United States Patent
Buenrostro et al.

(10) Patent No.: US 11,634,766 B2
(45) Date of Patent: Apr. 25, 2023

(54) METHODS AND COMPOSITIONS FOR ANALYZING NUCLEIC ACIDS

(71) Applicants: PRESIDENT AND FELLOWS OF HARVARD COLLEGE, Cambridge, MA (US); THE BROAD INSTITUTE, INC., Cambridge, MA (US); MASSACHUSETTS INSTITUTE OF TECHNOLOGY, Cambridge, MA (US)

(72) Inventors: Jason Daniel Buenrostro, Cambridge, MA (US); Sai Ma, Cambridge, MA (US); Aviv Regev, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 213 days.

(21) Appl. No.: 16/782,044

(22) Filed: Feb. 4, 2020

(65) Prior Publication Data

US 2020/0248255 A1  Aug. 6, 2020

Related U.S. Application Data

(60) Provisional application No. 62/951,880, filed on Dec. 20, 2019, provisional application No. 62/894,549, (Continued)

(51) Int. Cl.
*C12Q 1/68* (2018.01)
*C12Q 1/6874* (2018.01)
(Continued)

(52) U.S. Cl.
CPC ....... *C12Q 1/6874* (2013.01); *C12N 15/1065* (2013.01); *C12Q 1/6853* (2013.01);
(Continued)

(58) Field of Classification Search
CPC ..................................... C12Q 1/68
(Continued)

(56) References Cited

U.S. PATENT DOCUMENTS

| | | | |
|---|---|---|---|
| 11,198,910 B2 * | 12/2021 | Ponnaluri | C12Q 1/6886 |
| 2016/0138086 A1 * | 5/2016 | Seelig | C12Q 1/6806 |
| | | | 506/26 |
| 2017/0321251 A1 * | 11/2017 | Nolan | C12Q 1/6816 |

OTHER PUBLICATIONS

Cao et al, Joint profiling of chromatin accessibility and gene expression in thousands of single cells, Science. Sep. 28, 2018;361(6409):1380-1385. doi: 10.1126/science.aau0730. Epub Aug. 30, 2018.*

(Continued)

*Primary Examiner* — Aaron A Priest
(74) *Attorney, Agent, or Firm* — F Brent Nix, Esq.; Johnson, Marcou, Isaacs & Nix, LLC

(57) ABSTRACT

Provided herein include methods and compositions for analyzing nucleic acid in individual cells. In some embodiments, the methods herein include generating, within individual cells, fragmented cellular genomic DNA and cDNA copies of cellular RNA molecules, barcoding the fragmented genomic DNA and the cDNA within each cell such that the genomic DNA and the cDNA from the same cell receive the same unique barcode sequence, isolating the barcoded genomic DNA and cDNA, and characterizing one or more features of the individual cells based, at least in part, on sequencing of the isolated barcoded genomic DNA and the cDNA.

18 Claims, 23 Drawing Sheets

Specification includes a Sequence Listing.

Related U.S. Application Data filed on Aug. 30, 2019, provisional application No. 62/801,040, filed on Feb. 4, 2019.

(51) Int. Cl.
*C12N 15/10* (2006.01)
*C12Q 1/6853* (2018.01)

(52) U.S. Cl.
CPC . *C12Q 2525/131* (2013.01); *C12Q 2525/301* (2013.01); *C12Q 2563/179* (2013.01)

(58) Field of Classification Search
USPC .......................................................... 435/6
See application file for complete search history.

(56) References Cited

OTHER PUBLICATIONS

Angermueller, et al., "Parallel Single-Cell Sequencing Links Transcriptional and Epigenetic Heterogeneity", Nature Methods, vol. 13, No. 3, Mar. 2016, 11 pages.
Buenrostro, et al., "Integrated Single-Cell Analysis Maps the Continuous Regulatory Landscape of Human Hematopoietic Differentiation", Cell, vol. 173, No. 6, May 31, 2018, 29 pages.
Buenrostro, et al., "Single-Cell Chromatin Accessibility Reveals Principles of Regulatory Variation", Nature, vol. 523, No. 7561, Jul. 23, 2015, 20 pages.
Buenrostro, et al., "Transposition of Native Chromatin for Fast and Sensitive Epigenomic Profiling of Open Chromatin, DNA-Binding Proteins and Nucleosome Position", Nature Methods, vol. 10, No. 12, Dec. 2013, 15 pages.
Cao, et al., "Joint Profiling of Chromatin Accessibility and Gene Expression in Thousands of Single Cells", Science, vol. 361, No. 6409, Sep. 28, 2018, 14 pages.
Chen, et al., "High-Throughput Sequencing of the Transcriptome and Chromatin Accessibility in the Same Cell", Nature Biotechnology, vol. 37, No. 12, Dec. 2019, 10 pages.
Clark, et al., "ScNMT-seq Enables Joint Profiling of Chromatin Accessibility DNA Methylation and Transcription in Single Cells", Nature Communications, vol. 9, Article No. 781, 2018, 9 pages.
Cusanovich, et al., "Multiplex Single Cell Profiling of Chromatin Accessibility by Combinatorial Cellular Indexing", Science, vol. 348, No. 6237, May 22, 2015, 11 pages.
Datlinger, et al., "Pooled CRISPR Screening with Single-Cell Transcriptome Read-Out", Nature Methods, vol. 14, No. 3, Mar. 2017, 20 pages.
Dey, et al., "Integrated Genome and Transcriptome Sequencing of the Same Cell", Nature Biotechnology, vol. 33, No. 3, Mar. 2015, 7 pages.
Ding, et al., "Systematic Comparative Analysis of Single Cell RNA-Sequencing Methods", bioRxiv, May 9, 2019, 67 pages.
Dixit, et al., "Perturb-Seq; Dissecting Molecular Circuits with Scalable Single-Cell RNA Profiling of Pooled Genetic Screens", Cell, vol. 167, No. 7, Dec. 15, 2016, 40 pages.
Frei, et al., "Highly Multiplexed Simultaneous Detection of RNAs and Proteins in Single Cells", Nature Methods, vol. 13, No. 3, Mar. 2016, 19 pages.
Gasperini, et al., "A Genome-Wide Framework for Mapping Gene Regulation via Cellular Genetic Screens", Cell, vol. 176, No. (1-2), Jan. 10, 2019, 49 pages.
Gierahn, et al., "Seq-Well: Portable, Low-Cost RNA Sequencing of Single Cells at High Throughput", Nature Methods, vol. 14, No. 4, Apr. 2017., 9 pages.
Guo, et al., "Single-Cell Multi-Omics Sequencing of Mouse Early Embryos and Embryonic Stem Cells", Cell Research, vol. 27, No. 8, Aug. 2017, 22 pages.
Habib, et al., "Div-Seq: Single-Nucleus RNA-Seq Reveals Dynamics of Rare Adult Newborn Neurons", Science, vol. 353, No. 6302, Aug. 26, 2016, 5 pages.
Habib, et al., "Massively Parallel Single-Nucleus RNA-seq with DroNc-seq", Nature Methods, vol. 14, No. 10, Oct. 2017, 18 pages.
Hou, et al., "Single-Cell Triple Omics Sequencing Reveals Genetic, Epigenetic and Transcriptomic Heterogeneity in Hepatocellular Carcinomas", Cell Research, vol. 26, No. 3, Mar. 2016, 16 pages.
Joost, et al., "Single-Cell Transcriptomics Reveals that Differentiation and Spatial Signatures Shape Epidermal and Hair Follicle Heterogeneity", Cell Systems, vol. 3, No. 3, Sep. 28, 2016, 27 pages.
Kelsey, et al., "Single-Cell Epigenomics: Recording the Past and Predicting the Future", Science, vol. 358, No. 6359, Oct. 6, 2017, 8 pages.
Klein, et al., "Droplet Barcoding for Single-Cell Transcriptomics Applied to Embryonic Stem Cells", Cell, vol. 161, No. 5, May 21, 2015, 24 pages.
Kong, et al., "Concurrent Single-Cell RNA and Targeted DNA Sequencing on an Automated Platform for Comeasurement of Genomic and Transcriptomic Signatures", Clinical Chemistry, vol. 65, No. 2, Feb. 2019, 10 pages.
Lareau, et al., "Droplet-Based Combinatorial Indexing for Massive-Scale Single-Cell Chromatin Accessibility", Nature Biotechnology, vol. 37, No. 8, Aug. 2019, 15 pages.
Larsson, et al., "Genomic Encoding of Transcriptional Burst Kinetics", Nature. vol. 565, Jan. 10, 2019, 17 pages.
Liu, et al., "Deconvolution of Single-Cell Multi-Omics Layers Reveals Regulatory Heterogeneity", Nature Communications, vol. 10, No. 1, Jan. 28, 2019, 10 pages.
Ludwig, et al., "Lineage Tracing in Humans Enabled by Mitochondrial Mutations and Singe-Cell Genomics", Cell, vol. 176, No. 6, Mar. 7, 2019, 38 pages.
Macaulay, et al., "G&T-seq: Parallel Sequencing of Single-Cell Genomes and Transcriptomes", Nature Methods, vol. 12, No. 6, Jun. 2015, 7 pages.
Macosko, et al., "Highly Parallel Genome-Wide Expression Profiling of Individual Cells Using Nanoliter Droplets", Cell, vol. 161, No. 5, May 21, 2015, 25 pages.
Marinov, et al., "From Single-Cell to Cell-Pool Transcriptomes: Stochasticity in Gene Expression and RNA Splicing", Genome Research, vol. 24, No. 3, Mar. 2014, 496-510.
Mezger, et al., "High-Throughput Chromatin Accessibility Profiling at Single-Cell Resolution", Nature Communications, vol. 9, No. 3647, Sep. 7, 2018, 6 pages.
Mulqueen, et al., "Highly Scalable Generation of DNA Methylation Profiles in Single Cells", Nature Biotechnology, vol. 36, No. 5, Jun. 2018, 16 pages.
Olsson, et al., "Single-Cell Analysis of Mixed-Lineage States Leading to a Binary Cell Fate Choice", Nature, vol. 537, No. 7622, Sep. 29, 2016, 35 pages.
Picelli, et al., "Tn5 Transposase and Tagmentation Procedures for Massively Scaled Sequencing Projects", Genome Research, vol. 24, No. 12, Dec. 2014, 2033-2040.
Pott, et al., "Simultaneous Measurement of Chromatin Accessibility, DNA Methylation, and Nucleosome Phasing in Single Cells", eLife, vol. 6, Jun. 2017, 19 pages.
Preissl, et al., "Single-Nucleus Analysis of Accessible Chromatin in Developing Mouse Forebrain Reveals Cell-Type-Specific Transcriptional Regulation", Nature Neuroscience, vol. 21, No. 3, Mar. 2018, 14 pages.
Ramani, et al., "Massively Multiplex Single-Cell Hi-C", Nature Methods, vol. 14, No. 3, Mar. 2017, 13 pages.
Rodriguez-Fraticelli, et al., "Clonal Analysis of Lineage Fate in Native Haematopoiesis", Nature, vol. 553, Jan. 11, 2018, 22 pages.
Rodriguez-Meira, et al., "Unravelling Intratumoral Heterogeneity through High-Sensitivity Single-Cell Mutational Analysis and Parallel RNA Sequencing", Molecular Cell, vol. 73, No. 6, Mar. 21, 2019, 23 pages.
Rosenberg, et al., "Single-Cell Profiling of the Developing Mouse Brain and Spinal Cord with Split-Pool Barcoding", Science, vol. 360, No. 6385, Apr. 13, 2018, 8 pages.
Rusk, et al., "Multi-Omics Single-Cell Analysis", Nature Methods, vol. 16, No. 8, Aug. 2019, 679 page.

(56) References Cited

OTHER PUBLICATIONS

Satpathy, et al., "Massively Parallel Single-Cell Chromatin Landscapes of Human Immune Cell Development and Intratumoral T Cell Exhaustion", Nature Biotechnology, vol. 37, No. 8, Aug. 2019, 20 pages.

Shema, et al., "Single-Cell and Single-Molecule Epigenomics to Uncover Genome Regulation at Unprecedented Resolution", Nature Genetics, vol. 51, No. 1, Jan. 2019, 7 pages.

Stoeckius, et al., "Simultaneous Epitope and Transcriptome Measurement in Single Cells", Nature Methods, vol. 14, Jul. 31, 2017, 10 pages.

Vitak, et al., "Sequencing Thousands of Single-Cell Genomes with Combinatorial Indexing", Nature Methods, vol. 14, No. 3, Mar. 2017, 19 pages.

Yoshida, et al., "The cis-Regulatory Atlas of the Mouse Immune System", Cell, vol. 176, No. 4, Feb. 7, 2019, 897-912.

Zhu, et al., "An Ultra High-Throughput Method for Single-Cell Joint Analysis of Open Chromatin and Transcriptome", Nature Structural & Molecular Biology, vol. 26, No. 11, Nov. 2019, 1063-1070.

* cited by examiner

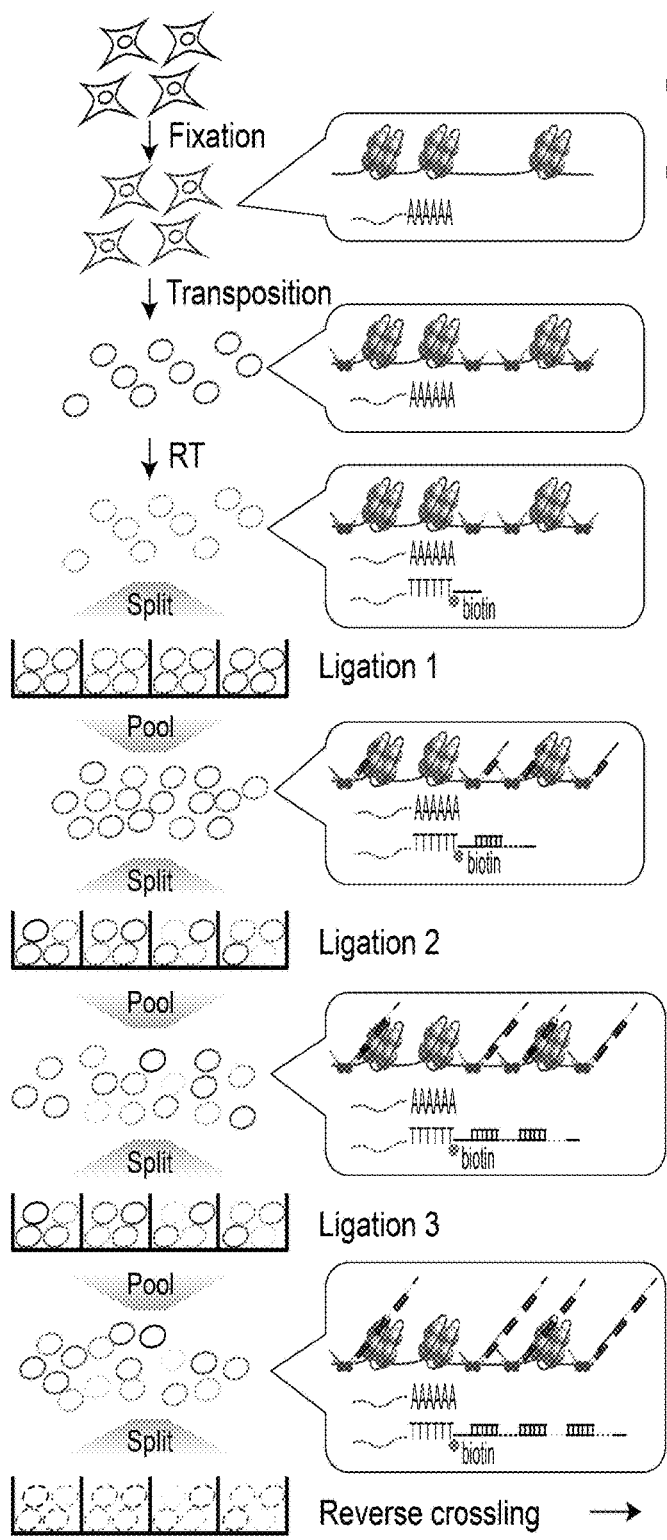
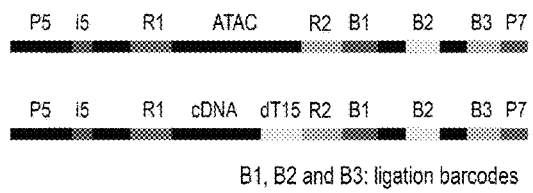
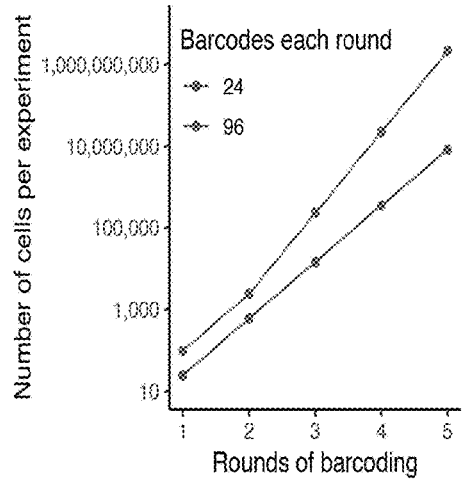
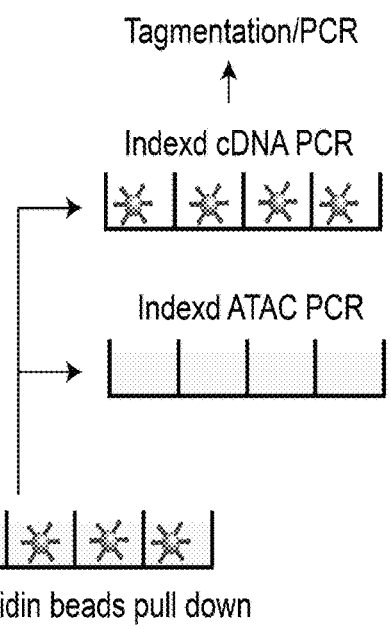
FIG. 1B
FIG. 1C
FIG. 1A

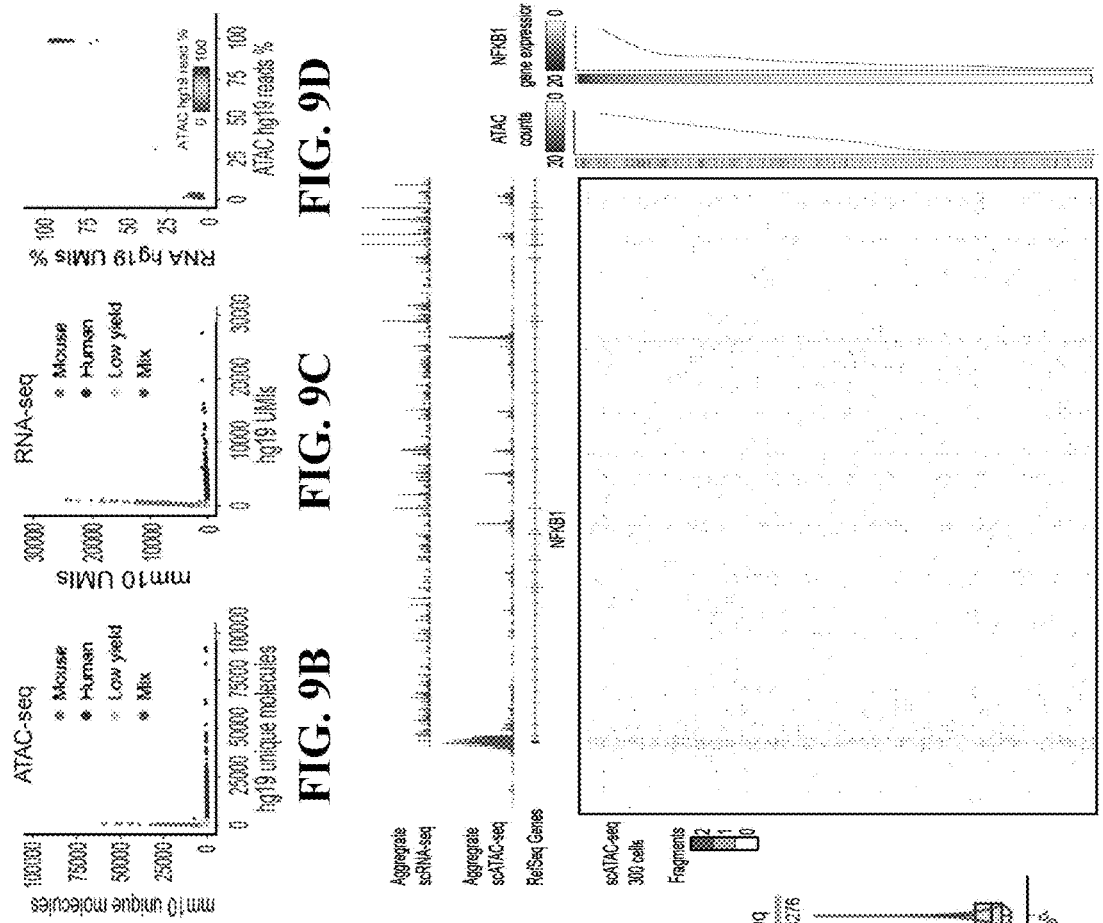
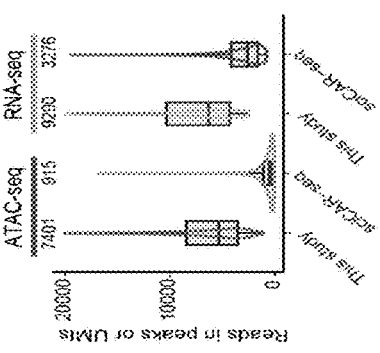
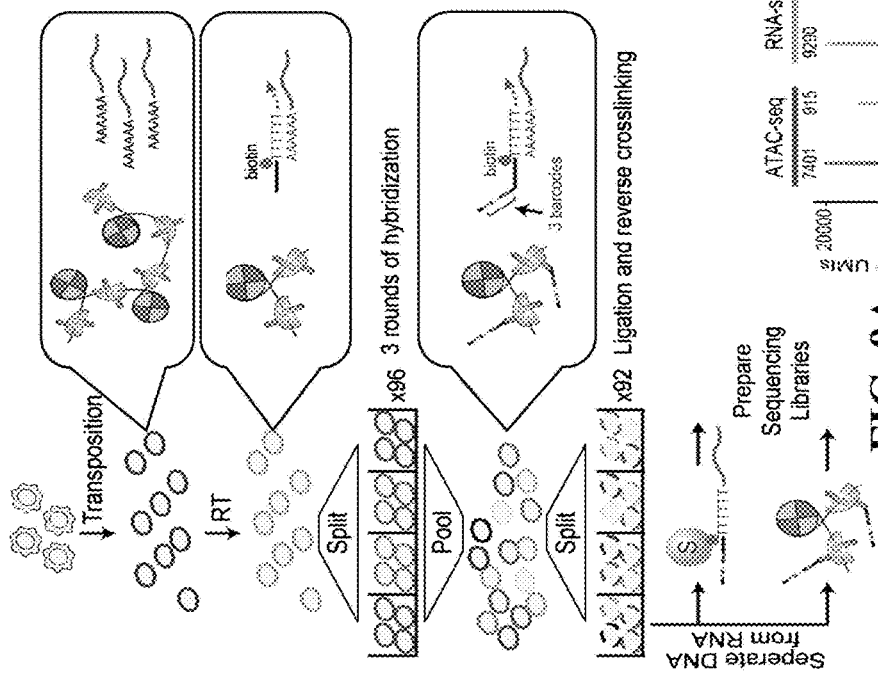
FIG. 9A  FIG. 9B  FIG. 9C  FIG. 9D  FIG. 9E  FIG. 9F

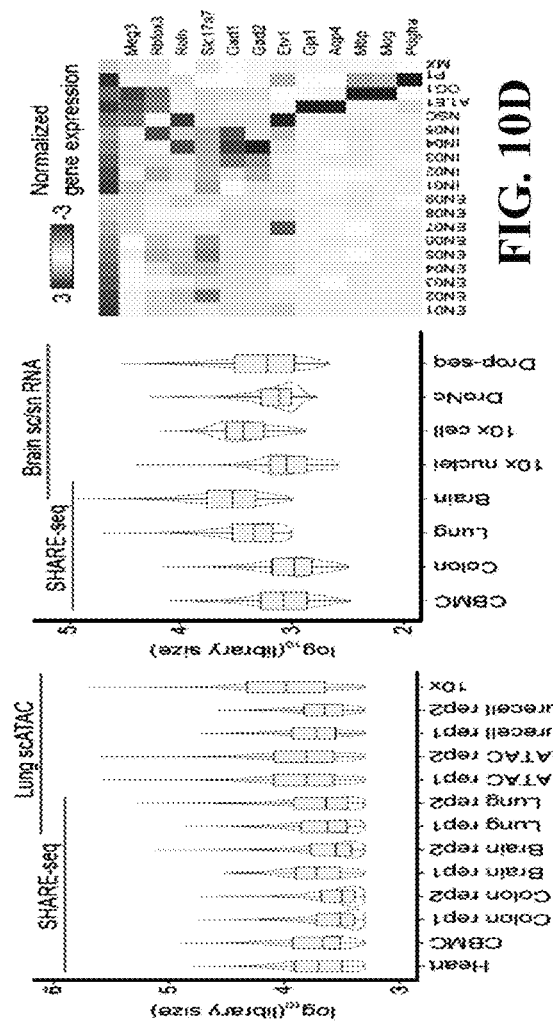
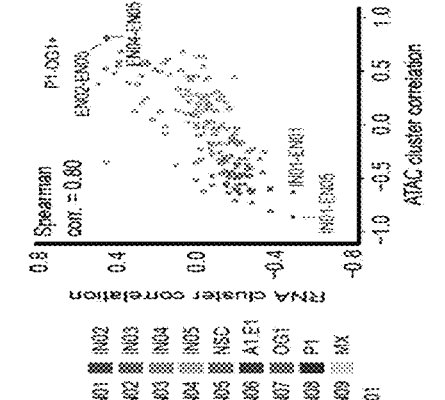
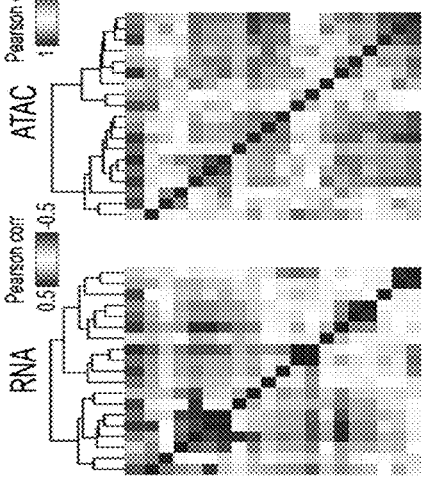
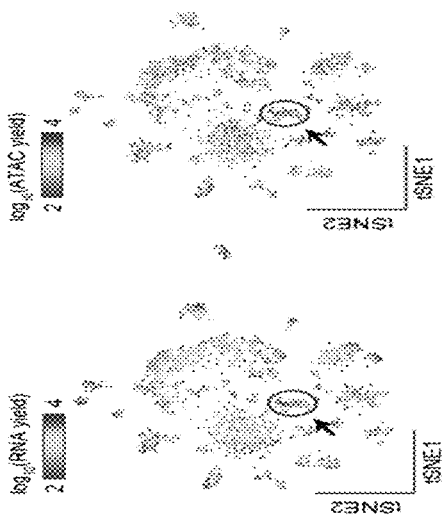
FIG. 10A FIG. 10B FIG. 10C FIG. 10D FIG. 10E FIG. 10F FIG. 10G FIG. 10H

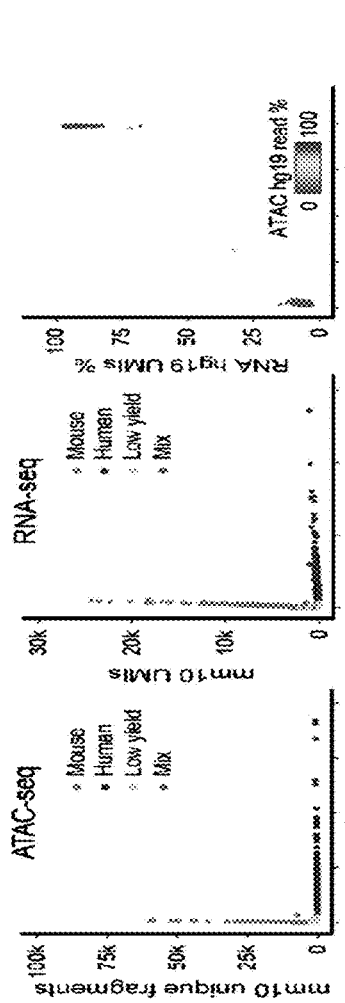
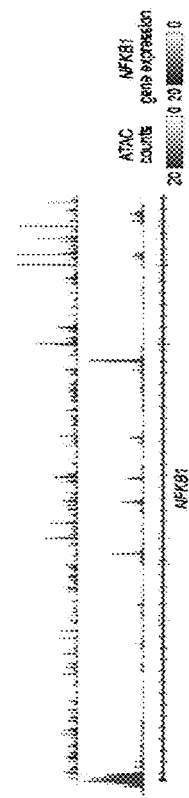
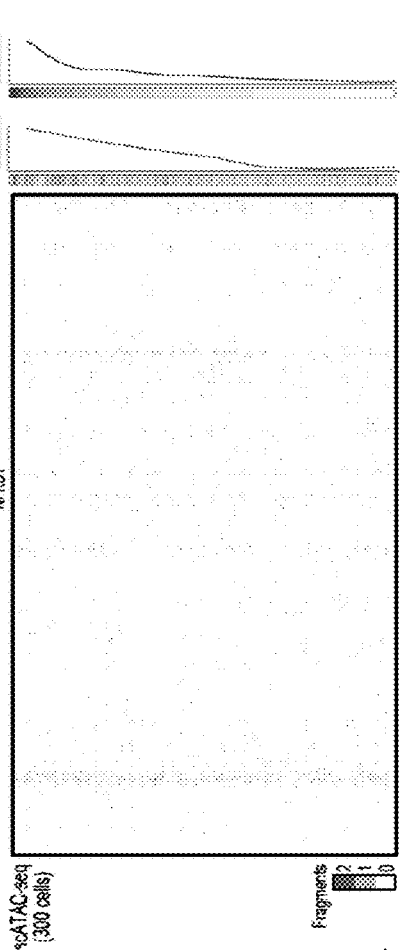
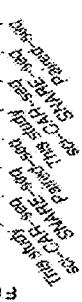
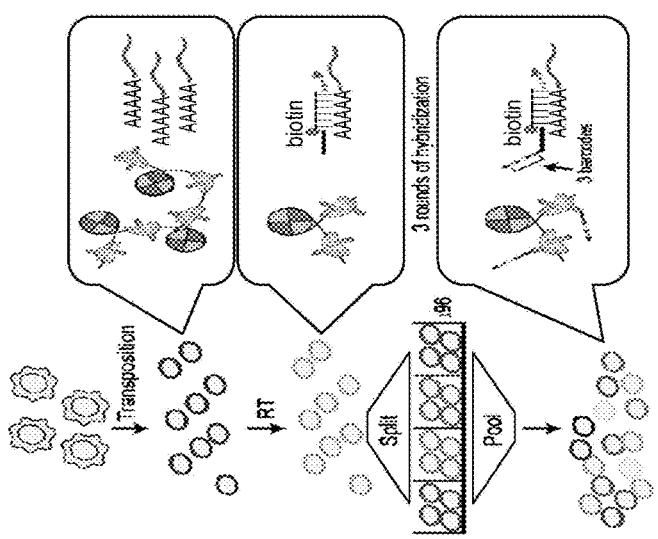
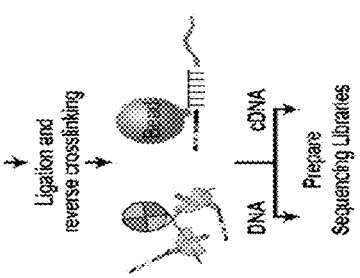
FIG. 11A
FIG. 11B
FIG. 11C
FIG. 11D
FIG. 11E
FIG. 11F

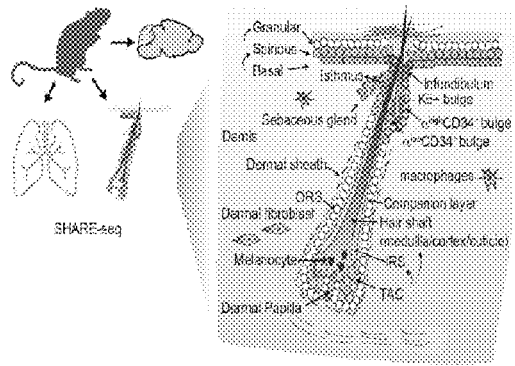
FIG. 12A
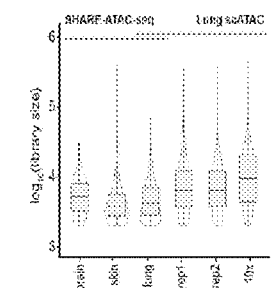
FIG. 12B
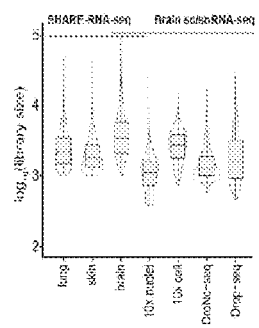
FIG. 12C
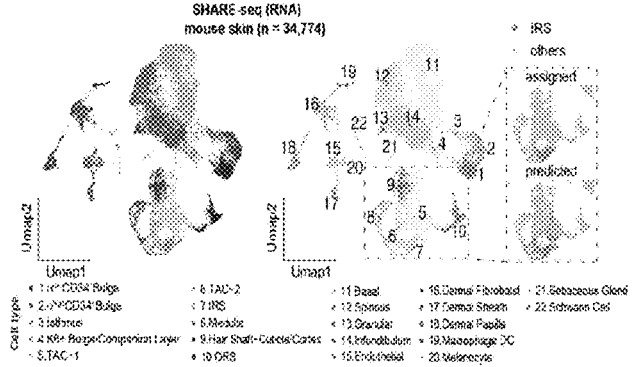
FIG. 12D
FIG. 12E
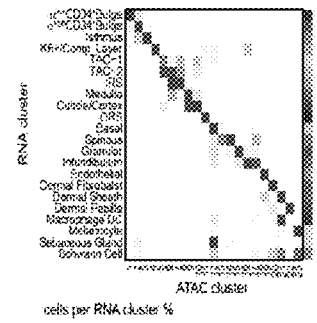
FIG. 12F
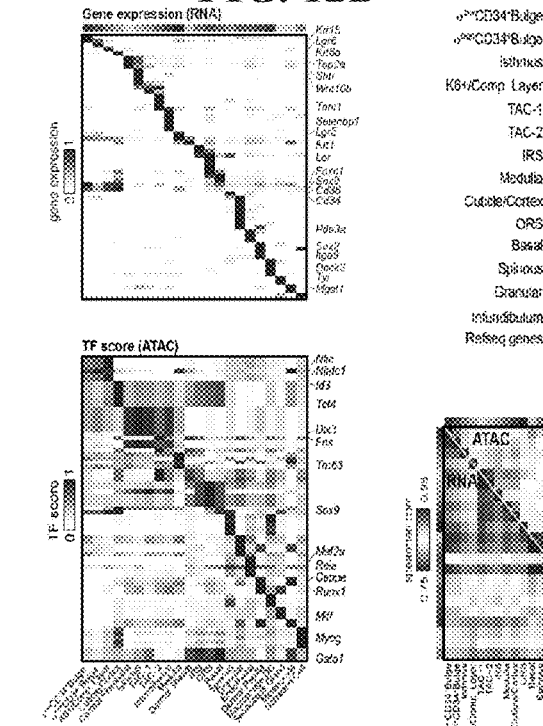
FIG. 12G
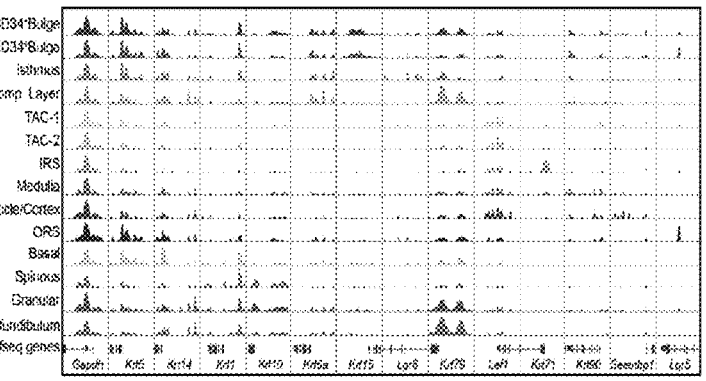
FIG. 12H
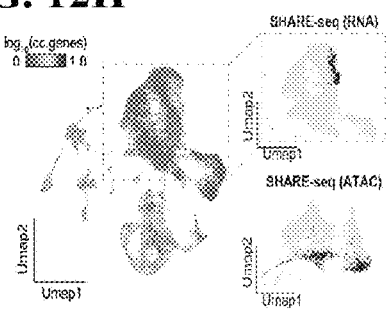
FIG. 12J
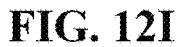
FIG. 12I

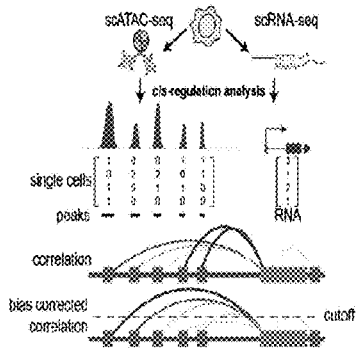
FIG. 13A
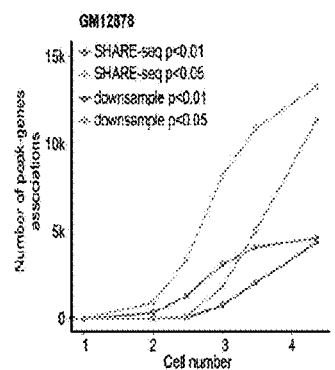
FIG. 13B
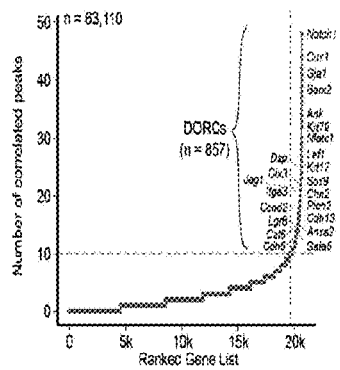
FIG. 13F
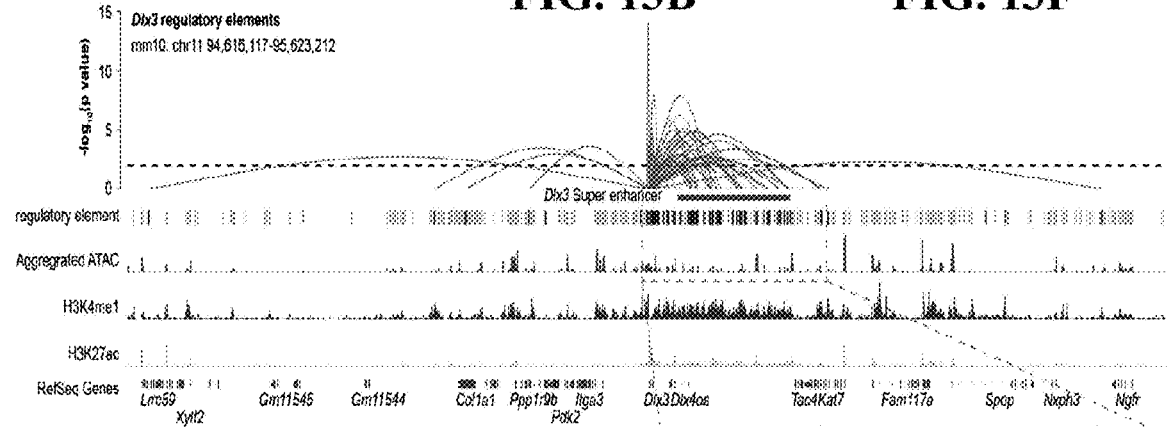
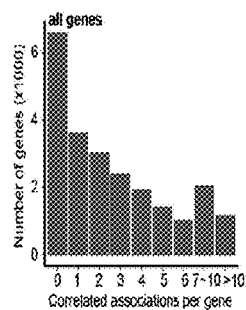
FIG. 13D
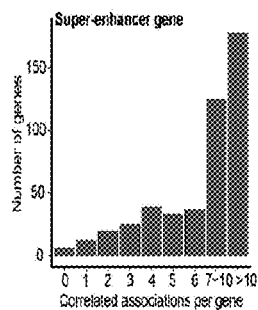
FIG. 13E
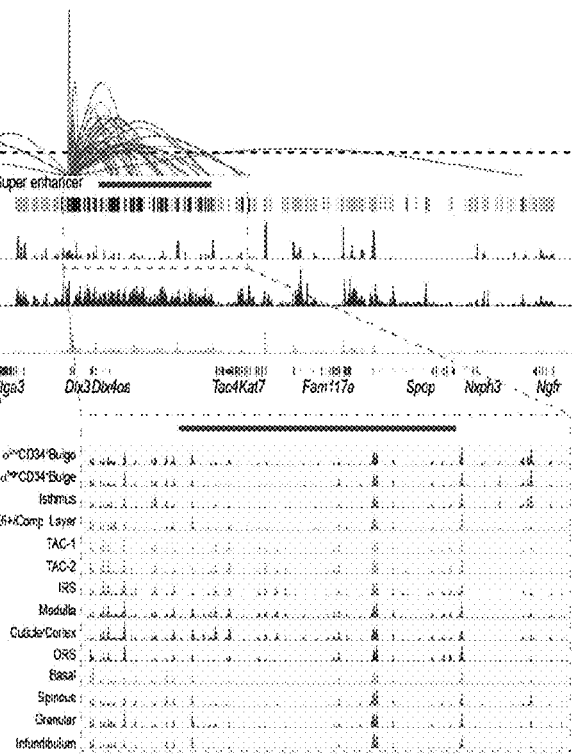
FIG. 13C
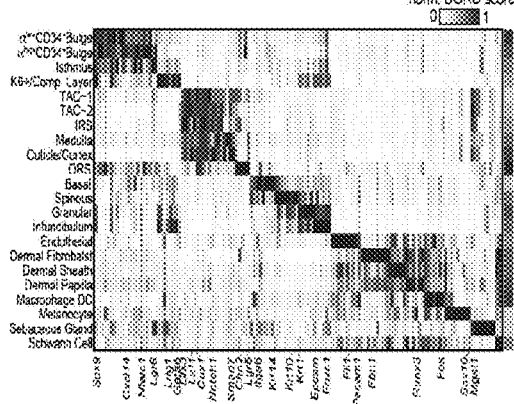
FIG. 13G
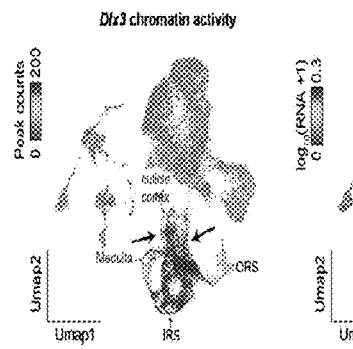
FIG. 13H

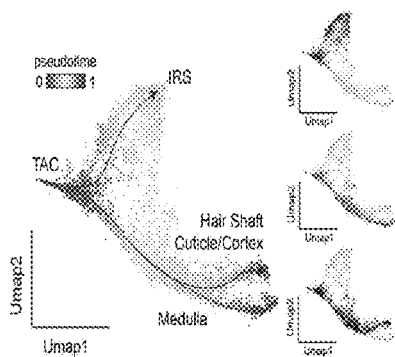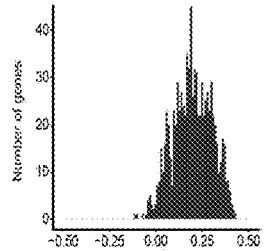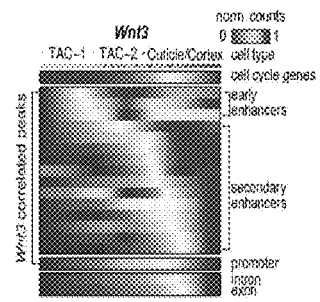
FIG. 14A   FIG. 14C   FIG. 14D
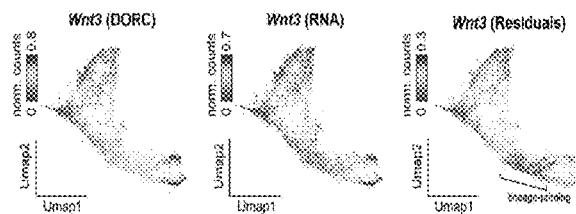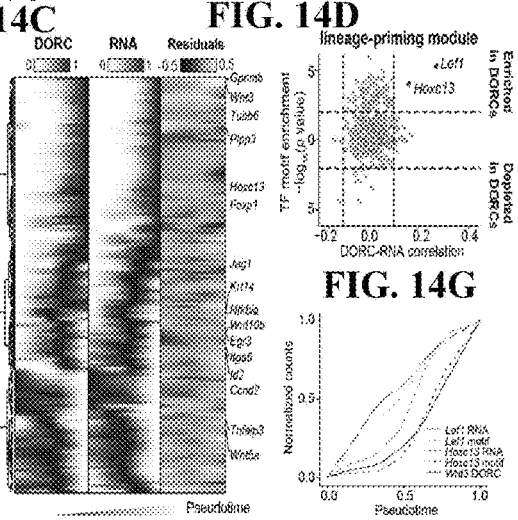
FIG. 14B
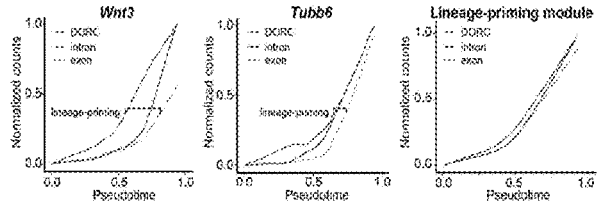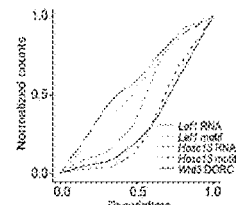
FIG. 14F   FIG. 14E   FIG. 14H
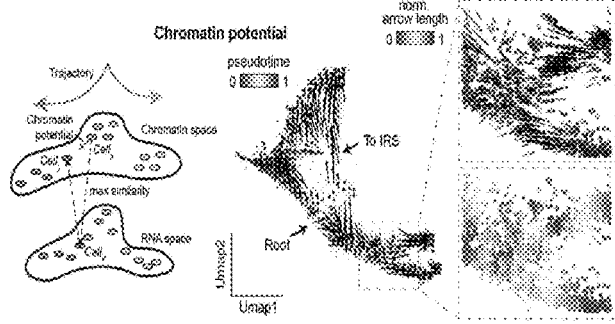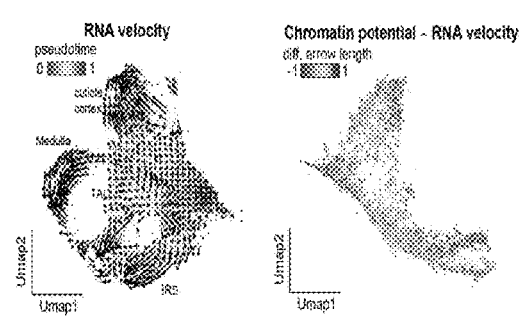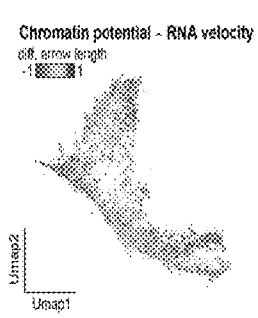
FIG. 14I   FIG. 14J   FIG. 14K
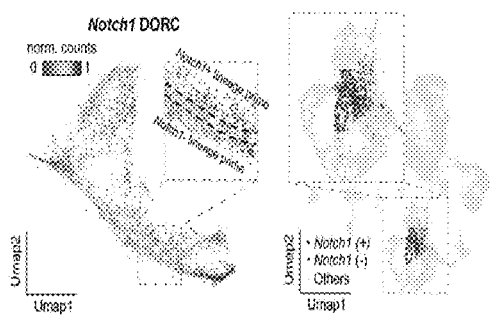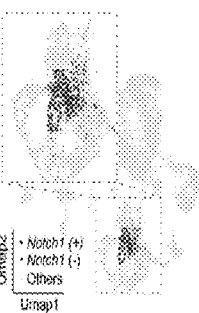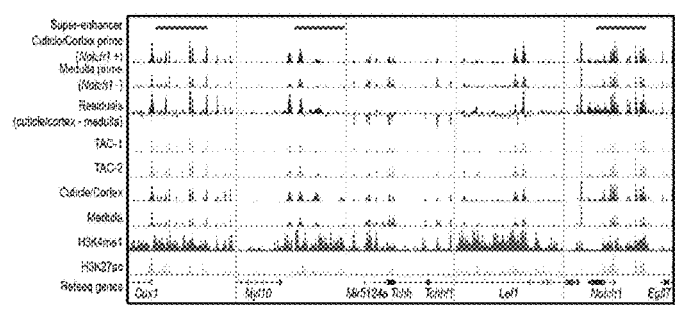
FIG. 14L   FIG. 14M   FIG. 14N

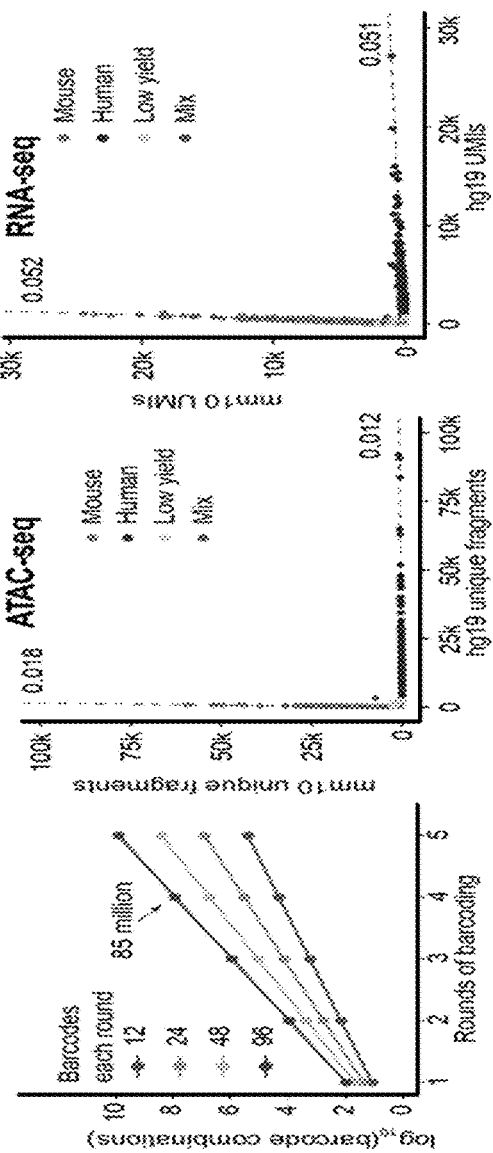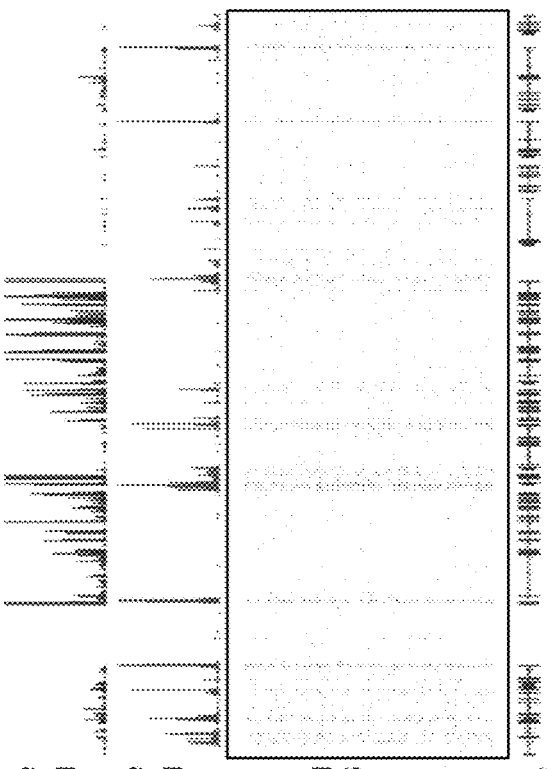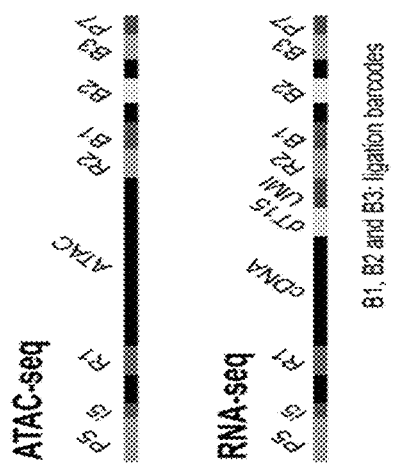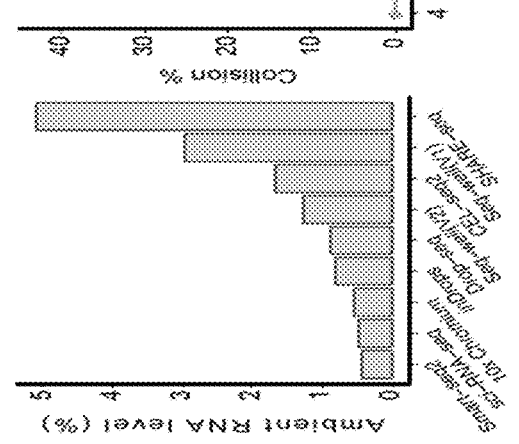
FIG. 15A
FIG. 15B
FIG. 15C
FIG. 15D
FIG. 15E
FIG. 15F
FIG. 15G

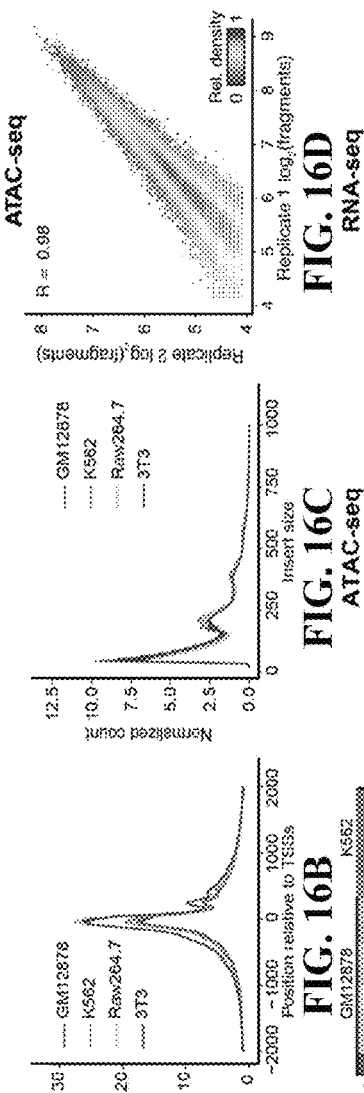
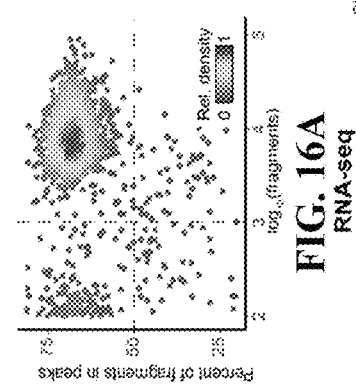
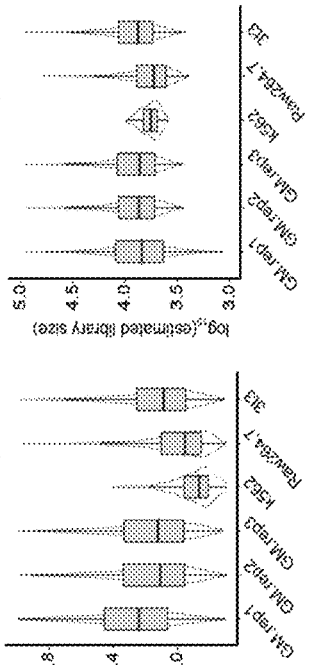
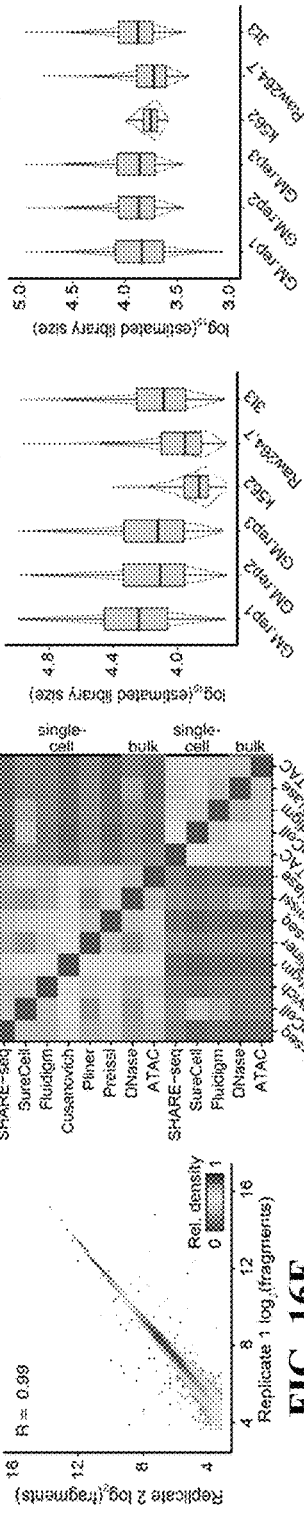
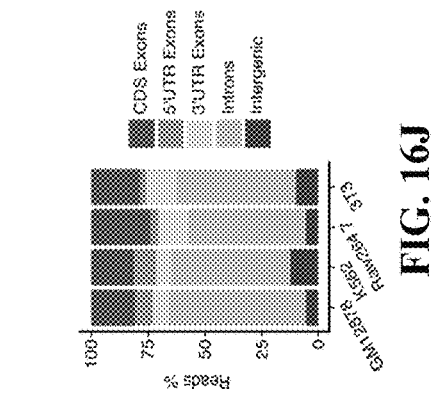
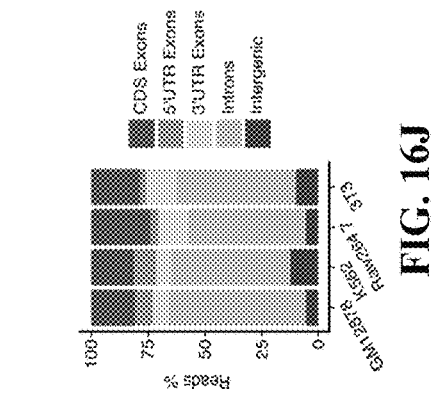
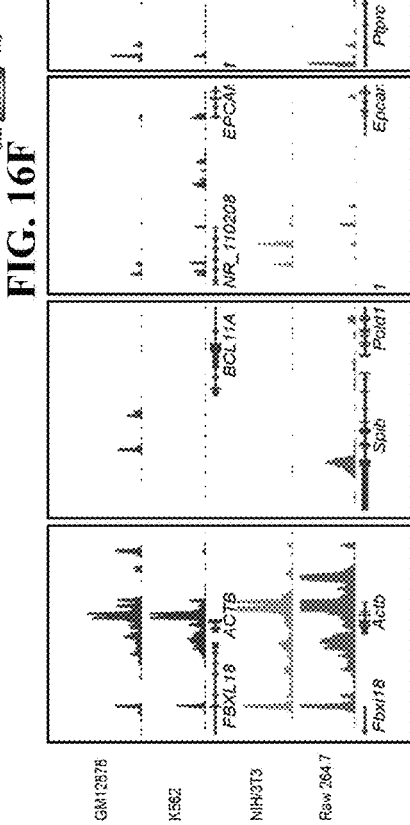

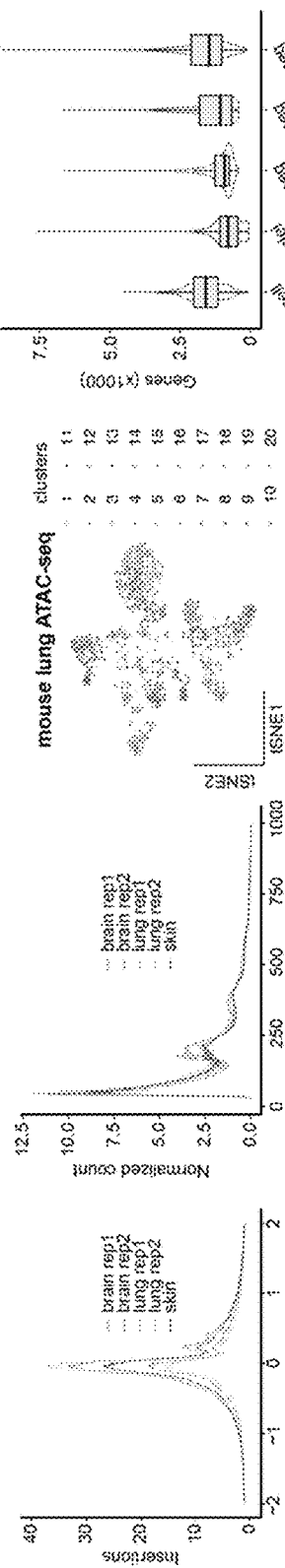
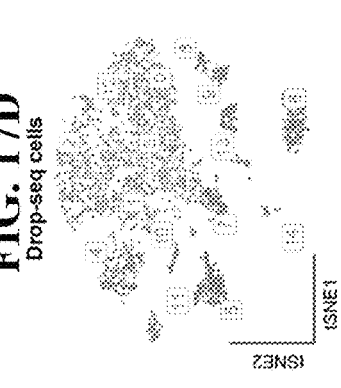
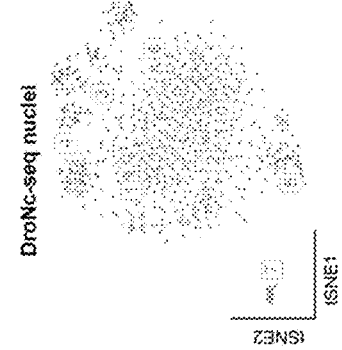
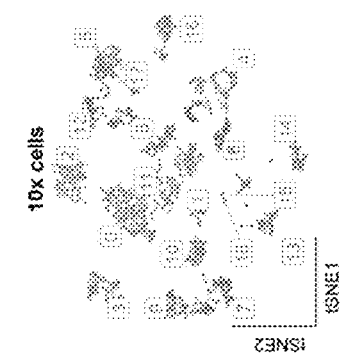
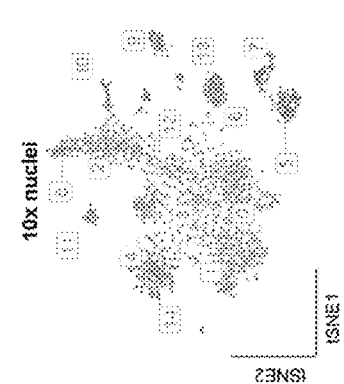
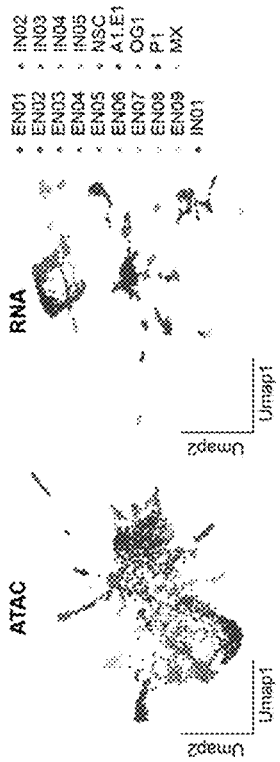

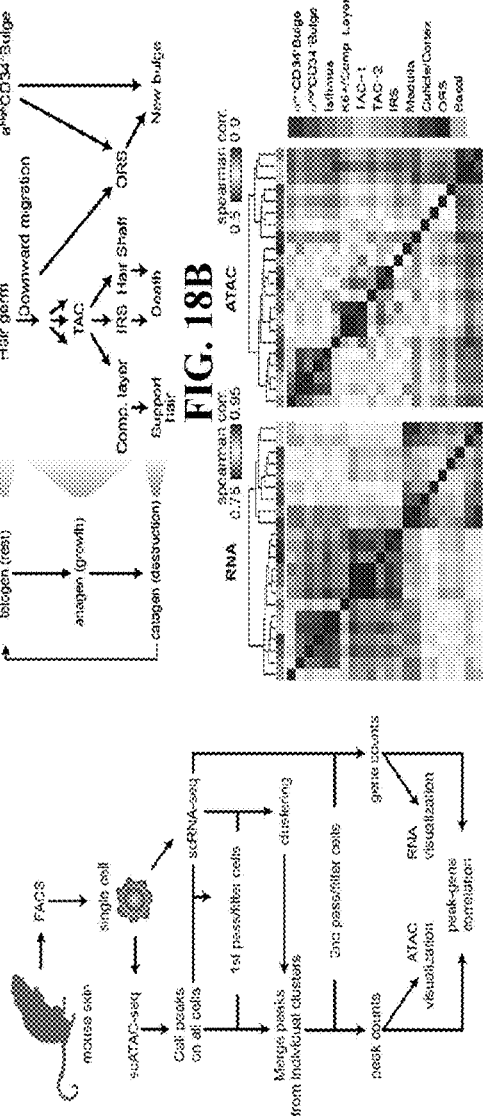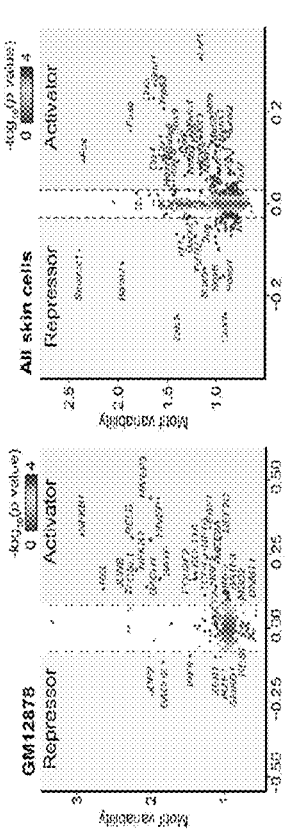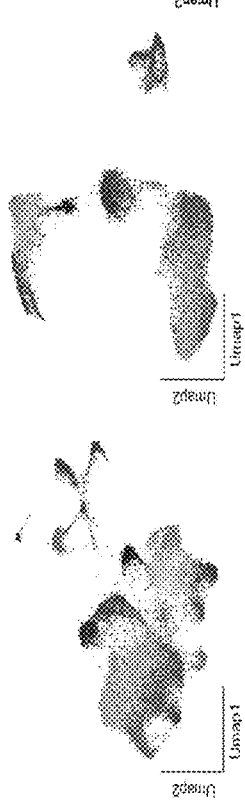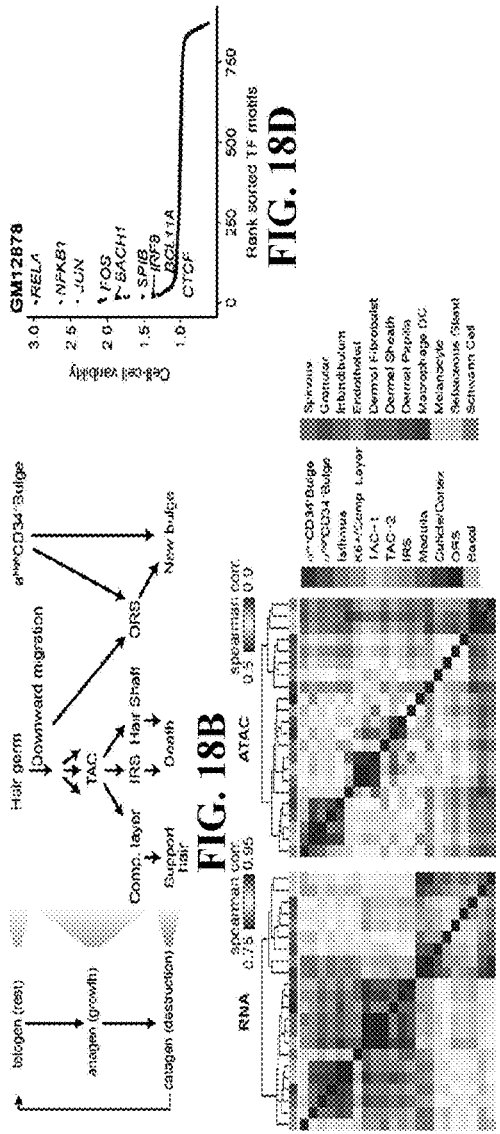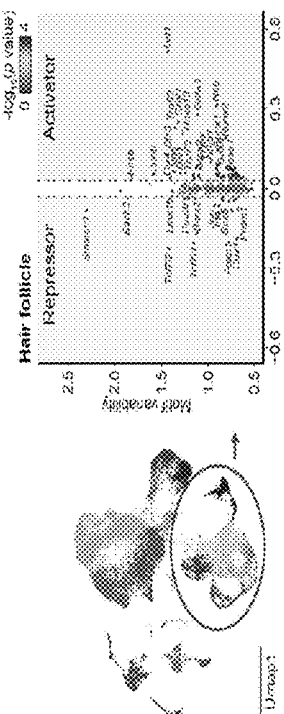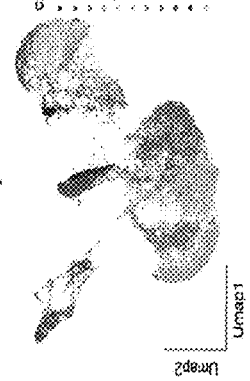
FIG. 18A — FIG. 18J

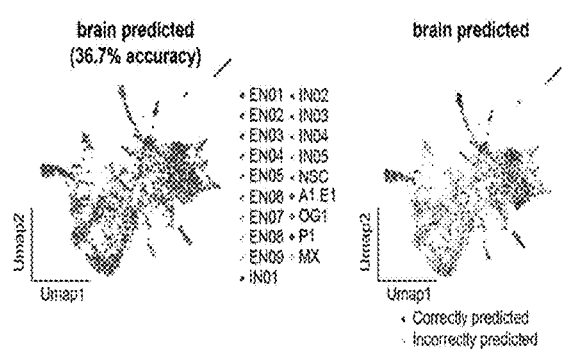
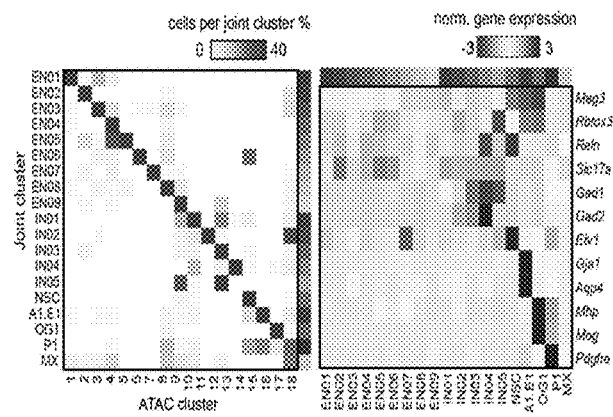
FIG. 19A  FIG. 19B  FIG. 19C
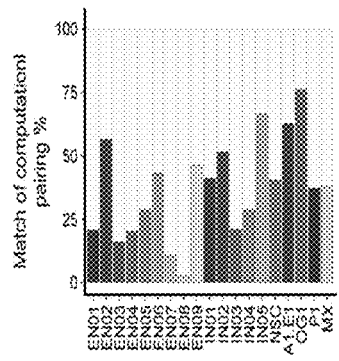
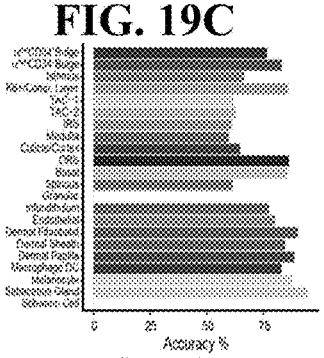
FIG. 19D  FIG. 19E  FIG. 19F
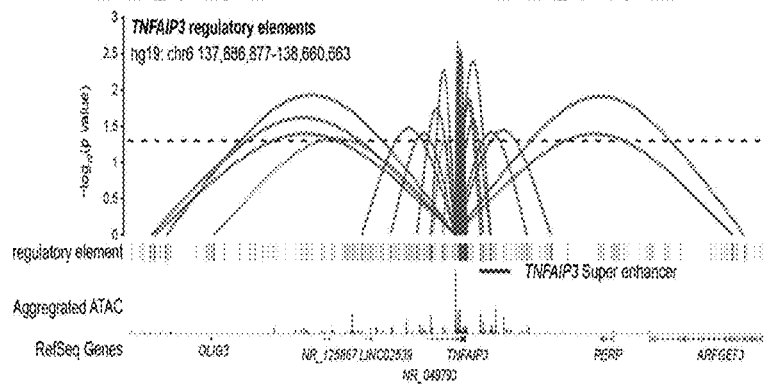
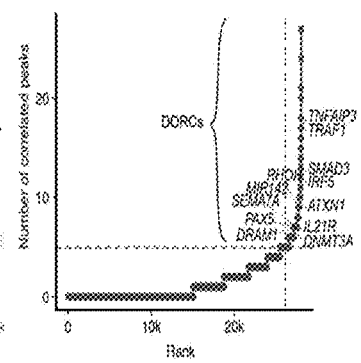
FIG. 20A  FIG. 20B
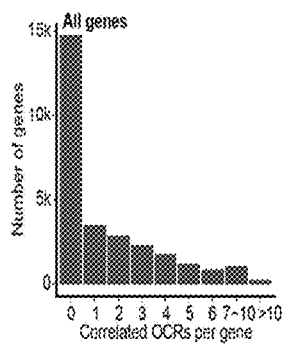
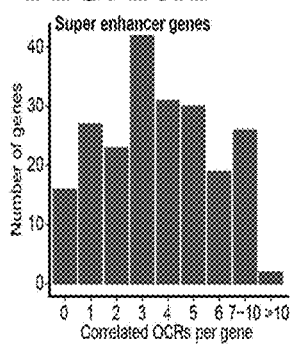
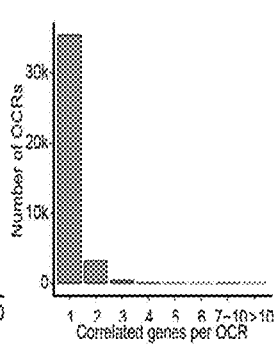
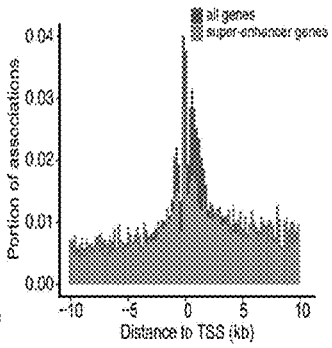
FIG. 20C  FIG. 20D  FIG. 20E  FIG. 20F

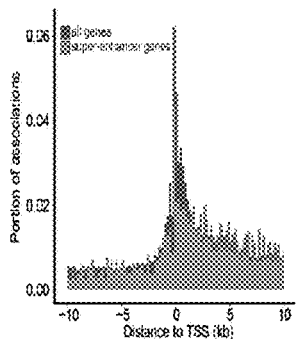 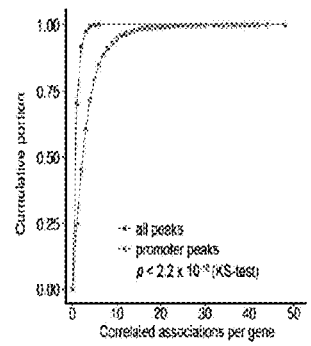 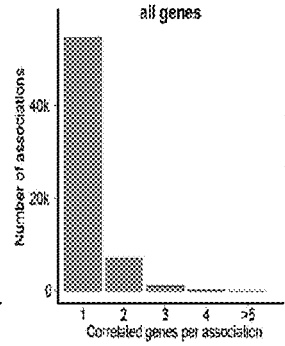 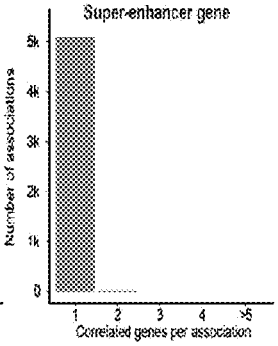
FIG. 21A FIG. 21B FIG. 21C FIG. 21D
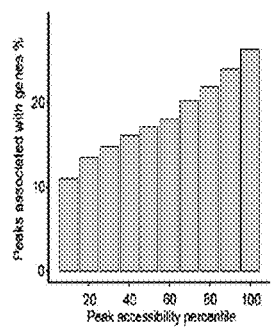 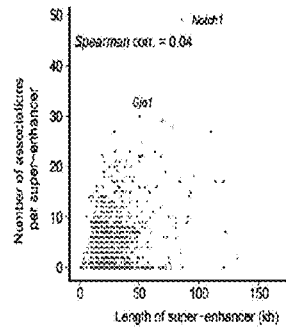 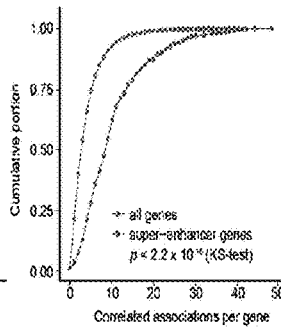 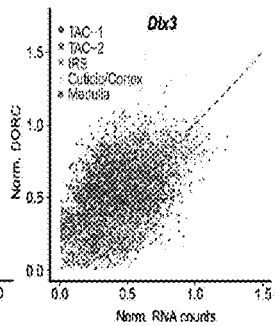
FIG. 21E FIG. 21G FIG. 21H FIG. 21K
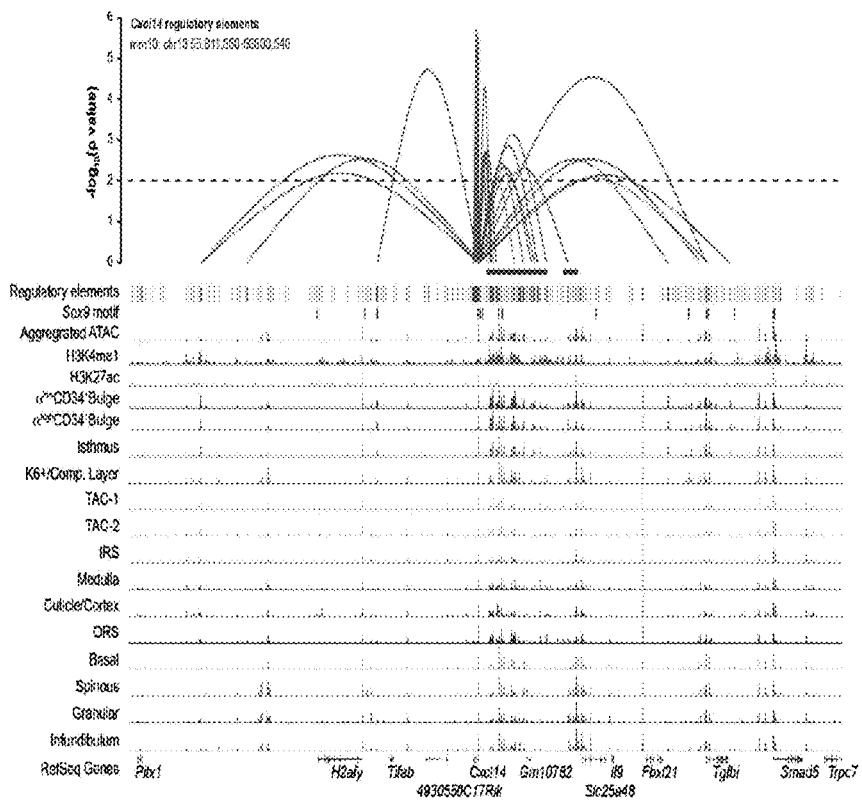 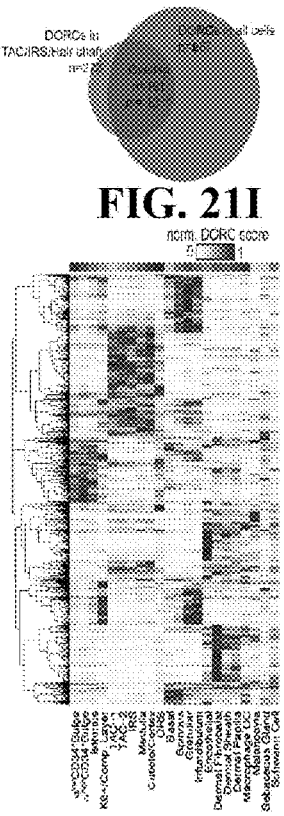
FIG. 21I
FIG. 21F FIG. 21J

SEQUENCE LISTING

```
<160> NUMBER OF SEQ ID NOS: 788

<210> SEQ ID NO 1
<211> LENGTH: 157
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(32)
<223> OTHER INFORMATION: n is a, c, g, or t
<220> FEATURE:
<221> NAME/KEY: misc_feature
<222> LOCATION: (63)..(70)
<223> OTHER INFORMATION: n is a, c, g, or t
<220> FEATURE:
<221> NAME/KEY: misc_feature
<222> LOCATION: (101)..(108)
<223> OTHER INFORMATION: n is a, c, g, or t

<400> SEQUENCE: 1
caagcagaag acggcatacg agatnnnnnn nngtggccga tgtttcgcat cggcgtacga      60
ctnnnnnnnn atccacgtgc ttgagcgcgc tgcatacttg nnnnnnnncc catgatcgtc     120
cgagtctcgt gggctcggag atgtgtataa gagacag                             157

<210> SEQ ID NO 2
<211> LENGTH: 12
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(12)
<223> OTHER INFORMATION: n is a, c, g, or t

<400> SEQUENCE: 2
nnnnnnnnnn nn                                                         12

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
ccgagcccac gagactcgga cgatcatggg                                      30

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 4
caagtatgca gcgcgctcaa gcacgtggat                                    30

<210> SEQ ID NO 5
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 5
agtcgtacgc cgatgcgaaa catcggccac                                    30

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 6
cccatgatcg tccgagtctc gtgggctcgg                                    30

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 7
atccacgtgc ttgagcgcgc tgcatacttg                                    30

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
gtggccgatg tttcgcatcg gcgtacgact                                    30

<210> SEQ ID NO 9
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 9
tcgtcggcag cgtcagatgt gtataagaga cag                                33

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(29)
<223> OTHER INFORMATION: RNA nucleotide

<400> SEQUENCE: 10
aagcagtggt atcaacgcag agtgaatggg                                    30
```

```
<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 11
aagcagtggt atcaacgcag agt                                              23

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 12
caagcagaag acggcatacg agat                                             24

<210> SEQ ID NO 13
<211> LENGTH: 34
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphate modification

<400> SEQUENCE: 13
gtctcgtggg ctcggagatg tgtataagag acag                                  34

<210> SEQ ID NO 14
<211> LENGTH: 60
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphate modification
<220> FEATURE:
<221> NAME/KEY: misc_feature
<222> LOCATION: (35)..(43)
<223> OTHER INFORMATION: n is a, c, g, or t
<220> FEATURE:
<221> NAME/KEY: misc_feature
<222> LOCATION: (44)..(45)
<223> OTHER INFORMATION: biotin linker
<220> FEATURE:
<221> NAME/KEY: misc_feature
<222> LOCATION: (60)..(60)
<223> OTHER INFORMATION: n is a, c, g, or t

<400> SEQUENCE: 14
gtctcgtggg ctcggagatg tgtataagag acagnnnnn nnnntttttt ttttttttvn       60

<210> SEQ ID NO 15
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
```

<223> OTHER INFORMATION: 5 prime phosphorylation
<220> FEATURE:
<221> NAME/KEY: misc_feature
<222> LOCATION: (14)..(14)
<223> OTHER INFORMATION: 3 prime 3ddC modification

<400> SEQUENCE: 15
ctgtctctta taca                                                          14

<210> SEQ ID NO 16
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 16
aatgatacgg cgaccaccga gatctacact agatcgctcg tcggcagcgt cagatgtgta        60
t                                                                        61

<210> SEQ ID NO 17
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 17
aatgatacgg cgaccaccga gatctacacc tctctattcg tcggcagcgt cagatgtgta        60
t                                                                        61

<210> SEQ ID NO 18
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 18
aatgatacgg cgaccaccga gatctacact atcctcttcg tcggcagcgt cagatgtgta        60
t                                                                        61

<210> SEQ ID NO 19
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 19
aatgatacgg cgaccaccga gatctacaca gagtagatcg tcggcagcgt cagatgtgta        60
t                                                                        61

<210> SEQ ID NO 20
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 20
aatgatacgg cgaccaccga gatctacacg taaggagtcg tcggcagcgt cagatgtgta        60
t                                                                        61

<210> SEQ ID NO 21
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 21
aatgatacgg cgaccaccga gatctacaca ctgcatatcg tcggcagcgt cagatgtgta     60
t                                                                    61

<210> SEQ ID NO 22
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 22
aatgatacgg cgaccaccga gatctacaca aggagtatcg tcggcagcgt cagatgtgta     60
t                                                                    61

<210> SEQ ID NO 23
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 23
aatgatacgg cgaccaccga gatctacacc taagccttcg tcggcagcgt cagatgtgta     60
t                                                                    61

<210> SEQ ID NO 24
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 24
aatgatacgg cgaccaccga gatctacact ggaaatctcg tcggcagcgt cagatgtgta     60
t                                                                    61

<210> SEQ ID NO 25
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 25
aatgatacgg cgaccaccga gatctacaca acatgattcg tcggcagcgt cagatgtgta     60
t                                                                    61

<210> SEQ ID NO 26
<211> LENGTH: 61
<212> TYPE: DNA
<213> ORGANISM: Artificial Sequence
<220> FEATURE:
<223> OTHER INFORMATION: Synthetic Oligonucleotide

```
<400> SEQUENCE: 26
aatgatacgg cgaccaccga gatctacact gatgaaatcg tcggcagcgt cagatgtgta    60
t                                                                   61

<210> SEQ ID NO 27
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 27
aatgatacgg cgaccaccga gatctacacg tcggacttcg tcggcagcgt cagatgtgta    60
t                                                                   61

<210> SEQ ID NO 28
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 28
aatgatacgg cgaccaccga gatctacact ttctagctcg tcggcagcgt cagatgtgta    60
t                                                                   61

<210> SEQ ID NO 29
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 29
aatgatacgg cgaccaccga gatctacact aaccaagtcg tcggcagcgt cagatgtgta    60
t                                                                   61

<210> SEQ ID NO 30
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 30
aatgatacgg cgaccaccga gatctacacg tgtatcgtcg tcggcagcgt cagatgtgta    60
t                                                                   61

<210> SEQ ID NO 31
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 31
aatgatacgg cgaccaccga gatctacact ccatcaatcg tcggcagcgt cagatgtgta    60
t                                                                   61

<210> SEQ ID NO 32
<211> LENGTH: 61
```

```
<212> TYPE: DNA
<213> ORGANISM: Artificial Sequence
<220> FEATURE:
<223> OTHER INFORMATION: Synthetic Oligonucleotide

<400> SEQUENCE: 32
aatgatacgg cgaccaccga gatctacact tcgtgcatcg tcggcagcgt cagatgtgta    60
t                                                                   61

<210> SEQ ID NO 33
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 33
aatgatacgg cgaccaccga gatctacaca ggttgcctcg tcggcagcgt cagatgtgta    60
t                                                                   61

<210> SEQ ID NO 34
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 34
aatgatacgg cgaccaccga gatctacacc cttatgttcg tcggcagcgt cagatgtgta    60
t                                                                   61

<210> SEQ ID NO 35
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 35
aatgatacgg cgaccaccga gatctacacc agcaacgtcg tcggcagcgt cagatgtgta    60
t                                                                   61

<210> SEQ ID NO 36
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 36
aatgatacgg cgaccaccga gatctacacg gttcaattcg tcggcagcgt cagatgtgta    60
t                                                                   61

<210> SEQ ID NO 37
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 37
aatgatacgg cgaccaccga gatctacaca cattcgttcg tcggcagcgt cagatgtgta    60
t    61

<210> SEQ ID NO 38
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 38
aatgatacgg cgaccaccga gatctacacg attcccatcg tcggcagcgt cagatgtgta    60
t    61

<210> SEQ ID NO 39
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 39
aatgatacgg cgaccaccga gatctacacc ggactgctcg tcggcagcgt cagatgtgta    60
t    61

<210> SEQ ID NO 40
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 40
aatgatacgg cgaccaccga gatctacaca gccgttctcg tcggcagcgt cagatgtgta    60
t    61

<210> SEQ ID NO 41
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 41
aatgatacgg cgaccaccga gatctacaca ttgggtctcg tcggcagcgt cagatgtgta    60
t    61

<210> SEQ ID NO 42
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 42
aatgatacgg cgaccaccga gatctacact gcatacttcg tcggcagcgt cagatgtgta    60
t    61

<210> SEQ ID NO 43

<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 43
aatgatacgg cgaccaccga gatctacacg ggcttggtcg tcggcagcgt cagatgtgta    60
t    61

<210> SEQ ID NO 44
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 44
aatgatacgg cgaccaccga gatctacacg acgtggctcg tcggcagcgt cagatgtgta    60
t    61

<210> SEQ ID NO 45
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 45
aatgatacgg cgaccaccga gatctacacg caaattttcg tcggcagcgt cagatgtgta    60
t    61

<210> SEQ ID NO 46
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 46
aatgatacgg cgaccaccga gatctacacg cagcctctcg tcggcagcgt cagatgtgta    60
t    61

<210> SEQ ID NO 47
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 47
aatgatacgg cgaccaccga gatctacact ccgagtttcg tcggcagcgt cagatgtgta    60
t    61

<210> SEQ ID NO 48
<211> LENGTH: 61
<212> TYPE: DNA
<213> ORGANISM: Artificial Sequence
<220> FEATURE:
<223> OTHER INFORMATION: Synthetic Oligonucleotide

```
<400> SEQUENCE: 48
aatgatacgg cgaccaccga gatctacacg cattaagtcg tcggcagcgt cagatgtgta    60
t                                                                   61

<210> SEQ ID NO 49
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 49
aatgatacgg cgaccaccga gatctacaca cgataactcg tcggcagcgt cagatgtgta    60
t                                                                   61

<210> SEQ ID NO 50
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 50
aatgatacgg cgaccaccga gatctacacc ctgcgggtcg tcggcagcgt cagatgtgta    60
t                                                                   61

<210> SEQ ID NO 51
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 51
aatgatacgg cgaccaccga gatctacact gattgtttcg tcggcagcgt cagatgtgta    60
t                                                                   61

<210> SEQ ID NO 52
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 52
aatgatacgg cgaccaccga gatctacacg gcacggatcg tcggcagcgt cagatgtgta    60
t                                                                   61

<210> SEQ ID NO 53
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 53
aatgatacgg cgaccaccga gatctacacg atcattctcg tcggcagcgt cagatgtgta    60
t                                                                   61

<210> SEQ ID NO 54
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 54
aatgatacgg cgaccaccga gatctacaca tggtcattcg tcggcagcgt cagatgtgta      60
t                                                                     61

<210> SEQ ID NO 55
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 55
aatgatacgg cgaccaccga gatctacacc gtaccaatcg tcggcagcgt cagatgtgta      60
t                                                                     61

<210> SEQ ID NO 56
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 56
aatgatacgg cgaccaccga gatctacacc cagtttatcg tcggcagcgt cagatgtgta      60
t                                                                     61

<210> SEQ ID NO 57
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 57
aatgatacgg cgaccaccga gatctacaca ccggccctcg tcggcagcgt cagatgtgta      60
t                                                                     61

<210> SEQ ID NO 58
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 58
aatgatacgg cgaccaccga gatctacacc tagaagttcg tcggcagcgt cagatgtgta      60
t                                                                     61

<210> SEQ ID NO 59
<211> LENGTH: 61
<212> TYPE: DNA
<213> ORGANISM: Artificial Sequence
<220> FEATURE:
<223> OTHER INFORMATION: Synthetic Oligonucleotide
```

```
<400> SEQUENCE: 59
aatgatacgg cgaccaccga gatctacacc gccagattcg tcggcagcgt cagatgtgta      60
t                                                                     61

<210> SEQ ID NO 60
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 60
aatgatacgg cgaccaccga gatctacact cacatggtcg tcggcagcgt cagatgtgta      60
t                                                                     61

<210> SEQ ID NO 61
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 61
aatgatacgg cgaccaccga gatctacacg aactcgatcg tcggcagcgt cagatgtgta      60
t                                                                     61

<210> SEQ ID NO 62
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 62
aatgatacgg cgaccaccga gatctacacc caccgtttcg tcggcagcgt cagatgtgta      60
t                                                                     61

<210> SEQ ID NO 63
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 63
aatgatacgg cgaccaccga gatctacact aagttactcg tcggcagcgt cagatgtgta      60
t                                                                     61

<210> SEQ ID NO 64
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 64
aatgatacgg cgaccaccga gatctacacg agacgtgtcg tcggcagcgt cagatgtgta      60
t                                                                     61

<210> SEQ ID NO 65
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 65
aatgatacgg cgaccaccga gatctacact tgcctaatcg tcggcagcgt cagatgtgta    60
t                                                                    61

<210> SEQ ID NO 66
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 66
aatgatacgg cgaccaccga gatctacact taacttgtcg tcggcagcgt cagatgtgta    60
t                                                                    61

<210> SEQ ID NO 67
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 67
aatgatacgg cgaccaccga gatctacacc tttaacatcg tcggcagcgt cagatgtgta    60
t                                                                    61

<210> SEQ ID NO 68
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 68
aatgatacgg cgaccaccga gatctacacc gtagacctcg tcggcagcgt cagatgtgta    60
t                                                                    61

<210> SEQ ID NO 69
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 69
aatgatacgg cgaccaccga gatctacact atttgcgtcg tcggcagcgt cagatgtgta    60
t                                                                    61

<210> SEQ ID NO 70
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 70
aatgatacgg cgaccaccga gatctacaca tccaggatcg tcggcagcgt cagatgtgta    60
t                                                                    61

<210> SEQ ID NO 71
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 71
aatgatacgg cgaccaccga gatctacact gttcctgtcg tcggcagcgt cagatgtgta    60
t                                                                    61

<210> SEQ ID NO 72
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 72
aatgatacgg cgaccaccga gatctacaca cgcgcagtcg tcggcagcgt cagatgtgta    60
t                                                                    61

<210> SEQ ID NO 73
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 73
aatgatacgg cgaccaccga gatctacact ctggcgatcg tcggcagcgt cagatgtgta    60
t                                                                    61

<210> SEQ ID NO 74
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 74
aatgatacgg cgaccaccga gatctacaca atctacatcg tcggcagcgt cagatgtgta    60
t                                                                    61

<210> SEQ ID NO 75
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 75
aatgatacgg cgaccaccga gatctacact actgacctcg tcggcagcgt cagatgtgta    60
t                                                                    61

<210> SEQ ID NO 76

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 76
aatgatacgg cgaccaccga gatctacacc gatagggtcg tcggcagcgt cagatgtgta      60
t                                                                     61

<210> SEQ ID NO 77
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 77
aatgatacgg cgaccaccga gatctacaca cttagaatcg tcggcagcgt cagatgtgta      60
t                                                                     61

<210> SEQ ID NO 78
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 78
aatgatacgg cgaccaccga gatctacaca gagatcttcg tcggcagcgt cagatgtgta      60
t                                                                     61

<210> SEQ ID NO 79
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 79
aatgatacgg cgaccaccga gatctacacg gtgaaggtcg tcggcagcgt cagatgtgta      60
t                                                                     61

<210> SEQ ID NO 80
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 80
aatgatacgg cgaccaccga gatctacaca tcgaatgtcg tcggcagcgt cagatgtgta      60
t                                                                     61

<210> SEQ ID NO 81
<211> LENGTH: 61
<212> TYPE: DNA
<213> ORGANISM: Artificial Sequence
<220> FEATURE:
<223> OTHER INFORMATION: Synthetic Oligonucleotide
```

```
<400> SEQUENCE: 81
aatgatacgg cgaccaccga gatctacact caagagctcg tcggcagcgt cagatgtgta    60
t                                                                    61

<210> SEQ ID NO 82
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 82
aatgatacgg cgaccaccga gatctacacg cccacgttcg tcggcagcgt cagatgtgta    60
t                                                                    61

<210> SEQ ID NO 83
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 83
aatgatacgg cgaccaccga gatctacact gggcggttcg tcggcagcgt cagatgtgta    60
t                                                                    61

<210> SEQ ID NO 84
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 84
aatgatacgg cgaccaccga gatctacacc ccttggatcg tcggcagcgt cagatgtgta    60
t                                                                    61

<210> SEQ ID NO 85
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 85
aatgatacgg cgaccaccga gatctacaca ttaccgttcg tcggcagcgt cagatgtgta    60
t                                                                    61

<210> SEQ ID NO 86
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 86
aatgatacgg cgaccaccga gatctacaca gtccgagtcg tcggcagcgt cagatgtgta    60
t                                                                    61

<210> SEQ ID NO 87
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 87
aatgatacgg cgaccaccga gatctacaca cttgttgtcg tcggcagcgt cagatgtgta      60
t                                                                     61

<210> SEQ ID NO 88
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 88
aatgatacgg cgaccaccga gatctacacg taatacatcg tcggcagcgt cagatgtgta      60
t                                                                     61

<210> SEQ ID NO 89
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 89
aatgatacgg cgaccaccga gatctacacg gcgtctatcg tcggcagcgt cagatgtgta      60
t                                                                     61

<210> SEQ ID NO 90
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 90
aatgatacgg cgaccaccga gatctacacg cgctgcttcg tcggcagcgt cagatgtgta      60
t                                                                     61

<210> SEQ ID NO 91
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 91
aatgatacgg cgaccaccga gatctacacg tgccatttcg tcggcagcgt cagatgtgta      60
t                                                                     61

<210> SEQ ID NO 92
<211> LENGTH: 61
<212> TYPE: DNA
<213> ORGANISM: Artificial Sequence
<220> FEATURE:
<223> OTHER INFORMATION: Synthetic Oligonucleotide
```

```
<400> SEQUENCE: 92
aatgatacgg cgaccaccga gatctacact aggtatgtcg tcggcagcgt cagatgtgta      60
t                                                                     61

<210> SEQ ID NO 93
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 93
aatgatacgg cgaccaccga gatctacaca acacctatcg tcggcagcgt cagatgtgta      60
t                                                                     61

<210> SEQ ID NO 94
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 94
aatgatacgg cgaccaccga gatctacacc tccgaactcg tcggcagcgt cagatgtgta      60
t                                                                     61

<210> SEQ ID NO 95
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 95
aatgatacgg cgaccaccga gatctacacc aacggcatcg tcggcagcgt cagatgtgta      60
t                                                                     61

<210> SEQ ID NO 96
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 96
aatgatacgg cgaccaccga gatctacacc aatgtagtcg tcggcagcgt cagatgtgta      60
t                                                                     61

<210> SEQ ID NO 97
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 97
aatgatacgg cgaccaccga gatctacacg gctaccctcg tcggcagcgt cagatgtgta      60
t                                                                     61

<210> SEQ ID NO 98
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 98
aatgatacgg cgaccaccga gatctacaca aagtccgtcg tcggcagcgt cagatgtgta    60
t                                                                   61

<210> SEQ ID NO 99
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 99
aatgatacgg cgaccaccga gatctacact tccgcggtcg tcggcagcgt cagatgtgta    60
t                                                                   61

<210> SEQ ID NO 100
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 100
aatgatacgg cgaccaccga gatctacaca ggcactttcg tcggcagcgt cagatgtgta    60
t                                                                   61

<210> SEQ ID NO 101
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 101
aatgatacgg cgaccaccga gatctacacc ttcagtgtcg tcggcagcgt cagatgtgta    60
t                                                                   61

<210> SEQ ID NO 102
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 102
aatgatacgg cgaccaccga gatctacacg ccggtagtcg tcggcagcgt cagatgtgta    60
t                                                                   61

<210> SEQ ID NO 103
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 103
aatgatacgg cgaccaccga gatctacact tcaatcctcg tcggcagcgt cagatgtgta    60
t    61

<210> SEQ ID NO 104
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 104
aatgatacgg cgaccaccga gatctacacc cacacactcg tcggcagcgt cagatgtgta    60
t    61

<210> SEQ ID NO 105
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 105
aatgatacgg cgaccaccga gatctacaca tattatctcg tcggcagcgt cagatgtgta    60
t    61

<210> SEQ ID NO 106
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 106
aatgatacgg cgaccaccga gatctacacc cgaagcatcg tcggcagcgt cagatgtgta    60
t    61

<210> SEQ ID NO 107
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 107
aatgatacgg cgaccaccga gatctacacg tatcggttcg tcggcagcgt cagatgtgta    60
t    61

<210> SEQ ID NO 108
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylation

<400> SEQUENCE: 108
cgcgctgcat acttgaacgt gatcccatga tcgtccga    38

```
<210> SEQ ID NO 109
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 109
cgcgctgcat acttgaaaca tcgcccatga tcgtccga                              38

<210> SEQ ID NO 110
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 110
cgcgctgcat acttgatgcc taacccatga tcgtccga                              38

<210> SEQ ID NO 111
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 111
cgcgctgcat acttgagtgg tcacccatga tcgtccga                              38

<210> SEQ ID NO 112
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 112
cgcgctgcat acttgaccac tgtcccatga tcgtccga                              38

<210> SEQ ID NO 113
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 113
cgcgctgcat acttgacatt ggcccatga tcgtccga                               38
```

<210> SEQ ID NO 114
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 114
cgcgctgcat acttgcagat ctgcccatga tcgtccga                              38

<210> SEQ ID NO 115
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(1)
<223> OTHER INFORMATION: 5 prime phosphorylated

<400> SEQUENCE: 115
cgcgctgcat acttgcatca agtcccatga tcgtccga                              38

<210> SEQ ID NO 116
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 116
cgcgctgcat acttgcgctg atccccatga tcgtccga                              38

<210> SEQ ID NO 117
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 117
cgcgctgcat acttgacaag ctacccatga tcgtccga                              38

<210> SEQ ID NO 118
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 118
cgcgctgcat acttgctgta gcccccatga tcgtccga                    38

<210> SEQ ID NO 119
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 119
cgcgctgcat acttgagtac aagcccatga tcgtccga                    38

<210> SEQ ID NO 120
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 120
cgcgctgcat acttgaacaa ccacccatga tcgtccga                    38

<210> SEQ ID NO 121
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 121
cgcgctgcat acttgaaccg agacccatga tcgtccga                    38

<210> SEQ ID NO 122
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 122
cgcgctgcat acttgaacgc ttacccatga tcgtccga                    38

<210> SEQ ID NO 123
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

```
<223> OTHER INFORMATION: 5 prime phosphorylated

<400> SEQUENCE: 123
cgcgctgcat acttgaagac ggacccatga tcgtccga                                    38

<210> SEQ ID NO 124
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 124
cgcgctgcat acttgaaggt acacccatga tcgtccga                                    38

<210> SEQ ID NO 125
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 125
cgcgctgcat acttgacaca gaacccatga tcgtccga                                    38

<210> SEQ ID NO 126
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 126
cgcgctgcat acttgacagc agacccatga tcgtccga                                    38

<210> SEQ ID NO 127
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 127
cgcgctgcat acttgacctc caacccatga tcgtccga                                    38

<210> SEQ ID NO 128
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(1)
<223> OTHER INFORMATION: 5 prime phosphorylated

<400> SEQUENCE: 128
cgcgctgcat acttgacgct cgacccatga tcgtccga                                  38

<210> SEQ ID NO 129
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 129
cgcgctgcat acttgacgta tcacccatga tcgtccga                                  38

<210> SEQ ID NO 130
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 130
cgcgctgcat acttgactat gcacccatga tcgtccga                                  38

<210> SEQ ID NO 131
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 131
cgcgctgcat acttgagagt caacccatga tcgtccga                                  38

<210> SEQ ID NO 132
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 132
cgcgctgcat acttgagatc gcacccatga tcgtccga                                  38

<210> SEQ ID NO 133
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<223> OTHER INFORMATION: 5 prime phosphorylated

<400> SEQUENCE: 133
cgcgctgcat acttgagcag gaacccatga tcgtccga                           38

<210> SEQ ID NO 134
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 134
cgcgctgcat acttgagtca ctacccatga tcgtccga                           38

<210> SEQ ID NO 135
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 135
cgcgctgcat acttgatcct gtacccatga tcgtccga                           38

<210> SEQ ID NO 136
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 136
cgcgctgcat acttgattga ggacccatga tcgtccga                           38

<210> SEQ ID NO 137
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 137
cgcgctgcat acttgcaacc acacccatga tcgtccga                           38

<210> SEQ ID NO 138
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: 5 prime phosphorylated

<400> SEQUENCE: 138
cgcgctgcat acttggacta gtacccatga tcgtccga                                   38

<210> SEQ ID NO 139
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 139
cgcgctgcat acttgcaatg gaacccatga tcgtccga                                   38

<210> SEQ ID NO 140
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 140
cgcgctgcat acttgcactt cgacccatga tcgtccga                                   38

<210> SEQ ID NO 141
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 141
cgcgctgcat acttgcagcg ttacccatga tcgtccga                                   38

<210> SEQ ID NO 142
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 142
cgcgctgcat acttgcatac caacccatga tcgtccga                                   38

<210> SEQ ID NO 143
<211> LENGTH: 38
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: 5 prime phosphorylated

<400> SEQUENCE: 143
cgcgctgcat acttgccagt tcacccatga tcgtccga                                38

<210> SEQ ID NO 144
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 144
cgcgctgcat acttgccgaa gtacccatga tcgtccga                                38

<210> SEQ ID NO 145
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 145
cgcgctgcat acttgccgtg agacccatga tcgtccga                                38

<210> SEQ ID NO 146
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 146
cgcgctgcat acttgcctcc tgacccatga tcgtccga                                38

<210> SEQ ID NO 147
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 147
cgcgctgcat acttgcgaac ttacccatga tcgtccga                                38

<210> SEQ ID NO 148
<211> LENGTH: 38
<212> TYPE: DNA
<213> ORGANISM: Artificial Sequence
<220> FEATURE:
```

<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 148
cgcgctgcat acttgcgact ggacccatga tcgtccga                                38

<210> SEQ ID NO 149
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 149
cgcgctgcat acttgcgcat acacccatga tcgtccga                                38

<210> SEQ ID NO 150
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 150
cgcgctgcat acttgctcaa tgacccatga tcgtccga                                38

<210> SEQ ID NO 151
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 151
cgcgctgcat acttgctgag ccacccatga tcgtccga                                38

<210> SEQ ID NO 152
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 152
cgcgctgcat acttgctggc atacccatga tcgtccga                                38

<210> SEQ ID NO 153
<211> LENGTH: 38
<212> TYPE: DNA
<213> ORGANISM: Artificial Sequence -continued

```
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 153
cgcgctgcat acttggaatc tgacccatga tcgtccga                              38

<210> SEQ ID NO 154
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 154
cgcgctgcat acttgcaaga ctacccatga tcgtccga                              38

<210> SEQ ID NO 155
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 155
cgcgctgcat acttggagct gaacccatga tcgtccga                              38

<210> SEQ ID NO 156
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 156
cgcgctgcat acttggatag acacccatga tcgtccga                              38

<210> SEQ ID NO 157
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 157
cgcgctgcat acttggccac atacccatga tcgtccga                              38

<210> SEQ ID NO 158
<211> LENGTH: 38
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 158
cgcgctgcat acttggcgag taacccatga tcgtccga                                38

<210> SEQ ID NO 159
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 159
cgcgctgcat acttggctaa cgacccatga tcgtccga                                38

<210> SEQ ID NO 160
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5 prime phosphorylated

<400> SEQUENCE: 160
cgcgctgcat acttggctcg gtacccatga tcgtccga                                38

<210> SEQ ID NO 161
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 161
cgcgctgcat acttgggaga acacccatga tcgtccga                                38

<210> SEQ ID NO 162
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 162
cgcgctgcat acttgggtgc gaacccatga tcgtccga                                38

<210> SEQ ID NO 163
<211> LENGTH: 38
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 163
cgcgctgcat acttggtacg caacccatga tcgtccga                              38

<210> SEQ ID NO 164
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 164
cgcgctgcat acttggtcgt agacccatga tcgtccga                              38

<210> SEQ ID NO 165
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 165
cgcgctgcat acttggtctg tcacccatga tcgtccga                              38

<210> SEQ ID NO 166
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 166
cgcgctgcat acttggtgtt ctacccatga tcgtccga                              38

<210> SEQ ID NO 167
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 167
cgcgctgcat acttgtagga tgacccatga tcgtccga                              38

<210> SEQ ID NO 168
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 168
cgcgctgcat acttgtatca gcacccatga tcgtccga                              38

<210> SEQ ID NO 169
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 169
cgcgctgcat acttgtccgt ctacccatga tcgtccga                              38

<210> SEQ ID NO 170
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 170
cgcgctgcat acttgtcttc acacccatga tcgtccga                              38

<210> SEQ ID NO 171
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 171
cgcgctgcat acttgtgaag agacccatga tcgtccga                              38

<210> SEQ ID NO 172
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 172
cgcgctgcat acttgtggaa caacccatga tcgtccga                              38
```

```
<210> SEQ ID NO 173
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 173
cgcgctgcat acttgtggct tcacccatga tcgtccga                                  38

<210> SEQ ID NO 174
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 174
cgcgctgcat acttgtggtg gtacccatga tcgtccga                                  38

<210> SEQ ID NO 175
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 175
cgcgctgcat acttgttcac gcacccatga tcgtccga                                  38

<210> SEQ ID NO 176
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 176
cgcgctgcat acttgaactc accccatga tcgtccga                                   38

<210> SEQ ID NO 177
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 177
cgcgctgcat acttgaagag atccccatga tcgtccga                                  38
```

<210> SEQ ID NO 178
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 178
cgcgctgcat acttgaagga caccccatga tcgtccga                           38

<210> SEQ ID NO 179
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 179
cgcgctgcat acttgaatcc gtccccatga tcgtccga                           38

<210> SEQ ID NO 180
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 180
cgcgctgcat acttgaatgt tgccccatga tcgtccga                           38

<210> SEQ ID NO 181
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 181
cgcgctgcat acttgacacg acccccatga tcgtccga                           38

<210> SEQ ID NO 182
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 182
cgcgctgcat acttgacaga ttccccatga tcgtccga                           38

<210> SEQ ID NO 183
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 183
cgcgctgcat acttgagatg tacccccatga tcgtccga                38

<210> SEQ ID NO 184
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 184
cgcgctgcat acttgagcac ctccccatga tcgtccga                38

<210> SEQ ID NO 185
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 185
cgcgctgcat acttgagcca tgccccatga tcgtccga                38

<210> SEQ ID NO 186
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 186
cgcgctgcat acttgaggct aaccccatga tcgtccga                38

<210> SEQ ID NO 187
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 187
cgcgctgcat acttgatagc gacccccatga tcgtccga        38

<210> SEQ ID NO 188
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 188
cgcgctgcat acttgatcat tcccccatga tcgtccga        38

<210> SEQ ID NO 189
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 189
cgcgctgcat acttgattgg ctcccccatga tcgtccga        38

<210> SEQ ID NO 190
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 190
cgcgctgcat acttgcaagg agcccccatga tcgtccga        38

<210> SEQ ID NO 191
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 191
cgcgctgcat acttgcacct tacccccatga tcgtccga        38

<210> SEQ ID NO 192
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

```
<223> OTHER INFORMATION: 5 prime phosphorylated

<400> SEQUENCE: 192
cgcgctgcat acttgccatc ctccccatga tcgtccga                               38

<210> SEQ ID NO 193
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 193
cgcgctgcat acttgccgac aaccccatga tcgtccga                               38

<210> SEQ ID NO 194
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 194
cgcgctgcat acttgcctaa tcccccatga tcgtccga                               38

<210> SEQ ID NO 195
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 195
cgcgctgcat acttgcctct atccccatga tcgtccga                               38

<210> SEQ ID NO 196
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 196
cgcgctgcat acttgcgaca caccccatga tcgtccga                               38

<210> SEQ ID NO 197
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(1)
<223> OTHER INFORMATION: 5 prime phosphorylated

<400> SEQUENCE: 197
cgcgctgcat acttgcggat tgccccatga tcgtccga                                    38

<210> SEQ ID NO 198
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 198
cgcgctgcat acttgctaag gtccccatga tcgtccga                                    38

<210> SEQ ID NO 199
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 199
cgcgctgcat acttggaaca ggccccatga tcgtccga                                    38

<210> SEQ ID NO 200
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 200
cgcgctgcat acttggacag tgccccatga tcgtccga                                    38

<210> SEQ ID NO 201
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 201
cgcgctgcat acttggagtt agccccatga tcgtccga                                    38

<210> SEQ ID NO 202
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: 5 prime phosphorylated

<400> SEQUENCE: 202
cgcgctgcat acttggatga atccccatga tcgtccga                              38

<210> SEQ ID NO 203
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 203
cgcgctgcat acttggccaa gaccccatga tcgtccga                              38

<210> SEQ ID NO 204
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 204
catcggcgta cgactaacgt gatatccacg tgcttgag                              38

<210> SEQ ID NO 205
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 205
catcggcgta cgactaaaca tcgatccacg tgcttgag                              38

<210> SEQ ID NO 206
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 206
catcggcgta cgactatgcc taaatccacg tgcttgag                              38

<210> SEQ ID NO 207
<211> LENGTH: 38
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: 5 prime phosphorylated

<400> SEQUENCE: 207
catcggcgta cgactagtgg tcaatccacg tgcttgag                              38

<210> SEQ ID NO 208
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 208
catcggcgta cgactaccac tgtatccacg tgcttgag                              38

<210> SEQ ID NO 209
<211> LENGTH: 37
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 209
atcggcgtac gactacattg gcatccacgt gcttgag                               37

<210> SEQ ID NO 210
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 210
catcggcgta cgactcagat ctgatccacg tgcttgag                              38

<210> SEQ ID NO 211
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 211
catcggcgta cgactcatca agtatccacg tgcttgag                              38

<210> SEQ ID NO 212
<211> LENGTH: 38
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 212
catcggcgta cgactcgctg atcatccacg tgcttgag                              38

<210> SEQ ID NO 213
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 213
catcggcgta cgactacaag ctaatccacg tgcttgag                              38

<210> SEQ ID NO 214
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 214
catcggcgta cgactctgta gccatccacg tgcttgag                              38

<210> SEQ ID NO 215
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 215
catcggcgta cgactagtac aagatccacg tgcttgag                              38

<210> SEQ ID NO 216
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 216
catcggcgta cgactaacaa ccaatccacg tgcttgag                              38

<210> SEQ ID NO 217
<211> LENGTH: 38
<212> TYPE: DNA
<213> ORGANISM: Artificial Sequence
```

```
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 217
catcggcgta cgactaaccg agaatccacg tgcttgag                                38

<210> SEQ ID NO 218
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 218
catcggcgta cgactaacgc ttaatccacg tgcttgag                                38

<210> SEQ ID NO 219
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 219
catcggcgta cgactaagac ggaatccacg tgcttgag                                38

<210> SEQ ID NO 220
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 220
catcggcgta cgactaaggt acaatccacg tgcttgag                                38

<210> SEQ ID NO 221
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 221
catcggcgta cgactacaca gaaatccacg tgcttgag                                38

<210> SEQ ID NO 222
<211> LENGTH: 38
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 222
catcggcgta cgactacagc agaatccacg tgcttgag                              38

<210> SEQ ID NO 223
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 223
catcggcgta cgactacctc caaatccacg tgcttgag                              38

<210> SEQ ID NO 224
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 224
catcggcgta cgactacgct cgaatccacg tgcttgag                              38

<210> SEQ ID NO 225
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 225
catcggcgta cgactacgta tcaatccacg tgcttgag                              38

<210> SEQ ID NO 226
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 226
catcggcgta cgactactat gcaatccacg tgcttgag                              38

<210> SEQ ID NO 227
<211> LENGTH: 38
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 227
catcggcgta cgactagagt caaatccacg tgcttgag                              38

<210> SEQ ID NO 228
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 228
catcggcgta cgactagatc gcaatccacg tgcttgag                              38

<210> SEQ ID NO 229
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 229
catcggcgta cgactagcag gaaatccacg tgcttgag                              38

<210> SEQ ID NO 230
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 230
catcggcgta cgactagtca ctaatccacg tgcttgag                              38

<210> SEQ ID NO 231
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 231
catcggcgta cgactatcct gtaatccacg tgcttgag                              38

<210> SEQ ID NO 232
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 232
catcggcgta cgactattga ggaatccacg tgcttgag                          38

<210> SEQ ID NO 233
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 233
catcggcgta cgactcaacc acaatccacg tgcttgag                          38

<210> SEQ ID NO 234
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 234
catcggcgta cgactgacta gtaatccacg tgcttgag                          38

<210> SEQ ID NO 235
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 235
catcggcgta cgactcaatg gaaatccacg tgcttgag                          38

<210> SEQ ID NO 236
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 236
catcggcgta cgactcactt cgaatccacg tgcttgag                          38
```

```
<210> SEQ ID NO 237
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 237
catcggcgta cgactcagcg ttaatccacg tgcttgag                              38

<210> SEQ ID NO 238
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 238
catcggcgta cgactcatac caaatccacg tgcttgag                              38

<210> SEQ ID NO 239
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 239
catcggcgta cgactccagt tcaatccacg tgcttgag                              38

<210> SEQ ID NO 240
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 240
catcggcgta cgactccgaa gtaatccacg tgcttgag                              38

<210> SEQ ID NO 241
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 241
catcggcgta cgactccgtg agaatccacg tgcttgag                              38
```

```
<210> SEQ ID NO 242
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 242
catcggcgta cgactcctcc tgaatccacg tgcttgag                            38

<210> SEQ ID NO 243
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 243
catcggcgta cgactcgaac ttaatccacg tgcttgag                            38

<210> SEQ ID NO 244
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 244
catcggcgta cgactcgact ggaatccacg tgcttgag                            38

<210> SEQ ID NO 245
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 245
catcggcgta cgactcgcat acaatccacg tgcttgag                            38

<210> SEQ ID NO 246
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 246
catcggcgta cgactctcaa tgaatccacg tgcttgag                            38
```

<210> SEQ ID NO 247
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 247
catcggcgta cgactctgag ccaatccacg tgcttgag                                38

<210> SEQ ID NO 248
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 248
catcggcgta cgactctggc ataatccacg tgcttgag                                38

<210> SEQ ID NO 249
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 249
catcggcgta cgactgaatc tgaatccacg tgcttgag                                38

<210> SEQ ID NO 250
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 250
catcggcgta cgactcaaga ctaatccacg tgcttgag                                38

<210> SEQ ID NO 251
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 251
catcggcgta cgactgagct gaaatccacg tgcttgag                              38

<210> SEQ ID NO 252
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 252
catcggcgta cgactgatag acaatccacg tgcttgag                              38

<210> SEQ ID NO 253
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 253
catcggcgta cgactgccac ataatccacg tgcttgag                              38

<210> SEQ ID NO 254
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 254
catcggcgta cgactgcgag taaatccacg tgcttgag                              38

<210> SEQ ID NO 255
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 255
catcggcgta cgactgctaa cgaatccacg tgcttgag                              38

<210> SEQ ID NO 256
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

<223> OTHER INFORMATION: 5 prime phosphorylated

<400> SEQUENCE: 256
catcggcgta cgactgctcg gtaatccacg tgcttgag                              38

<210> SEQ ID NO 257
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 257
catcggcgta cgactggaga acaatccacg tgcttgag                              38

<210> SEQ ID NO 258
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 258
catcggcgta cgactggtgc gaaatccacg tgcttgag                              38

<210> SEQ ID NO 259
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 259
catcggcgta cgactgtacg caaatccacg tgcttgag                              38

<210> SEQ ID NO 260
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 260
catcggcgta cgactgtcgt agaatccacg tgcttgag                              38

<210> SEQ ID NO 261
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature

```
<222> LOCATION: (1)..(1)
<223> OTHER INFORMATION: 5 prime phosphorylated

<400> SEQUENCE: 261
catcggcgta cgactgtctg tcaatccacg tgcttgag                              38

<210> SEQ ID NO 262
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 262
catcggcgta cgactgtgtt ctaatccacg tgcttgag                              38

<210> SEQ ID NO 263
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 263
catcggcgta cgacttagga tgaatccacg tgcttgag                              38

<210> SEQ ID NO 264
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 264
catcggcgta cgacttatca gcaatccacg tgcttgag                              38

<210> SEQ ID NO 265
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 265
catcggcgta cgacttccgt ctaatccacg tgcttgag                              38

<210> SEQ ID NO 266
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

<221> NAME/KEY: misc_feature
<222> LOCATION: (1)..(1)
<223> OTHER INFORMATION: 5 prime phosphorylated

<400> SEQUENCE: 266
catcggcgta cgacttcttc acaatccacg tgcttgag                         38

<210> SEQ ID NO 267
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 267
catcggcgta cgacttgaag agaatccacg tgcttgag                         38

<210> SEQ ID NO 268
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 268
catcggcgta cgacttggaa caaatccacg tgcttgag                         38

<210> SEQ ID NO 269
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 269
catcggcgta cgacttggct tcaatccacg tgcttgag                         38

<210> SEQ ID NO 270
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 270
catcggcgta cgacttggtg gtaatccacg tgcttgag                         38

<210> SEQ ID NO 271
<211> LENGTH: 38
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (1)..(1)
<223> OTHER INFORMATION: 5 prime phosphorylated

<400> SEQUENCE: 271
catcggcgta cgactttcac gcaatccacg tgcttgag                            38

<210> SEQ ID NO 272
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 272
catcggcgta cgactaactc accatccacg tgcttgag                            38

<210> SEQ ID NO 273
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 273
catcggcgta cgactaagag atcatccacg tgcttgag                            38

<210> SEQ ID NO 274
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..()
<223> OTHER INFORMATION: 5 prime phosphorylated

<400> SEQUENCE: 274
catcggcgta cgactaagga cacatccacg tgcttgag                            38

<210> SEQ ID NO 275
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 275
catcggcgta cgactaatcc gtcatccacg tgcttgag                            38

<210> SEQ ID NO 276
<211> LENGTH: 38
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 276
catcggcgta cgactaatgt tgcatccacg tgcttgag                              38

<210> SEQ ID NO 277
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 277
catcggcgta cgactacacg accatccacg tgcttgag                              38

<210> SEQ ID NO 278
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 278
catcggcgta cgactacaga ttcatccacg tgcttgag                              38

<210> SEQ ID NO 279
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 279
catcggcgta cgactagatg tacatccacg tgcttgag                              38

<210> SEQ ID NO 280
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 280
catcggcgta cgactagcac ctcatccacg tgcttgag                              38

<210> SEQ ID NO 281
<211> LENGTH: 38
<212> TYPE: DNA
<213> ORGANISM: Artificial Sequence
```

```
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 281
catcggcgta cgactagcca tgcatccacg tgcttgag                              38

<210> SEQ ID NO 282
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 282
catcggcgta cgactaggct aacatccacg tgcttgag                              38

<210> SEQ ID NO 283
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 283
catcggcgta cgactatagc gacatccacg tgcttgag                              38

<210> SEQ ID NO 284
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 284
catcggcgta cgactatcat tccatccacg tgcttgag                              38

<210> SEQ ID NO 285
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 285
catcggcgta cgactattgg ctcatccacg tgcttgag                              38

<210> SEQ ID NO 286
<211> LENGTH: 38
<212> TYPE: DNA
```

<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 286
catcggcgta cgactcaagg agcatccacg tgcttgag        38

<210> SEQ ID NO 287
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 287
catcggcgta cgactcacct tacatccacg tgcttgag        38

<210> SEQ ID NO 288
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 288
catcggcgta cgactccatc ctcatccacg tgcttgag        38

<210> SEQ ID NO 289
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 289
catcggcgta cgactccgac aacatccacg tgcttgag        38

<210> SEQ ID NO 290
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 290
catcggcgta cgactcctaa tccatccacg tgcttgag        38

<210> SEQ ID NO 291
<211> LENGTH: 38

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..()
<223> OTHER INFORMATION: 5 prime phosphorylated

<400> SEQUENCE: 291
catcggcgta cgactcctct atcatccacg tgcttgag                               38

<210> SEQ ID NO 292
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 292
catcggcgta cgactcgaca cacatccacg tgcttgag                               38

<210> SEQ ID NO 293
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 293
catcggcgta cgactcggat tgcatccacg tgcttgag                               38

<210> SEQ ID NO 294
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 294
catcggcgta cgactctaag gtcatccacg tgcttgag                               38

<210> SEQ ID NO 295
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 295
catcggcgta cgactgaaca ggcatccacg tgcttgag                               38

<210> SEQ ID NO 296
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 296
catcggcgta cgactgacag tgcatccacg tgcttgag                              38

<210> SEQ ID NO 297
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 297
catcggcgta cgactgagtt agcatccacg tgcttgag                              38

<210> SEQ ID NO 298
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 298
catcggcgta cgactgatga atcatccacg tgcttgag                              38

<210> SEQ ID NO 299
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 299
catcggcgta cgactgccaa gacatccacg tgcttgag                              38

<210> SEQ ID NO 300
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 300
caagcagaag acggcatacg agataacgtg atgtggccga tgtttcg                    47

<210> SEQ ID NO 301
<211> LENGTH: 47
<212> TYPE: DNA
<213> ORGANISM: Artificial Sequence
<220> FEATURE:
<223> OTHER INFORMATION: Synthetic Oligonucleotide
```

```
<400> SEQUENCE: 301
caagcagaag acggcatacg agataaacat cggtggccga tgtttcg         47

<210> SEQ ID NO 302
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 302
caagcagaag acggcatacg agatatgcct aagtggccga tgtttcg         47

<210> SEQ ID NO 303
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 303
caagcagaag acggcatacg agatagtggt cagtggccga tgtttcg         47

<210> SEQ ID NO 304
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 304
caagcagaag acggcatacg agataccact gtgtggccga tgtttcg         47

<210> SEQ ID NO 305
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 305
caagcagaag acggcatacg agatacattg gcgtggccga tgtttcg         47

<210> SEQ ID NO 306
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 306
caagcagaag acggcatacg agatcagatc tggtggccga tgtttcg         47

<210> SEQ ID NO 307
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 307
caagcagaag acggcatacg agatcgctga tcgtggccga tgtttcg         47

<210> SEQ ID NO 308
```

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 308
caagcagaag acggcatacg agatcgctga tcgtggccga tgtttcg          47

<210> SEQ ID NO 309
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 309
caagcagaag acggcatacg agatacaagc tagtggccga tgtttcg          47

<210> SEQ ID NO 310
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 310
caagcagaag acggcatacg agatctgtag ccgtggccga tgtttcg          47

<210> SEQ ID NO 311
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 311
caagcagaag acggcatacg agatagtaca aggtggccga tgtttcg          47

<210> SEQ ID NO 312
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 312
caagcagaag acggcatacg agataacaac cagtggccga tgtttcg          47

<210> SEQ ID NO 313
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 313
caagcagaag acggcatacg agataaccga gagtggccga tgtttcg          47

<210> SEQ ID NO 314
<211> LENGTH: 47
<212> TYPE: DNA
<213> ORGANISM: Artificial Sequence
<220> FEATURE:
<223> OTHER INFORMATION: Synthetic Oligonucleotide
```

-continued

<400> SEQUENCE: 314
caagcagaag acggcatacg agataacgct tagtggccga tgtttcg    47

<210> SEQ ID NO 315
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 315
caagcagaag acggcatacg agataagacg gagtggccga tgtttcg    47

<210> SEQ ID NO 316
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 316
caagcagaag acggcatacg agataaggta cagtggccga tgtttcg    47

<210> SEQ ID NO 317
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 317
caagcagaag acggcatacg agatacacag aagtggccga tgtttcg    47

<210> SEQ ID NO 318
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 318
caagcagaag acggcatacg agatacagca gagtggccga tgtttcg    47

<210> SEQ ID NO 319
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 319
caagcagaag acggcatacg agatacctcc aagtggccga tgtttcg    47

<210> SEQ ID NO 320
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 320
caagcagaag acggcatacg agatacgctc gagtggccga tgtttcg    47

<210> SEQ ID NO 321

<210> SEQ ID NO 321
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 321
caagcagaag acggcatacg agatacgtat cagtggccga tgtttcg        47

<210> SEQ ID NO 322
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 322
caagcagaag acggcatacg agatactatg cagtggccga tgtttcg        47

<210> SEQ ID NO 323
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 323
caagcagaag acggcatacg agatagagtc aagtggccga tgtttcg        47

<210> SEQ ID NO 324
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 324
caagcagaag acggcatacg agatagatcg cagtggccga tgtttcg        47

<210> SEQ ID NO 325
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 325
caagcagaag acggcatacg agatagcagg aagtggccga tgtttcg        47

<210> SEQ ID NO 326
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 326
caagcagaag acggcatacg agatagtcac tagtggccga tgtttcg        47

<210> SEQ ID NO 327
<211> LENGTH: 47
<212> TYPE: DNA
<213> ORGANISM: Artificial Sequence
<220> FEATURE:
<223> OTHER INFORMATION: Synthetic Oligonucleotide -continued

<400> SEQUENCE: 327
caagcagaag acggcatacg agatatcctg tagtggccga tgtttcg     47

<210> SEQ ID NO 328
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 328
caagcagaag acggcatacg agatattgag gagtggccga tgtttcg     47

<210> SEQ ID NO 329
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 329
caagcagaag acggcatacg agatcaacca cagtggccga tgtttcg     47

<210> SEQ ID NO 330
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 330
caagcagaag acggcatacg agatgactag tagtggccga tgtttcg     47

<210> SEQ ID NO 331
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 331
caagcagaag acggcatacg agatcaatgg aagtggccga tgtttcg     47

<210> SEQ ID NO 332
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 332
caagcagaag acggcatacg agatcacttc gagtggccga tgtttcg     47

<210> SEQ ID NO 333
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 333
caagcagaag acggcatacg agatcagcgt tagtggccga tgtttcg     47

<210> SEQ ID NO 334

<210> SEQ ID NO 334
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 334
caagcagaag acggcatacg agatcatacc aagtggccga tgtttcg     47

<210> SEQ ID NO 335
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 335
caagcagaag acggcatacg agatccagtt cagtggccga tgtttcg     47

<210> SEQ ID NO 336
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 336
caagcagaag acggcatacg agatccgaag tagtggccga tgtttcg     47

<210> SEQ ID NO 337
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 337
caagcagaag acggcatacg agatccgtga gagtggccga tgtttcg     47

<210> SEQ ID NO 338
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 338
caagcagaag acggcatacg agatcctcct gagtggccga tgtttcg     47

<210> SEQ ID NO 339
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 339
caagcagaag acggcatacg agatcgaact tagtggccga tgtttcg     47

<210> SEQ ID NO 340
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 340
caagcagaag acggcatacg agatcgactg gagtggccga tgtttcg          47

<210> SEQ ID NO 341
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 341
caagcagaag acggcatacg agatcgcata cagtggccga tgtttcg          47

<210> SEQ ID NO 342
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 342
caagcagaag acggcatacg agatctcaat gagtggccga tgtttcg          47

<210> SEQ ID NO 343
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 343
caagcagaag acggcatacg agatctgagc cagtggccga tgtttcg          47

<210> SEQ ID NO 344
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 344
caagcagaag acggcatacg agatctggca tagtggccga tgtttcg          47

<210> SEQ ID NO 345
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 345
caagcagaag acggcatacg agatgaatct gagtggccga tgtttcg          47

<210> SEQ ID NO 346
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 346
caagcagaag acggcatacg agatcaagac tagtggccga tgtttcg          47

<210> SEQ ID NO 347

<210> SEQ ID NO 347
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 347
caagcagaag acggcatacg agatgagctg aagtggccga tgtttcg         47

<210> SEQ ID NO 348
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 348
caagcagaag acggcatacg agatgataga cagtggccga tgtttcg         47

<210> SEQ ID NO 349
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 349
caagcagaag acggcatacg agatgccaca tagtggccga tgtttcg         47

<210> SEQ ID NO 350
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 350
caagcagaag acggcatacg agatgcgagt aagtggccga tgtttcg         47

<210> SEQ ID NO 351
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 351
caagcagaag acggcatacg agatgctaac gagtggccga tgtttcg         47

<210> SEQ ID NO 352
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 352
caagcagaag acggcatacg agatgctcgg tagtggccga tgtttcg         47

<210> SEQ ID NO 353
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 353
caagcagaag acggcatacg agatggagaa cagtggccga tgtttcg         47

<210> SEQ ID NO 354
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 354
caagcagaag acggcatacg agatggtgcg aagtggccga tgtttcg         47

<210> SEQ ID NO 355
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 355
caagcagaag acggcatacg agatgtacgc aagtggccga tgtttcg         47

<210> SEQ ID NO 356
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 356
caagcagaag acggcatacg agatgtcgta gagtggccga tgtttcg         47

<210> SEQ ID NO 357
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 357
caagcagaag acggcatacg agatgtctgt cagtggccga tgtttcg         47

<210> SEQ ID NO 358
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 358
caagcagaag acggcatacg agatgtgttc tagtggccga tgtttcg         47

<210> SEQ ID NO 359
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 359
caagcagaag acggcatacg agattaggat gagtggccga tgtttcg         47

<210> SEQ ID NO 360

<210> SEQ ID NO 360
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 360
caagcagaag acggcatacg agattatcag cagtggccga tgtttcg                47

<210> SEQ ID NO 361
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 361
caagcagaag acggcatacg agattccgtc tagtggccga tgtttcg                47

<210> SEQ ID NO 362
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 362
caagcagaag acggcatacg agattcttca cagtggccga tgtttcg                47

<210> SEQ ID NO 363
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 363
caagcagaag acggcatacg agattgaaga gagtggccga tgtttcg                47

<210> SEQ ID NO 364
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 364
caagcagaag acggcatacg agattggaac aagtggccga tgtttcg                47

<210> SEQ ID NO 365
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 365
caagcagaag acggcatacg agattggctt cagtggccga tgtttcg                47

<210> SEQ ID NO 366
<211> LENGTH: 47
<212> TYPE: DNA
<213> ORGANISM: Artificial Sequence
<220> FEATURE:
<223> OTHER INFORMATION: Synthetic Oligonucleotide

```
<400> SEQUENCE: 366
caagcagaag acggcatacg agattggtgg tagtggccga tgtttcg              47

<210> SEQ ID NO 367
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 367
caagcagaag acggcatacg agatttcacg cagtggccga tgtttcg              47

<210> SEQ ID NO 368
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 368
caagcagaag acggcatacg agataactca ccgtggccga tgtttcg              47

<210> SEQ ID NO 369
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 369
caagcagaag acggcatacg agataagaga tcgtggccga tgtttcg              47

<210> SEQ ID NO 370
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 370
caagcagaag acggcatacg agataaggac acgtggccga tgtttcg              47

<210> SEQ ID NO 371
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 371
caagcagaag acggcatacg agataatccg tcgtggccga tgtttcg              47

<210> SEQ ID NO 372
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 372
caagcagaag acggcatacg agataatgtt gcgtggccga tgtttcg              47

<210> SEQ ID NO 373
```

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 373
caagcagaag acggcatacg agatacacga ccgtggccga tgtttcg          47

<210> SEQ ID NO 374
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 374
caagcagaag acggcatacg agatacagat cgtggccga tgtttcg           47

<210> SEQ ID NO 375
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 375
caagcagaag acggcatacg agatagatgt acgtggccga tgtttcg          47

<210> SEQ ID NO 376
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 376
caagcagaag acggcatacg agatagcacc tcgtggccga tgtttcg          47

<210> SEQ ID NO 377
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 377
caagcagaag acggcatacg agatagccat gcgtggccga tgtttcg          47

<210> SEQ ID NO 378
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 378
caagcagaag acggcatacg agataggcta acgtggccga tgtttcg          47

<210> SEQ ID NO 379
<211> LENGTH: 47
<212> TYPE: DNA
<213> ORGANISM: Artificial Sequence
<220> FEATURE:
<223> OTHER INFORMATION: Synthetic Oligonucleotide
```

```
<400> SEQUENCE: 379
caagcagaag acggcatacg agatatagcg acgtggccga tgtttcg         47

<210> SEQ ID NO 380
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 380
caagcagaag acggcatacg agatatcatt ccgtggccga tgtttcg         47

<210> SEQ ID NO 381
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 381
caagcagaag acggcatacg agatattggc tcgtggccga tgtttcg         47

<210> SEQ ID NO 382
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 382
caagcagaag acggcatacg agatcaagga gcgtggccga tgtttcg         47

<210> SEQ ID NO 383
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 383
caagcagaag acggcatacg agatcacctt acgtggccga tgtttcg         47

<210> SEQ ID NO 384
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 384
caagcagaag acggcatacg agatccatcc tcgtggccga tgtttcg         47

<210> SEQ ID NO 385
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 385
caagcagaag acggcatacg agatccgaca acgtggccga tgtttcg         47

<210> SEQ ID NO 386
```

<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 386
caagcagaag acggcatacg agatcctaat ccgtggccga tgtttcg            47

<210> SEQ ID NO 387
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 387
caagcagaag acggcatacg agatcctcta tcgtggccga tgtttcg            47

<210> SEQ ID NO 388
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 388
caagcagaag acggcatacg agatcgacac acgtggccga tgtttcg            47

<210> SEQ ID NO 389
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 389
caagcagaag acggcatacg agatcggatt gcgtggccga tgtttcg            47

<210> SEQ ID NO 390
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 390
caagcagaag acggcatacg agatctaagg tcgtggccga tgtttcg            47

<210> SEQ ID NO 391
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 391
caagcagaag acggcatacg agatgaacag gcgtggccga tgtttcg            47

<210> SEQ ID NO 392
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 392
caagcagaag acggcatacg agatgacagt gcgtggccga tgtttcg          47

<210> SEQ ID NO 393
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 393
caagcagaag acggcatacg agatgagtta gcgtggccga tgtttcg          47

<210> SEQ ID NO 394
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 394
caagcagaag acggcatacg agatgatgaa tcgtggccga tgtttcg          47

<210> SEQ ID NO 395
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 395
caagcagaag acggcatacg agatgccaag acgtggccga tgtttcg          47

<210> SEQ ID NO 396
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 396
ccgagcccac gagactcgga cgatcatggg                              30

<210> SEQ ID NO 397
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 397
caagtatgca gcgcgctcaa gcacgtggat                              30

<210> SEQ ID NO 398
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 398
agtcgtacgc cgatgcgaaa catcggccac                              30

<210> SEQ ID NO 399

```
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 399
cccatgatcg tccgagtctc gtgggctcgg                                              30

<210> SEQ ID NO 400
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 400
atccacgtgc ttgagcgcgc tgcatacttg                                              30

<210> SEQ ID NO 401
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 401
gtggccgatg tttcgcatcg gcgtacgact                                              30

<210> SEQ ID NO 402
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 402
tcgtcggcag cgtcagatgt gtataagaga cag                                          33

<210> SEQ ID NO 403
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(31)
<223> OTHER INFORMATION: RNA nucleotide

<400> SEQUENCE: 403
aagcagtggt atcaacgcag agtgaatggg                                              30

<210> SEQ ID NO 404
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 404
aagcagtggt atcaacgcag agt                                                     23

<210> SEQ ID NO 405
<211> LENGTH: 24
<212> TYPE: DNA
<213> ORGANISM: Artificial Sequence
```

```
<220> FEATURE:
<223> OTHER INFORMATION: Synthetic Oligonucleotide

<400> SEQUENCE: 405
caagcagaag acggcatacg agat                                           24

<210> SEQ ID NO 406
<211> LENGTH: 34
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 406
gtctcgtggg ctcggagatg tgtataagag acag                                34

<210> SEQ ID NO 407
<211> LENGTH: 60
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated
<220> FEATURE:
<221> NAME/KEY: misc_feature
<222> LOCATION: (35)..(43)
<223> OTHER INFORMATION: n is a, c, g, or t
<220> FEATURE:
<221> NAME/KEY: misc_feature
<222> LOCATION: (44)..(45)
<223> OTHER INFORMATION: biotin linker
<220> FEATURE:
<221> NAME/KEY: misc_feature
<222> LOCATION: (60)..(60)
<223> OTHER INFORMATION: n is a, c, g, or t

<400> SEQUENCE: 407
gtctcgtggg ctcggagatg tgtataagag acagnnnnnn nnnntttttt ttttttttvn    60

<210> SEQ ID NO 408
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated
<220> FEATURE:
<221> NAME/KEY: misc_feature
<222> LOCATION: (14)..(14)
<223> OTHER INFORMATION: 3 prime di-deoxy C modification

<400> SEQUENCE: 408
ctgtctctta taca                                                      14

<210> SEQ ID NO 409
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 409
aatgatacgg cgaccaccga gatctacact agatcgctcg tcggcagcgt cagatgtgta    60
t                                                                  61

<210> SEQ ID NO 410
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 410
aatgatacgg cgaccaccga gatctacacc tctctattcg tcggcagcgt cagatgtgta    60
t                                                                  61

<210> SEQ ID NO 411
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 411
aatgatacgg cgaccaccga gatctacact atcctcttcg tcggcagcgt cagatgtgta    60
t                                                                  61

<210> SEQ ID NO 412
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 412
aatgatacgg cgaccaccga gatctacaca gagtagatcg tcggcagcgt cagatgtgta    60
t                                                                  61

<210> SEQ ID NO 413
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 413
aatgatacgg cgaccaccga gatctacacg taaggagtcg tcggcagcgt cagatgtgta    60
t                                                                  61

<210> SEQ ID NO 414
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 414
aatgatacgg cgaccaccga gatctacaca ctgcatatcg tcggcagcgt cagatgtgta    60
t                                                                  61

<210> SEQ ID NO 415
<211> LENGTH: 61

<212> TYPE: DNA
<213> ORGANISM: Artificial Sequence
<220> FEATURE:
<223> OTHER INFORMATION: Synthetic Oligonucleotide

<400> SEQUENCE: 415
aatgatacgg cgaccaccga gatctacaca aggagtatcg tcggcagcgt cagatgtgta    60
t                                                                    61

<210> SEQ ID NO 416
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 416
aatgatacgg cgaccaccga gatctacacc taagccttcg tcggcagcgt cagatgtgta    60
t                                                                    61

<210> SEQ ID NO 417
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 417
aatgatacgg cgaccaccga gatctacact ggaaatctcg tcggcagcgt cagatgtgta    60
t                                                                    61

<210> SEQ ID NO 418
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 418
aatgatacgg cgaccaccga gatctacaca acatgattcg tcggcagcgt cagatgtgta    60
t                                                                    61

<210> SEQ ID NO 419
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 419
aatgatacgg cgaccaccga gatctacact gatgaaatcg tcggcagcgt cagatgtgta    60
t                                                                    61

<210> SEQ ID NO 420
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 420
aatgatacgg cgaccaccga gatctacacg tcggacttcg tcggcagcgt cagatgtgta    60
t    61

<210> SEQ ID NO 421
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 421
aatgatacgg cgaccaccga gatctacact ttctagctcg tcggcagcgt cagatgtgta    60
t    61

<210> SEQ ID NO 422
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 422
aatgatacgg cgaccaccga gatctacact aaccaagtcg tcggcagcgt cagatgtgta    60
t    61

<210> SEQ ID NO 423
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 423
aatgatacgg cgaccaccga gatctacacg tgtatcgtcg tcggcagcgt cagatgtgta    60
t    61

<210> SEQ ID NO 424
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 424
aatgatacgg cgaccaccga gatctacact ccatcaatcg tcggcagcgt cagatgtgta    60
t    61

<210> SEQ ID NO 425
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 425
aatgatacgg cgaccaccga gatctacact tcgtgcatcg tcggcagcgt cagatgtgta    60
t    61

<210> SEQ ID NO 426

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 426
aatgatacgg cgaccaccga gatctacaca ggttgcctcg tcggcagcgt cagatgtgta    60
t                                                                    61

<210> SEQ ID NO 427
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 427
aatgatacgg cgaccaccga gatctacacc cttatgttcg tcggcagcgt cagatgtgta    60
t                                                                    61

<210> SEQ ID NO 428
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 428
aatgatacgg cgaccaccga gatctacacc agcaacgtcg tcggcagcgt cagatgtgta    60
t                                                                    61

<210> SEQ ID NO 429
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 429
aatgatacgg cgaccaccga gatctacacg gttcaattcg tcggcagcgt cagatgtgta    60
t                                                                    61

<210> SEQ ID NO 430
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 430
aatgatacgg cgaccaccga gatctacaca cattcgttcg tcggcagcgt cagatgtgta    60
t                                                                    61

<210> SEQ ID NO 431
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 431
aatgatacgg cgaccaccga gatctacacg attcccatcg tcggcagcgt cagatgtgta    60
t    61

<210> SEQ ID NO 432
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 432
aatgatacgg cgaccaccga gatctacacc ggactgctcg tcggcagcgt cagatgtgta    60
t    61

<210> SEQ ID NO 433
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 433
aatgatacgg cgaccaccga gatctacaca gccgttctcg tcggcagcgt cagatgtgta    60
t    61

<210> SEQ ID NO 434
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 434
aatgatacgg cgaccaccga gatctacaca ttgggtctcg tcggcagcgt cagatgtgta    60
t    61

<210> SEQ ID NO 435
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 435
aatgatacgg cgaccaccga gatctacact gcatacttcg tcggcagcgt cagatgtgta    60
t    61

<210> SEQ ID NO 436
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 436
aatgatacgg cgaccaccga gatctacacg ggcttggtcg tcggcagcgt cagatgtgta    60
t    61

<210> SEQ ID NO 437

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 437
aatgatacgg cgaccaccga gatctacacg acgtggctcg tcggcagcgt cagatgtgta    60
t                                                                    61

<210> SEQ ID NO 438
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 438
aatgatacgg cgaccaccga gatctacacg caaattttcg tcggcagcgt cagatgtgta    60
t                                                                    61

<210> SEQ ID NO 439
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 439
aatgatacgg cgaccaccga gatctacacg cagcctctcg tcggcagcgt cagatgtgta    60
t                                                                    61

<210> SEQ ID NO 440
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 440
aatgatacgg cgaccaccga gatctacact ccgagtttcg tcggcagcgt cagatgtgta    60
t                                                                    61

<210> SEQ ID NO 441
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 441
aatgatacgg cgaccaccga gatctacacg cattaagtcg tcggcagcgt cagatgtgta    60
t                                                                    61

<210> SEQ ID NO 442
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 442
aatgatacgg cgaccaccga gatctacaca cgataactcg tcggcagcgt cagatgtgta    60
t    61

<210> SEQ ID NO 443
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 443
aatgatacgg cgaccaccga gatctacacc ctgcgggtcg tcggcagcgt cagatgtgta    60
t    61

<210> SEQ ID NO 444
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 444
aatgatacgg cgaccaccga gatctacact gattgtttcg tcggcagcgt cagatgtgta    60
t    61

<210> SEQ ID NO 445
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 445
aatgatacgg cgaccaccga gatctacacg gcacggatcg tcggcagcgt cagatgtgta    60
t    61

<210> SEQ ID NO 446
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 446
aatgatacgg cgaccaccga gatctacacg atcattctcg tcggcagcgt cagatgtgta    60
t    61

<210> SEQ ID NO 447
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 447
aatgatacgg cgaccaccga gatctacaca tggtcattcg tcggcagcgt cagatgtgta    60
t    61

<210> SEQ ID NO 448

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 448
aatgatacgg cgaccaccga gatctacacc gtaccaatcg tcggcagcgt cagatgtgta      60
t                                                                     61

<210> SEQ ID NO 449
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 449
aatgatacgg cgaccaccga gatctacacc cagtttatcg tcggcagcgt cagatgtgta      60
t                                                                     61

<210> SEQ ID NO 450
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 450
aatgatacgg cgaccaccga gatctacaca ccggccctcg tcggcagcgt cagatgtgta      60
t                                                                     61

<210> SEQ ID NO 451
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 451
aatgatacgg cgaccaccga gatctacacc tagaagttcg tcggcagcgt cagatgtgta      60
t                                                                     61

<210> SEQ ID NO 452
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 452
aatgatacgg cgaccaccga gatctacacc gccagattcg tcggcagcgt cagatgtgta      60
t                                                                     61

<210> SEQ ID NO 453
<211> LENGTH: 61
<212> TYPE: DNA
<213> ORGANISM: Artificial Sequence
<220> FEATURE:
<223> OTHER INFORMATION: Synthetic Oligonucleotide
```

```
<400> SEQUENCE: 453
aatgatacgg cgaccaccga gatctacact cacatggtcg tcggcagcgt cagatgtgta    60
t                                                                   61

<210> SEQ ID NO 454
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 454
aatgatacgg cgaccaccga gatctacacg aactcgatcg tcggcagcgt cagatgtgta    60
t                                                                   61

<210> SEQ ID NO 455
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 455
aatgatacgg cgaccaccga gatctacacc caccgtttcg tcggcagcgt cagatgtgta    60
t                                                                   61

<210> SEQ ID NO 456
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 456
aatgatacgg cgaccaccga gatctacact aagttactcg tcggcagcgt cagatgtgta    60
t                                                                   61

<210> SEQ ID NO 457
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 457
aatgatacgg cgaccaccga gatctacacg agacgtgtcg tcggcagcgt cagatgtgta    60
t                                                                   61

<210> SEQ ID NO 458
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 458
aatgatacgg cgaccaccga gatctacact tgcctaatcg tcggcagcgt cagatgtgta    60
t                                                                   61

<210> SEQ ID NO 459
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 459
aatgatacgg cgaccaccga gatctacact taacttgtcg tcggcagcgt cagatgtgta     60
t                                                                    61

<210> SEQ ID NO 460
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 460
aatgatacgg cgaccaccga gatctacacc tttaacatcg tcggcagcgt cagatgtgta     60
t                                                                    61

<210> SEQ ID NO 461
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 461
aatgatacgg cgaccaccga gatctacacc gtagacctcg tcggcagcgt cagatgtgta     60
t                                                                    61

<210> SEQ ID NO 462
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 462
aatgatacgg cgaccaccga gatctacact atttgcgtcg tcggcagcgt cagatgtgta     60
t                                                                    61

<210> SEQ ID NO 463
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 463
aatgatacgg cgaccaccga gatctacaca tccaggatcg tcggcagcgt cagatgtgta     60
t                                                                    61

<210> SEQ ID NO 464
<211> LENGTH: 61
<212> TYPE: DNA
<213> ORGANISM: Artificial Sequence
<220> FEATURE:
<223> OTHER INFORMATION: Synthetic Oligonucleotide
```

<400> SEQUENCE: 464
aatgatacgg cgaccaccga gatctacact gttcctgtcg tcggcagcgt cagatgtgta    60
t                                                                    61

<210> SEQ ID NO 465
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 465
aatgatacgg cgaccaccga gatctacaca cgcgcagtcg tcggcagcgt cagatgtgta    60
t                                                                    61

<210> SEQ ID NO 466
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 466
aatgatacgg cgaccaccga gatctacact ctggcgatcg tcggcagcgt cagatgtgta    60
t                                                                    61

<210> SEQ ID NO 467
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 467
aatgatacgg cgaccaccga gatctacaca atctacatcg tcggcagcgt cagatgtgta    60
t                                                                    61

<210> SEQ ID NO 468
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 468
aatgatacgg cgaccaccga gatctacact actgacctcg tcggcagcgt cagatgtgta    60
t                                                                    61

<210> SEQ ID NO 469
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 469
aatgatacgg cgaccaccga gatctacacc gatagggtcg tcggcagcgt cagatgtgta    60
t                                                                    61

<210> SEQ ID NO 470

<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 470
aatgatacgg cgaccaccga gatctacaca cttagaatcg tcggcagcgt cagatgtgta    60
t                                                                    61

<210> SEQ ID NO 471
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 471
aatgatacgg cgaccaccga gatctacaca gagatcttcg tcggcagcgt cagatgtgta    60
t                                                                    61

<210> SEQ ID NO 472
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 472
aatgatacgg cgaccaccga gatctacacg gtgaaggtcg tcggcagcgt cagatgtgta    60
t                                                                    61

<210> SEQ ID NO 473
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 473
aatgatacgg cgaccaccga gatctacaca tcgaatgtcg tcggcagcgt cagatgtgta    60
t                                                                    61

<210> SEQ ID NO 474
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 474
aatgatacgg cgaccaccga gatctacact caagagctcg tcggcagcgt cagatgtgta    60
t                                                                    61

<210> SEQ ID NO 475
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 475
aatgatacgg cgaccaccga gatctacacg cccacgttcg tcggcagcgt cagatgtgta    60
t    61

<210> SEQ ID NO 476
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 476
aatgatacgg cgaccaccga gatctacact gggcggttcg tcggcagcgt cagatgtgta    60
t    61

<210> SEQ ID NO 477
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 477
aatgatacgg cgaccaccga gatctacacc ccttggatcg tcggcagcgt cagatgtgta    60
t    61

<210> SEQ ID NO 478
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 478
aatgatacgg cgaccaccga gatctacaca ttaccgttcg tcggcagcgt cagatgtgta    60
t    61

<210> SEQ ID NO 479
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 479
aatgatacgg cgaccaccga gatctacaca gtccgagtcg tcggcagcgt cagatgtgta    60
t    61

<210> SEQ ID NO 480
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 480
aatgatacgg cgaccaccga gatctacaca cttgttgtcg tcggcagcgt cagatgtgta    60
t    61

<210> SEQ ID NO 481

<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 481
aatgatacgg cgaccaccga gatctacacg taatacatcg tcggcagcgt cagatgtgta    60
t                                                                    61

<210> SEQ ID NO 482
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 482
aatgatacgg cgaccaccga gatctacacg gcgtctatcg tcggcagcgt cagatgtgta    60
t                                                                    61

<210> SEQ ID NO 483
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 483
aatgatacgg cgaccaccga gatctacacg cgctgcttcg tcggcagcgt cagatgtgta    60
t                                                                    61

<210> SEQ ID NO 484
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 484
aatgatacgg cgaccaccga gatctacacg tgccatttcg tcggcagcgt cagatgtgta    60
t                                                                    61

<210> SEQ ID NO 485
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 485
aatgatacgg cgaccaccga gatctacact aggtatgtcg tcggcagcgt cagatgtgta    60
t                                                                    61

<210> SEQ ID NO 486
<211> LENGTH: 61
<212> TYPE: DNA
<213> ORGANISM: Artificial Sequence
<220> FEATURE:
<223> OTHER INFORMATION: Synthetic Oligonucleotide -continued

```
<400> SEQUENCE: 486
aatgatacgg cgaccaccga gatctacaca acacctatcg tcggcagcgt cagatgtgta    60
t                                                                   61

<210> SEQ ID NO 487
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 487
aatgatacgg cgaccaccga gatctacacc tccgaactcg tcggcagcgt cagatgtgta    60
t                                                                   61

<210> SEQ ID NO 488
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 488
aatgatacgg cgaccaccga gatctacacc aacggcatcg tcggcagcgt cagatgtgta    60
t                                                                   61

<210> SEQ ID NO 489
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 489
aatgatacgg cgaccaccga gatctacacc aatgtagtcg tcggcagcgt cagatgtgta    60
t                                                                   61

<210> SEQ ID NO 490
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 490
aatgatacgg cgaccaccga gatctacacg gctaccctcg tcggcagcgt cagatgtgta    60
t                                                                   61

<210> SEQ ID NO 491
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 491
aatgatacgg cgaccaccga gatctacaca aagtccgtcg tcggcagcgt cagatgtgta    60
t                                                                   61

<210> SEQ ID NO 492
```

```
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 492
aatgatacgg cgaccaccga gatctacact tccgcggtcg tcggcagcgt cagatgtgta      60
t                                                                     61

<210> SEQ ID NO 493
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 493
aatgatacgg cgaccaccga gatctacaca ggcactttcg tcggcagcgt cagatgtgta      60
t                                                                     61

<210> SEQ ID NO 494
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 494
aatgatacgg cgaccaccga gatctacacc ttcagtgtcg tcggcagcgt cagatgtgta      60
t                                                                     61

<210> SEQ ID NO 495
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 495
aatgatacgg cgaccaccga gatctacacg ccggtagtcg tcggcagcgt cagatgtgta      60
t                                                                     61

<210> SEQ ID NO 496
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 496
aatgatacgg cgaccaccga gatctacact tcaatcctcg tcggcagcgt cagatgtgta      60
t                                                                     61

<210> SEQ ID NO 497
<211> LENGTH: 61
<212> TYPE: DNA
<213> ORGANISM: Artificial Sequence
<220> FEATURE:
<223> OTHER INFORMATION: Synthetic Oligonucleotide
```

```
<400> SEQUENCE: 497
aatgatacgg cgaccaccga gatctacacc cacacactcg tcggcagcgt cagatgtgta    60
t                                                                   61

<210> SEQ ID NO 498
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 498
aatgatacgg cgaccaccga gatctacaca tattatctcg tcggcagcgt cagatgtgta    60
t                                                                   61

<210> SEQ ID NO 499
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 499
aatgatacgg cgaccaccga gatctacacc cgaagcatcg tcggcagcgt cagatgtgta    60
t                                                                   61

<210> SEQ ID NO 500
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 500
aatgatacgg cgaccaccga gatctacacg tatcggttcg tcggcagcgt cagatgtgta    60
t                                                                   61

<210> SEQ ID NO 501
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 501
cgcgctgcat acttgaacgt gatcccatga tcgtccga                           38

<210> SEQ ID NO 502
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated
```

<400> SEQUENCE: 502
cgcgctgcat acttgaaaca tcgcccatga tcgtccga                                  38

<210> SEQ ID NO 503
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 503
cgcgctgcat acttgatgcc taacccatga tcgtccga                                  38

<210> SEQ ID NO 504
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..()
<223> OTHER INFORMATION: 5 prime phosphorylated

<400> SEQUENCE: 504
cgcgctgcat acttgagtgg tcacccatga tcgtccga                                  38

<210> SEQ ID NO 505
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 505
cgcgctgcat acttgaccac tgtcccatga tcgtccga                                  38

<210> SEQ ID NO 506
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 506
cgcgctgcat acttgacatt ggcccatga tcgtccga                                   38

<210> SEQ ID NO 507
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

```
<223> OTHER INFORMATION: 5 prime phosphorylated

<400> SEQUENCE: 507
cgcgctgcat acttgcagat ctgcccatga tcgtccga                              38

<210> SEQ ID NO 508
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 508
cgcgctgcat acttgcatca agtcccatga tcgtccga                              38

<210> SEQ ID NO 509
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 509
cgcgctgcat acttgcgctg atccccatga tcgtccga                              38

<210> SEQ ID NO 510
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 510
cgcgctgcat acttgacaag ctacccatga tcgtccga                              38

<210> SEQ ID NO 511
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 511
cgcgctgcat acttgctgta gcccccatga tcgtccga                              38

<210> SEQ ID NO 512
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(1)
<223> OTHER INFORMATION: 5 prime phosphorylated

<400> SEQUENCE: 512
cgcgctgcat acttgagtac aagcccatga tcgtccga                              38

<210> SEQ ID NO 513
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 513
cgcgctgcat acttgaacaa ccacccatga tcgtccga                              38

<210> SEQ ID NO 514
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 514
cgcgctgcat acttgaaccg agacccatga tcgtccga                              38

<210> SEQ ID NO 515
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 515
cgcgctgcat acttgaacgc ttacccatga tcgtccga                              38

<210> SEQ ID NO 516
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 516
cgcgctgcat acttgaagac ggacccatga tcgtccga                              38

<210> SEQ ID NO 517
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: 5 prime phosphorylated

<400> SEQUENCE: 517
cgcgctgcat acttgaaggt acacccatga tcgtccga                              38

<210> SEQ ID NO 518
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 518
cgcgctgcat acttgacaca gaacccatga tcgtccga                              38

<210> SEQ ID NO 519
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 519
cgcgctgcat acttgacagc agacccatga tcgtccga                              38

<210> SEQ ID NO 520
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 520
cgcgctgcat acttgacctc caacccatga tcgtccga                              38

<210> SEQ ID NO 521
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 521
cgcgctgcat acttgacgct cgacccatga tcgtccga                              38

<210> SEQ ID NO 522
<211> LENGTH: 38
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: 5 prime phosphorylated

<400> SEQUENCE: 522
cgcgctgcat acttgacgta tcacccatga tcgtccga                                    38

<210> SEQ ID NO 523
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 523
cgcgctgcat acttgactat gcacccatga tcgtccga                                    38

<210> SEQ ID NO 524
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 524
cgcgctgcat acttgagagt caacccatga tcgtccga                                    38

<210> SEQ ID NO 525
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 525
cgcgctgcat acttgagatc gcacccatga tcgtccga                                    38

<210> SEQ ID NO 526
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 526
cgcgctgcat acttgagcag gaacccatga tcgtccga                                    38

<210> SEQ ID NO 527
<211> LENGTH: 38
<212> TYPE: DNA
<213> ORGANISM: Artificial Sequence
<220> FEATURE:
```

<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 527
cgcgctgcat acttgagtca ctacccatga tcgtccga                              38

<210> SEQ ID NO 528
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 528
cgcgctgcat acttgatcct gtacccatga tcgtccga                              38

<210> SEQ ID NO 529
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 529
cgcgctgcat acttgattga ggacccatga tcgtccga                              38

<210> SEQ ID NO 530
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 530
cgcgctgcat acttgcaacc acacccatga tcgtccga                              38

<210> SEQ ID NO 531
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 531
cgcgctgcat acttggacta gtacccatga tcgtccga                              38

<210> SEQ ID NO 532
<211> LENGTH: 38
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 532
cgcgctgcat acttgcaatg gaacccatga tcgtccga                                 38

<210> SEQ ID NO 533
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 533
cgcgctgcat acttgcactt cgacccatga tcgtccga                                 38

<210> SEQ ID NO 534
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 534
cgcgctgcat acttgcagcg ttacccatga tcgtccga                                 38

<210> SEQ ID NO 535
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 535
cgcgctgcat acttgcatac caacccatga tcgtccga                                 38

<210> SEQ ID NO 536
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 536
cgcgctgcat acttgccagt tcacccatga tcgtccga                                 38

<210> SEQ ID NO 537
<211> LENGTH: 38
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 537
cgcgctgcat acttgccgaa gtacccatga tcgtccga                              38

<210> SEQ ID NO 538
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 538
cgcgctgcat acttgccgtg agacccatga tcgtccga                              38

<210> SEQ ID NO 539
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 539
cgcgctgcat acttgcctcc tgacccatga tcgtccga                              38

<210> SEQ ID NO 540
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 540
cgcgctgcat acttgcgaac ttacccatga tcgtccga                              38

<210> SEQ ID NO 541
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 541
cgcgctgcat acttgcgact ggacccatga tcgtccga                              38

<210> SEQ ID NO 542
<211> LENGTH: 37
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 542
cgcgctgcat acttgcgcat acacccatga tcgtccg                              37

<210> SEQ ID NO 543
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 543
cgcgctgcat acttgctcaa tgacccatga tcgtccga                             38

<210> SEQ ID NO 544
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 544
cgcgctgcat acttgctgag ccacccatga tcgtccga                             38

<210> SEQ ID NO 545
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 545
cgcgctgcat acttgctggc atacccatga tcgtccga                             38

<210> SEQ ID NO 546
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 546
cgcgctgcat acttggaatc tgacccatga tcgtccga                             38

<210> SEQ ID NO 547
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 547
cgcgctgcat acttgcaaga ctacccatga tcgtccga                              38

<210> SEQ ID NO 548
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 548
cgcgctgcat acttggagct gaacccatga tcgtccga                              38

<210> SEQ ID NO 549
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 549
cgcgctgcat acttggatag acacccatga tcgtccga                              38

<210> SEQ ID NO 550
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 550
cgcgctgcat acttggccac atacccatga tcgtccga                              38

<210> SEQ ID NO 551
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 551
cgcgctgcat acttggcgag taacccatga tcgtccga                              38
```

-continued

```
<210> SEQ ID NO 552
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 552
cgcgctgcat acttggctaa cgacccatga tcgtccga                          38

<210> SEQ ID NO 553
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 553
cgcgctgcat acttggctcg gtacccatga tcgtccga                          38

<210> SEQ ID NO 554
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 554
cgcgctgcat acttgggaga acacccatga tcgtccga                          38

<210> SEQ ID NO 555
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 555
cgcgctgcat acttgggtgc gaacccatga tcgtccga                          38

<210> SEQ ID NO 556
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 556
cgcgctgcat acttggtacg caacccatga tcgtccga                          38

<210> SEQ ID NO 557
<211> LENGTH: 38
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 557
cgcgctgcat acttggtcgt agacccatga tcgtccga                                  38

<210> SEQ ID NO 558
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 558
cgcgctgcat acttggtctg tcacccatga tcgtccga                                  38

<210> SEQ ID NO 559
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 559
cgcgctgcat acttggtgtt ctacccatga tcgtccga                                  38

<210> SEQ ID NO 560
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 560
cgcgctgcat acttgtagga tgacccatga tcgtccga                                  38

<210> SEQ ID NO 561
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 561
cgcgctgcat acttgtatca gcacccatga tcgtccga                                  38

<210> SEQ ID NO 562
<211> LENGTH: 38
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 562
cgcgctgcat acttgtccgt ctacccatga tcgtccga                              38

<210> SEQ ID NO 563
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 563
cgcgctgcat acttgtcttc acacccatga tcgtccga                              38

<210> SEQ ID NO 564
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 564
cgcgctgcat acttgtgaag agacccatga tcgtccga                              38

<210> SEQ ID NO 565
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 565
cgcgctgcat acttgtggaa caacccatga tcgtccga                              38

<210> SEQ ID NO 566
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 566
cgcgctgcat acttgtggct tcacccatga tcgtccga                              38

<210> SEQ ID NO 567
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 567
cgcgctgcat acttgtggtg gtacccatga tcgtccga                              38

<210> SEQ ID NO 568
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 568
cgcgctgcat acttgttcac gcacccatga tcgtccga                              38

<210> SEQ ID NO 569
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 569
cgcgctgcat acttgaactc accccatga tcgtccga                               38

<210> SEQ ID NO 570
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 570
cgcgctgcat acttgaagag atccccatga tcgtccga                              38

<210> SEQ ID NO 571
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 571
cgcgctgcat acttgaagga cacccatga tcgtccga                               38
```

```
<210> SEQ ID NO 572
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 572
cgcgctgcat acttgaatcc gtccccatga tcgtccga                               38

<210> SEQ ID NO 573
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 573
cgcgctgcat acttgaatgt tgccccatga tcgtccga                               38

<210> SEQ ID NO 574
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 574
cgcgctgcat acttgacacg accccatga tcgtccga                                38

<210> SEQ ID NO 575
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 575
cgcgctgcat acttgacaga ttccccatga tcgtccga                               38

<210> SEQ ID NO 576
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 576
cgcgctgcat acttgagatg taccccatga tcgtccga                               38
```

<210> SEQ ID NO 577
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 577
cgcgctgcat acttgagcac ctccccatga tcgtccga                           38

<210> SEQ ID NO 578
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 578
cgcgctgcat acttgagcca tgccccatga tcgtccga                           38

<210> SEQ ID NO 579
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 579
cgcgctgcat acttgaggct aaccccatga tcgtccga                           38

<210> SEQ ID NO 580
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 580
cgcgctgcat acttgatagc gaccccatga tcgtccga                           38

<210> SEQ ID NO 581
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 581
cgcgctgcat acttgatcat tccccatga tcgtccga                            38

<210> SEQ ID NO 582
<211> LENGTH: 38

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 582
cgcgctgcat acttgattgg ctccccatga tcgtccga                              38

<210> SEQ ID NO 583
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 583
cgcgctgcat acttgcaagg agccccatga tcgtccga                              38

<210> SEQ ID NO 584
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 584
cgcgctgcat acttgcacct taccccatga tcgtccga                              38

<210> SEQ ID NO 585
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 585
cgcgctgcat acttgccatc ctccccatga tcgtccga                              38

<210> SEQ ID NO 586
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 586
cgcgctgcat acttgccgac aaccccatga tcgtccga                              38

<210> SEQ ID NO 587
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 587
cgcgctgcat acttgcctaa tcccccatga tcgtccga                              38

<210> SEQ ID NO 588
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 588
cgcgctgcat acttgcctct atccccatga tcgtccga                              38

<210> SEQ ID NO 589
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 589
cgcgctgcat acttgcgaca caccccatga tcgtccga                              38

<210> SEQ ID NO 590
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 590
cgcgctgcat acttgcggat tgccccatga tcgtccga                              38

<210> SEQ ID NO 591
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 591
cgcgctgcat acttgctaag gtccccatga tcgtccga                              38
```

```
<210> SEQ ID NO 592
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 592
cgcgctgcat acttggaaca ggccccatga tcgtccga                                38

<210> SEQ ID NO 593
<211> LENGTH: 37
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 593
cgcgctgcat acttggacag tgccccatga tcgtccg                                 37

<210> SEQ ID NO 594
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 594
cgcgctgcat acttggagtt agccccatga tcgtccga                                38

<210> SEQ ID NO 595
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 595
cgcgctgcat acttggatga atccccatga tcgtccga                                38

<210> SEQ ID NO 596
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 596
cgcgctgcat acttggccaa gaccccatga tcgtccga                                38
```

```
<210> SEQ ID NO 597
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 597
catcggcgta cgactaacgt gatatccacg tgcttgag                              38

<210> SEQ ID NO 598
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 598
catcggcgta cgactaaaca tcgatccacg tgcttgag                              38

<210> SEQ ID NO 599
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 599
catcggcgta cgactatgcc taaatccacg tgcttgag                              38

<210> SEQ ID NO 600
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 600
catcggcgta cgactagtgg tcaatccacg tgcttgag                              38

<210> SEQ ID NO 601
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 601
catcggcgta cgactaccac tgtatccacg tgcttgag                              38
```

<210> SEQ ID NO 602
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 602
catcggcgta cgactacatt ggcatccacg tgcttgag                                    38

<210> SEQ ID NO 603
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 603
catcggcgta cgactcagat ctgatccacg tgcttgag                                    38

<210> SEQ ID NO 604
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 604
catcggcgta cgactcatca agtatccacg tgcttgag                                    38

<210> SEQ ID NO 605
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 605
catcggcgta cgactcgctg atcatccacg tgcttgag                                    38

<210> SEQ ID NO 606
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 606
catcggcgta cgactacaag ctaatccacg tgcttgag                    38

<210> SEQ ID NO 607
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 607
catcggcgta cgactctgta gccatccacg tgcttgag                    38

<210> SEQ ID NO 608
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 608
catcggcgta cgactagtac aagatccacg tgcttgag                    38

<210> SEQ ID NO 609
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 609
catcggcgta cgactaacaa ccaatccacg tgcttgag                    38

<210> SEQ ID NO 610
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 610
catcggcgta cgactaaccg agaatccacg tgcttgag                    38

<210> SEQ ID NO 611
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

<223> OTHER INFORMATION: 5 prime phosphorylated

<400> SEQUENCE: 611
catcggcgta cgactaacgc ttaatccacg tgcttgag                              38

<210> SEQ ID NO 612
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 612
catcggcgta cgactaagac ggaatccacg tgcttgag                              38

<210> SEQ ID NO 613
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 613
catcggcgta cgactaaggt acaatccacg tgcttgag                              38

<210> SEQ ID NO 614
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 614
catcggcgta cgactacaca gaaatccacg tgcttgag                              38

<210> SEQ ID NO 615
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 615
catcggcgta cgactacagc agaatccacg tgcttgag                              38

<210> SEQ ID NO 616
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 616
catcggcgta cgactacctc caaatccacg tgcttgag                           38

<210> SEQ ID NO 617
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 617
catcggcgta cgactacgct cgaatccacg tgcttgag                           38

<210> SEQ ID NO 618
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 618
catcggcgta cgactacgta tcaatccacg tgcttgag                           38

<210> SEQ ID NO 619
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 619
catcggcgta cgactactat gcaatccacg tgcttgag                           38

<210> SEQ ID NO 620
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 620
catcggcgta cgactagagt caaatccacg tgcttgag                           38

<210> SEQ ID NO 621
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:

<221> NAME/KEY: misc_feature
<222> LOCATION: (1)..(1)
<223> OTHER INFORMATION: 5 prime phosphorylated

<400> SEQUENCE: 621
catcggcgta cgactagatc gcaatccacg tgcttgag        38

<210> SEQ ID NO 622
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 622
catcggcgta cgactagcag gaaatccacg tgcttgag        38

<210> SEQ ID NO 623
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 623
catcggcgta cgactagtca ctaatccacg tgcttgag        38

<210> SEQ ID NO 624
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 624
catcggcgta cgactatcct gtaatccacg tgcttgag        38

<210> SEQ ID NO 625
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 625
catcggcgta cgactattga ggaatccacg tgcttgag        38

<210> SEQ ID NO 626
<211> LENGTH: 38
<212> TYPE: DNA
<213> ORGANISM: Artificial Sequence
<220> FEATURE:
<223> OTHER INFORMATION: Synthetic Oligonucleotide -continued

```
<220> FEATURE:
<221> NAME/KEY: misc_feature
<222> LOCATION: (1)..(1)
<223> OTHER INFORMATION: 5 prime phosphorylated

<400> SEQUENCE: 626
catcggcgta cgactcaacc acaatccacg tgcttgag                                   38

<210> SEQ ID NO 627
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 627
catcggcgta cgactgacta gtaatccacg tgcttgag                                   38

<210> SEQ ID NO 628
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 628
catcggcgta cgactcaatg gaaatccacg tgcttgag                                   38

<210> SEQ ID NO 629
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 629
catcggcgta cgactcactt cgaatccacg tgcttgag                                   38

<210> SEQ ID NO 630
<211> LENGTH: 37
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 630
catcggcgta cgactcagcg ttaatccacg tgcttga                                    37

<210> SEQ ID NO 631
<211> LENGTH: 38
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 631
catcggcgta cgactcatac caaatccacg tgcttgag                              38

<210> SEQ ID NO 632
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 632
catcggcgta cgactccagt tcaatccacg tgcttgag                              38

<210> SEQ ID NO 633
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 633
catcggcgta cgactccgaa gtaatccacg tgcttgag                              38

<210> SEQ ID NO 634
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..()
<223> OTHER INFORMATION: 5 prime phosphorylated

<400> SEQUENCE: 634
catcggcgta cgactccgtg agaatccacg tgcttgag                              38

<210> SEQ ID NO 635
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 635
catcggcgta cgactcctcc tgaatccacg tgcttgag                              38

<210> SEQ ID NO 636
<211> LENGTH: 38
<212> TYPE: DNA
<213> ORGANISM: Artificial Sequence
```

-continued

```
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 636
catcggcgta cgactcgaac ttaatccacg tgcttgag                              38

<210> SEQ ID NO 637
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 637
catcggcgta cgactcgact ggaatccacg tgcttgag                              38

<210> SEQ ID NO 638
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 638
catcggcgta cgactcgcat acaatccacg tgcttgag                              38

<210> SEQ ID NO 639
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 639
catcggcgta cgactctcaa tgaatccacg tgcttgag                              38

<210> SEQ ID NO 640
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 640
catcggcgta cgactctgag ccaatccacg tgcttgag                              38

<210> SEQ ID NO 641
<211> LENGTH: 38
<212> TYPE: DNA
```

<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 641
catcggcgta cgactctggc ataatccacg tgcttgag                    38

<210> SEQ ID NO 642
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 642
catcggcgta cgactgaatc tgaatccacg tgcttgag                    38

<210> SEQ ID NO 643
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 643
catcggcgta cgactcaaga ctaatccacg tgcttgag                    38

<210> SEQ ID NO 644
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 644
catcggcgta cgactgagct gaaatccacg tgcttgag                    38

<210> SEQ ID NO 645
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 645
catcggcgta cgactgatag acaatccacg tgcttgag                    38

<210> SEQ ID NO 646
<211> LENGTH: 38

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 646
catcggcgta cgactgccac ataatccacg tgcttgag                          38

<210> SEQ ID NO 647
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 647
catcggcgta cgactgcgag taaatccacg tgcttgag                          38

<210> SEQ ID NO 648
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 648
catcggcgta cgactgctaa cgaatccacg tgcttgag                          38

<210> SEQ ID NO 649
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 649
catcggcgta cgactgctcg gtaatccacg tgcttgag                          38

<210> SEQ ID NO 650
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 650
catcggcgta cgactggaga acaatccacg tgcttgag                          38

<210> SEQ ID NO 651
```

```
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 651
catcggcgta cgactggtgc gaaatccacg tgcttgag                              38

<210> SEQ ID NO 652
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 652
catcggcgta cgactgtacg caaatccacg tgcttgag                              38

<210> SEQ ID NO 653
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 653
catcggcgta cgactgtcgt agaatccacg tgcttgag                              38

<210> SEQ ID NO 654
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 654
catcggcgta cgactgtctg tcaatccacg tgcttgag                              38

<210> SEQ ID NO 655
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 655
catcggcgta cgactgtgtt ctaatccacg tgcttgag                              38
```

```
<210> SEQ ID NO 656
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 656
catcggcgta cgacttagga tgaatccacg tgcttgag                              38

<210> SEQ ID NO 657
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 657
catcggcgta cgacttatca gcaatccacg tgcttgag                              38

<210> SEQ ID NO 658
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 658
catcggcgta cgacttccgt ctaatccacg tgcttgag                              38

<210> SEQ ID NO 659
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 659
catcggcgta cgacttcttc acaatccacg tgcttgag                              38

<210> SEQ ID NO 660
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 660
catcggcgta cgacttgaag agaatccacg tgcttgag                              38
```

<210> SEQ ID NO 661
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 661
catcggcgta cgacttggaa caaatccacg tgcttgag         38

<210> SEQ ID NO 662
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 662
catcggcgta cgacttggct tcaatccacg tgcttgag         38

<210> SEQ ID NO 663
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 663
catcggcgta cgacttggtg gtaatccacg tgcttgag         38

<210> SEQ ID NO 664
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 664
catcggcgta cgactttcac gcaatccacg tgcttgag         38

<210> SEQ ID NO 665
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 665
catcggcgta cgactaactc accatccacg tgcttgag         38

<210> SEQ ID NO 666
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 666
catcggcgta cgactaagag atcatccacg tgcttgag                                  38

<210> SEQ ID NO 667
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 667
catcggcgta cgactaagga cacatccacg tgcttgag                                  38

<210> SEQ ID NO 668
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 668
catcggcgta cgactaatcc gtcatccacg tgcttgag                                  38

<210> SEQ ID NO 669
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 669
catcggcgta cgactaatgt tgcatccacg tgcttgag                                  38

<210> SEQ ID NO 670
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 670
catcggcgta cgactacacg accatccacg tgcttgag            38

<210> SEQ ID NO 671
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 671
catcggcgta cgactacaga ttcatccacg tgcttgag            38

<210> SEQ ID NO 672
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 672
catcggcgta cgactagatg tacatccacg tgcttgag            38

<210> SEQ ID NO 673
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 673
catcggcgta cgactagcac ctcatccacg tgcttgag            38

<210> SEQ ID NO 674
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 674
catcggcgta cgactagcca tgcatccacg tgcttgag            38

<210> SEQ ID NO 675
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)

```
<223> OTHER INFORMATION: 5 prime phosphorylated

<400> SEQUENCE: 675
catcggcgta cgactaggct aacatccacg tgcttgag                              38

<210> SEQ ID NO 676
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 676
catcggcgta cgactatagc gacatccacg tgcttgag                              38

<210> SEQ ID NO 677
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 677
catcggcgta cgactatcat tccatccacg tgcttgag                              38

<210> SEQ ID NO 678
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 678
catcggcgta cgactattgg ctcatccacg tgcttgag                              38

<210> SEQ ID NO 679
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 679
catcggcgta cgactcaagg agcatccacg tgcttgag                              38

<210> SEQ ID NO 680
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(1)
<223> OTHER INFORMATION: 5 prime phosphorylated

<400> SEQUENCE: 680
catcggcgta cgactcacct tacatccacg tgcttgag                                    38

<210> SEQ ID NO 681
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 681
catcggcgta cgactccatc ctcatccacg tgcttgag                                    38

<210> SEQ ID NO 682
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 682
catcggcgta cgactccgac aacatccacg tgcttgag                                    38

<210> SEQ ID NO 683
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 683
catcggcgta cgactcctaa tccatccacg tgcttgag                                    38

<210> SEQ ID NO 684
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 684
catcggcgta cgactcctct atcatccacg tgcttgag                                    38

<210> SEQ ID NO 685
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: 5 prime phosphorylated

<400> SEQUENCE: 685
catcggcgta cgactcgaca cacatccacg tgcttgag                              38

<210> SEQ ID NO 686
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 686
catcggcgta cgactcggat tgcatccacg tgcttgag                              38

<210> SEQ ID NO 687
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 687
catcggcgta cgactctaag gtcatccacg tgcttgag                              38

<210> SEQ ID NO 688
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 688
catcggcgta cgactgaaca ggcatccacg tgcttgag                              38

<210> SEQ ID NO 689
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 689
catcggcgta cgactgacag tgcatccacg tgcttgag                              38

<210> SEQ ID NO 690
<211> LENGTH: 38
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: 5 prime phosphorylated

<400> SEQUENCE: 690
catcggcgta cgactgagtt agcatccacg tgcttgag                              38

<210> SEQ ID NO 691
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 691
catcggcgta cgactgatga atcatccacg tgcttgag                              38

<210> SEQ ID NO 692
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime phosphorylated

<400> SEQUENCE: 692
catcggcgta cgactgccaa gacatccacg tgcttgag                              38

<210> SEQ ID NO 693
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 693
caagcagaag acggcatacg agataacgtg atgtggccga tgtttcg                    47

<210> SEQ ID NO 694
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 694
caagcagaag acggcatacg agataaacat cggtggccga tgtttcg                    47

<210> SEQ ID NO 695
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 695
caagcagaag acggcatacg agatatgcct aagtggccga tgtttcg                    47

<210> SEQ ID NO 696
```

<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 696
caagcagaag acggcatacg agatagtggt cagtggccga tgtttcg         47

<210> SEQ ID NO 697
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 697
caagcagaag acggcatacg agataccact gtgtggccga tgtttcg         47

<210> SEQ ID NO 698
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 698
caagcagaag acggcatacg agatacattg gcgtggccga tgtttcg         47

<210> SEQ ID NO 699
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 699
caagcagaag acggcatacg agatcagatc tggtggccga tgtttcg         47

<210> SEQ ID NO 700
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 700
caagcagaag acggcatacg agatcatcaa gtgtggccga tgtttcg         47

<210> SEQ ID NO 701
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 701
caagcagaag acggcatacg agatcgctga tcgtggccga tgtttcg         47

<210> SEQ ID NO 702
<211> LENGTH: 47
<212> TYPE: DNA
<213> ORGANISM: Artificial Sequence
<220> FEATURE:
<223> OTHER INFORMATION: Synthetic Oligonucleotide

```
<400> SEQUENCE: 702
caagcagaag acggcatacg agatacaagc tagtggccga tgtttcg                    47

<210> SEQ ID NO 703
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 703
caagcagaag acggcatacg agatctgtag ccgtggccga tgtttcg                    47

<210> SEQ ID NO 704
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 704
caagcagaag acggcatacg agatagtaca aggtggccga tgtttcg                    47

<210> SEQ ID NO 705
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 705
caagcagaag acggcatacg agataacaac cagtggccga tgtttcg                    47

<210> SEQ ID NO 706
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 706
caagcagaag acggcatacg agataaccga gagtggccga tgtttcg                    47

<210> SEQ ID NO 707
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 707
caagcagaag acggcatacg agataacgct tagtggccga tgtttcg                    47

<210> SEQ ID NO 708
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 708
caagcagaag acggcatacg agataagacg gagtggccga tgtttcg                    47

<210> SEQ ID NO 709
```

<210> SEQ ID NO 709
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 709
caagcagaag acggcatacg agataaggta cagtggccga tgtttcg                47

<210> SEQ ID NO 710
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 710
caagcagaag acggcatacg agatacacag aagtggccga tgtttcg                47

<210> SEQ ID NO 711
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 711
caagcagaag acggcatacg agatacagca gagtggccga tgtttcg                47

<210> SEQ ID NO 712
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 712
caagcagaag acggcatacg agatacctcc aagtggccga tgtttcg                47

<210> SEQ ID NO 713
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 713
caagcagaag acggcatacg agatacgctc gagtggccga tgtttcg                47

<210> SEQ ID NO 714
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 714
caagcagaag acggcatacg agatacgtat cagtggccga tgtttcg                47

<210> SEQ ID NO 715
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 715
caagcagaag acggcatacg agatactatg cagtggccga tgtttcg      47

<210> SEQ ID NO 716
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 716
caagcagaag acggcatacg agatagagtc aagtggccga tgtttcg      47

<210> SEQ ID NO 717
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 717
caagcagaag acggcatacg agatagatcg cagtggccga tgtttcg      47

<210> SEQ ID NO 718
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 718
caagcagaag acggcatacg agatagcagg aagtggccga tgtttcg      47

<210> SEQ ID NO 719
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 719
caagcagaag acggcatacg agatagtcac tagtggccga tgtttcg      47

<210> SEQ ID NO 720
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 720
caagcagaag acggcatacg agatatcctg tagtggccga tgtttcg      47

<210> SEQ ID NO 721
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 721
caagcagaag acggcatacg agatattgag gagtggccga tgtttcg      47

<210> SEQ ID NO 722

<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 722
caagcagaag acggcatacg agatcaacca cagtggccga tgtttcg        47

<210> SEQ ID NO 723
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 723
caagcagaag acggcatacg agatgactag tagtggccga tgtttcg        47

<210> SEQ ID NO 724
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 724
caagcagaag acggcatacg agatcaatgg aagtggccga tgtttcg        47

<210> SEQ ID NO 725
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 725
caagcagaag acggcatacg agatcacttc gagtggccga tgtttcg        47

<210> SEQ ID NO 726
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 726
caagcagaag acggcatacg agatcagcgt tagtggccga tgtttcg        47

<210> SEQ ID NO 727
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 727
caagcagaag acggcatacg agatcatacc aagtggccga tgtttcg        47

<210> SEQ ID NO 728
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 728
caagcagaag acggcatacg agatccagtt cagtggccga tgtttcg          47

<210> SEQ ID NO 729
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 729
caagcagaag acggcatacg agatccgaag tagtggccga tgtttcg          47

<210> SEQ ID NO 730
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 730
caagcagaag acggcatacg agatccgtga gagtggccga tgtttcg          47

<210> SEQ ID NO 731
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 731
caagcagaag acggcatacg agatcctcct gagtggccga tgtttcg          47

<210> SEQ ID NO 732
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 732
caagcagaag acggcatacg agatcgaact tagtggccga tgtttcg          47

<210> SEQ ID NO 733
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 733
caagcagaag acggcatacg agatcgactg gagtggccga tgtttcg          47

<210> SEQ ID NO 734
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 734
caagcagaag acggcatacg agatcgcata cagtggccga tgtttcg          47

<210> SEQ ID NO 735

<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 735
caagcagaag acggcatacg agatctcaat gagtggccga tgtttcg                47

<210> SEQ ID NO 736
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 736
caagcagaag acggcatacg agatctgagc cagtggccga tgtttcg                47

<210> SEQ ID NO 737
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 737
caagcagaag acggcatacg agatctggca tagtggccga tgtttcg                47

<210> SEQ ID NO 738
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 738
caagcagaag acggcatacg agatgaatct gagtggccga tgtttcg                47

<210> SEQ ID NO 739
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 739
caagcagaag acggcatacg agatcaagac tagtggccga tgtttcg                47

<210> SEQ ID NO 740
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 740
caagcagaag acggcatacg agatgagctg aagtggccga tgtttcg                47

<210> SEQ ID NO 741
<211> LENGTH: 47
<212> TYPE: DNA
<213> ORGANISM: Artificial Sequence
<220> FEATURE:
<223> OTHER INFORMATION: Synthetic Oligonucleotide -continued

<400> SEQUENCE: 741
caagcagaag acggcatacg agatgataga cagtggccga tgtttcg        47

<210> SEQ ID NO 742
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 742
caagcagaag acggcatacg agatgccaca tagtggccga tgtttcg        47

<210> SEQ ID NO 743
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 743
caagcagaag acggcatacg agatgcgagt aagtggccga tgtttcg        47

<210> SEQ ID NO 744
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 744
caagcagaag acggcatacg agatgctaac gagtggccga tgtttcg        47

<210> SEQ ID NO 745
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 745
caagcagaag acggcatacg agatgctcgg tagtggccga tgtttcg        47

<210> SEQ ID NO 746
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 746
caagcagaag acggcatacg agatggagaa cagtggccga tgtttcg        47

<210> SEQ ID NO 747
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 747
caagcagaag acggcatacg agatggtgcg aagtggccga tgtttcg        47

<210> SEQ ID NO 748

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 748
caagcagaag acggcatacg agatgtacgc aagtggccga tgtttcg                47

<210> SEQ ID NO 749
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 749
caagcagaag acggcatacg agatgtcgta gagtggccga tgtttcg                47

<210> SEQ ID NO 750
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 750
caagcagaag acggcatacg agatgtctgt cagtggccga tgtttcg                47

<210> SEQ ID NO 751
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 751
caagcagaag acggcatacg agatgtgttc tagtggccga tgtttcg                47

<210> SEQ ID NO 752
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 752
caagcagaag acggcatacg agattaggat gagtggccga tgtttcg                47

<210> SEQ ID NO 753
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 753
caagcagaag acggcatacg agattatcag cagtggccga tgtttcg                47

<210> SEQ ID NO 754
<211> LENGTH: 47
<212> TYPE: DNA
<213> ORGANISM: Artificial Sequence
<220> FEATURE:
<223> OTHER INFORMATION: Synthetic Oligonucleotide
```

-continued

<400> SEQUENCE: 754
caagcagaag acggcatacg agattccgtc tagtggccga tgtttcg         47

<210> SEQ ID NO 755
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 755
caagcagaag acggcatacg agattcttca cagtggccga tgtttcg         47

<210> SEQ ID NO 756
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 756
caagcagaag acggcatacg agattgaaga gagtggccga tgtttcg         47

<210> SEQ ID NO 757
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 757
caagcagaag acggcatacg agattggaac aagtggccga tgtttcg         47

<210> SEQ ID NO 758
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 758
caagcagaag acggcatacg agattggctt cagtggccga tgtttcg         47

<210> SEQ ID NO 759
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 759
caagcagaag acggcatacg agattggtgg tagtggccga tgtttcg         47

<210> SEQ ID NO 760
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 760
caagcagaag acggcatacg agatttcacg cagtggccga tgtttcg         47

<210> SEQ ID NO 761

<210> SEQ ID NO 761
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 761
caagcagaag acggcatacg agataactca ccgtggccga tgtttcg         47

<210> SEQ ID NO 762
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 762
caagcagaag acggcatacg agataagaga tcgtggccga tgtttcg         47

<210> SEQ ID NO 763
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 763
caagcagaag acggcatacg agataaggac acgtggccga tgtttcg         47

<210> SEQ ID NO 764
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 764
caagcagaag acggcatacg agataatccg tcgtggccga tgtttcg         47

<210> SEQ ID NO 765
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 765
caagcagaag acggcatacg agataatgtt gcgtggccga tgtttcg         47

<210> SEQ ID NO 766
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 766
caagcagaag acggcatacg agatacacga ccgtggccga tgtttcg         47

<210> SEQ ID NO 767
<211> LENGTH: 47
<212> TYPE: DNA
<213> ORGANISM: Artificial Sequence
<220> FEATURE:
<223> OTHER INFORMATION: Synthetic Oligonucleotide -continued

<400> SEQUENCE: 767
caagcagaag acggcatacg agatacagat tcgtggccga tgtttcg          47

<210> SEQ ID NO 768
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 768
caagcagaag acggcatacg agatagatgt acgtggccga tgtttcg          47

<210> SEQ ID NO 769
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 769
caagcagaag acggcatacg agatagcacc tcgtggccga tgtttcg          47

<210> SEQ ID NO 770
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 770
caagcagaag acggcatacg agatagccat gcgtggccga tgtttcg          47

<210> SEQ ID NO 771
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 771
caagcagaag acggcatacg agataggcta acgtggccga tgtttcg          47

<210> SEQ ID NO 772
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 772
caagcagaag acggcatacg agatatagcg acgtggccga tgtttcg          47

<210> SEQ ID NO 773
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 773
caagcagaag acggcatacg agatatcatt ccgtggccga tgtttcg          47

<210> SEQ ID NO 774

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 774
caagcagaag acggcatacg agatattggc tcgtggccga tgtttcg         47

<210> SEQ ID NO 775
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 775
caagcagaag acggcatacg agatcaagga gcgtggccga tgtttcg         47

<210> SEQ ID NO 776
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 776
caagcagaag acggcatacg agatcacctt acgtggccga tgtttcg         47

<210> SEQ ID NO 777
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 777
caagcagaag acggcatacg agatccatcc tcgtggccga tgtttcg         47

<210> SEQ ID NO 778
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 778
caagcagaag acggcatacg agatccgaca acgtggccga tgtttcg         47

<210> SEQ ID NO 779
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 779
caagcagaag acggcatacg agatcctaat ccgtggccga tgtttcg         47

<210> SEQ ID NO 780
<211> LENGTH: 47
<212> TYPE: DNA
<213> ORGANISM: Artificial Sequence
<220> FEATURE:
<223> OTHER INFORMATION: Synthetic Oligonucleotide
```

-continued

<400> SEQUENCE: 780
caagcagaag acggcatacg agatcctcta tcgtggccga tgtttcg          47

<210> SEQ ID NO 781
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 781
caagcagaag acggcatacg agatcgacac acgtggccga tgtttcg          47

<210> SEQ ID NO 782
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 782
caagcagaag acggcatacg agatcggatt gcgtggccga tgtttcg          47

<210> SEQ ID NO 783
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 783
caagcagaag acggcatacg agatctaagg tcgtggccga tgtttcg          47

<210> SEQ ID NO 784
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 784
caagcagaag acggcatacg agatgaacag gcgtggccga tgtttcg          47

<210> SEQ ID NO 785
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 785
caagcagaag acggcatacg agatgacagt gcgtggccga tgtttcg          47

<210> SEQ ID NO 786
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 786
caagcagaag acggcatacg agatgagtta gcgtggccga tgtttcg          47

<210> SEQ ID NO 787

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 787
caagcagaag acggcatacg agatgatgaa tcgtggccga tgtttcg                47

<210> SEQ ID NO 788
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 788
caagcagaag acggcatacg agatgccaag acgtggccga tgtttcg                47
```

METHODS AND COMPOSITIONS FOR ANALYZING NUCLEIC ACIDS

CROSS-REFERENCE TO RELATED APPLICATIONS

This application claims the benefit of U.S. Provisional Application No. 62/801,040, filed Feb. 4, 2019, U.S. Provisional Application No. 62/894,549, Aug. 30, 2019, and U.S. Provisional Application No. 62/951,880, filed Dec. 20, 2019. The entire contents of the above-identified applications are hereby fully incorporated herein by reference.

REFERENCE TO AN ELECTRONIC SEQUENCE LISTING

The contents of the electronic sequence listing ("BROD-3970US_replacement_ST25"; Size is 205 kilobytes and it was created on Apr. 9, 2020) is herein incorporated by reference in its entirety.

TECHNICAL FIELD

The subject matter disclosed herein is generally directed to analyzing nucleic acids in single cells.

BACKGROUND

Recent development of methods such as RNA-seq and ATAC-seq (Assay for Transposase-Accessible Chromatin using sequencing) have provided the ability to analyze different types of nucleic acids in cells. However, simultaneous analysis of different types of nucleic acids in single cells remain underdeveloped due to challenges such as making the processing cross compatible between the two approaches. Thus, there is a need for methods that allow for simultaneous analysis and processing of different types of nucleic acids within single cells.

Citation or identification of any document in this application is not an admission that such document is available as prior art to the present invention.

SUMMARY

The present disclosure provides methods and compositions for analyzing different types of nucleic acids in single cells. In one aspect, the present disclosure provides a method for single cell analysis of genomic DNA accessibility and RNA expression in a cell, the method comprising generating, within individual cells, fragmented cellular genomic DNA and cDNA copies of cellular RNA molecules; barcoding the fragmented genomic DNA and the cDNA within each cell such that the genomic DNA and the cDNA from the same cell receive the same unique cell barcode sequence; isolating the barcoded genomic DNA and the cDNA; and characterizing one or more features of the individual cells based, at least in part, on sequencing of the isolated barcoded genomic DNA and the cDNA.

In some embodiments, the method further comprises fragmenting the cellular genomic DNA and/or the cDNA using an insertional enzyme. In some embodiments, the fragmented cellular genomic DNA is generated by contacting chromatin in the individual cells with an insertional enzyme. In some embodiments, the insertional enzyme is a transposase. In some embodiments, the transposase is an engineered transposase with an activity higher than a wild type counterpart. In some embodiments, the insertional enzyme comprises two or more enzymatic moieties. In some embodiments, the insertional enzyme forms a complex with a phosphorylated oligonucleotide. In some embodiments, the method further comprises generating cDNA from the RNA in the cell using a primer comprising i) a unique molecular identifier (UMI), ii) an affinity tag, and/or iii) a poly(T) sequence. In some embodiments, the cDNA comprises an affinity tag. In some embodiments, the barcoded cDNA is isolated by capturing the affinity tag on a solid support. In some embodiments, before isolation, the genomic DNA forms a complex with one or more proteins, and the genomic DNA is isolated by capturing the one or more proteins on a solid support. In some embodiments, the method further comprises amplifying the genomic DNA, the cDNA, or a combination thereof. In some embodiments, the sequencing comprises sequencing a portion of the genomic DNA fragments, a portion of the cDNA molecules, and/or a portion of the barcode attached thereof. In some embodiments, the one or more features comprise an epigenetic feature of a genomic DNA region in the cell. In some embodiments, the epigenetic feature comprises a profile of chromatin accessibility along the genomic DNA region; a DNA binding protein occupancy for a binding site in the genomic DNA region; a nucleosome-free DNA in the genomic DNA region; a positioning of nucleosomes along the genomic DNA region; chromatin states; or a combination thereof. In some embodiments, the one or more features comprise an expression profile of the cellular RNA. In some embodiments, the genomic DNA is tagged. In some embodiments, the method further comprises fixing the individual cells before generating the genomic DNA and cDNA. In some embodiments, the method further comprises lysing the individual cells in the presence of an RNase inhibitor. In some embodiments, the RNase inhibitor is compatible with an insertional enzyme.

In another aspect, the present disclosure further provides a method of diagnosing a condition in a subject, comprising characterizing a feature of one or more cells in the subject using the method and compositions described herein; and providing a diagnosis or prognosis based on the feature.

In another aspect, the present disclosure provides a kit for analyzing single cell genomic accessibility and RNA expression comprising a transposase, reverse transcription reagents, buffers for performing transposition and reverse transcription in a single reaction within an individual discrete volume; barcoding reagents; and RNA capture oligos comprising a capture moiety.

In some embodiments, the kit further comprises cell fixation reagents and/or reverse cross-linking reagents. In some embodiments, the kit further comprises a transposase compatible RNase inhibitor. In some embodiments, the kit further comprises an isolation reagent comprising a binding binder that bind the capture moiety. In some embodiments, the capture moiety is a biotinylated nucleotide and the isolation reagent is a streptavidin coated solid support.

In another aspect, the invention also provides a method for single cell analysis of genomic DNA accessibility and mRNA expression, comprising contacting chromatin within individual cells with a transposase to generate fragmented cellular genomic DNA; reverse transcribing the mRNA to generate cDNA; isolating the individual cells in separate individual discrete volumes, each of the individual discrete volumes further comprising a primer pair and a volume-specific barcode that hybridizes to both fragmented cellular genomic DNA and cDNA; using combinatorial split-and-pool strategies, such as ligation, to add sequential barcodes to the cellular genomic DNA fragments; amplifying the cellular genomic DNA fragments using the primer pair to generate amplicons; and sequencing the amplicons.

In some embodiments, the transposase is a Tn5 transposase.

In some embodiments, the mRNA is reverse transcribed using an oligonucleotide comprising a poly(dT) sequence. In some embodiments, the oligonucleotide further comprises a unique molecular identifier (UMI) and a biotin tag. In some embodiments, the hybridization is repeated three or more times.

In some embodiments, the method further comprises crosslinking the cells prior to fragmenting them. In some embodiments, the method further comprises reversing the crosslinks prior to amplifying the genomic DNA fragments.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1C—provide a workflow overview of a method for detection of genomic accessibility and RNA expression within single cells, in accordance with an example embodiment.

FIGS. 9A-9F—SHARE-seq provides an accurate co-measure of genome-wide chromatin accessibility and gene expression. (FIG. 9A) Workflow for measuring scATAC and scRNA from the same cell using SHARE-seq. (FIGS. 9B, 9C) Unique ATAC fragments (FIG. 9B), or RNA UMIs (FIG. 9C), aligning to either the human or mouse genome; experiment is performed using a mix of human (GM12878) and mouse (NIH/3T3) cell lines. (FIG. 9D) Proportion of ATAC or RNA human reads relative to all reads mapping uniquely to the human or mouse genomes. (FIG. 9E) Number of ATAC reads in peaks or RNA UMIs for SHARE-seq (this study) or sciCAR-seq (Cao et al. Science 361:1380-1385 (2018)). (FIG. 9F) Aggregate single-cell accessibility and gene expression profiles in GM12878 cells (top), individual cell profiles (bottom) and single-cell average (right). Single-cells are sorted by the ATAC yield of the depicted NFKB1 locus.

FIGS. 10A-10H—SHARE-seq enables joint profiling of chromatin accessibility and transcription in adult mouse brain. (FIG. 10A) ATAC and RNA-seq t-SNE visualization of mouse adult brain nuclei; points are colored by clusters labels. Clusters are assigned to cell types on the basis of established marker genes and chromatin peaks. (FIG. 10B) The violin and box plot of library complexity of SHARE-seq and other single cell ATAC-seq approaches. (FIG. 10C) The violin and box plot of library complexity of SHARE-seq and other single cell/nuclei RNA-seq approaches. (FIG. 10D) Marker genes for each assigned cell type. (FIGS. 10E-10F) The RNA yield (UMIs, FIG. 10E) and ATAC yield (unique fragments, FIG. 10F) labelled on RNA tSNE. The NSC cluster is highlighted. (FIG. 10G) The pairwise similarity across RNA and ATAC clusters. TF motif scores are used for computing correlation of the ATAC-seq data. (FIG. 10H) Pairwise correlations across clusters, correlated using either the ATAC or RNA data.

FIGS. 11A-11F SHARE-seq provided an accurate co-measure of genome-wide chromatin accessibility and gene expression. (FIG. 11A) Exemplary workflow for measuring scATAC and scRNA from the same cell using SHARE-seq. (FIGS. 11B, 11C) Unique ATAC fragments (FIG. 11B), or RNA UMIs (FIG. 11C), aligning to either the human or mouse genome. The experiment was performed using a mix of human (GM12878) and mouse (NIH/3T3) cell lines. (FIG. 11D) The proportion of ATAC or RNA human reads relative to all reads mapping uniquely to the human or mouse genomes. (FIG. 11E) Number of ATAC reads in peaks or RNA UMIs for SHARE-seq (the study in Example 3), sci-CAR10, SNARE-seq11, or Paired-seq12. Boxplots denote the medians and the interquartile ranges (IQRs). The whiskers of each boxplot are the lowest datum still within 1.5×IQR of the lower quartile and the highest datum still within 1.5×IQR of the upper quartile. The median fragments are labeled for each assay. (FIG. 11F) Aggregated single-cell chromatin accessibility and gene expression profiles in GM12878 cells (top), individual cell profiles (bottom) and single-cell average (right). Single-cells were sorted by the ATAC-seq yield of the depicted NFKB1 locus.

FIGS. 12A-12J. SHARE-seq enabled joint profiling of chromatin accessibility and transcription in tissues. (FIG. 12A) A schematic of tissues profiled with SHARE-seq, highlighting the cellular diversity within mouse skin. (FIGS. 12B-12C) Comparison of library size estimates of SHARE-seq and other single-cell or nuclei based approaches for scATAC-seq (FIG. 12B) and scRNA-seq (FIG. 12C) approaches. Boxplots denote the medians and the interquartile ranges (IQRs). The whiskers of each boxplot are the lowest datum still within 1.5×IQR of the lower quartile and the highest datum still within 1.5×IQR of the upper quartile. (FIG. 12D) SHARE-seq UMAP visualization of single-cells derived from mouse skin showing UMAP coordinates defined by RNA. Points are colored by assigned cell types. Clusters are defined by RNA clustering. Cell types are assigned on the basis of marker genes, TF motifs, and chromatin accessibility peaks. Computational pairing8 of scATAC-seq to scRNA-seq (right), colored by predicted cell type. The IRS cluster is highlighted. (FIG. 12E) SHARE-seq UMAP visualization of single-cells derived from mouse skin showing UMAP coordinates defined by ATAC. (FIG. 12F) Heatmap showing the proportion of cells in the RNA cluster that overlaps with ATAC clusters. (FIG. 12G) Marker gene expression and TF motif scores for each cluster. (FIG. 12H) Aggregated ATAC-seq tracks denoting marker chromatin accessibility peaks for each cluster. (FIG. 12I) The cluster-cluster correlation of scATAC-seq (top right) and scRNA-seq (bottom left). (FIG. 12J) Cells colored by the activity of cell cycle genes (left panel). An RNA cluster marked by high expression of cell cycle genes is highlighted in RNA UMAP (top right panel) and ATAC UMAP space (bottom right panel).

FIGS. 13A-13H. Cis-regulation determined Domains of Regulatory Chromatin (DORCs) that largely overlap with known super-enhancers. (FIG. 13A) Schematic depicting distal regulatory elements modulating the expression of genes. (FIG. 13B) Number of peak-gene associations after down-sampling the number of cells or reads within the GM12878 SHARE-seq data set. Reads are down-sampled to match the number of reads recovered to match the sciCAR-seq dataset. (FIG. 13C) Loops denote the p-value of chromatin accessibility of each peak and Dlx3 RNA expression. Loop height represents the significance of the correlation. H3K4me1 and H3K27ac ChIP-seq tracks and super-enhancer annotation generated from isolated TAC population[14]. (FIG. 13D, FIG. 13E) The number of significant peak-gene associations for all genes (FIG. 13D) and previously defined[14] super-enhancer genes (FIG. 13E). (FIG. 13F) The number of significantly correlated peaks (p<0.05) for each gene. Known super-enhancer regulated genes are highlighted. (FIG. 13G) Representative DORCs for each defined cluster; values are normalized by the min and max activity. (FIG. 13H) The peak counts of all Dlx3 correlated peaks (left) and Dlx3 gene expression (right) colored in UMAP. The arrows point to regions with differential signals.

FIGS. 14A-14N. Lineage dynamics of chromatin and expression defines lineage priming and lineage memory. (FIG. 14A) Pseudotime for three cell fate decisions shown on ATAC UMAP coordinates. (FIG. 14B) Difference (residuals) for Wnt3 between chromatin accessibility and gene expression for the regenerative portion of the hair follicle. (FIG. 14C) Histogram of the average difference (residuals) for each gene between chromatin accessibility and gene expression. (FIG. 14D) Dynamics of gene expression (intron and exon) and individual chromatin accessibility peaks for the Cuticle/cortex lineage. (FIG. 14E) Hierarchical clustering of chromatin accessibility, expression of DORC regulated genes and the difference between chromatin accessibility and gene expression (residuals) for the cuticle/cortex lineage. Cells are ordered by pseudotime. (FIG. 14F) Lineage dynamics for individual DORC regulated genes highlighting lineage-priming in Wnt3 (left), Tubb6 (middle), and the lineage-priming module (cluster in panel e). (FIG. 14G) TF motif enrichment in lineage-priming DORCs plotted against Spearman correlation of DORC score and gene expression of TFs. (FIG. 14H) Lef1 and Hoxc13 TFs drive lineage-priming in hair shaft lineage. (FIG. 14I) Chromatin potential visualized on a regular grid. Arrows denote the extrapolated gene expression state of the cell. (FIG. 14J) RNA velocity visualized on RNA UMAP coordinates. (FIG. 14K) The difference between the neighborhood predicted by chromatin potential and RNA velocity. (FIG. 14L) Differential chromatin accessibility of Notch1 DORC in lineage priming region. (FIG. 14M) Distribution of Notch1 (+/−) lineage primed cells in RNA UMAP. (FIG. 14N) Aggregated chromatin accessibility profiles of lineage prime cells (Notch1+/−), progenitor cells (TACs), and differentiated cells (cuticle/cortex, medulla).

FIGS. 15A-15G. The principle of SHARE-seq. (FIG. 15A) The structure of scATAC-seq and scRNA-seq sequencing library. (FIG. 15B) The expected number of barcode combinations exponentially scales with the rounds of barcoding. (FIGS. 15C-15D) Estimation of ambient DNA (c), RNA (d) level in species mixing experiments. (FIG. 15E) Comparison of ambient RNA level to the previous approaches 16. (FIG. 15F) Expected barcode collision happens with a large number of cells (>105). (FIG. 15G) Aggregate single-cell accessibility and gene expression profiles in GM12878 cells.

FIGS. 16A-16J. Data quality control on cell line datasets. (FIG. 16A) Scatter plot of the portion of reads in peaks (FRIP) of GM12878 ATAC-seq data. (FIG. 16B) The enrichment of ATAC-seq reads around TSSs. (FIG. 16C) The insert size distribution of ATAC-seq fragments. (FIGS. 16D-16E) The SHARE-seq reproducibility between biological replicates on ATAC-seq (FIG. 16D) and RNA-seq (FIG. 16E). (FIG. 16F) Aggregated ATAC-seq portion of SHARE-seq profile compares to Cusanovich59, Pliner60, Preiss161, SureCel121, sci-ATAC-seq (LaFave et al. under review), Flugidm C1 dataset36, and DNase-seq (ENCODE). (FIGS. 16G-16H) The estimated library size (the unique molecules could be recovered by sequencing to saturation, estimated based on the duplication rate and recovered unique molecule) in SHARE-ATAC-seq (FIG. 16G) and SHARE-RNA-seq (FIG. 16H). (FIG. 16I) The aggregated single-cell SHARE-seq accessibility profiles across different cell lines. (FIG. 16J) The RNA reads distribution of SHARE-seq in the genome.

FIGS. 17A-17I. Quality control for scATAC libraries on multiple tissues generated using SHARE-seq protocol. (FIG. 17A) The enrichment of ATAC-seq reads around TSSs. (FIG. 17B) The insert size distribution of ATAC-seq fragments. (FIG. 17C) t-SNE clustering of SHARE-ATAC-seq on adult mouse lung. (FIG. 17D) Comparison of SHARE-RNA-seq to previous deposited 3' single cell/nuclei adult mouse brain datasets (Methods) in terms of the number of genes detected. (FIGS. 17E-17H) t-SNE visualizations of other 3' single cell/nuclei adult mouse brain dataset to compare to SHARE-RNA-seq. The numbers denote the clusters identified with Louvain community detection algorithm. (FIG. 17I) ATAC UMAP and RNA UMAP colored by the cell type assigned by the joint clustering of ATAC-seq and RNA-seq data in the mouse brain.

FIGS. 18A-18J. SHARE-seq enables joint profiling of chromatin accessibility and transcription in adult mouse skin. (FIG. 18A) Schematic of a computational pipeline to process SHARE-seq data on adult mouse skin. (FIG. 18B) The hair follicle cell types shift during hair follicle cycles. (FIG. 18C) The pairwise similarity across RNA and ATAC clusters. Peak counts are used for computing correlation of the ATAC-seq data. (FIG. 18D) The cell-cell variability of TF motif scores in the GM12878 cell line. (FIGS. 18E-18G) The TF motif score to gene correlation in GM12878 cells (FIG. 18E), all skin cells (FIG. 18F), and hair follicle cells (FIG. 18G). The dots color denotes the significance of the correlation. (FIGS. 18H-18J) ATAC UMAP visualization with Seurat LSI (FIG. 18H), chromVAR Kmer (FIG. 18I), and snapATAC (FIG. 18J) approaches (Methods). Points are colored by clusters labels.

FIGS. 19A-19F. The computational paring of ATAC-RNA mis-assigns cell types. (FIG. 19A) ATAC UMAP colored by computationally inferred cell type in mouse brain. The computational paring was performed by transferring the assigned cluster label to the ATAC cluster using Seurat8. (FIG. 19B) Heatmap showing the proportion of cells in the joint cluster that overlaps in ATAC clusters in mouse brain. (FIG. 19C) Marker genes for each assigned cell type in the mouse brain. (FIG. 19D) Histogram showing the percentage of cells that are correctly computationally assigned for each cell type in the mouse brain. (FIG. 19E) UMAP visualization of computationally inferred cell type in mouse skin. The cell type labels are transferred from RNA-seq to ATAC-seq using Seurat8. (FIG. 19F) Histogram showing the percentage of cells that are correctly computationally assigned for each cell type in mouse skin.

FIGS. 20A-20F. SHARE-seq reveals cis-regulation within a cell line (GM12878). (FIG. 20A) Loops denote the correlation of peak accessibility and RNA expression at the TNFAIP3 locus; loop height represents the significance of the correlation. Super-enhancer annotation generated from GM12878 cell line62. (FIG. 20B) The number of significant peak-gene associations for each gene. (FIGS. 20C-20D) Histogram of the number of significant peak-gene associations per gene for all the genes (FIG. 20C) super-enhancer related genes (FIG. 20D). (FIG. 20E) The number of genes associated with each significant peak. (FIG. 20F) The distance of each significant peak-gene association (p<0.05) to the TSS of each gene.

FIGS. 21A-21K. Cis-regulation regions overlap with known super-enhancers, and are gene- and cell stage-specific. (FIG. 21A) Distance of each significant peak-gene association (p<0.05) to the TSS of each gene. (FIG. 21B) A cumulative distribution function plot of peak-gene associations across all peaks and promoter peaks. (FIGS. 21-21D) The number of genes associated with each significant peak for all genes (FIG. 21C) and super-enhancer related genes (FIG. 21D). (FIG. 21E) The portion of peaks associated with genes varies with chromatin accessibility level. (FIG. 21F) Loops denote the correlation of peak accessibility and RNA expression around the Cxcl14 locus, loop height represents the significance of the correlation. H3K4me1 and H3K27ac ChIP-seq tracks and super-enhancer annotation generated from isolated TAC population14. (FIG. 21G) The scatter plot showing the length of super-enhancer is not correlated with the number of associated peaks. (FIG. 21H) A cumulative distribution function plot of peak-gene associations for each gene. (FIG. 21I) The overlapping between DORCs identified in TAC/IRS/Hair shaft and in all cells. (FIG. 21J) DORC activity for each defined cluster, values are normalized by the min and max activity. (FIG. 21K) Scatter plot of the Dlx3 DORC score and Dlx3 gene expression.

(FIGS. 22A-22E) RNA UMAP visualization of the percentage of intronic RNA-seq reads, (FIG. 22A), total intronic RNA-seq reads, (FIG. 22B), the percentage of promoter ATAC-seq reads, (FIG. 22C), the yield of unique transcripts, (FIG. 22D), and total exonic RNA-seq reads (FIG. 22E). (FIG. 22F) Immuno-staining of PolI, PolII S2, and PolII S5 in the late anagen stage.

(FIG. 23A) The scatter plot of the Wnt3 DORC score and Wnt3 gene expression. (FIG. 23B) The distribution of Spearman correlation between DORC and DORC-regulated genes. A background correlation was calculated by permuting peaks with matched GC-content and accessibility. (FIG. 23C) Normalized residuals between chromatin accessibility and gene expression for hair-shaft lineages. (FIG. 23D) ATAC UMAP visualization of gene expression (top) and motif score (bottom) inferred from ATAC-seq. (FIG. 23E) The raw chromatin potential. The arrow denotes the distance between a cell in chromatin accessibility space to its most similar cell in RNA space. (FIG. 23F) Raw chromatin potential was smoothed by averaging 15 k-nearest neighbors for each given cell. (FIG. 23G) The arrows denote the potential "future" RNA state (observed in another cell) which is best predicted by the current RNA state. The arrows show the most correlated neighbor in RNA space for a given cell in RNA space. (FIG. 23H) The arrows denote the potential "future" chromatin state (observed in another cell) which is best predicted by the current chromatin state. The arrows show the most correlated neighbor in chromatin space for a given cell in chromatin space. (FIG. 23I) Comparison of the arrow lengths between chromatin potential (FIG. 23I), RNA-RNA prediction, (FIG. 23J) and chromatin-chromatin prediction (FIG. 23K). (FIG. 23J) The Pearson correlations between chromatin state of a cell and the potential "future" RNA state of the given cell, predicted by either chromatin potential (left) or RNA velocity (right). (FIG. 23K) A scatter plot shows the differences in arrow length between chromatin potential or RNA velocity. The dot color denotes pseudotime. (FIG. 23L) Volcano plot of differentially enriched DORCs between Notch1+ and Notch1– lineage-prime cells. (FIG. 23M) Volcano plot of differentially enriched DORC-regulated gene between Notch1+ and Notch1– lineage-priming cells.

Figure 2:
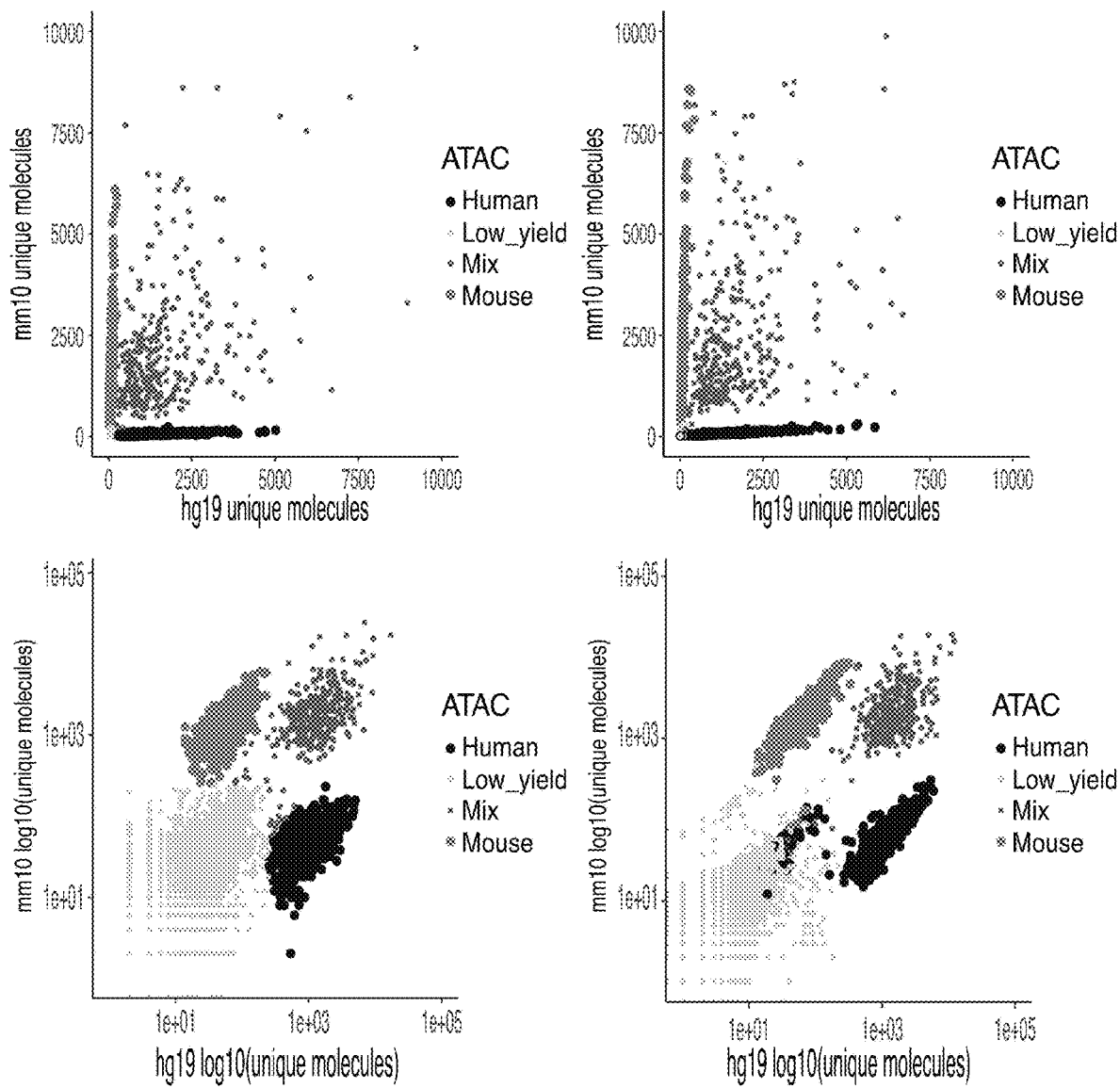
FIG. 2—demonstrates the ability to detect genomic accessibility and RNA expression in accordance with an example embodiment. Mouse and human cells were mixed at equal portions and profiled using the methods disclosed herein. Individual cells were resolved and the number of UMIs detected are plotted. A clean separation of cells with human and mouse only reads were obtained with only a small portion of barcodes representing two cells.
Figure 3:
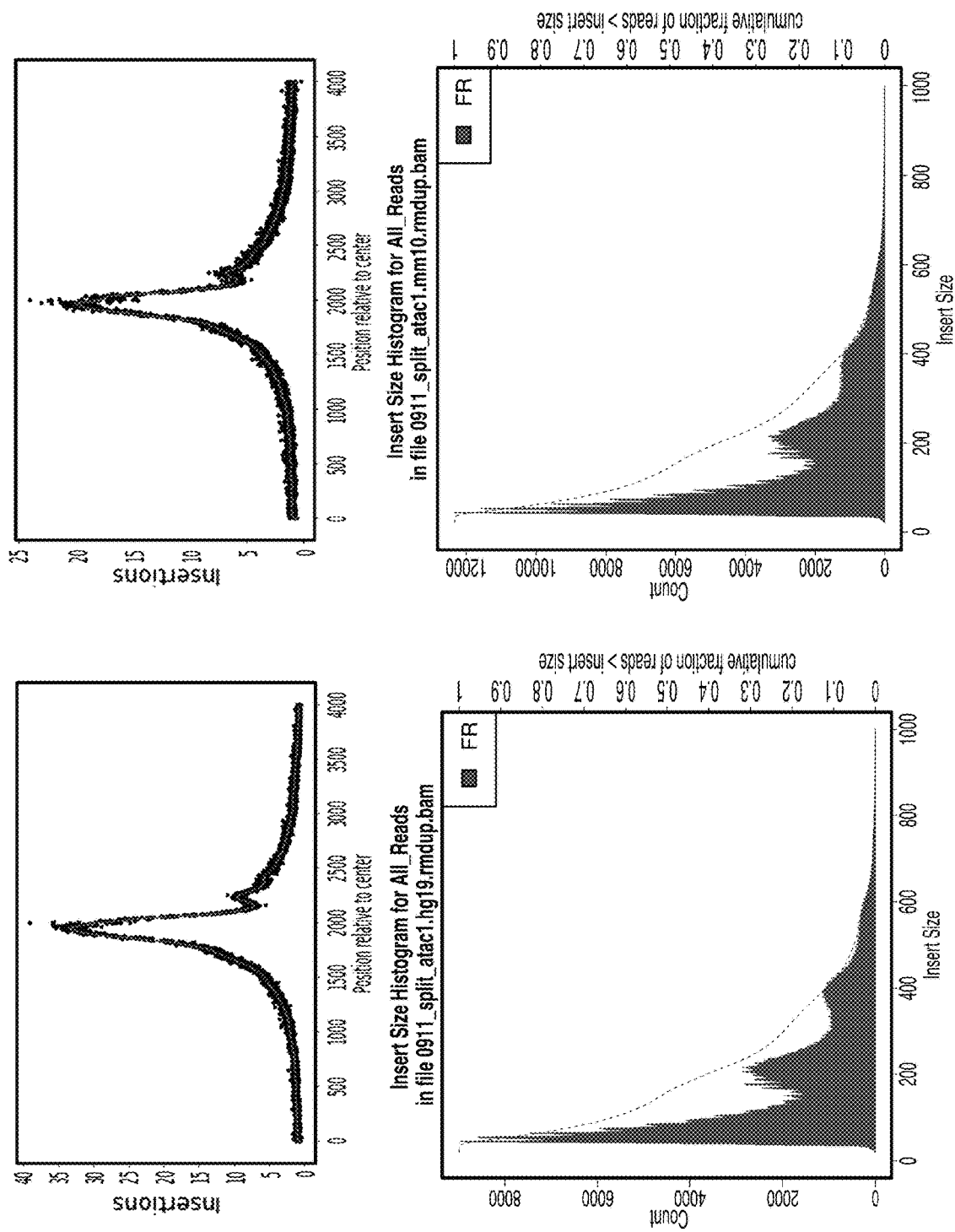
FIG. 3—provides QC metrics supporting the quality of ATAC-seq data generated in accordance with certain example embodiments.
Figure 4:
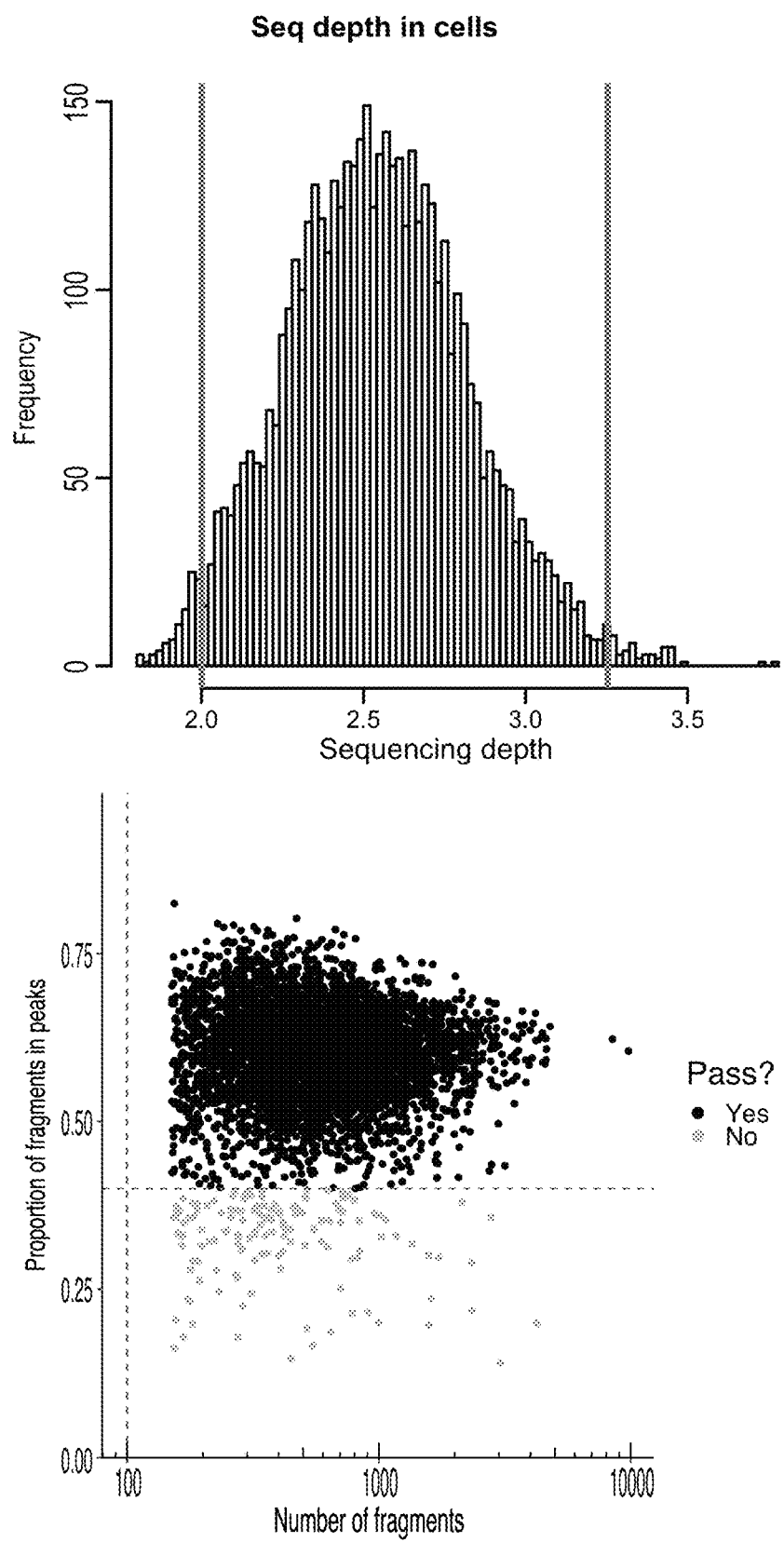
FIG. 4—provides additional QC metrics supporting the yield and quality of the ATAC-seq data generated in accordance with certain example embodiments.
Figure 5:
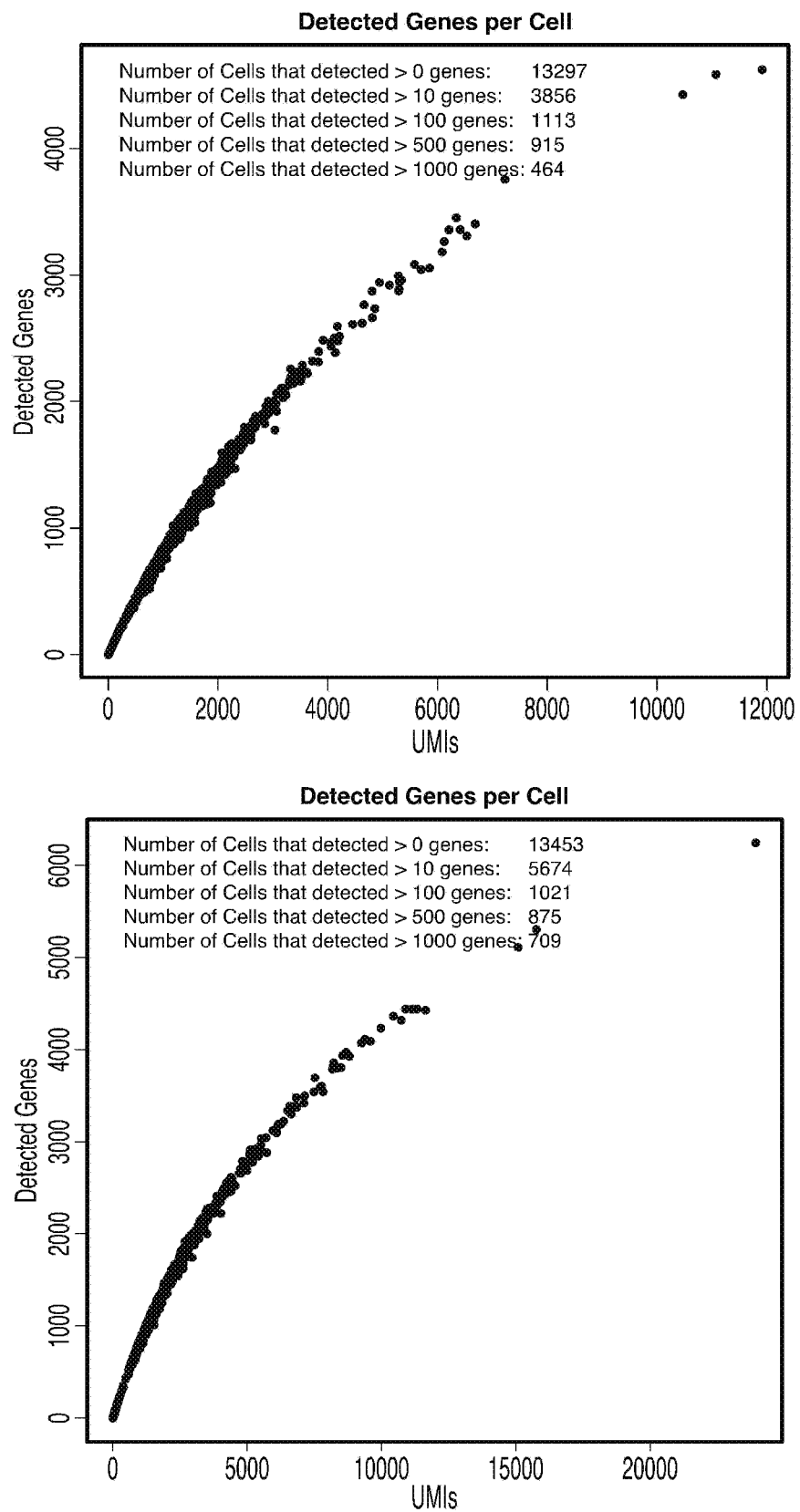
FIG. 5—provides QC metrics supporting the quality of RNA-seq data generated in accordance with certain example embodiments.
Figure 6:
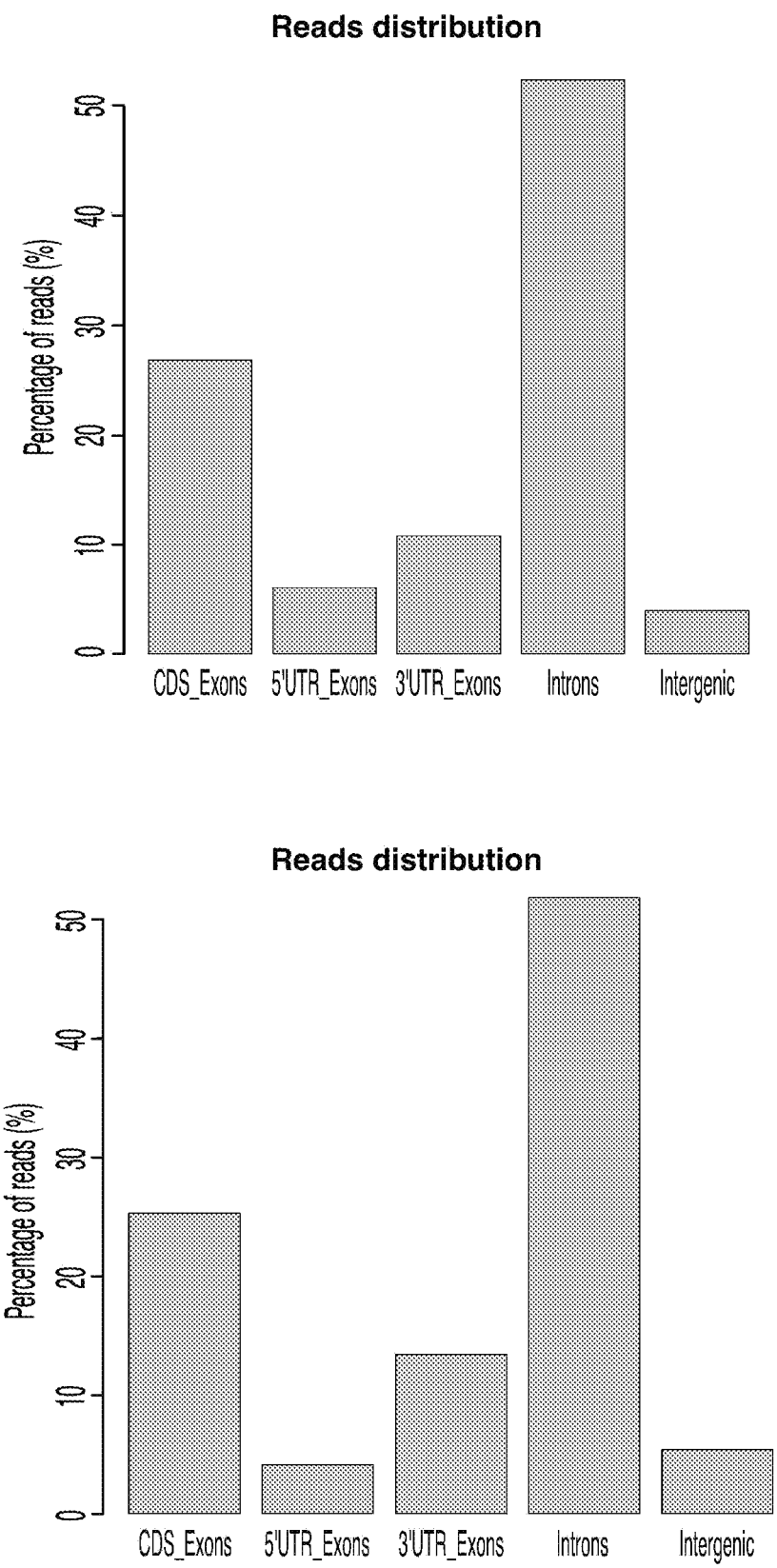
FIG. 6—provides additional QC metrics supporting the quality of RNA-seq data generated in accordance with certain example embodiments.
Figure 7:
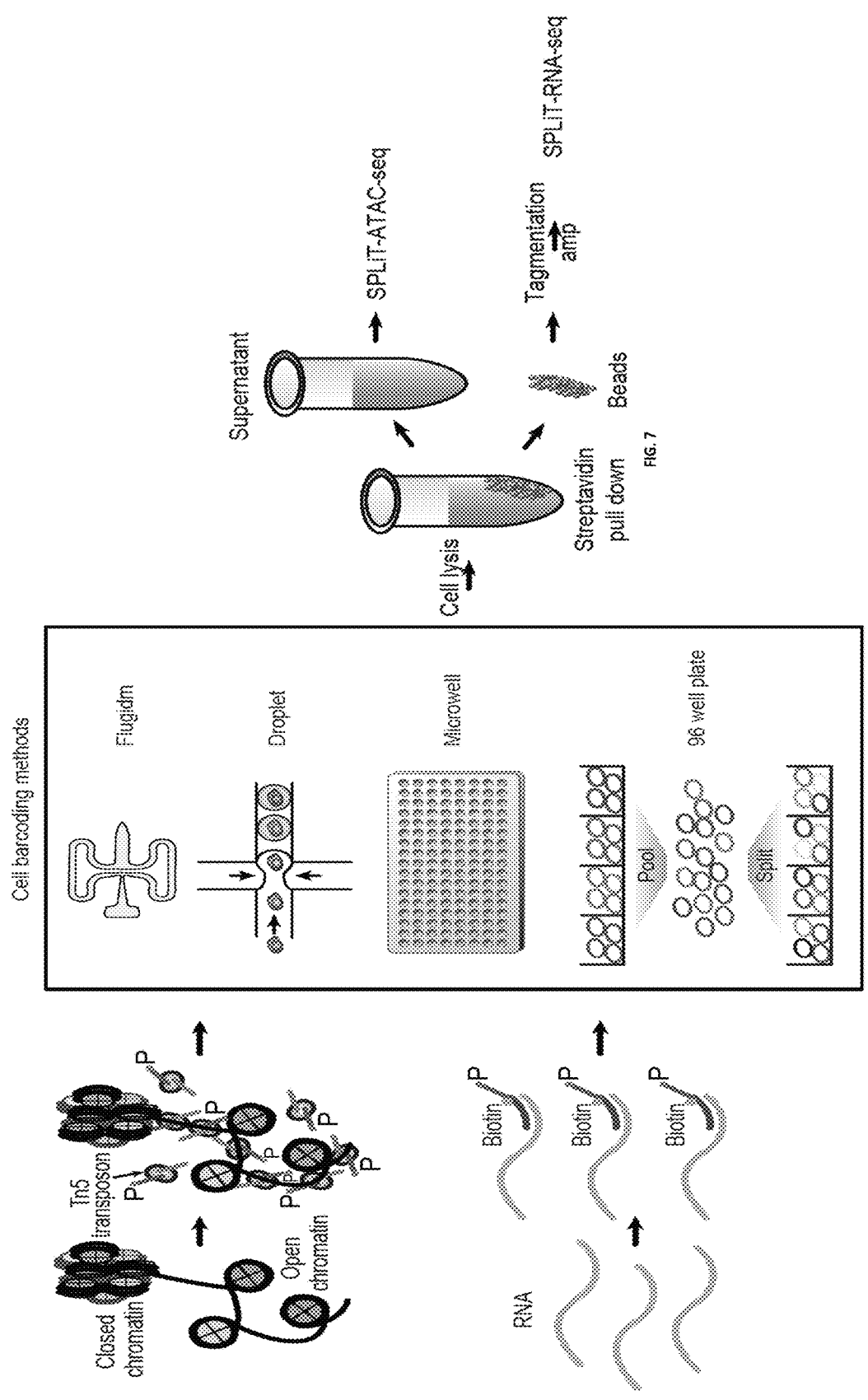
FIG. 7—shows a graphic abstract of exemplary approaches for analyzing nucleic acids, denoting that the approach described herein is compatible with various methods for cell barcoding.
Figure 8:
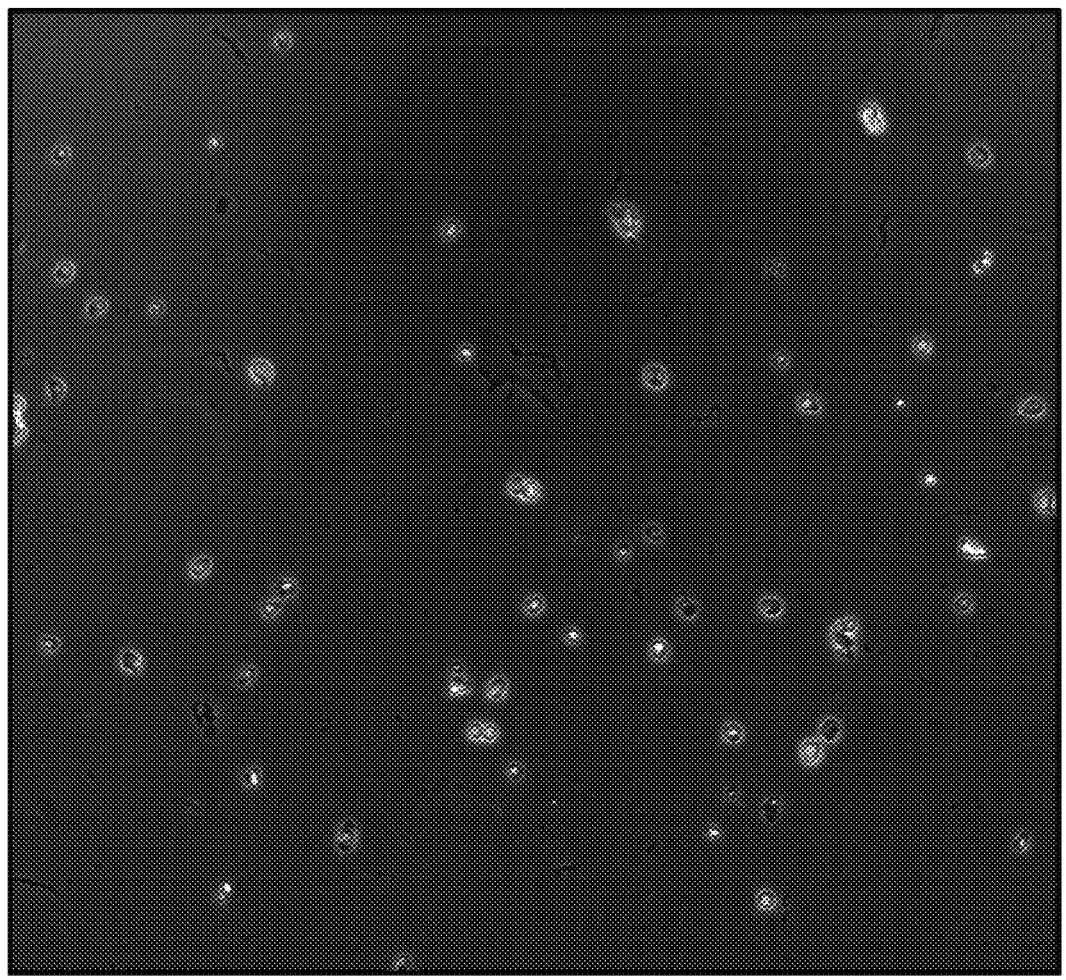
FIG. 8—The microscopic image of nuclei from Gm12878 and 3T3 cell lines after transposition, reverse transcription and ligation.
Figure 22A:
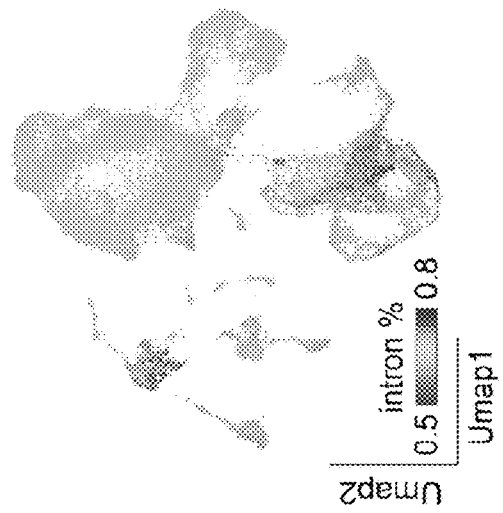
FIGS. 22A-22F. TACs show a low percentage of RNA intronic reads.
Figure 22B:
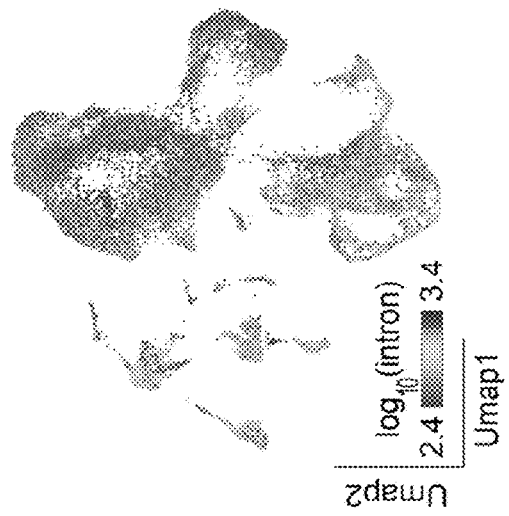
Figure 22C:
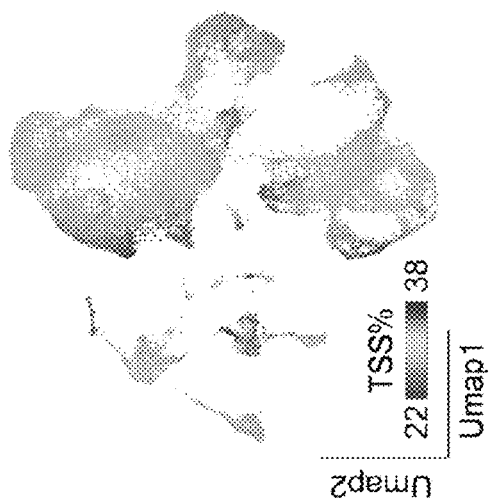
Figure 22D:
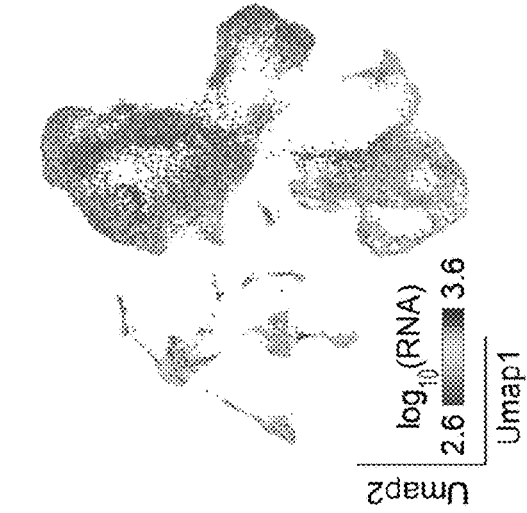
Figure 22E:
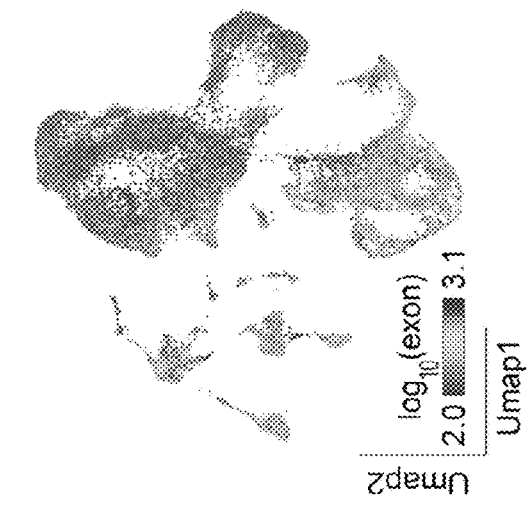
Figure 22F:
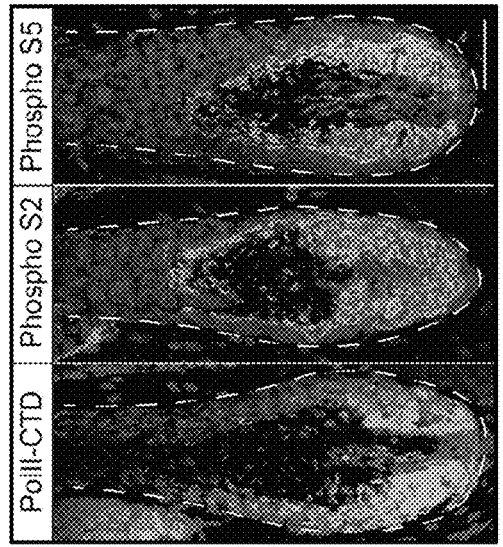

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides methods and compositions for processing and analyzing different types of nucleic acid molecules (e.g., genomic DNA, RNA, and/or cDNA) in a single cell. The strategies herein allow for high throughput single cell analysis of different types of nucleic acids simultaneously.

Cell differentiation and function are regulated at multiple layers and their simultaneous molecule profiling can help infer mechanistic relationships and understand their distinct contributions to cellular phenotype. In particular, chromatin organization has been postulated to prime changes in gene expression, especially during differentiation, but tracing this synchronous process has remained challenging. The embodiments disclosed herein provide a highly scalable, sensitive, and cost-effective approach for measurement of chromatin accessibility and gene expression from the same single cell. The combined scalability and depth provides an extensive platform to study regulatory circuitry and cellular dynamics across diverse cells within tissues.

In general, the methods herein include generating fragmented genomic DNA and cDNA copies of RNA in the nuclei of individual cells, barcoding the fragmented genomic DNA and the cDNA with one or more barcodes such that nucleic acids from or derived from the same cell receive the same unique barcode sequence, separating the barcoded cDNA and the barcoded genomic DNA, and characterizing one or more features of the individual cells based, at least in part, on sequencing of the barcoded cDNA and barcoded genomic DNA.

In some embodiments, the cells are fixed and lysed such that the nuclei have access to reagents (e.g., transposase, reverse transcriptase, ligase, etc.) and remain intact. The genomic DNA may remain part of chromatin when being fragmented. The fragmentation may be performed using a transposase. The transposase may also attach the fragmented genomic DNA with phosphorylated oligonucleotides, which may be ligated to one or more barcodes. In some cases, RNase inhibitor(s) is used when the cells are lysed. The RNase inhibitor(s) may be transposase compatible, e.g., the RNase inhibitor(s) does not reduce or inhibit the activity of a transposase.

Methods

The present disclosure includes methods for analyzing nucleic acids. The methods may allow processing and analyzing different types of nucleic acids (e.g., DNA and RNA) at the same time. In some cases, the methods may be used for single cell analysis, e.g., for analyzing genomic DNA and/or chromatin accessibility and RNA expression, and their correlations.

In some embodiments, the methods herein may include generating a library of genomic DNA and a library of RNA or cDNA derived from the RNA. The libraries may be used for sequencing. Nucleic acids in the libraries may be barcoded, e.g., by one or more barcodes. In some cases, the nucleic acids from or derived from the same cell may comprise the same unique barcode sequences. In such cases, the nucleic acids may be pooled together and sequenced. Sequence reads of nucleic acids from or derived from the same cell may be identified by the unique barcode sequences.

In one example embodiment, a method for single cell analysis of genomic DNA accessibility and RNA expression may comprise generating, within individual cell, fragmented genomic DNA and cDNA copies of cellular RNA molecules. The fragmented genomic DNA and the cDNA within each cell may be barcoded such that the genomic DNA and the cDNA from the same cell receive the same unique barcode cell sequence. The barcoded genomic DNA and the cDNA may then be isolated. Features of the individual cells may then be characterized, based at least in part, on sequencing of the isolated barcoded genomic DNA and the cDNA. The following paragraphs provide extended details on the steps outlined in this paragraph and possible variations and modifications thereof.

Cell Fixation

The method may be used for analyzing nucleic acids in cells. In some embodiments, the cells may be fixed. Fixation may be carried out to preserve the intactness of the cells, organelles, and/or nuclei in the cells. In some cases, once fixed, the cells, organelles, and/or nuclei in the cells remain intact during reactions and handling. In some examples, once fixed, the nuclei of the cells remain intact during reactions such as reverse transcription, ligation, sample splitting/pooling, etc. The methods herein may be used on any types of cells types, e.g., cell lines (GM12878, 3T3, TH1, TH17), mouse brain, human postmodern brain, PBMCs, bone marrow, mouse lung etc.

Fixation of cells may involve the use of cross-linking agents, such as formaldehyde, paraformaldehyde, alcohol (e.g., methanol), and may involve embedding cells or tissue in a paraffin wax or polyacrylamide support matrix.

In some cases, the cells are fixed using formaldehyde. The concentration of formaldehyde used for fixing the cells may be from 0.01% to 2%, e.g., from 0.05% to 0.15%, from 0.07% to 0.13%, from 0.08% to 0.12%, from 0.09% to 0.11%, from 0.05% to 0.15%, from 0.1% to 0.2%, from 0.15% to 0.25%, from 0.2% to 0.3%, from 0.25% to 0.35%, from 0.3% to 0.4%, from 0.35% to 0.45%, from 0.4% to 0.5%, from 0.45% to 0.55%, from 0.5% to 0.6%, from 0.5% to 0.7%, from 0.6% to 0.8%, from 0.7% to 0.9%, or from 0.8% to 1.0%. For example, the concentration of formaldehyde may be about 0.05%, about 0.06%, about 0.07%, about 0.08%, about 0.09%, about 0.1%, about 0.11%, about 0.12%, about 0.13%, about 0.14%, or about 0.15%. In some examples, the concentration of formaldehyde may be about 0.1%.

For fixation, the cells may be incubated with a cross-linking agent (e.g., formaldehyde) for from 0.5 to 20, from 1 to 10, from 2 to 8, from 1 to 3, from 2 to 4, from 3 to 5, from 4 to 6, from 5 to 7, from 6 to 8, from 7 to 9, from 8 to 10 minutes. In some cases, the cells may be incubated with formaldehyde from 4 to 6 minutes. For example, the cells may be incubated with formaldehyde for about 5 minutes.

Cell fixation may be performed prior to generating fragmented cellular genomic DNA and cDNA copies of cellular RNA molecules.

Cell Permeabilization

In some cases, the cells, organelle, and/or nuclei may be permeabilized to allow access for nucleic acid processing reagents. The permeabilization may be performed in a way to minimally perturb the cells, organelles, and/or nuclei. In some instances, the cells may be permeabilized using a permeabilization agent. Examples of permeabilization agents include NP40, digitonin, tween, triton, SDS, streptolysin, and cationic lipids. In other instances, the cells, organelles, and/or nuclei may be permeabilized using hypotonic shock and/or ultrasonication. In other cases, the nucleic acid processing reagents e.g., enzymes such as insertional enzyme, may be highly charged, which may allow them to permeabilize through the membranes of the cells, organelles, or nuclei. In certain examples, the methods include permeabilizing nuclei.

Cell permeabilization may be completed after cell fixation and prior to generating fragmented cellular genomic DNA and cDNA copies of cellular RNA copies.

Cell Lysis

The methods may include lysing the cells. After lysis, molecules, organelles and/or nuclei may be released from the cells for further analysis. In some embodiments, cells may be lysed under conditions that preserve the molecules, organelles, and/or nuclei in other lysis may be performed. In some embodiments, the cell lysis is performed to release nuclei from cells. In certain embodiments, the cell lysis is performed to release molecules, e.g., RNA or DNA from cells, organelles, and/or nuclei. In certain embodiments, the cells lysis is performed to separate RNA molecules from DNA molecules.

Cells may be lysed using a lysis agent. Examples of lysis agents include a detergent, a salt, and a combination thereof. Examples of salts include NaCl, KCl, ammonium sulfate [(NH4)2SO4], and others. Examples of detergents include Triton X-100, sodium dodecyl sulfate (SDS), CHAPS (3-[(3-cholamidopropyl)dimethylammonio]-1-propane-sulfonate), ethyl trimethyl ammonium bromide, nonyl phenoxypolyethoxylethanol (NP-40), digitonin and any combination thereof. In some cases, the detergent may be SDS.

Concentrations of detergents may depend on the particular application, and may be specific to the reaction in some cases. For example, the concentration of detergent (e.g., SDS) used herein may be from 0.005% to 1%, from 0.01% to 0.8%, from 0.01% to 0.6%, from 0.01% to 0.4%, from 0.01% to 0.2%, from 0.01% to 0.1%, from 0.00%5 to 0.05%, from 0.01% to 0.03%, from 0.015% to 0.025%, from 0.018% to 0.022%, from 0.015% to 0.017%, from 0.016% to 0.018%, from 0.017% to 0.019%, from 0.018% to 0.02%, from 0.019% to 0.021%, from 0.02% to 0.022%, or from 0.021% to 0.023%. In some cases, the concentration of the detergent may be about 0.01%, about 0.015%, about 0.02%, about 0.02%5, or about 0.0%3. For example, the concentration of the detergent may be about 0.02%.

For lysis, the cells may be incubated with the detergent for from 0.5 to 20, e.g., from 0.5 hour to 2 hours, from 1 hour to 3 hours, from 2 hours to 4 hours, from 3 hours to 5 hours, from 4 hours to 6 hours, from 5 hours to 7 hours, from 6 hours to 8 hours, from 7 hours to 9 hours, from 8 hours to 10 hours, from 9 hours to 11 hours, from 10 hours to 12 hours, from 11 hours to 13 hours, from 12 hours to 14 hours, from 13 hours to 15 hours, from 14 hours to 16 hours, from 15 hours to 17 hours, or from 16 hours to 18 hours. In some cases, the cells may be incubated with the detergent for about 1, about 2, about 3, about 4, about 5, about 6, about 7, about 8, about 9, about 10, about 11, about 12, about 13, about 14, about 15, about 16, about 17, or about 18 hours.

For lysis, the cells may be incubated with the detergent at a temperature ranging from 50° C. to 80° C., from 50° C. to 70° C., from 50° C. to 60° C., from 52° C. to 58° C., or from 54° C. to 56° C. In some examples, the temperature may be about 50° C., about 51° C., about 52° C., about 53° C., about 54° C., about 55° C., about 56° C., about 57° C., about 58° C., about 59° C., or about 60° C. For example, the temperature may be from 54° C. to 56° C. In one example, the temperature may be about 55° C.

In some embodiments, the cells are lysed in the presence of one or more inhibitors, which preserve molecules from the cells from degradation by enzymes. Such inhibitors may be protease inhibitors and nuclease inhibitors, e.g., RNase inhibitors and DNase inhibitors.

In certain cases, the cells are lysed in the presence of one or more RNase inhibitors. The RNase inhibitors may be compatible with enzymes used for further analysis. For example, the RNase inhibitors do not alter (e.g., reduce) the activity of other enzymes. In some cases, the RNase may be compatible with insertional enzymes such as transposases (e.g., Tn5).

In some examples, the RNase inhibitors may be RNAse inhibitor (Cat No. Y9240L, Enzymatics) or SUPERase• In™ RNase Inhibitor (Cat No. AM2694, Invitrogen). Other RNase inhibitors, such as RNaseOUT (Thermo Fisher) and Recombinant RNase Inhibitor (Takara) may also be used.

Cell lysis may also be performed in the presence of one or more protease inhibitors. Examples of protease inhibitors include Protease inhibitor Cocktail (P8340, Sigma), complete ULTRA and PhosSTOP (Roche Applied Science), Protease Inhibitor Set (EMD Chemicals); and Phosphatase Inhibitor Cocktail Set I-IV (EMD Chemicals).

Generating Fragmented DNA

In some embodiments, the methods include generating fragmented DNA. The DNA may include genomic DNA, DNA in organelles (e.g., mitochondrial DNA or chloroplast DNA), DNA derived from templates such as RNA, cell-free DNA, and any combination thereof. In some examples, the DNA is genomic DNA. In certain embodiments, the fragmented DNA is tagged, e.g., by attaching one or more barcodes.

DNA Tagmentation

In some embodiments, the fragmented DNA is generated by DNA tagmentation. In such cases, the DNA may be fragmented and tagged with one or more oligonucleotides. In some examples, the fragmentation and tagging may be performed in the same reaction or by the same enzyme.

Insertional Enzyme

Tagmentation may include contacting DNA with an insertional enzyme. The insertional enzyme may be any enzyme capable of inserting a nucleic acid sequence into a polynucleotide. In some examples, the DNA may be fragmented into a plurality of fragments during the insertion. In some cases, the insertional enzyme may insert the nucleic acid sequence into the polynucleotide in a substantially sequence-independent manner. The insertional enzyme may be prokaryotic or eukaryotic. Examples of insertional enzymes include transposases, HERMES, and HIV integrase.

In some cases, the insertional enzyme may be a transposase. The transposase may be an enzyme that binds to the end of a transposon and catalyzes its movement to another part of the genome by a cut and paste mechanism. Examples of transposases include a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnlO, Tyl, any prokaryotic transposase, or any transposase related to and/or derived from those listed above. In certain cases, the transposase may be Tn5. For example, the Tn5 may be the one described in Picelli, S. et al. Tn5 transposase and tagmentation procedures for massively scaled sequencing projects. *Genome Res.* 24, 2033-2040, doi:10.1101/gr.177881.114 (2014).

In certain instances, a transposase is related to and/or derived from a parent transposase, which comprises a peptide fragment with at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% amino acid sequence homology to a corresponding peptide fragment of the parent transposase. The peptide fragment can be at least 5, 10, 15, 20, 25, 30, 35, 40, 45, 50, 60, 70, 80, 90, 100, 150, 200, 250, 300, 400, or 500 amino acids in length. For example, a transposase derived from Tn5 may comprise a peptide fragment that is 50 amino acids in length and about 80% homologous to a corresponding fragment in a parent Tn5 transposase. In some cases, the insertion is facilitated and/or triggered by addition of one or more cations. The cations may be divalent cations such as, for example, $Ca^{2+}$, $Mg^{2+}$ and $Mn^{2+}$.

In some cases, tagmentation include contacting DNA with an insertional enzyme complex. The term "insertional enzyme complex," as used herein, refers to a complex comprising an insertional enzyme and one or more (e.g., two) adaptor molecules (the "transposon tags") that are combined with polynucleotides to fragment and add adaptors to the polynucleotides. Such a system is described in a variety of publications, including Caruccio (Methods Mol. Biol. 2011 733: 241-55) and US20100120098, which are incorporated by reference herein.

The tags attached to the DNA during tagmentation may be any barcode described herein. In some examples, the tags may comprise sequencing adaptors, locked nucleic acids (LNAs), zip nucleic acids (ZNAs), RNAs, affinity reactive molecules (e.g. biotin, dig), self-complementary molecules, phosphorothioate modifications, azide or alkyne groups. In some cases, the sequencing adaptors further comprise a barcode label. Further, the barcode labels may comprise a unique sequence. The unique sequences can be used to identify the individual insertion events. Any of the tags can further comprise fluorescence tags (e.g. fluorescein, rhodamine, Cy3, Cy5, thiazole orange, etc.).

The insertional enzyme may be assembled with one or more tags to be attached to the nucleic acids. One or more oligonucleotides may be assembled with the insertional enzyme. In some cases, the oligonucleotides comprise a first, a second and a third oligonucleotides. The second oligonucleotide may be phosphorylated, e.g., at the 5' end. The phosphorylated oligonucleotide may be used for downstream ligation of cell barcodes. The third oligonucleotide may be a mosaic end compliment oligo (ME-comp). The ME-comp may be phosphorylated. Alternatively or additionally, the ME-comp may be modified to reduce extension of oligo by polymerase. For example, the ME-comp may comprise 3' ddC modification. One or more nucleotides in the ME-comp may be modified to prevent tagmentation of the oligo itself. For example, the one or more nucleotides in the ME-comp may have phosphorothioation. The first and the third, and the second and the third may be annealed before assembling with the insertional enzyme.

The insertional enzyme may further comprise an affinity tag. In some cases, the affinity tag is an antibody. The antibody may bind to, for example, a transcription factor, a modified nucleosome or a modified nucleic acid. Examples of modified nucleic acids include, but are not limited to, methylated or hydroxymethylated DNA. In other cases, the affinity tag may be a single-stranded nucleic acid (e.g. ssDNA, ssRNA). In some examples, the single-stranded nucleic acid may bind to a target nucleic acid. In further cases, the insertional enzyme may further comprise a nuclear localization signal. In some cases, the affinity tag may be one of the capture moieties or labels described herein. For example, the affinity tag may be biotin, FLAG tag, HaloTag, or V5 tag.

The insertional enzyme may be one used for Assay for Transposase Accessible Chromatin, e.g., as described in Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature Methods 2013; 10 (12): 1213-1218). For example, the insertional enzyme may be a hyperactive Tn5 transposase loaded in vitro with adapters for high-throughput DNA sequencing, can simultaneously fragment and tag a genome with sequencing adapters. In one embodiment, the adapters are compatible with the methods described herein.

In some cases, the insertional enzyme may comprise two or more enzymatic moieties and the enzymatic moieties are linked together. An insert element can be bound to the insertional enzyme. The enzymatic moieties may be linked by using any suitable chemical synthesis or bioconjugation methods. For example, the enzymatic moieties may be linked via an ester/amide bond, a thiol addition into a maleimide, Native Chemical Ligation (NCL) techniques, Click Chemistry (i.e. an alkyne-azide pair), or a biotin-streptavidin pair. In some cases, each of the enzymatic moieties may insert a common sequence into the polynucleotide. The common sequence can comprise a common barcode. The enzymatic moieties may comprise transposases or derivatives thereof. In some embodiments, the polynucleotide may be fragmented into a plurality of fragments during the insertion. The fragments comprising the common barcode may be determined to be in proximity in the three-dimensional structure of the polynucleotide. The insertional enzyme may also be bound to the polynucleotide. In some cases, the polynucleotide may be further bound to a plurality of association molecules. The association molecules can be proteins (e.g. histones) or nucleic acids (e.g. aptamers).

Complementary DNA (cDNA) Generation

The methods may include generating cDNA using RNA as templates. In some cases, the cDNA molecules may be generated using mRNA as templates. In some cases, the RNA and/or the generated cDNA may be generated and remain in nuclei.

As used herein, the term "cDNA" refers to a strand of DNA copied from an RNA template and may be complementary to the RNA template. As used herein, the term "template" refers to the substrate RNA for the reverse transcriptase to make cDNA. A template may be complex (e.g., total RNA, polyA+ RNA, mRNA, etc.) or not complex (e.g., an enriched RNA or an in vitro transcribed product).

The cDNA may be generated using reverse transcription. In some cases, the cDNA is generated using RT-PCR. As used herein, the term "RT-PCR" or "reverse transcription polymerase chain reaction", refers to a technique for synthesizing a cDNA from RNA and amplifying the cDNA molecule. RT-PCR is useful for detecting RNA species such as in quantitative analysis of gene expression and for producing DNA copies of RNA for use in cloning, cDNA library construction, probe synthesis, and signal amplification in in situ hybridizations. In general, the technique comprises two parts: 1) synthesis of cDNA from RNA by reverse transcription (RT); and 2) amplification of a specific cDNA by polymerase chain reaction (PCR). Reverse transcriptase is an RNA dependent DNA polymerase that catalyzes the polymerization of nucleotides using template RNA or the RNA molecule in an RNA:DNA hybrid. Examples of reverse transcriptases include retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechoccus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (e.g., retrons, group II introns, and diversity-generating retroelements among others). In some examples, the transcriptase is Maxima H Minus Reverse Transcriptase. In some cases, RT mix, e.g., M-MLV, SensiScript, ProtoScript II, Superscript II, Superscript III, and SuperScrip IV, may be used for the reverse transcription reaction.

Primer for RT-PCR

One or more primers may be used in the synthesis of first strand cDNA. In some cases, the primers may comprise an oligo-d(T), e.g., 12-18 nucleotides in length, that initiates synthesis by annealing to the poly-A tract at the 3' terminus of eukaryotic messenger RNA molecules. The primers may further comprise an affinity tag. In these cases, the resulting cDNA comprise the affinity tag. The affinity tag may be used for isolating the cDNA in further processing and analysis. Other primers, including short random oligonucleotide primers, may be used to prime complementary DNA synthesis. In some instances, gene-specific primers may be used to prime cDNA synthesis. In some examples, the primers for RT-PCR may contain one or more of a poly-T tail, a unique molecular identifier (UMI), a universal ligation overhand, and an affinity tag described herein (e.g., biotin molecule). In some cases, the primers may be phosphorylated (e.g., at 5' end).

After synthesis of a double stranded cDNA, the synthesized cDNA may comprise one or more tags. The tags may be introduced to the cDNA by primers comprising such tags. Alternatively or additionally, the tags may be introduced to the cDNA after synthesis, e.g., by ligation. In some cases, the tags may comprise an affinity tag. In certain cases, the tags may comprise one or more sequences recognized by restriction endonuclease(s). In certain cases, the tags may comprise one or more sequences recognized by other types of enzymes such as methylase. In some examples, the cDNA may comprise multiple types of tags. For example, the cDNA may comprise an affinity tag and one or more sequences that can be recognized by restriction endonuclease(s).

Barcode Attachment

The method may further comprise attaching one or more barcodes to the fragmented DNA and the cDNA. In some examples, the fragmented DNA and the cDNA from or derived from the same cell may receive a unique barcode sequence, which may comprise one or more barcodes. When the nucleic acids are sequenced, the unique barcode sequence may be used to identify sequence reads identifying a single cell. In some examples, a barcode may be a unique cell barcode, e.g., molecules from the same cell comprises the same unique cell barcode. In such cases, molecules from different cells may be distinguished and/or identified based on the unique cell barcodes. In some examples, a barcode may be a unique molecular identifier (UMI), e.g., two different molecules comprise different UMIs and can be distinguished based on the UMIs.

Barcodes

As used herein, the term "barcode" refers to a sequence of nucleotides (for example, DNA or RNA) that is used as an identifier. For example, barcodes may be identifier for the associated molecule, such as a target molecule and/or target nucleic acid, or as an identifier of the source of an associated molecule, such as a cell-of-origin. In some cases, a tag described herein may be a barcode. A barcode may also refer to any unique, non-naturally occurring, nucleic acid sequence that may be used to identify the originating source of a nucleic acid fragment. Barcoding may be performed based on any of the compositions or methods disclosed in patent publication WO 2014047561 A1, Compositions and methods for labeling of agents, incorporated herein in its entirety. In certain embodiments, barcoding uses an error correcting scheme (T. K. Moon, Error Correction Coding: Mathematical Methods and Algorithms (Wiley, New York, ed. 1, 2005)). Not being bound by a theory, amplified sequences from single cells may be sequenced together and resolved based on the barcode associated with each cell.

A barcode or can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides. A barcode may be in single- or double-stranded form. Target molecule and/or target nucleic acids can be labeled with multiple nucleic acid barcodes in combinatorial fashion, such as a nucleic acid barcode concatemer. In some cases, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple barcodes to provide information about all of these features (and more).

In certain embodiments, a barcode may identify the type of nucleic acids molecules. For example, all DNA molecules may comprise a first common barcode sequence and all RNA molecules or cDNA molecules generated from RNA molecules may comprise a second common barcode sequence, which is different from the first common barcode sequence. In some cases, a barcode may identify the individual discrete volume.

In some examples, a cell barcode may have one or more of the following structures:

```
                                            (SEQ ID NO: 1)
CAAGCAGAAGACGGCATACGAGATNNNNNNNNNGTGGCCGATGTTTCGCAT

CGGCGTACGACTNNNNNNNNNATCCACGTGCTTGAGCGCGCTGCATACTTG

NNNNNNNNNCCCATGATCGTCCGAGTCTCGTGGGCTCGGAGATGTGTATAA

GAGACAG;
```

P7-Barcode3-Overhang-Barocde2-Overhang-Barcode1-read2-ME.

One or more barcodes may be attached to a target molecule. This attachment can be direct (for example, covalent or noncovalent binding of the barcodes to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents. In certain embodiments, barcode tagging can occur via a barcode receiving adapter associate with (for example, attached to) a target molecule, as described herein.

Nucleic acid molecules may be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool.

In some embodiments, a barcode may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type (SEQ ID NO:2).

A barcode may further include an identifier specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semi-solid support can be added to the discreet volume sequentially after introduction of the target molecule pool), such that the precise combination of conditions to which a given target molecule was exposed can be subsequently determined by sequencing the unique molecular identifiers associated with it.

Nucleic acid molecules associated barcode(s) may be amplified by methods known in the art, such as polymerase chain reaction (PCR). For example, the nucleic acid barcode may contain universal primer recognition sequences that may be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode may be amplified, for example using PCR. In some embodiments, an origin-specific barcode further comprises a sequencing adaptor. In some embodiments, an origin-specific barcode further comprises universal priming sites.

Barcodes Reversibly Coupled to Solid Substrate

In some embodiments, one or more barcodes may be reversibly coupled to a solid or semisolid substrate. In some embodiments, the barcodes further comprise a nucleic acid capture sequence that specifically binds to the nucleic acids and/or a specific binding agent that specifically binds to the target molecules. In specific embodiments, the barcodes include two or more populations of barcodes, wherein a first population comprises the nucleic acid capture sequence and a second population comprises the specific binding agent that specifically binds to the target molecules. In some examples, the first population of barcodes further comprises a target nucleic acid barcode, wherein the nucleic acid barcode identifies the population as one that labels nucleic acids. In some examples, the second population of barcodes further comprises a target molecule barcode, wherein the target molecule barcode identifies the population as one that labels target molecules.

Barcode with Cleavage Sites

A barcode may be cleavable from a specific binding agent, for example, after the specific binding agent has bound to a target molecule. In some embodiments, the barcode further comprises one or more cleavage sites. In some examples, at least one cleavage site is oriented such that cleavage at that site releases the barcode from a substrate, such as a bead, for example a hydrogel bead, to which it is coupled. In some examples, at least one cleavage site is oriented such that the cleavage at the site releases the barcode from the target molecule specific binding agent. In some examples, a cleavage site is an enzymatic cleavage site, such an endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Barcode Adapters

In some embodiments, a nucleic acid molecule is attached to a barcode via an adapter. An adapter may be a molecule configured to accept or receive a barcode, such as an barcode. In some examples, the adapter comprises an overhang, and the barcode comprises a sequence capable of hybridizing to the overhang. For example, an adapter can include a single-stranded nucleic acid sequence (for example, an overhang) capable of hybridizing to a given barcode (for example, a barcode), for example, via a sequence complementary to a portion or the entirety of the nucleic acid barcode. In certain embodiments, this portion of the barcode is a standard sequence held constant between individual barcodes. The hybridization couples the adapter to the barcode. In some embodiments, the adapter may be associated with (for example, attached to) a target molecule. As such, the adapter may serve as the means through which a barcode is attached to a target molecule. An adapter may be attached to a target molecule according to methods known in the art. For example, a barcode receiving adapter can be attached to a polypeptide target molecule at a cysteine residue (for example, a C-terminal cysteine residue). An adapter may be used to identify a particular condition related to one or more target molecules, such as a cell of origin or a discreet volume of origin. For example, a target molecule can be a cell surface protein expressed by a cell, which receives a cell-specific adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, a barcode further includes a capture moiety (e.g., affinity tags described herein), covalently or non-covalently linked. In specific embodiments, a targeting probe is labeled with biotin, for instance by incorporation of biotin-16-UTP during in vitro transcription, allowing later capture by streptavidin. Other means for labeling, capturing, and detecting a barcode include: incorporation of aminoallyl-labeled nucleotides, incorporation of sulfhydryl-labeled nucleotides, incorporation of allyl- or azide-containing nucleotides.

Barcode with Detectable Tags

The barcodes herein may comprise one or more detectable tags. In some examples, a detectable tag may comprise a detectable oligonucleotide tag is an oligonucleotide that can be detected by sequencing of its nucleotide sequence and/or by detecting non-nucleic acid detectable moieties it may be attached to.

The oligonucleotide tags may be randomly selected from a diverse plurality of oligonucleotide tags. In some instances, an oligonucleotide tag may be present once in a plurality or it may be present multiple times in a plurality. In the latter instance, the plurality of tags may be comprised of a number of subsets each comprising a plurality of identical tags. In some important embodiments, these subsets are physically separate from each other. Physical separation may be achieved by providing the subsets in separate wells of a multiwell plate or separate droplets from an emulsion. It is the random selection and thus combination of oligonucleotide tags that results in a unique label. Accordingly, the number of distinct (i.e., different) oligonucleotide tags required to uniquely label a plurality of agents can be far less than the number of agents being labeled. This is particularly advantageous when the number of agents is large (e.g., when the agents are members of a library).

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety.

In some embodiments, a detectable oligonucleotide tag comprises one or more non-oligonucleotide detectable moieties. Examples of detectable moieties include fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides comprising unique nucleotide sequences, oligonucleotides comprising detectable moieties, and oligonucleotides comprising both unique nucleotide sequences and detectable moieties.

In some cases, the detectable tag comprises a labeling substance, which is detectable by spectroscopic, photochemical, biochemical, immunochemical, electrical, optical or chemical means. Such tags include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Detectable tags may be detected by many methods. For example, radiolabels may be detected using photographic film or scintillation counters, and fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I, $^{3}$H, and $^{131}$I) fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinyl sulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAN/IRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. A fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code. Advantageously, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation. In some embodiments, the detectable moieties may be quantum dots.

Split-Pool Barcoding

In some embodiments, the nucleic acids molecules, e.g., the fragmented genomic DNA and the cDNA, may be barcoded by a split-pool method. In some embodiments, the split-pool method may be performed on a sample comprising nuclei containing the fragmented genomic DNA and the cDNA herein. In such cases, the fragmented genomic DNA and the cDNA remain in nuclei after generation. The nuclei may remain intact during the split-pool process. In certain examples, the nuclei are isolated from cells. For example, the cells may be lysed and the nuclei are released, but remain intact and contain the fragmented genomic DNA and the cDNA. In certain examples, the nuclei remain in the cells, which are made permeable so the nucleic acids in the cells (e.g., in the nuclei) can access reaction reagents and the fragmented DNA and the cDNA can be generated inside cells.

In general, the split-pool method may comprise splitting a sample comprising nuclei into discrete volumes in partitions, each partition containing a unique first barcode; ligating the first barcode to nucleic acids in each partition; and pooling the discrete partitions to a first pooled sample. The process may be performed once. The process may be repeated. For example, the split-pool method may further comprise splitting the first pooled sample into discrete partitions, each partition containing a unique second barcode; ligating the second barcode to nucleic acids in each partition; and pooling the discrete partitions to make a second pooled sample. The splitting and pooling steps may be repeated for at least 1, at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 100, at least 200, or at least 500 times. In some cases, the splitting and pooling steps may be repeated once, twice, three times, or four times. In some cases, the pooled sample may be used for further processing and analysis. In certain cases, the split samples in partitions may be used for further processing and analysis. In some cases, the split-pooling (one or multiple rounds) may be performed for barcode ligation. Multiple rounds of split-pooling may create barcode possibilities to identify cells, thus increase the throughput of analysis methods.

After split-pool steps, each nucleic acid molecule may comprise one or a combination of barcodes. In a split-pool step, nucleic acid molecules in a nucleus or cell are split together, nucleic acid molecules from or derived from the same cell may receive the same barcode or barcode combination. Such barcode or barcode combination may comprise a unique barcode sequence, which may be used as an identifier of cell origin of the nucleic acid molecules. In some embodiments, the split-pool-ligation approach may be modified to a split-pool-hybridization-ligation approach. For example, the barcodes may be hybridized to nuclei during each round without adding ligase. After several rounds of hybridization, the nuclei may be washed and then resuspended in ligation mixture. This approach may provide similar or better yield than split-pool-ligation approach. The overall cost for ligase may be much lower.

In some embodiments, nucleic acids in the split-pool process may comprise ligation handles. The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. The ligation handles may be generated before the split-pool process. For example, the ligation handles may be generated during the fragmentation, tagmentation, and/or RT-PCR process. Alternatively or additionally, the ligation handles may be generated during the split-pool process.

Discrete Volumes

The partitions in the split-pool method may be discrete volumes in any container or on any support. A "discrete volume" or "partition" as used herein may be discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electromagnetic, or light illumination, or any combination thereof. By "diffusion rate limited" (for example, diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents may be passed out through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

Droplets

In some cases, an individual discrete volume is in a droplet. The present disclosure enables high throughput and high-resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets may be carried in a flowing oil phase and stabilized by a surfactant. In one aspect, single cells or single organelles or single nuclei or single molecules (proteins, RNA, DNA) are encapsulated into uniform droplets from an aqueous solution/dispersion. In a related aspect, multiple cells or multiple nuclei or multiple molecules may take the place of single cells or single nuclei or single molecules. The aqueous droplets of volume ranging from 1 pL to 10 nL work as individual reactors. Disclosed embodiments provide 104 to 105 single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet may be introduced at a confluence point in a main microfluidic channel from separate inlet microfluidic channels. In some cases, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length may be selected such that faster species of droplets catch up to the slowest species. Size constraints of the channel may prevent the faster moving droplets from passing the slower moving droplets resulting in a train of droplets entering a merge zone. Multi-step chemical reactions, biochemical reactions, or assay detection chemistries may involve a fixed reaction time before species of different type may be added to a reaction. Multi-step reactions may be achieved by repeating the process multiple times with a second, third or more confluence points each with a separate merge point. Highly efficient and precise reactions and analysis of reactions may be achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in some embodiments, a fluidic droplet may be steered or sorted by directing the liquid surrounding the fluidic droplet into a first channel, a second channel, etc. In certain embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels may be controlled to direct the droplet selectively into one of the channels, and changes in pressure can be affected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets, preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example, if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet, and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

Solid Support

In some embodiments, an individual discrete volume is on a solid support. A solid support may be a bead or micro-bead, or a plurality of micro-beads, micro-arrays, micro-wells, or micro-lids. The solid support can be shaped in any manner required for an end use application and may have a shape that is circular, square, star, or porous. Examples of suitable solid supports include, but are not limited to, inert polymers (preferably non-nucleic acid polymers), beads, glass, or peptides. In some embodiments, the solid support is an inert polymer or a bead. The bead is a silica bead, a hydrogel bead or a magnetic bead. In some embodiments, the solid support comprises a magnetic core. Examples of suitable polymers include a hydroxylated methacrylic polymer, a hydroxylated poly(methyl methacrylate), a polystyrene polymer, a polypropylene polymer, a polyethylene polymer agarose, or cellulose. In one example, the solid support may be wells in a microwell plate. In another example, the solid support may be particles, e.g., beads.

In cases where the solid support is particles, the solid support has an average particle size between about 10 microns to 200 microns, about 10 microns to 190 microns, about 10 microns to 180 microns, about 10 microns to 170 microns, about 10 microns to 160 microns, about 10 microns to 150 microns, about 10 microns to about 140 microns, about 10 to about 130 microns, about 10 to about 120 microns, about 10 microns to about 110 microns, about 10 microns to about 100 microns, about 10 microns to about 90 microns, about 10 microns to about 80 microns, about 10 microns to about 70 microns, about 10 microns to about 60 microns, about 10 microns to about 50 microns, about 10 microns to about 40 microns, about 10 microns to 30 microns, about 10 microns to about 20 microns, about 20 microns to about 30 microns, about 20 microns to about 40 microns, about 20 microns to about 50 microns, about 20 microns to about 60 microns, about 20 microns to about 70 microns, about 20 microns to about 80 microns, about 20 microns to about 100 microns, about 20 microns to about 100 microns, about 50 microns to about 100 microns, about 100 microns to 200 microns, or about 30 microns. In some embodiments, the bead or micro-bead has an average size, measured as average diameter of 20-40 μm.

In some embodiments, the solid support may be functionalized, e.g., to permit covalent attachment of the agent and/or label. Such functionalization on the support may comprise reactive groups that permit covalent attachment to an agent and/or a label.

Features of Discrete Volumes

The slip steps may comprise splitting a sample into a number of discrete volumes, e.g., in at least 2, at least 4, at least 6, at least 8, at least 10, at least 20, at least 30, at least 40, at least 50, at least 60, at least 70, at least 80, at least 90, at least 100, at least 200, at least 300, at least 400, or at least 500 discrete volumes.

Each discrete volume may have a suitable number of cells or nuclei for the number of barcodes available to avoid excessive barcode collision. For example, the number of cells in each volume and the number of barcodes available may be used to reach a barcode collision rate less than 10%, 9%, 8%, 7%, 6%, 5%, 4%, 3%, 2%, or 1%. In one example, the collision rate may be less than 5%. In another example, the barcode collision rate may be less than 1%.

Ligation

Barcodes herein may be attached nucleic acid molecules using ligation. As used herein, the term "ligation" refers to joining two or more nucleic acid molecules.

The ligation may be performed using a ligase. A ligase may refer to an enzyme that is capable of ligating nucleic acid. For example, a ligase may be capable of ligating the 3'-end of an acceptor polynucleotide to a the 5'-end of a donor polynucleotide. Examples of ligases include bacteriophage T4 DNA ligase, *Escherichia coli* (*E. coli*) DNA ligase, *Aquifex aeolicus* DNA ligase, *Thermus aquaticus* (Taq) DNA ligase, 9° N™ DNA ligase, *Methanobacterium thermoautotrophicum* RNA ligase, *Ferroplasma acidiphilum* DNA ligase, Human DNA ligase I, Human DNA ligase II, Human DNA ligase III, Human DNA ligase IV, Vaccinia virus DNA ligase, *Chlorella* virus DNA ligase, *Pyrococcus furiosis* DNA ligase, *Haloferax volcanii* DNA ligase, *Acidianus ambivalens* DNA ligase, *Archaeoglobus fulgidus* DNA ligase, *Aeropyrum pernix* DNA ligase, *Cenarcheon symbiosum* DNA ligase, *Haloarcula marismortui* DNA ligase, *Ferroplasma acidarmanus* DNA ligase, *Natronomonas pharaosis* DNA ligase, *Haloquadratum walsbyi* DNA ligase, *Halobacterium salinarum* DNA ligase, *Methanosarcina acetivorans* DNA ligase, *Methanosarcina barkeri* DNA ligase, *Methanococcoides burtonii* DNA ligase, *Methanospirillum hungatei* DNA ligase, *Methanocaldococcus jannaschii* DNA ligase, *Methanopyrus kandleri* DNA ligase, *Methanosarcina mazei* DNA ligase, *Methanococcus maripaludis* DNA ligase, *Methanosaeta thermophile* DNA ligase, *Methanosphaera stadtmanae* DNA ligase, *Methanothermobacter thermautotrophicus* DNA ligase, *Nanoarchaeum equitans* DNA ligase, *Pyrococcus abyssi* DNA ligase, *Pyrobaculum aerophilum* DNA ligase, *Pyrococcus horikoshii* DNA ligase, *Picrophilus torridus* DNA ligase, *Sulfolobus acidocaldarius* DNA ligase, *Sulfolobus shibatae* DNA ligase, *Sulfolobus solfataricus* DNA ligase, *Sulfolobus tokodaii* DNA ligase, *Thermoplasma acidophilum* DNA ligase, *Thermococcus fumicolans* DNA ligase, *Thermococcus kodakarensis* DNA ligase, *Thermococcus* sp. NA 1 DNA ligase, *Thermoplasma volcanium* DNA ligase, *Staphylococcus aureus* DNA ligase, *Thermus scotoductus* NAD$^+$-DNA ligase, T4 RNA ligase, *Staphylococcus aureus* DNA ligase, *Methanobacterium thermoautotrophicum* DNA ligase, *Thermus* species AK16D DNA ligase, *Haemophilus influenzae* DNA ligase, *Thermus thermophilus* DNA ligase, bacteriophage T7 DNA ligase, *Haemophilus influenzae* DNA ligase, *Mycobacterium tuberculosis* DNA ligase, *Deinococcus radiodurans* RNA ligase, *Methanobacterium thermoautotrophicum* RNA ligase, *Rhodothermus marinus* RNA ligase, *Trypanosoma brucei* RNA ligase, bacteriophage T4 RNA ligase 1, Ampligase, and bacteriophage T4 RNA ligase 2. In some example, the ligase may be T4 DNA ligase (M0202L, NEB).

In some embodiments, barcodes may be attached to nucleic acids by synthesis, e.g., using a DNA polymerase.

For example, barcodes may be attached by polymerase chain reaction (PCR) using primers with the barcode sequences.

Reverse Crosslinking

In cases where the cells or nuclei are fixed, the method may further comprise reverse crosslinking. Reverse crosslinking may be performed after the cells are lysed to release molecules from the cells. In some examples, reverse crosslinking may be performed after RNA molecules and DNA molecules are separated. For reverse crosslinking may be performed by incubating the cells with detergent (e.g., SDS) and proteinase (e.g., proteinase K).

Nucleic Acid Isolation

The methods may further include isolating one or more types of nucleic acid molecules from other type(s) of nucleic acid molecules. For examples, the methods may include isolating cDNA molecules from genomic DNA molecules in a sample.

In some embodiments, the isolation may be performed by capturing a tag (e.g., an affinity tag) on the nucleic acid molecules so they can be separated from nucleic acids that do not have such tag. The tag may specifically bind to a capture agent. The capture agent may be immobilized or linked to a solid support. Examples of such tags may include biotin, digoxygenin, peptide tags, and protein tags (e.g., his-tags and the like). In some cases, the tag may be an antibody.

In some cases, certain types of nucleic acids may be in a complex with one or more proteins. For example, the genomic DNA (or fragmented, tagmented, and/or barcoded forms thereof) may be part of chromatin. In some cases, such genomic DNA (or fragmented, tagmented, and/or barcoded forms thereof) may be isolated from other nucleic acids that are not in chromatin by capturing one or more proteins in chromatin (e.g., histones). Such isolation may be performed using antibodies.

Sequencing

The methods herein may further include sequencing one or more nucleic acids processed by the steps herein. For example, after barcoded and isolated, the genomic DNA, cDNA, the barcode sequence(s), and a portion thereof, may be sequenced.

In some cases, the sequencing may be next generation sequencing. The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences. Any method of sequencing known in the art can be used before and after isolation. In certain embodiments, a sequencing library is generated and sequenced.

At least a part of the processed nucleic acids and/or barcodes attached thereto may be sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513: 19-39) and Morozova et al (Genomics. 2008 92:255-64), which are incorporated by reference for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. In certain cases, the primers used may contain a molecular barcode (an "index") so that different pools can be pooled together before sequencing, and the sequence reads can be traced to a particular sample using the barcode sequence.

In some cases, the sequencing may be performed at certain "depth." The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads(N), and the average read length(L) as N×L/G. For example, a hypothetical genome with 2,000 base pairs reconstructed from 8 reads with an average length of 500 nucleotides will have 2× redundancy.

In some cases, the sequencing herein may be low-pass sequencing. The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

In some cases, the sequencing herein may deep sequencing or ultra-deep sequencing. The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell). The term "ultra-deep" as used herein refers to higher coverage (>100-fold), which allows for detection of sequence variants in mixed populations.

Analysis of Sequence Reads

Sequence reads obtained using methods herein may be analyzed, e.g., for characterizing one or more features of the cells, tissues, or subject from which the nucleic acid molecules are from or derived from.

In some embodiments, the sequence reads may be analyzed for determining one or more epigenetic features in genomic DNA, expression profiles of one or more genes, or a combination thereof. In some examples, the sequence reads may comprise sequence information of different types of nucleic acids, e.g., genomic DNA and cDNA. In such cases, the sequence reads may be analyzed for determining a correlation of one or more epigenetic features and expression profiles of one or more genes in the same cell. The sequence reads of nucleic acids from or derived from the same cell may be identified using the unique barcode sequence described herein.

The epigenetic features may include a profile of chromatin accessibility along a region of interest, DNA binding protein (e.g., transcription factors) occupancy for a site in the region, nucleosome-free DNA in the region, positioning of nucleosomes along the region, a profile of chromatin states along the region, global occupancy of a binding site for the DNA binding protein by, e.g., aggregating data for one DNA binding protein over a plurality of sites to which that protein binds. Information about the sequence analyzed may also be obtained. Such information may include the positions of promoters, introns, exons, known enhancers, transcriptional start sites, untranslated regions, terminators, etc.

The term "chromatin accessibility," as used herein, refers to how accessible a nucleic acid site is within a polynucleotide, such as in genomic DNA, e.g., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins). The term "DNA binding protein occupancy," as used herein, refers to whether a binding site for a sequence specific DNA binding protein (e.g., a binding site for a transcription factor) is occupied by the DNA binding protein. DNA binding protein occupancy can be measured quantitatively or qualitatively. The term "global occupancy," as used herein, refers to whether a plurality of different binding sites for a DNA binding protein that are distributed throughout the genome (e.g., a binding site for a transcription factor) are bound by the DNA binding protein. DNA binding protein occupancy can be measured quantitatively or qualitatively.

The epigenetic features may be analyzed in the context with the sequence information. The epigenetic features may provide information regarding active regulatory regions and/or the transcription factors that are bound to the regulatory regions. For example, nucleosome positions may be inferred from the lengths of sequencing reads generated. Alternatively and additionally, transcription factor binding sites may be inferred from the size, distribution and/or position of the sequencing reads generated. In some cases, novel transcription factor binding sites may be inferred from sequencing reads generated. In other cases, novel transcription factors can be inferred from sequencing reads generated.

In some embodiments, the correlation between the epigenetic feature(s) of a region of interest and the expression profile of one or more genes in the region may be obtained. The expression profile may be obtained using sequence reads of cDNA or RNA transcribed from the one or more genes.

The methods may be used for performing any assays that involve analyzing nucleic acids. In some embodiments, the methods may be used for determining chromatin accessibility or chromatin remodeling. In these cases, the methods, the methods may be used for identifying and analyzing molecules in or derived from open chromatin regions. In some embodiments, the methods may be used for performing whole genome sequencing. For example, for performing whole genome sequencing, the methods may comprise pretreating cells with detergents (e.g., SDS), and depleting nucleosome (e.g., using Lithium Assisted Nucleosome Depletion (LAND)). In some examples, the nucleosome depletion may be performed as described in Vitak S A et al., Sequencing thousands of single-cell genomes with combinatorial indexing, Nat Methods. 2017 March; 14(3): 302-308.

Systems and Kits

In certain aspects, the present disclosure provides systems and kits for analyzing nucleic acids in single cells. The systems and kits may be used for performing the methods described herein. The systems and kits may comprise one or more compositions and reagents described herein.

In some examples, the system and kits may comprise cell fixation reagents, DNA tagmentation reagents (e.g., transposase), RT-PCR reagents (e.g., primers for reverse transcription), devices and/or reagents for performing split-pool barcoding, devices and/or reagents for sequencing and sequence reads analysis, or any combination thereof.

In addition to reagents and devices, the kits may further include instructions for using the components of the kit to practice the methods. The instructions for practicing the subject methods may be generally recorded on a suitable recording medium. For example, the instructions may be printed on a substrate, such as paper or plastic, etc. As such, the instructions may be present in the kits as a package insert, in the labeling of the container of the kit or components thereof. In other embodiments, the instructions are present as an electronic storage data file present on a suitable computer readable storage medium, e.g., CD-ROM, diskette, etc. In certain embodiments, the instructions are not present in the kit, but means for obtaining the instructions from a remote source, e.g., via the internet, are provided.

The invention is further described in the following examples, which do not limit the scope of the invention described in the claims.

EXAMPLES

Example 1—Methods for Analyzing Genomic DNA and mRNA in Single Cells Preparing Oligonucleotides for Ligations There were three barcoding rounds of ligation reactions. Each round used a different set of 96 well barcoding plates. Ligation rounds had a universal linker strand with partial complementarity to a second strand containing the unique well-specific barcode sequence added to each well. These strands were annealed together prior to cellular barcoding to create a DNA molecule with three distinct functional domains: a 5' overhang that is complementary to the 3' overhang present on the cDNA molecule or transposed DNA molecules (may originate from RT primer, transposition adapter or previous barcoding round), a unique well-specific barcode sequence, and a 3' overhang complementary to the 5' overhang present on the DNA molecule to be subsequently ligated. Linker strands and barcode strands for the ligation rounds were added to RNase-free 96 well plates to a total volume of 10 µl/well with the following concentrations: round 1 plates contained 9 µM round 2 linker strand and 10 µM barcodes, round 2 plates contained 11 µM round 2 linker strand and 12 µM barcodes, and round 3 plates contained 13 µM round 3 linker strand and 14 µM barcodes. Strands for ligation barcoding rounds were annealed by heating plates to 95° C. for 2 min and cooling down to 20° C. at a rate of −1° C. per min.

Blocking strands were complementary to the 3' overhang present on the DNA barcodes used during hybridization barcoding rounds. Blocking occurred after well-specific barcodes had hybridized to cDNA molecules, but before all cells were pooled back together. Blocking ensured that unbound DNA barcodes could not mislabel cells in future barcoding rounds. 10 µl, 10 µl, and 20 µl of blocking strand solution was added to each of the 96 wells after first, second, and third round of hybridization of DNA barcodes, respectively. Blocking strand solutions were prepared at a concentration of 22 µM for round 1, 26.4 µM for round 2, and 11.5 µM for round 3. Blocking strands for the first two rounds were in a 2λT4 DNA Ligase buffer (NEB) while the third round was in a water. Both ligation reaction and blocking strands reaction were incubated with cells for 30 min at 37° C. with gentle shaking (300 rpm).

Fixation

Cells or nuclei were centrifuged at 300 g for 5 min and resuspended to 1 million cells/ml in 1 ml PBS with 0.1 U/µl Enzymatics RNase Inhibitor. Cells were fixed by adding 66.7 µl of 1.6% formaldehyde (final concentration 0.1%) and incubated at room temperature for 5 min. The final concentration of formaldehyde ranging from 0.1% to 1%, 0.1% was the optimal for most of the cell types. The fixation was stopped by adding 56.1 µl of 2.5 M glycine. The sample was incubated at room temperature for 5 min and then centrifuged at 500 g for 5 min to move supernatant. The cell pellet was washed twice with 1 ml of PBS with 0.1 U/µl Enzymatics RNase Inhibitor and 0.025 U/µl SUPERase RNase Inhibitor, and centrifuged at 500 g for 5 min between washings. The cells were resuspended in PBS with 0.1 U/µl Enzymatics RNase Inhibitor and used for transposition.

Transposition

All the oligos used in this protocol can be found in Tables 1-5 below.

TABLE 1

| Name | Sequence | Scale | Purification | Specific oligos | |
|---|---|---|---|---|---|
| Round 1 linker | CCGAGCCCACGAGACTCGGACGATCATGGG (SEQ ID NO: 3) | 1 µm | STD | | Note: Oligos specific to ATAC-RNA protocol is labelled with * |
| Round 2 linker | CAAGTATGCAGCGCGCTCAAGCACGTGGAT (SEQ ID NO: 4) | 1 µm | STD | | Other oligos are designed for split-pool-ligation |
| Round 3 linker | AGTCGTACGCCGATGCGAAACATCGGCCAC (SEQ ID NO: 5) | 1 µm | STD | | |
| Round 1 blocking | CCCATGATCGTCCGAGTCTCGTGGGCTCGG (SEQ ID NO: 6) | 1 µm | STD | | |
| Round 2 blocking | ATCCACGTGCTTGAGCGCGCTGCATACTTG (SEQ ID NO: 7) | 1 µum | STD | | |
| Round 3 blocking | GTGGCCGATGTTTCGCATCGGCGTACGACT (SEQ ID NO: 8) | 1 µm | STD | | |
| Read1 | TCGTCGGCAGCGTCAGATGTGTATAAGAGACAG (SEQ ID NO: 9) | 100 nm | HPLC | * | |
| TSO | AAGCAGTGGTATCAACGCAGAGTGAATrGrG+G (SEQ ID NO: 10) | 100 nm | HPLC | * | |
| RNA_PCR_primer | AAGCAGTGGTATCAACGCAGAGT (SEQ ID NO: 11) | 100 nm | STD | * | |
| P7 | CAAGCAGAAGACGGCATACGAGAT (SEQ ID NO: 12) | 100 nm | STD | * | |
| Phosphorylated_Read2 | /5Phos/GTCTCGTGGGCTCGGAGATGTGTATAAGAGACAG (SEQ ID NO: 13) | 100 nm | HPLC | * | The phosphorylation is used for following ligation step |
| RT_primer | /5Phos/GTCTCGTGGGCTCGGAGATGTGTATAAGAGACAGNNNNNNNNNN/iBiodT/TTTTTTTTTTTTTVN (SEQ ID NO: 14) | 100 nm | HPLC | * | The phosphorylation is used for following ligation step |
| Blocked_ME_Comp | /5Phos/C*T*G* T*C*T* C*T*T* A*T*A* C*A*/3ddC/ (SEQ ID NO: 15) | 100 nm | HPLC | * | The phosphorylation is used for following ligation step. The 3ddC modification reduces extension of oligo by polymerase |

TABLE 1-continued

| Name | Sequence | Scale | Purification | Specific oligos |
|------|----------|-------|--------------|-----------------|
|      |          |       |              | The phosphorothioation prevents the tagmentation of the oligo itself |

TABLE 2

| 96 Well Columns | (plate Ad1) Custom Barcodes Adapter 1 (index i5): | sequence |
|---|---|---|
| A1 | v2_Ad1.01_TAGATCGC | AATGATACGGCGACCACCGAGATCTACACTAGATCGCTCGTCGGCAGCGTCAGATGTGTAT (SEQ ID NO: 16) |
| B1 | v2_Ad1.02_CTCTCTAT | AATGATACGGCGACCACCGAGATCTACACCTCTCTATTCGTCGGCAGCGTCAGATGTGTAT (SEQ ID NO: 17) |
| C1 | v2_Ad1.03_TATCCTCT | AATGATACGGCGACCACCGAGATCTACACTATCCTCTTCGTCGGCAGCGTCAGATGTGTAT (SEQ ID NO: 18) |
| D1 | v2_Ad1.04_AGAGTAGA | AATGATACGGCGACCACCGAGATCTACACAGAGTAGATCGTCGGCAGCGTCAGATGTGTAT (SEQ ID NO: 19) |
| E1 | v2_Ad1.05_GTAAGGAG | AATGATACGGCGACCACCGAGATCTACACGTAAGGAGTCGTCGGCAGCGTCAGATGTGTAT (SEQ ID NO: 20) |
| F1 | v2_Ad1.06_ACTGCATA | AATGATACGGCGACCACCGAGATCTACACACTGCATATCGTCGGCAGCGTCAGATGTGTAT (SEQ ID NO: 21) |
| G1 | v2_Ad1.07_AAGGAGTA | AATGATACGGCGACCACCGAGATCTACACAAGGAGTATCGTCGGCAGCGTCAGATGTGTAT (SEQ ID NO: 22) |
| H1 | v2_Ad1.08_CTAAGCCT | AATGATACGGCGACCACCGAGATCTACACCTAAGCCTTCGTCGGCAGCGTCAGATGTGTAT (SEQ ID NO: 23) |
| A2 | v2_Ad1.09_TGGAAATC | AATGATACGGCGACCACCGAGATCTACACTGGAAATCTCGTCGGCAGCGTCAGATGTGTAT (SEQ ID NO: 24) |
| B2 | v2_Ad1.10_AACATGAT | AATGATACGGCGACCACCGAGATCTACACAACATGATTCGTCGGCAGCGTCAGATGTGTAT (SEQ ID NO: 25) |
| C2 | v2_Ad1.11_TGATGAAA | AATGATACGGCGACCACCGAGATCTACACTGATGAAATCGTCGGCAGCGTCAGATGTGTAT (SEQ ID NO: 26) |
| D2 | v2_Ad1.12_GTCGGACT | AATGATACGGCGACCACCGAGATCTACACGTCGGACTTCGTCGGCAGCGTCAGATGTGTAT (SEQ ID NO: 27) |
| E2 | v2_Ad1.13_TTTCTAGC | AATGATACGGCGACCACCGAGATCTACACTTTCTAGCTCGTCGGCAGCGTCAGATGTGTAT (SEQ ID NO: 28) |
| F2 | v2_Ad1.14_TAACCAAG | AATGATACGGCGACCACCGAGATCTACACTAACCAAGTCGTCGGCAGCGTCAGATGTGTAT (SEQ ID NO: 29) |
| G2 | v2_Ad1.15_GTGTATCG | AATGATACGGCGACCACCGAGATCTACACGTGTATCGTCGTCGGCAGCGTCAGATGTGTAT (SEQ ID NO: 30) |
| H2 | v2_Ad1.16_TCCATCAA | AATGATACGGCGACCACCGAGATCTACACTCCATCAATCGTCGGCAGCGTCAGATGTGTAT (SEQ ID NO: 31) |
| A3 | v2_Ad1.17_TTCGTGCA | AATGATACGGCGACCACCGAGATCTACACTTCGTGCATCGTCGGCAGCGTCAGATGTGTAT (SEQ ID NO: 32) |
| B3 | v2_Ad1.18_AGGTTGCC | AATGATACGGCGACCACCGAGATCTACACAGGTTGCCTCGTCGGCAGCGTCAGATGTGTAT (SEQ ID NO: 33) |
| C3 | v2_Ad1.19_CCTTATGT | AATGATACGGCGACCACCGAGATCTACACCCTTATGTTCGTCGGCAGCGTCAGATGTGTAT (SEQ ID NO: 34) |
| D3 | v2_Ad1.20_CAGCAACG | AATGATACGGCGACCACCGAGATCTACACCAGCAACGTCGTCGGCAGCGTCAGATGTGTAT (SEQ ID NO: 35) |
| E3 | v2_Ad1.21_GGTTCAAT | AATGATACGGCGACCACCGAGATCTACACGGTTCAATTCGTCGGCAGCGTCAGATGTGTAT (SEQ ID NO: 36) |

TABLE 2-continued

| 96 Well Columns | (plate Ad1) Custom Barcodes Adapter 1 (index i5): | sequence |
|---|---|---|
| F3 | v2_Ad1.22_ACATTCGT | AATGATACGGCGACCACCGAGATCTACACACATTCGTTCGTCGGCAGCGTCAGATGTGTAT (SEQ ID NO: 37) |
| G3 | v2_Ad1.23_GATTCCCA | AATGATACGGCGACCACCGAGATCTACACGATTCCCATCGTCGGCAGCGTCAGATGTGTAT (SEQ ID NO: 38) |
| H3 | v2_Ad1.24_CGGACTGC | AATGATACGGCGACCACCGAGATCTACACCGGACTGCTCGTCGGCAGCGTCAGATGTGTAT (SEQ ID NO: 39) |
| A4 | v2_Ad1.25_AGCCGTTC | AATGATACGGCGACCACCGAGATCTACACAGCCGTTCTCGTCGGCAGCGTCAGATGTGTAT (SEQ ID NO: 40) |
| B4 | v2_Ad1.26_ATTGGGTC | AATGATACGGCGACCACCGAGATCTACACATTGGGTCTCGTCGGCAGCGTCAGATGTGTAT (SEQ ID NO: 41) |
| C4 | v2_Ad1.27_TGCATACT | AATGATACGGCGACCACCGAGATCTACACTGCATACTTCGTCGGCAGCGTCAGATGTGTAT (SEQ ID NO: 42) |
| D4 | v2_Ad1.28_GGGCTTGG | AATGATACGGCGACCACCGAGATCTACACGGGCTTGGTCGTCGGCAGCGTCAGATGTGTAT (SEQ ID NO: 43) |
| E4 | v2_Ad1.29_GACGTGGC | AATGATACGGCGACCACCGAGATCTACACGACGTGGCTCGTCGGCAGCGTCAGATGTGTAT (SEQ ID NO: 44) |
| F4 | v2_Ad1.30_GCAAATTT | AATGATACGGCGACCACCGAGATCTACACGCAAATTTTCGTCGGCAGCGTCAGATGTGTAT (SEQ ID NO: 45) |
| G4 | v2_Ad1.31_GCAGCCTC | AATGATACGGCGACCACCGAGATCTACACGCAGCCTCTCGTCGGCAGCGTCAGATGTGTAT (SEQ ID NO: 46) |
| H4 | v2_Ad1.32_TCCGAGTT | AATGATACGGCGACCACCGAGATCTACACTCCGAGTTTCGTCGGCAGCGTCAGATGTGTAT (SEQ ID NO: 47) |
| A5 | v2_Ad1.33_GCATTAAG | AATGATACGGCGACCACCGAGATCTACACGCATTAAGTCGTCGGCAGCGTCAGATGTGTAT (SEQ ID NO: 48) |
| B5 | v2_Ad1.34_ACGATAAC | AATGATACGGCGACCACCGAGATCTACACACGATAACTCGTCGGCAGCGTCAGATGTGTAT (SEQ ID NO: 49) |
| C5 | v2_Ad1.35_CCTGCGGG | AATGATACGGCGACCACCGAGATCTACACCCTGCGGGTCGTCGGCAGCGTCAGATGTGTAT (SEQ ID NO: 50) |
| D5 | v2_Ad1.36_TGATTGTT | AATGATACGGCGACCACCGAGATCTACACTGATTGTTTCGTCGGCAGCGTCAGATGTGTAT (SEQ ID NO: 51) |
| E5 | v2_Ad1.37_GGCACGGA | AATGATACGGCGACCACCGAGATCTACACGGCACGGATCGTCGGCAGCGTCAGATGTGTAT (SEQ ID NO: 52) |
| F5 | v2_Ad1.38_GATCATTC | AATGATACGGCGACCACCGAGATCTACACGATCATTCTCGTCGGCAGCGTCAGATGTGTAT (SEQ ID NO: 53) |
| G5 | v2_Ad1.39_ATGGTCAT | AATGATACGGCGACCACCGAGATCTACACATGGTCATTCGTCGGCAGCGTCAGATGTGTAT (SEQ ID NO: 54) |
| H5 | v2_Ad1.40_CGTACCAA | AATGATACGGCGACCACCGAGATCTACACCGTACCAATCGTCGGCAGCGTCAGATGTGTAT (SEQ ID NO: 55) |
| A6 | v2_Ad1.41_CCAGTTTA | AATGATACGGCGACCACCGAGATCTACACCCAGTTTATCGTCGGCAGCGTCAGATGTGTAT (SEQ ID NO: 56) |
| B6 | v2_Ad1.42_ACCGGCCC | AATGATACGGCGACCACCGAGATCTACACACCGGCCCTCGTCGGCAGCGTCAGATGTGTAT (SEQ ID NO: 57) |
| C6 | v2_Ad1.43_CTAGAAGT | AATGATACGGCGACCACCGAGATCTACACCTAGAAGTTCGTCGGCAGCGTCAGATGTGTAT (SEQ ID NO: 58) |
| D6 | v2_Ad1.44_CGCCAGAT | AATGATACGGCGACCACCGAGATCTACACCGCCAGATTCGTCGGCAGCGTCAGATGTGTAT (SEQ ID NO: 59) |
| E6 | v2_Ad1.45_TCACATGG | AATGATACGGCGACCACCGAGATCTACACTCACATGGTCGTCGGCAGCGTCAGATGTGTAT (SEQ ID NO: 60) |
| F6 | v2_Ad1.46_GAACTCGA | AATGATACGGCGACCACCGAGATCTACACGAACTCGATCGTCGGCAGCGTCAGATGTGTAT (SEQ ID NO: 61) |

TABLE 2-continued

| 96 Well Columns | (plate Ad1) Custom Barcodes Adapter 1 (index i5): | sequence |
|---|---|---|
| G6 | v2_Ad1.47_CCACCGTT | AATGATACGGCGACCACCGAGATCTACACCCACCGTTTCGTCGGCAGCGTCAGATGTGTAT (SEQ ID NO: 62) |
| H6 | v2_Ad1.48_TAAGTTAC | AATGATACGGCGACCACCGAGATCTACACTAAGTTACTCGTCGGCAGCGTCAGATGTGTAT (SEQ ID NO: 63) |
| A7 | v2_Ad1.49_GAGACGTG | AATGATACGGCGACCACCGAGATCTACACGAGACGTGTCGTCGGCAGCGTCAGATGTGTAT (SEQ ID NO: 64) |
| B7 | v2_Ad1.50_TTGCCTAA | AATGATACGGCGACCACCGAGATCTACACTTGCCTAATCGTCGGCAGCGTCAGATGTGTAT (SEQ ID NO: 65) |
| C7 | v2_Ad1.51_TTAACTTG | AATGATACGGCGACCACCGAGATCTACACTTAACTTGTCGTCGGCAGCGTCAGATGTGTAT (SEQ ID NO: 66) |
| D7 | v2_Ad1.52_CTTTAACA | AATGATACGGCGACCACCGAGATCTACACCTTTAACATCGTCGGCAGCGTCAGATGTGTAT (SEQ ID NO: 67) |
| E7 | v2_Ad1.53_CGTAGACC | AATGATACGGCGACCACCGAGATCTACACCGTAGACCTCGTCGGCAGCGTCAGATGTGTAT (SEQ ID NO: 68) |
| F7 | v2_Ad1.54_TATTTGCG | AATGATACGGCGACCACCGAGATCTACACTATTTGCGTCGTCGGCAGCGTCAGATGTGTAT (SEQ ID NO: 69) |
| G7 | v2_Ad1.55_ATCCAGGA | AATGATACGGCGACCACCGAGATCTACACATCCAGGATCGTCGGCAGCGTCAGATGTGTAT (SEQ ID NO: 70) |
| H7 | v2_Ad1.56_TGTTCCTG | AATGATACGGCGACCACCGAGATCTACACTGTTCCTGTCGTCGGCAGCGTCAGATGTGTAT (SEQ ID NO: 71) |
| A8 | v2_Ad1.57_ACGCGCAG | AATGATACGGCGACCACCGAGATCTACACACGCGCAGTCGTCGGCAGCGTCAGATGTGTAT (SEQ ID NO: 72) |
| B8 | v2_Ad1.58_TCTGGCGA | AATGATACGGCGACCACCGAGATCTACACTCTGGCGATCGTCGGCAGCGTCAGATGTGTAT (SEQ ID NO: 73) |
| C8 | v2_Ad1.59_AATCTACA | AATGATACGGCGACCACCGAGATCTACACAATCTACATCGTCGGCAGCGTCAGATGTGTAT (SEQ ID NO: 74) |
| D8 | v2_Ad1.60_TACTGACC | AATGATACGGCGACCACCGAGATCTACACTACTGACCTCGTCGGCAGCGTCAGATGTGTAT (SEQ ID NO: 75) |
| E8 | v2_Ad1.61_CGATAGGG | AATGATACGGCGACCACCGAGATCTACACCGATAGGGTCGTCGGCAGCGTCAGATGTGTAT (SEQ ID NO: 76) |
| F8 | v2_Ad1.62_ACTTAGAA | AATGATACGGCGACCACCGAGATCTACACACTTAGAATCGTCGGCAGCGTCAGATGTGTAT (SEQ ID NO: 77) |
| G8 | v2_Ad1.63_AGAGATCT | AATGATACGGCGACCACCGAGATCTACACAGAGATCTTCGTCGGCAGCGTCAGATGTGTAT (SEQ ID NO: 78) |
| H8 | v2_Ad1.64_GGTGAAGG | AATGATACGGCGACCACCGAGATCTACACGGTGAAGGTCGTCGGCAGCGTCAGATGTGTAT (SEQ ID NO: 79) |
| A9 | v2_Ad1.65_ATCGAATG | AATGATACGGCGACCACCGAGATCTACACATCGAATGTCGTCGGCAGCGTCAGATGTGTAT (SEQ ID NO: 80) |
| B9 | v2_Ad1.66_TCAAGAGC | AATGATACGGCGACCACCGAGATCTACACTCAAGAGCTCGTCGGCAGCGTCAGATGTGTAT (SEQ ID NO: 81) |
| C9 | v2_Ad1.67_GCCCACGT | AATGATACGGCGACCACCGAGATCTACACGCCCACGTTCGTCGGCAGCGTCAGATGTGTAT (SEQ ID NO: 82) |
| D9 | v2_Ad1.68_TGGGCGGT | AATGATACGGCGACCACCGAGATCTACACTGGGCGGTTCGTCGGCAGCGTCAGATGTGTAT (SEQ ID NO: 83) |
| E9 | v2_Ad1.69_CCCTTGGA | AATGATACGGCGACCACCGAGATCTACACCCCTTGGATCGTCGGCAGCGTCAGATGTGTAT (SEQ ID NO: 84) |
| F9 | v2_Ad1.70_ATTACCGT | AATGATACGGCGACCACCGAGATCTACACATTACCGTTCGTCGGCAGCGTCAGATGTGTAT (SEQ ID NO: 85) |
| G9 | v2_Ad1.71_AGTCCGAG | AATGATACGGCGACCACCGAGATCTACACAGTCCGAGTCGTCGGCAGCGTCAGATGTGTAT (SEQ ID NO: 86) |

TABLE 2-continued

| 96 Well Columns | (plate Ad1) Custom Barcodes Adapter 1 (index i5): | sequence |
|---|---|---|
| H9 | v2_Ad1.72_ACTTGTTG | AATGATACGGCGACCACCGAGATCTACACACTTGTTGTCGTCGGCAGCGTCAGATGTGTAT (SEQ ID NO: 87) |
| A10 | v2_Ad1.73_GTAATACA | AATGATACGGCGACCACCGAGATCTACACGTAATACATCGTCGGCAGCGTCAGATGTGTAT (SEQ ID NO: 88) |
| B10 | v2_Ad1.74_GGCGTCTA | AATGATACGGCGACCACCGAGATCTACACGGCGTCTATCGTCGGCAGCGTCAGATGTGTAT (SEQ ID NO: 89) |
| C10 | v2_Ad1.75_GCGCTGCT | AATGATACGGCGACCACCGAGATCTACACGCGCTGCTTCGTCGGCAGCGTCAGATGTGTAT (SEQ ID NO: 90) |
| D10 | v2_Ad1.76_GTGCCATT | AATGATACGGCGACCACCGAGATCTACACGTGCCATTTCGTCGGCAGCGTCAGATGTGTAT (SEQ ID NO: 91) |
| E10 | v2_Ad1.77_TAGGTATG | AATGATACGGCGACCACCGAGATCTACACTAGGTATGTCGTCGGCAGCGTCAGATGTGTAT (SEQ ID NO: 92) |
| F10 | v2_Ad1.78_AACACCTA | AATGATACGGCGACCACCGAGATCTACACAACACCTATCGTCGGCAGCGTCAGATGTGTAT (SEQ ID NO: 93) |
| G10 | v2_Ad1.79_CTCCGAAC | AATGATACGGCGACCACCGAGATCTACACCTCCGAACTCGTCGGCAGCGTCAGATGTGTAT (SEQ ID NO: 94) |
| H10 | v2_Ad1.80_CAACGGCA | AATGATACGGCGACCACCGAGATCTACACCAACGGCATCGTCGGCAGCGTCAGATGTGTAT (SEQ ID NO: 95) |
| A11 | v2_Ad1.81_CAATGTAG | AATGATACGGCGACCACCGAGATCTACACCAATGTAGTCGTCGGCAGCGTCAGATGTGTAT (SEQ ID NO: 96) |
| B11 | v2_Ad1.82_GGCTACCC | AATGATACGGCGACCACCGAGATCTACACGGCTACCCTCGTCGGCAGCGTCAGATGTGTAT (SEQ ID NO: 97) |
| C11 | v2_Ad1.83_AAAGTCCG | AATGATACGGCGACCACCGAGATCTACACAAAGTCCGTCGTCGGCAGCGTCAGATGTGTAT (SEQ ID NO: 98) |
| D11 | v2_Ad1.84_TTCCGCGG | AATGATACGGCGACCACCGAGATCTACACTTCCGCGGTCGTCGGCAGCGTCAGATGTGTAT (SEQ ID NO: 99) |
| E11 | v2_Ad1.85_AGGCACTT | AATGATACGGCGACCACCGAGATCTACACAGGCACTTTCGTCGGCAGCGTCAGATGTGTAT (SEQ ID NO: 100) |
| F11 | v2_Ad1.86_CTTCAGTG | AATGATACGGCGACCACCGAGATCTACACCTTCAGTGTCGTCGGCAGCGTCAGATGTGTAT (SEQ ID NO: 101) |
| G11 | v2_Ad1.87_GCCGGTAG | AATGATACGGCGACCACCGAGATCTACACGCCGGTAGTCGTCGGCAGCGTCAGATGTGTAT (SEQ ID NO: 102) |
| H11 | v2_Ad1.88_TTCAATCC | AATGATACGGCGACCACCGAGATCTACACTTCAATCCTCGTCGGCAGCGTCAGATGTGTAT (SEQ ID NO: 103) |
| A12 | v2_Ad1.89_CCACACAC | AATGATACGGCGACCACCGAGATCTACACCCACACACTCGTCGGCAGCGTCAGATGTGTAT (SEQ ID NO: 104) |
| B12 | v2_Ad1.90_ATATTATC | AATGATACGGCGACCACCGAGATCTACACATATTATCTCGTCGGCAGCGTCAGATGTGTAT (SEQ ID NO: 105) |
| C12 | v2_Ad1.91_CCGAAGCA | AATGATACGGCGACCACCGAGATCTACACCCGAAGCATCGTCGGCAGCGTCAGATGTGTAT (SEQ ID NO: 106) |
| D12 | v2_Ad1.92_GTATCGGT | AATGATACGGCGACCACCGAGATCTACACGTATCGGTTCGTCGGCAGCGTCAGATGTGTAT (SEQ ID NO: 107) |

TABLE 3

| Well Position | Name | Sequence |
|---|---|---|
| A1 | Round1_01 | /5Phos/CGCGCTGCATACTTGAACGTGATCCCATGATCGTCCGA (SEQ ID NO: 108) |
| B1 | Round1_02 | /5Phos/CGCGCTGCATACTTGAAACATCGCCCATGATCGTCCGA (SEQ ID NO: 109) |

TABLE 3-continued

| Well Position | Name | Sequence |
|---|---|---|
| C1 | Round1_03 | /5Phos/CGCGCTGCATACTTGATGCCTAACCCATGATCGTCCGA (SEQ ID NO: 110) |
| D1 | Round1_04 | /5Phos/CGCGCTGCATACTTGAGTGGTCACCCATGATCGTCCGA (SEQ ID NO: 111) |
| E1 | Round1_05 | /5Phos/CGCGCTGCATACTTGACCACTGTCCCATGATCGTCCGA (SEQ ID NO: 112) |
| F1 | Round1_06 | /5Phos/CGCGCTGCATACTTGACATTGGCCCCATGATCGTCCGA (SEQ ID NO: 113) |
| G1 | Round1_07 | /5Phos/CGCGCTGCATACTTGCAGATCTGCCCATGATCGTCCGA (SEQ ID NO: 114) |
| H1 | Round1_08 | /5Phos/CGCGCTGCATACTTGCATCAAGTCCCATGATCGTCCGA (SEQ ID NO: 115) |
| A2 | Round1_09 | /5Phos/CGCGCTGCATACTTGCGCTGATCCCCATGATCGTCCGA (SEQ ID NO: 116) |
| B2 | Round1_10 | /5Phos/CGCGCTGCATACTTGACAAGCTACCCATGATCGTCCGA (SEQ ID NO: 117) |
| C2 | Round1_11 | /5Phos/CGCGCTGCATACTTGCTGTAGCCCCCATGATCGTCCGA (SEQ ID NO: 118) |
| D2 | Round1_12 | /5Phos/CGCGCTGCATACTTGAGTACAAGCCCATGATCGTCCGA (SEQ ID NO: 119) |
| E2 | Round1_13 | /5Phos/CGCGCTGCATACTTGAACAACCACCCATGATCGTCCGA (SEQ ID NO: 120) |
| F2 | Round1_14 | /5Phos/CGCGCTGCATACTTGAACCGAGACCCATGATCGTCCGA (SEQ ID NO: 121) |
| G2 | Round1_15 | /5Phos/CGCGCTGCATACTTGAACGCTTACCCATGATCGTCCGA (SEQ ID NO: 122) |
| H2 | Round1_16 | /5Phos/CGCGCTGCATACTTGAAGACGGACCCATGATCGTCCGA (SEQ ID NO: 123) |
| A3 | Round1_17 | /5Phos/CGCGCTGCATACTTGAAGGTACACCCATGATCGTCCGA (SEQ ID NO: 124) |
| B3 | Round1_18 | /5Phos/CGCGCTGCATACTTGACACAGAACCCATGATCGTCCGA (SEQ ID NO: 125) |
| C3 | Round1_19 | /5Phos/CGCGCTGCATACTTGACAGCAGACCCATGATCGTCCGA (SEQ ID NO: 126) |
| D3 | Round1_20 | /5Phos/CGCGCTGCATACTTGACCTCCAACCCATGATCGTCCGA (SEQ ID NO: 127) |
| E3 | Round1_21 | /5Phos/CGCGCTGCATACTTGACGCTCGACCCATGATCGTCCGA (SEQ ID NO: 128) |
| F3 | Round1_22 | /5Phos/CGCGCTGCATACTTGACGTATCACCCATGATCGTCCGA (SEQ ID NO: 129) |
| G3 | Round1_23 | /5Phos/CGCGCTGCATACTTGACTATGCACCCATGATCGTCCGA (SEQ ID NO: 130) |
| H3 | Round1_24 | /5Phos/CGCGCTGCATACTTGAGAGTCAACCCATGATCGTCCGA (SEQ ID NO: 131) |
| A4 | Round1_25 | /5Phos/CGCGCTGCATACTTGAGATCGCACCCATGATCGTCCGA (SEQ ID NO: 132) |
| B4 | Round1_26 | /5Phos/CGCGCTGCATACTTGAGCAGGAACCCATGATCGTCCGA (SEQ ID NO: 133) |
| C4 | Round1_27 | /5Phos/CGCGCTGCATACTTGAGTCACTACCCATGATCGTCCGA (SEQ ID NO: 134) |
| D4 | Round1_28 | /5Phos/CGCGCTGCATACTTGATCCTGTACCCATGATCGTCCGA (SEQ ID NO: 135) |
| E4 | Round1_29 | /5Phos/CGCGCTGCATACTTGATTGAGGACCCATGATCGTCCGA (SEQ ID NO: 136) |
| F4 | Round1_30 | /5Phos/CGCGCTGCATACTTGCAACCACACCCATGATCGTCCGA (SEQ ID NO: 137) |
| G4 | Round1_31 | /5Phos/CGCGCTGCATACTTGGACTAGTACCCATGATCGTCCGA (SEQ ID NO: 138) |
| H4 | Round1_32 | /5Phos/CGCGCTGCATACTTGCAATGGAACCCATGATCGTCCGA (SEQ ID NO: 139) |
| A5 | Round1_33 | /5Phos/CGCGCTGCATACTTGCACTTCGACCCATGATCGTCCGA (SEQ ID NO: 140) |
| B5 | Round1_34 | /5Phos/CGCGCTGCATACTTGCAGCGTTACCCATGATCGTCCGA (SEQ ID NO: 141) |
| C5 | Round1_35 | /5Phos/CGCGCTGCATACTTGCATACCAACCCATGATCGTCCGA (SEQ ID NO: 142) |
| D5 | Round1_36 | /5Phos/CGCGCTGCATACTTGCCAGTTCACCCATGATCGTCCGA (SEQ ID NO: 143) |
| E5 | Round1_37 | /5Phos/CGCGCTGCATACTTGCCGAAGTACCCATGATCGTCCGA (SEQ ID NO: 144) |
| F5 | Round1_38 | /5Phos/CGCGCTGCATACTTGCCGTGAGACCCATGATCGTCCGA (SEQ ID NO: 145) |
| G5 | Round1_39 | /5Phos/CGCGCTGCATACTTGCCTCCTGACCCATGATCGTCCGA (SEQ ID NO: 146) |
| H5 | Round1_40 | /5Phos/CGCGCTGCATACTTGCGAACTTACCCATGATCGTCCGA (SEQ ID NO: 147) |

TABLE 3-continued

| Well Position | Name | Sequence |
|---|---|---|
| A6 | Round1_41 | /5Phos/CGCGCTGCATACTTGCGACTGGACCCATGATCGTCCGA (SEQ ID NO: 148) |
| B6 | Round1_42 | /5Phos/CGCGCTGCATACTTGCGCATACACCCATGATCGTCCGA (SEQ ID NO: 149) |
| C6 | Round1_43 | /5Phos/CGCGCTGCATACTTGCTCAATGACCCATGATCGTCCGA (SEQ ID NO: 150) |
| D6 | Round1_44 | /5Phos/CGCGCTGCATACTTGCTGAGCCACCCATGATCGTCCGA (SEQ ID NO: 151) |
| E6 | Round1_45 | /5Phos/CGCGCTGCATACTTGCTGGCATACCCATGATCGTCCGA (SEQ ID NO: 152) |
| F6 | Round1_46 | /5Phos/CGCGCTGCATACTTGGAATCTGACCCATGATCGTCCGA (SEQ ID NO: 153) |
| G6 | Round1_47 | /5Phos/CGCGCTGCATACTTGCAAGACTACCCATGATCGTCCGA (SEQ ID NO: 154) |
| H6 | Round1_48 | /5Phos/CGCGCTGCATACTTGGAGCTGAACCCATGATCGTCCGA (SEQ ID NO: 155) |
| A7 | Round1_49 | /5Phos/CGCGCTGCATACTTGGATAGACACCCATGATCGTCCGA (SEQ ID NO: 156) |
| B7 | Round1_50 | /5Phos/CGCGCTGCATACTTGGCCACATACCCATGATCGTCCGA (SEQ ID NO: 157) |
| C7 | Round1_51 | /5Phos/CGCGCTGCATACTTGGCGAGTAACCCATGATCGTCCGA (SEQ ID NO: 158) |
| D7 | Round1_52 | /5Phos/CGCGCTGCATACTTGGCTAACGACCCATGATCGTCCGA (SEQ ID NO: 159) |
| E7 | Round1_53 | /5Phos/CGCGCTGCATACTTGGCTCGGTACCCATGATCGTCCGA (SEQ ID NO: 160) |
| F7 | Round1_54 | /5Phos/CGCGCTGCATACTTGGGAGAACACCCATGATCGTCCGA (SEQ ID NO: 161) |
| G7 | Round1_55 | /5Phos/CGCGCTGCATACTTGGGTGCGAACCCATGATCGTCCGA (SEQ ID NO: 162) |
| H7 | Round1_56 | /5Phos/CGCGCTGCATACTTGGTACGCAACCCATGATCGTCCGA (SEQ ID NO: 163) |
| A8 | Round1_57 | /5Phos/CGCGCTGCATACTTGGTCGTAGACCCATGATCGTCCGA (SEQ ID NO: 164) |
| B8 | Round1_58 | /5Phos/CGCGCTGCATACTTGGTCTGTCACCCATGATCGTCCGA (SEQ ID NO: 165) |
| C8 | Round1_59 | /5Phos/CGCGCTGCATACTTGGTGTTCTACCCATGATCGTCCGA (SEQ ID NO: 166) |
| D8 | Round1_60 | /5Phos/CGCGCTGCATACTTGTAGGATGACCCATGATCGTCCGA (SEQ ID NO: 167) |
| E8 | Round1_61 | /5Phos/CGCGCTGCATACTTGTATCAGCACCCATGATCGTCCGA (SEQ ID NO: 168) |
| F8 | Round1_62 | /5Phos/CGCGCTGCATACTTGTCCGTCTACCCATGATCGTCCGA (SEQ ID NO: 169) |
| G8 | Round1_63 | /5Phos/CGCGCTGCATACTTGTCTTCACACCCATGATCGTCCGA (SEQ ID NO: 170) |
| H8 | Round1_64 | /5Phos/CGCGCTGCATACTTGTGAAGAGACCCATGATCGTCCGA (SEQ ID NO: 171) |
| A9 | Round1_65 | /5Phos/CGCGCTGCATACTTGTGGAACAACCCATGATCGTCCGA (SEQ ID NO: 172) |
| B9 | Round1_66 | /5Phos/CGCGCTGCATACTTGTGGCTTCACCCATGATCGTCCGA (SEQ ID NO: 173) |
| C9 | Round1_67 | /5Phos/CGCGCTGCATACTTGTGGTGGTACCCATGATCGTCCGA (SEQ ID NO: 174) |
| D9 | Round1_68 | /5Phos/CGCGCTGCATACTTGTTCACGCACCCATGATCGTCCGA (SEQ ID NO: 175) |
| E9 | Round1_69 | /5Phos/CGCGCTGCATACTTGAACTCACCCCATGATCGTCCGA (SEQ ID NO: 176) |
| F9 | Round1_70 | /5Phos/CGCGCTGCATACTTGAAGAGATCCCCATGATCGTCCGA (SEQ ID NO: 177) |
| G9 | Round1_71 | /5Phos/CGCGCTGCATACTTGAAGGACACCCCATGATCGTCCGA (SEQ ID NO: 178) |
| H9 | Round1_72 | /5Phos/CGCGCTGCATACTTGAATCCGTCCCCATGATCGTCCGA (SEQ ID NO: 179) |
| A10 | Round1_73 | /5Phos/CGCGCTGCATACTTGAATGTTGCCCCATGATCGTCCGA (SEQ ID NO: 180) |
| B10 | Round1_74 | /5Phos/CGCGCTGCATACTTGACACGACCCCCATGATCGTCCGA (SEQ ID NO: 181) |
| C10 | Round1_75 | /5Phos/CGCGCTGCATACTTGACAGATTCCCCATGATCGTCCGA (SEQ ID NO: 182) |
| D10 | Round1_76 | /5Phos/CGCGCTGCATACTTGAGATGTACCCCATGATCGTCCGA (SEQ ID NO: 183) |
| E10 | Round1_77 | /5Phos/CGCGCTGCATACTTGAGCACCTCCCCATGATCGTCCGA (SEQ ID NO: 184) |
| F10 | Round1_78 | /5Phos/CGCGCTGCATACTTGAGCCATGCCCCATGATCGTCCGA (SEQ ID NO: 185) |

TABLE 3-continued

| Well Position | Name | Sequence |
|---|---|---|
| G10 | Round1_79 | /5Phos/CGCGCTGCATACTTGAGGCTAACCCCATGATCGTCCGA (SEQ ID NO: 186) |
| H10 | Round1_80 | /5Phos/CGCGCTGCATACTTGATAGCGACCCCATGATCGTCCGA (SEQ ID NO: 187) |
| A11 | Round1_81 | /5Phos/CGCGCTGCATACTTGATCATTCCCCATGATCGTCCGA (SEQ ID NO: 188) |
| B11 | Round1_82 | /5Phos/CGCGCTGCATACTTGATTGGCTCCCCATGATCGTCCGA (SEQ ID NO: 189) |
| C11 | Round1_83 | /5Phos/CGCGCTGCATACTTGCAAGGAGCCCCATGATCGTCCGA (SEQ ID NO: 190) |
| D11 | Round1_84 | /5Phos/CGCGCTGCATACTTGCACCTTACCCCATGATCGTCCGA (SEQ ID NO: 191) |
| E11 | Round1_85 | /5Phos/CGCGCTGCATACTTGCCATCCTCCCCATGATCGTCCGA (SEQ ID NO: 192) |
| F11 | Round1_86 | /5Phos/CGCGCTGCATACTTGCCGACAACCCCATGATCGTCCGA (SEQ ID NO: 193) |
| G11 | Round1_87 | /5Phos/CGCGCTGCATACTTGCCTAATCCCCATGATCGTCCGA (SEQ ID NO: 194) |
| H11 | Round1_88 | /5Phos/CGCGCTGCATACTTGCCTCTATCCCCATGATCGTCCGA (SEQ ID NO: 195) |
| A12 | Round1_89 | /5Phos/CGCGCTGCATACTTGCGACACACCCCATGATCGTCCGA (SEQ ID NO: 196) |
| B12 | Round1_90 | /5Phos/CGCGCTGCATACTTGCGGATTGCCCCATGATCGTCCGA (SEQ ID NO: 197) |
| C12 | Round1_91 | /5Phos/CGCGCTGCATACTTGCTAAGGTCCCCATGATCGTCCGA (SEQ ID NO: 198) |
| D12 | Round1_92 | /5Phos/CGCGCTGCATACTTGGAACAGGCCCCATGATCGTCCGA (SEQ ID NO: 199) |
| E12 | Round1_93 | /5Phos/CGCGCTGCATACTTGGACAGTGCCCCATGATCGTCCGA (SEQ ID NO: 200) |
| F12 | Round1_94 | /5Phos/CGCGCTGCATACTTGGAGTTAGCCCCATGATCGTCCGA (SEQ ID NO: 201) |
| G12 | Round1_95 | /5Phos/CGCGCTGCATACTTGGATGAATCCCCATGATCGTCCGA (SEQ ID NO: 202) |
| H12 | Round1_96 | /5Phos/CGCGCTGCATACTTGGCCAAGACCCCATGATCGTCCGA (SEQ ID NO: 203) |

TABLE 4

| Well Position | Name | Sequence |
|---|---|---|
| A1 | Round2_01 | /5Phos/CATCGGCGTACGACTAACGTGATATCCACGTGCTTGAG (SEQ ID NO: 204) |
| B1 | Round2_02 | /5Phos/CATCGGCGTACGACTAAACATCGATCCACGTGCTTGAG (SEQ ID NO: 205) |
| C1 | Round2_03 | /5Phos/CATCGGCGTACGACTATGCCTAAATCCACGTGCTTGAG (SEQ ID NO: 206) |
| D1 | Round2_04 | /5Phos/CATCGGCGTACGACTAGTGGTCAATCCACGTGCTTGAG (SEQ ID NO: 207) |
| E1 | Round2_05 | /5Phos/CATCGGCGTACGACTACCACTGTATCCACGTGCTTGAG (SEQ ID NO: 208) |
| F1 | Round2_06 | /5Phos/CATCGGCGTACGACTACATTGGCATCCACGTGCTTGAG (SEQ ID NO: 209) |
| G1 | Round2_07 | /5Phos/CATCGGCGTACGACTCAGATCTGATCCACGTGCTTGAG (SEQ ID NO: 210) |
| H1 | Round2_08 | /5Phos/CATCGGCGTACGACTCATCAAGTATCCACGTGCTTGAG (SEQ ID NO: 211) |
| A2 | Round2_09 | /5Phos/CATCGGCGTACGACTCGCTGATCATCCACGTGCTTGAG (SEQ ID NO: 212) |
| B2 | Round2_10 | /5Phos/CATCGGCGTACGACTACAAGCTAATCCACGTGCTTGAG (SEQ ID NO: 213) |
| C2 | Round2_11 | /5Phos/CATCGGCGTACGACTCTGTAGCCATCCACGTGCTTGAG (SEQ ID NO: 214) |
| D2 | Round2_12 | /5Phos/CATCGGCGTACGACTAGTACAAGATCCACGTGCTTGAG (SEQ ID NO: 215) |
| E2 | Round2_13 | /5Phos/CATCGGCGTACGACTAACAACCAATCCACGTGCTTGAG (SEQ ID NO: 216) |
| F2 | Round2_14 | /5Phos/CATCGGCGTACGACTAACCGAGAATCCACGTGCTTGAG (SEQ ID NO: 217) |
| G2 | Round2_15 | /5Phos/CATCGGCGTACGACTAACGCTTAATCCACGTGCTTGAG (SEQ ID NO: 218) |
| H2 | Round2_16 | /5Phos/CATCGGCGTACGACTAAGACGGAATCCACGTGCTTGAG (SEQ ID NO: 219) |
| A3 | Round2_17 | /5Phos/CATCGGCGTACGACTAAGGTACAATCCACGTGCTTGAG (SEQ ID NO: 220) |
| B3 | Round2_18 | /5Phos/CATCGGCGTACGACTACACAGAAATCCACGTGCTTGAG (SEQ ID NO: 221) |
| C3 | Round2_19 | /5Phos/CATCGGCGTACGACTACAGCAGAATCCACGTGCTTGAG (SEQ ID NO: 222) |

TABLE 4-continued

| Well Position | Name | Sequence |
|---|---|---|
| D3 | Round2_20 | /5Phos/CATCGGCGTACGACTACCTCCAAATCCACGTGCTTGAG (SEQ ID NO: 223) |
| E3 | Round2_21 | /5Phos/CATCGGCGTACGACTACGCTCGAATCCACGTGCTTGAG (SEQ ID NO: 224) |
| F3 | Round2_22 | /5Phos/CATCGGCGTACGACTACGTATCAATCCACGTGCTTGAG (SEQ ID NO: 225) |
| G3 | Round2_23 | /5Phos/CATCGGCGTACGACTACTATGCAATCCACGTGCTTGAG (SEQ ID NO: 226) |
| H3 | Round2_24 | /5Phos/CATCGGCGTACGACTAGAGTCAAATCCACGTGCTTGAG (SEQ ID NO: 227) |
| A4 | Round2_25 | /5Phos/CATCGGCGTACGACTAGATCGCAATCCACGTGCTTGAG (SEQ ID NO: 228) |
| B4 | Round2_26 | /5Phos/CATCGGCGTACGACTAGCAGGAAATCCACGTGCTTGAG (SEQ ID NO: 229) |
| C4 | Round2_27 | /5Phos/CATCGGCGTACGACTAGTCACTAATCCACGTGCTTGAG (SEQ ID NO: 230) |
| D4 | Round2_28 | /5Phos/CATCGGCGTACGACTATCCTGTAATCCACGTGCTTGAG (SEQ ID NO: 231) |
| E4 | Round2_29 | /5Phos/CATCGGCGTACGACTATTGAGGAATCCACGTGCTTGAG (SEQ ID NO: 232) |
| F4 | Round2_30 | /5Phos/CATCGGCGTACGACTCAACCACAATCCACGTGCTTGAG (SEQ ID NO: 233) |
| G4 | Round2_31 | /5Phos/CATCGGCGTACGACTGACTAGTAATCCACGTGCTTGAG (SEQ ID NO: 234) |
| H4 | Round2_32 | /5Phos/CATCGGCGTACGACTCAATGGAAATCCACGTGCTTGAG (SEQ ID NO: 235) |
| A5 | Round2_33 | /5Phos/CATCGGCGTACGACTCACTTCGAATCCACGTGCTTGAG (SEQ ID NO: 236) |
| B5 | Round2_34 | /5Phos/CATCGGCGTACGACTCAGCGTTAATCCACGTGCTTGAG (SEQ ID NO: 237) |
| C5 | Round2_35 | /5Phos/CATCGGCGTACGACTCATACCAAATCCACGTGCTTGAG (SEQ ID NO: 238) |
| D5 | Round2_36 | /5Phos/CATCGGCGTACGACTCCAGTTCAATCCACGTGCTTGAG (SEQ ID NO: 239) |
| E5 | Round2_37 | /5Phos/CATCGGCGTACGACTCCGAAGTAATCCACGTGCTTGAG (SEQ ID NO: 240) |
| F5 | Round2_38 | /5Phos/CATCGGCGTACGACTCCGTGAGAATCCACGTGCTTGAG (SEQ ID NO: 241) |
| G5 | Round2_39 | /5Phos/CATCGGCGTACGACTCCTCCTGAATCCACGTGCTTGAG (SEQ ID NO: 242) |
| H5 | Round2_40 | /5Phos/CATCGGCGTACGACTCGAACTTAATCCACGTGCTTGAG (SEQ ID NO: 243) |
| A6 | Round2_41 | /5Phos/CATCGGCGTACGACTCGACTGGAATCCACGTGCTTGAG (SEQ ID NO: 244) |
| B6 | Round2_42 | /5Phos/CATCGGCGTACGACTCGCATACAATCCACGTGCTTGAG (SEQ ID NO: 245) |
| C6 | Round2_43 | /5Phos/CATCGGCGTACGACTCTCAATGAATCCACGTGCTTGAG (SEQ ID NO: 246) |
| D6 | Round2_44 | /5Phos/CATCGGCGTACGACTCTGAGCCAATCCACGTGCTTGAG (SEQ ID NO: 247) |
| E6 | Round2_45 | /5Phos/CATCGGCGTACGACTCTGGCATAATCCACGTGCTTGAG (SEQ ID NO: 248) |
| F6 | Round2_46 | /5Phos/CATCGGCGTACGACTGAATCTGAATCCACGTGCTTGAG (SEQ ID NO: 249) |
| G6 | Round2_47 | /5Phos/CATCGGCGTACGACTCAAGACTAATCCACGTGCTTGAG (SEQ ID NO: 250) |
| H6 | Round2_48 | /5Phos/CATCGGCGTACGACTGAGCTGAAATCCACGTGCTTGAG (SEQ ID NO: 251) |
| A7 | Round2_49 | /5Phos/CATCGGCGTACGACTGATAGACAATCCACGTGCTTGAG (SEQ ID NO: 252) |
| B7 | Round2_50 | /5Phos/CATCGGCGTACGACTGCCACATAATCCACGTGCTTGAG (SEQ ID NO: 253) |
| C7 | Round2_51 | /5Phos/CATCGGCGTACGACTGCGAGTAAATCCACGTGCTTGAG (SEQ ID NO: 254) |
| D7 | Round2_52 | /5Phos/CATCGGCGTACGACTGCTAACGAATCCACGTGCTTGAG (SEQ ID NO: 255) |
| E7 | Round2_53 | /5Phos/CATCGGCGTACGACTGCTCGGTAATCCACGTGCTTGAG (SEQ ID NO: 256) |
| F7 | Round2_54 | /5Phos/CATCGGCGTACGACTGGAGAACAATCCACGTGCTTGAG (SEQ ID NO: 257) |
| G7 | Round2_55 | /5Phos/CATCGGCGTACGACTGGTGCGAAATCCACGTGCTTGAG (SEQ ID NO: 258) |
| H7 | Round2_56 | /5Phos/CATCGGCGTACGACTGTACGCAAATCCACGTGCTTGAG (SEQ ID NO: 259) |
| A8 | Round2_57 | /5Phos/CATCGGCGTACGACTGTCGTAGAATCCACGTGCTTGAG (SEQ ID NO: 260) |

TABLE 4-continued

| Well Position | Name | Sequence |
|---|---|---|
| B8 | Round2_58 | /5Phos/CATCGGCGTACGACTGTCTGTCAATCCACGTGCTTGAG (SEQ ID NO: 261) |
| C8 | Round2_59 | /5Phos/CATCGGCGTACGACTGTGTTCTAATCCACGTGCTTGAG (SEQ ID NO: 262) |
| D8 | Round2_60 | /5Phos/CATCGGCGTACGACTTAGGATGAATCCACGTGCTTGAG (SEQ ID NO: 263) |
| E8 | Round2_61 | /5Phos/CATCGGCGTACGACTTATCAGCAATCCACGTGCTTGAG (SEQ ID NO: 264) |
| F8 | Round2_62 | /5Phos/CATCGGCGTACGACTTCCGTCTAATCCACGTGCTTGAG (SEQ ID NO: 265) |
| G8 | Round2_63 | /5Phos/CATCGGCGTACGACTTCTTCACAATCCACGTGCTTGAG (SEQ ID NO: 266) |
| H8 | Round2_64 | /5Phos/CATCGGCGTACGACTTGAAGAGAATCCACGTGCTTGAG (SEQ ID NO: 267) |
| A9 | Round2_65 | /5Phos/CATCGGCGTACGACTTGGAACAAATCCACGTGCTTGAG (SEQ ID NO: 268) |
| B9 | Round2_66 | /5Phos/CATCGGCGTACGACTTGGCTTCAATCCACGTGCTTGAG (SEQ ID NO: 269) |
| C9 | Round2_67 | /5Phos/CATCGGCGTACGACTTGGTGGTAATCCACGTGCTTGAG (SEQ ID NO: 270) |
| D9 | Round2_68 | /5Phos/CATCGGCGTACGACTTTCACGCAATCCACGTGCTTGAG (SEQ ID NO: 271) |
| E9 | Round2_69 | /5Phos/CATCGGCGTACGACTAACTCACCATCCACGTGCTTGAG (SEQ ID NO: 272) |
| F9 | Round2_70 | /5Phos/CATCGGCGTACGACTAAGAGATCATCCACGTGCTTGAG (SEQ ID NO: 273) |
| G9 | Round2_71 | /5Phos/CATCGGCGTACGACTAAGGACACATCCACGTGCTTGAG (SEQ ID NO: 274) |
| H9 | Round2_72 | /5Phos/CATCGGCGTACGACTAATCCGTCATCCACGTGCTTGAG (SEQ ID NO: 275) |
| A10 | Round2_73 | /5Phos/CATCGGCGTACGACTAATGTTGCATCCACGTGCTTGAG (SEQ ID NO: 276) |
| B10 | Round2_74 | /5Phos/CATCGGCGTACGACTACACGACCATCCACGTGCTTGAG (SEQ ID NO: 277) |
| C10 | Round2_75 | /5Phos/CATCGGCGTACGACTACAGATTCATCCACGTGCTTGAG (SEQ ID NO: 278) |
| D10 | Round2_76 | /5Phos/CATCGGCGTACGACTAGATGTACATCCACGTGCTTGAG (SEQ ID NO: 279) |
| E10 | Round2_77 | /5Phos/CATCGGCGTACGACTAGCACCTCATCCACGTGCTTGAG (SEQ ID NO: 280) |
| F10 | Round2_78 | /5Phos/CATCGGCGTACGACTAGCCATGCATCCACGTGCTTGAG (SEQ ID NO: 281) |
| G10 | Round2_79 | /5Phos/CATCGGCGTACGACTAGGCTAACATCCACGTGCTTGAG (SEQ ID NO: 282) |
| H10 | Round2_80 | /5Phos/CATCGGCGTACGACTATAGCGACATCCACGTGCTTGAG (SEQ ID NO: 283) |
| A11 | Round2_81 | /5Phos/CATCGGCGTACGACTATCATTCCATCCACGTGCTTGAG (SEQ ID NO: 284) |
| B11 | Round2_82 | /5Phos/CATCGGCGTACGACTATTGGCTCATCCACGTGCTTGAG (SEQ ID NO: 285) |
| C11 | Round2_83 | /5Phos/CATCGGCGTACGACTCAAGGAGCATCCACGTGCTTGAG (SEQ ID NO: 286) |
| D11 | Round2_84 | /5Phos/CATCGGCGTACGACTCACCTTACATCCACGTGCTTGAG (SEQ ID NO: 287) |
| E11 | Round2_85 | /5Phos/CATCGGCGTACGACTCCATCCTCATCCACGTGCTTGAG (SEQ ID NO: 288) |
| F11 | Round2_86 | /5Phos/CATCGGCGTACGACTCCGACAACATCCACGTGCTTGAG (SEQ ID NO: 289) |
| G11 | Round2_87 | /5Phos/CATCGGCGTACGACTCCTAATCATCCACGTGCTTGAG (SEQ ID NO: 290) |
| H11 | Round2_88 | /5Phos/CATCGGCGTACGACTCCTCTATCATCCACGTGCTTGAG (SEQ ID NO: 291) |
| A12 | Round2_89 | /5Phos/CATCGGCGTACGACTCGACACACATCCACGTGCTTGAG (SEQ ID NO: 292) |
| B12 | Round2_90 | /5Phos/CATCGGCGTACGACTCGGATTGCATCCACGTGCTTGAG (SEQ ID NO: 293) |
| C12 | Round2_91 | /5Phos/CATCGGCGTACGACTCTAAGGTCATCCACGTGCTTGAG (SEQ ID NO: 294) |
| D12 | Round2_92 | /5Phos/CATCGGCGTACGACTGAACAGGCATCCACGTGCTTGAG (SEQ ID NO: 295) |
| E12 | Round2_93 | /5Phos/CATCGGCGTACGACTGACAGTGCATCCACGTGCTTGAG (SEQ ID NO: 296) |
| F12 | Round2_94 | /5Phos/CATCGGCGTACGACTGAGTTAGCATCCACGTGCTTGAG (SEQ ID NO: 297) |
| G12 | Round2_95 | /5Phos/CATCGGCGTACGACTGATGAATCATCCACGTGCTTGAG (SEQ ID NO: 298) |

TABLE 4-continued

| Well Position | Name | Sequence |
|---|---|---|
| H12 | Round2_96 | /5Phos/CATCGGCGTACGACTG CCAAGACATCCACGTGCTTGAG (SEQ ID NO: 299) |

TABLE 5

| Well Position | Name | Sequence |
|---|---|---|
| A1 | Round3_01 | CAAGCAGAAGACGGCATACGAGAT AACGTGATGTGGCCGATGTTTCG (SEQ ID NO: 300) |
| B1 | Round3_02 | CAAGCAGAAGACGGCATACGAGAT AAACATCGGTGGCCGATGTTTCG (SEQ ID NO: 301) |
| C1 | Round3_03 | CAAGCAGAAGACGGCATACGAGAT ATGCCTAAGTGGCCGATGTTTCG (SEQ ID NO: 302) |
| D1 | Round3_04 | CAAGCAGAAGACGGCATACGAGAT AGTGGTCAGTGGCCGATGTTTCG (SEQ ID NO: 303) |
| E1 | Round3_05 | CAAGCAGAAGACGGCATACGAGAT ACCACTGTGTGGCCGATGTTTCG (SEQ ID NO: 304) |
| F1 | Round3_06 | CAAGCAGAAGACGGCATACGAGAT ACATTGGCGTGGCCGATGTTTCG (SEQ ID NO: 305) |
| G1 | Round3_07 | CAAGCAGAAGACGGCATACGAGAT CAGATCTGGTGGCCGATGTTTCG (SEQ ID NO: 306) |
| H1 | Round3_08 | CAAGCAGAAGACGGCATACGAGAT CATCAAGTGTGGCCGATGTTTCG (SEQ ID NO: 307) |
| A2 | Round3_09 | CAAGCAGAAGACGGCATACGAGAT CGCTGATCGTGGCCGATGTTTCG (SEQ ID NO: 308) |
| B2 | Round3_10 | CAAGCAGAAGACGGCATACGAGAT ACAAGCTAGTGGCCGATGTTTCG (SEQ ID NO: 309) |
| C2 | Round3_11 | CAAGCAGAAGACGGCATACGAGAT CTGTAGCCGTGGCCGATGTTTCG (SEQ ID NO: 310) |
| D2 | Round3_12 | CAAGCAGAAGACGGCATACGAGAT AGTACAAGGTGGCCGATGTTTCG (SEQ ID NO: 311) |
| E2 | Round3_13 | CAAGCAGAAGACGGCATACGAGAT AACAACCAGTGGCCGATGTTTCG (SEQ ID NO: 312) |
| F2 | Round3_14 | CAAGCAGAAGACGGCATACGAGAT AACCGAGAGTGGCCGATGTTTCG (SEQ ID NO: 313) |
| G2 | Round3_15 | CAAGCAGAAGACGGCATACGAGAT AACGCTTAGTGGCCGATGTTTCG (SEQ ID NO: 314) |
| H2 | Round3_16 | CAAGCAGAAGACGGCATACGAGAT AAGACGGAGTGGCCGATGTTTCG (SEQ ID NO: 315) |
| A3 | Round3_17 | CAAGCAGAAGACGGCATACGAGAT AAGGTACAGTGGCCGATGTTTCG (SEQ ID NO: 316) |
| B3 | Round3_18 | CAAGCAGAAGACGGCATACGAGAT ACACAGAAGTGGCCGATGTTTCG (SEQ ID NO: 317) |
| C3 | Round3_19 | CAAGCAGAAGACGGCATACGAGAT ACAGCAGAGTGGCCGATGTTTCG (SEQ ID NO: 318) |
| D3 | Round3_20 | CAAGCAGAAGACGGCATACGAGAT ACCTCCAGTGTGGCCGATGTTTCG (SEQ ID NO: 319) |
| E3 | Round3_21 | CAAGCAGAAGACGGCATACGAGAT ACGCTCGAGTGGCCGATGTTTCG (SEQ ID NO: 320) |
| F3 | Round3_22 | CAAGCAGAAGACGGCATACGAGAT ACGTATCAGTGGCCGATGTTTCG (SEQ ID NO: 321) |
| G3 | Round3_23 | CAAGCAGAAGACGGCATACGAGAT ACTATGCAGTGGCCGATGTTTCG (SEQ ID NO: 322) |
| H3 | Round3_24 | CAAGCAGAAGACGGCATACGAGAT AGAGTCAAGTGGCCGATGTTTCG (SEQ ID NO: 323) |
| A4 | Round3_25 | CAAGCAGAAGACGGCATACGAGAT AGATCGCAGTGGCCGATGTTTCG (SEQ ID NO: 324) |
| B4 | Round3_26 | CAAGCAGAAGACGGCATACGAGAT AGCAGGAAGTGGCCGATGTTTCG (SEQ ID NO: 325) |
| C4 | Round3_27 | CAAGCAGAAGACGGCATACGAGAT AGTCACTAGTGGCCGATGTTTCG (SEQ ID NO: 326) |
| D4 | Round3_28 | CAAGCAGAAGACGGCATACGAGAT ATCCTGTAGTGGCCGATGTTTCG (SEQ ID NO: 327) |
| E4 | Round3_29 | CAAGCAGAAGACGGCATACGAGAT ATTGAGGAGTGGCCGATGTTTCG (SEQ ID NO: 328) |
| F4 | Round3_30 | CAAGCAGAAGACGGCATACGAGAT CAACCACGTGGCCGATGTTTCG (SEQ ID NO: 329) |
| G4 | Round3_31 | CAAGCAGAAGACGGCATACGAGAT GACTAGTAGTGGCCGATGTTTCG (SEQ ID NO: 330) |
| H4 | Round3_32 | CAAGCAGAAGACGGCATACGAGAT CAATGGAAGTGGCCGATGTTTCG (SEQ ID NO: 331) |
| A5 | Round3_33 | CAAGCAGAAGACGGCATACGAGAT CACTTCGAGTGGCCGATGTTTCG (SEQ ID NO: 332) |
| B5 | Round3_34 | CAAGCAGAAGACGGCATACGAGAT CAGCGTTAGTGGCCGATGTTTCG (SEQ ID NO: 333) |
| C5 | Round3_35 | CAAGCAGAAGACGGCATACGAGAT CATACCAAGTGGCCGATGTTTCG (SEQ ID NO: 334) |

TABLE 5-continued

| Well Position | Name | Sequence |
|---|---|---|
| D5 | Round3_36 | CAAGCAGAAGACGGCATACGAGATCCAGTTCAGTGGCCGATGTTTCG (SEQ ID NO: 335) |
| E5 | Round3_37 | CAAGCAGAAGACGGCATACGAGATCCGAAGTAGTGGCCGATGTTTCG (SEQ ID NO: 336) |
| F5 | Round3_38 | CAAGCAGAAGACGGCATACGAGATCCGTGAGAGTGGCCGATGTTTCG (SEQ ID NO: 337) |
| G5 | Round3_39 | CAAGCAGAAGACGGCATACGAGATCCTCCTGAGTGGCCGATGTTTCG (SEQ ID NO: 338) |
| H5 | Round3_40 | CAAGCAGAAGACGGCATACGAGATCGAACTTAGTGGCCGATGTTTCG (SEQ ID NO: 339) |
| A6 | Round3_41 | CAAGCAGAAGACGGCATACGAGATCGACTGGAGTGGCCGATGTTTCG (SEQ ID NO: 340) |
| B6 | Round3_42 | CAAGCAGAAGACGGCATACGAGATCGCATACAGTGGCCGATGTTTCG (SEQ ID NO: 341) |
| C6 | Round3_43 | CAAGCAGAAGACGGCATACGAGATCTCAATGAGTGGCCGATGTTTCG (SEQ ID NO: 342) |
| D6 | Round3_44 | CAAGCAGAAGACGGCATACGAGATCTGAGCCAGTGGCCGATGTTTCG (SEQ ID NO: 343) |
| E6 | Round3_45 | CAAGCAGAAGACGGCATACGAGATCTGGCATAGTGGCCGATGTTTCG (SEQ ID NO: 344) |
| F6 | Round3_46 | CAAGCAGAAGACGGCATACGAGATGAATCTGAGTGGCCGATGTTTCG (SEQ ID NO: 345) |
| G6 | Round3_47 | CAAGCAGAAGACGGCATACGAGATCAAGACTAGTGGCCGATGTTTCG (SEQ ID NO: 346) |
| H6 | Round3_48 | CAAGCAGAAGACGGCATACGAGATGAGCTGAAGTGGCCGATGTTTCG (SEQ ID NO: 347) |
| A7 | Round3_49 | CAAGCAGAAGACGGCATACGAGATGATAGACAGTGGCCGATGTTTCG (SEQ ID NO: 348) |
| B7 | Round3_50 | CAAGCAGAAGACGGCATACGAGATGCCACATAGTGGCCGATGTTTCG (SEQ ID NO: 349) |
| C7 | Round3_51 | CAAGCAGAAGACGGCATACGAGATGCGAGTAAGTGGCCGATGTTTCG (SEQ ID NO: 350) |
| D7 | Round3_52 | CAAGCAGAAGACGGCATACGAGATGCTAACGAGTGGCCGATGTTTCG (SEQ ID NO: 351) |
| E7 | Round3_53 | CAAGCAGAAGACGGCATACGAGATGCTCGGTAGTGGCCGATGTTTCG (SEQ ID NO: 352) |
| F7 | Round3_54 | CAAGCAGAAGACGGCATACGAGATGGAGAACAGTGGCCGATGTTTCG (SEQ ID NO: 353) |
| G7 | Round3_55 | CAAGCAGAAGACGGCATACGAGATGGTGCGAAGTGGCCGATGTTTCG (SEQ ID NO: 354) |
| H7 | Round3_56 | CAAGCAGAAGACGGCATACGAGATGTACGCAAGTGGCCGATGTTTCG (SEQ ID NO: 355) |
| A8 | Round3_57 | CAAGCAGAAGACGGCATACGAGATGTCGTAGAGTGGCCGATGTTTCG (SEQ ID NO: 356) |
| B8 | Round3_58 | CAAGCAGAAGACGGCATACGAGATGTCTGTCAGTGGCCGATGTTTCG (SEQ ID NO: 357) |
| C8 | Round3_59 | CAAGCAGAAGACGGCATACGAGATGTGTTCTAGTGGCCGATGTTTCG (SEQ ID NO: 358) |
| D8 | Round3_60 | CAAGCAGAAGACGGCATACGAGATTAGGATGAGTGGCCGATGTTTCG (SEQ ID NO: 359) |
| E8 | Round3_61 | CAAGCAGAAGACGGCATACGAGATTATCAGCAGTGGCCGATGTTTCG (SEQ ID NO: 360) |
| F8 | Round3_62 | CAAGCAGAAGACGGCATACGAGATTCCGTCTAGTGGCCGATGTTTCG (SEQ ID NO: 361) |
| G8 | Round3_63 | CAAGCAGAAGACGGCATACGAGATTCTTCACAGTGGCCGATGTTTCG (SEQ ID NO: 362) |
| H8 | Round3_64 | CAAGCAGAAGACGGCATACGAGATTGAAGAGAGTGGCCGATGTTTCG (SEQ ID NO: 363) |
| A9 | Round3_65 | CAAGCAGAAGACGGCATACGAGATTGGAACAAGTGGCCGATGTTTCG (SEQ ID NO: 364) |
| B9 | Round3_66 | CAAGCAGAAGACGGCATACGAGATTGGCTTCAGTGGCCGATGTTTCG (SEQ ID NO: 365) |
| C9 | Round3_67 | CAAGCAGAAGACGGCATACGAGATTGGTGGTAGTGGCCGATGTTTCG (SEQ ID NO: 366) |
| D9 | Round3_68 | CAAGCAGAAGACGGCATACGAGATTTCACGCAGTGGCCGATGTTTCG (SEQ ID NO: 367) |
| E9 | Round3_69 | CAAGCAGAAGACGGCATACGAGATAACTCACCGTGGCCGATGTTTCG (SEQ ID NO: 368) |
| F9 | Round3_70 | CAAGCAGAAGACGGCATACGAGATAAGAGATCGTGGCCGATGTTTCG (SEQ ID NO: 369) |
| G9 | Round3_71 | CAAGCAGAAGACGGCATACGAGATAAGGACACGTGGCCGATGTTTCG (SEQ ID NO: 370) |
| H9 | Round3_72 | CAAGCAGAAGACGGCATACGAGATAATCCGTCGTGGCCGATGTTTCG (SEQ ID NO: 371) |
| A10 | Round3_73 | CAAGCAGAAGACGGCATACGAGATAATGTTGCGTGGCCGATGTTTCG (SEQ ID NO: 372) |

TABLE 5-continued

| Well Position | Name | Sequence |
|---|---|---|
| B10 | Round3_74 | CAAGCAGAAGACGGCATACGAGAT ACACGACCGTGGCCGATGTTTCG (SEQ ID NO: 373) |
| C10 | Round3_75 | CAAGCAGAAGACGGCATACGAGAT ACAGATTCGTGGCCGATGTTTCG (SEQ ID NO: 374) |
| D10 | Round3_76 | CAAGCAGAAGACGGCATACGAGAT AGATGTACGTGGCCGATGTTTCG (SEQ ID NO: 375) |
| E10 | Round3_77 | CAAGCAGAAGACGGCATACGAGAT AGCACCTCGTGGCCGATGTTTCG (SEQ ID NO: 376) |
| F10 | Round3_78 | CAAGCAGAAGACGGCATACGAGAT AGCCATGCGTGGCCGATGTTTCG (SEQ ID NO: 377) |
| G10 | Round3_79 | CAAGCAGAAGACGGCATACGAGAT AGGCTAACGTGGCCGATGTTTCG (SEQ ID NO: 378) |
| H10 | Round3_80 | CAAGCAGAAGACGGCATACGAGAT ATAGCGACGTGGCCGATGTTTCG (SEQ ID NO: 379) |
| A11 | Round3_81 | CAAGCAGAAGACGGCATACGAGAT ATCATTCCGTGGCCGATGTTTCG (SEQ ID NO: 380) |
| B11 | Round3_82 | CAAGCAGAAGACGGCATACGAGAT ATTGGCTCGTGGCCGATGTTTCG (SEQ ID NO: 381) |
| C11 | Round3_83 | CAAGCAGAAGACGGCATACGAGAT CAAGGAGCGTGGCCGATGTTTCG (SEQ ID NO: 382) |
| D11 | Round3_84 | CAAGCAGAAGACGGCATACGAGAT CACCTTACGTGGCCGATGTTTCG (SEQ ID NO: 383) |
| E11 | Round3_85 | CAAGCAGAAGACGGCATACGAGAT CCATCCTCGTGGCCGATGTTTCG (SEQ ID NO: 384) |
| F11 | Round3_86 | CAAGCAGAAGACGGCATACGAGAT CCGACAACGTGGCCGATGTTTCG (SEQ ID NO: 385) |
| G11 | Round3_87 | CAAGCAGAAGACGGCATACGAGAT CCTAATCCGTGGCCGATGTTTCG (SEQ ID NO: 386) |
| H11 | Round3_88 | CAAGCAGAAGACGGCATACGAGAT CCTCTATCGTGGCCGATGTTTCG (SEQ ID NO: 387) |
| A12 | Round3_89 | CAAGCAGAAGACGGCATACGAGAT CGACACACGTGGCCGATGTTTCG (SEQ ID NO: 388) |
| B12 | Round3_90 | CAAGCAGAAGACGGCATACGAGAT CGGATTGCGTGGCCGATGTTTCG (SEQ ID NO: 389) |
| C12 | Round3_91 | CAAGCAGAAGACGGCATACGAGAT CTAAGGTCGTGGCCGATGTTTCG (SEQ ID NO: 390) |
| D12 | Round3_92 | CAAGCAGAAGACGGCATACGAGAT GAACAGGCGTGGCCGATGTTTCG (SEQ ID NO: 391) |
| E12 | Round3_93 | CAAGCAGAAGACGGCATACGAGAT GACAGTGCGTGGCCGATGTTTCG (SEQ ID NO: 392) |
| F12 | Round3_94 | CAAGCAGAAGACGGCATACGAGAT GAGTTAGCGTGGCCGATGTTTCG (SEQ ID NO: 393) |
| G12 | Round3_95 | CAAGCAGAAGACGGCATACGAGAT GATGAATCGTGGCCGATGTTTCG (SEQ ID NO: 394) |
| H12 | Round3_96 | CAAGCAGAAGACGGCATACGAGAT GCCAAGACGTGGCCGATGTTTCG (SEQ ID NO: 395) |

The 100 µM Read1 and Phosphorylated Read2 oligos were annealed with equal amount of 100 µM blocked ME-compliment oligo by heating at 85° C. for 2 min and slowly cooling down to 20° C. at a ramp rate of −1° C./min. The annealed oligos were mixed with equal volume of cold glycerol and stored at −80° C. until use. In-house produced Tn5[3], was mixed with equal volume of dilution buffer (50 mM Tris, 100 mM NaCl, 0.1 mM EDTA, 1 mM DTT, 0.1% NP-40, and 50% glycerol). The diluted Tn5 was then mixed with equal volume of annealed oligos and incubated at room temperature for 30 min before transposition.

Cells (50k-1k cells in 5 µl PBS) and 42.5 µl of transposition buffer (38.8 mM Tris-acetate, 77.6 mM K-acetate, 11.8 mM Mg-acetate, 18.8% DIME, 0.12% NP-40, 0.47% Protease Inhibitor Cocktail, and 0.8 U/µl Enzymatics RNase Inhibitor) were mixed and incubated at room temperature for 10 min. 2.5 µl of assembled Tn5 was added to the transposition reaction. As an alternative SUPERase In RNase inhibitor (Thermo Fisher) could be used. Other RNase inhibitors, including RNaseOUT (Thermo fisher) and Recombinant RNase Inhibitor (Takara), could reduce transposition efficiency. The transposition was carried out at 37° C. for 30 min with shaking at 300 rpm. The reaction was stopped by adding 5 µl of 0.5 M EDTA and incubated at 37° C. for 15 minutes with gentle shaking at 300 rpm. All the cells were then pooled and 2 µl of 1 M MgCl2 was added to the pooled sample. The sample was centrifuged at 500 g for 5 min and then washed with 1 ml washing buffer (10 mM Tris buffer (pH 7.5), 10 mM NaCl, 3 mM MgCl, and 0.1% NP40). The sample was resuspended to 10 µl of Tris buffer (pH 8.0) and proceed to reverse transcription.

Reverse Transcription

Transposed cells (10 µl) were mixed with 40 µl of RT mix (1×RT buffer, 0.5 U/µl Enzymatics RNase Inhibitor, 625 µM dNTP, 12.5 µM RT primer with affinity tag, 18.75% PEG 6000, and 25 U/µl Maxima H Minus Reverse Transcriptase). The final concentration of PEG can be in the range of 3-15%. The RT primer contains a poly-T tail, a unique molecular identifier (UMI), a universal ligation overhand, and a biotin molecule. The sample was heated at 50° C. for 10 min, then went through 3 thermal cycles (8° C. for 12s, 15° C. for 45s, 20° C. for 45s, 30° C. for 30s, 42° C. for 120s and 50° C. for 180s), and finally incubated at 50° C. for 5 min. Alternatively, other RT mix (M-MLV, SensiScript, ProtoScript II, Superscript II, Superscript III, and SuperScrip IV) and temperature conditions can also be used. While RT primer with biotin tag is used in this protocol, other affinity tags (FLAG, HaloTag, V5, etc.) could also be used. After reverse transcription, 1 µl of 5% Triton X-100 was added and the sample was centrifuged at 1000 g for 3 min to move supernatant. The cell pellet was washed twice with 1 ml of washing buffer and centrifuged at 1000 g for 3 min between washings. The cells were resuspended in hybridization mix (1×T4 ligation buffer, 0.32 U/µl Enzymatics RNase Inhibitor, 8 U/µl T4 ligase (M0202L, NEB), 0.1% Triton X-100).

Hybridization and Ligation

The cells can be barcoded using various existing technologies, including plate-based methods 1,4,5, droplet-based methods 6,7*(SureCell from Biorad, 10× Genomics), microwell-based methods 8,9, or microfluidic chip based methods 10. As an example, Applicants chose plate-based methods.

40 µl of cells in ligation mix were added to each of the 96 wells in the first-round barcoding plate. Each well already contained 10 µl of the appropriate DNA barcodes. The round 1 barcoding plate was incubated for 30 min at 37° C. with gentle shaking (300 rpm) to allow hybridization to occur before adding blocking strands. 10 µl of round 1 blocking oligo was added and the plate was incubated for 30 min at 37° C. with gentle shaking (300 rpm). Cells from all 96 wells were combined into a single multichannel basin. Subsequent steps in round 2 and round 3 were identical to round 1, except that 50 µl and 60 µl of pooled cells was split and added to barcodes in round 2 (total volume of 60 µl/well) and round 3 (total volume of 70 µl/well), respectively. After adding the round 3 blocking oligo (no incubation is needed), the cells from all wells were combined and centrifuged at 1000 g for 3 min to move supernatant. The cell pellet was washed twice with 0.5 ml of resuspension buffer (Tris with 0.1% Triton X-100 and 2 U/µl SUPERase inhibitor), and centrifuged at 1000 g for 3 min between washings. The cells were re-suspended in ligation mix (1×T4 ligation buffer, 0.32 U/µl Enzymatics RNase Inhibitor, 20 U/µl T4 DNA ligase (NEB), 0.1% Triton X-100) and incubated for 30 min at 37° C. with gentle shaking (300 rpm). The ligation was terminated by adding 2.5 µl of 0.5 M EDTA. The cells were washed once with washing buffer and resuspended in 60 µl of resuspension buffer, counted and aliquoted to 0.2 ml PCR tubes with desired number of cells.

Reverse Crosslinking and Affinity Pull Down

Tris buffer (pH 8.0) was added to each sample to 48 µl in total. 50 µl of 2× reverse crosslinking buffer (100 mM Tris pH 8.0, 100 mM NaCl, and 0.04% SDS) and 2 µl of 20 mg/ml proteinase K was mixed with each sample and incubated at 55° C. for 1-2 hours. 5 µl of 100 mM PMSF was added to the reverse crosslinked sample to inactive proteinase K and incubated at room temperature for 10 min. For each sample, 10 µl of MyOne C1 Dynabeads were washed three times with 1× B&W-T buffer (5 mM Tris pH 8.0, 1 M NaCl, 0.5 mM EDTA, 0.05% Tween 20, and 2 U/µl SUPERase inhibitor). After washing, the beads were resuspended in 100 µl of 2×B&W buffer (10 mM Tris pH 8.0, 2 M NaCl, 1 mM EDTA, and 4 U/µl SUPERase inhibitor) and mixed with the sample. The sample and beads mixture were rotated on an end-to-end rotator at 10 rpm for 60 min at room temperature. The lysate was put on a magnetic stand to separate supernatant and beads.

ATAC-Seq Library Preparation

The supernatant that contained the transposed DNA fragments was purified with Zymo DNA clean and concentrator and eluted to 10 µl of Tris buffer (pH 8.0). The fragments were PCR amplified with Ad1 primer with sample barcodes and P7 primer. The amplification procedure was similar to standard bulk ATAC-seq library with minor modifications. The annealing temperature was set to 65° C. instead of 72° C. The primer concentration was reduced to 0.5 µM instead of 1.25 µM.

cDNA Library Preparation

The beads were washed three times with 1×B&W-T buffer and once with $H_2O$ containing 1 U/µl SUPERase inhibitor. The beads were resuspended in 50 µl of template switch mix (15% PEG 6000, 1× Maxima RT buffer, 4% Ficoll PM-400, 1 mM dNTPs, 1 U/µl Enzymatics RNase-In, 2.5 µM TSO, and 10 U/µl Maxima H Minus Reverse Transcriptase). The beads were rotated on an end-to-end rotator at 10 rpm for 30 min at room temperature, and then shaken at 300 rpm for 90 min at 42° C. The beads were resuspended by pipetting every 30 min during agitation. After template switching, 100 µl of $H_2O$ was added to each tube to dilute sample. The supernatant was removed by placing the sample on a magnetic stand. The beads were washed with 200 µl of $H_2O$ without disturbing the beads pellet. The beads were then resuspended in 55 µl of PCR mix (1× Kapa Hifi PCR mix, 400 nM P7 primer, and 400 nM RNA PCR primer). The PCR reaction was carried out at following condition: 95° C. for 3 min, and then thermocycling at 98° C. for 30 s, 65° C. for 45 s and 72° C. for 3 min. After 5 cycles, Applicants took 2.5 µl sample and added 7.5 µl of PCR cocktail with 1× EvaGreen (Biotium). The 10 µl reactions were amplified to saturation to determine the number of cycles required for the remaining samples on the plate. The qPCR reaction was carried out at following condition: 95° C. for 3 min, and then 20 thermal cycles at 98° C. for 30 s, 65° C. for 20 s and 72° C. for 3 min. Libraries were amplified for 12 cycles in total for 1000 cells. The amplified cDNA was purified by 0.8× AMpure beads and eluted to 10 µl of Tris pH 8.0 buffer. The amount of cDNA was quantified by qubit.

Tagmentation and RNA-Seq Library Preparation

The 100 µM Read1 were annealed with equal amount of 100 µM blocked ME-compliment oligo and assembled with Tn5 as described above. For each sample, 50 ng cDNA was tagmented in 50 µl tagmentation mix (1×TD buffer from Illumina Nextera Kit, and 5 µl assembled Tn5) at 55° C. for 5 min. The tagmented cDNA was purified with Zymo DNA clean and concentrator and eluted to 10 µl of Tris pH 8.0 buffer. The purified cDNA was then mixed with tagmentation PCR mix (25 µl of NEBNext High-Fidelity 2×PCR Master Mix, 1 µl of 25 µM P7 primer and 1 µl of 25 µM Ad1 primer with sample barcodes). The PCR reaction was carried out at following condition: 72° C. for 5 min, 98° C. for 30 s, and then 7 cycles at 98° C. for 10 s, 65° C. for 30 s and 72° C. for 1 min. The amplified library was purified by 0.7× AMpure beads and eluted to 10 µl of Tris pH 8.0 buffer.

Quantification and Sequencing

Both ATAC-seq and RNA-seq libraries were quantified with KAPA Library Quantification Kit. Libraries were sequenced on the Next-seq platform (Illumina) using a 150-cycle kit (Read 1: 30 cycles, Index 1: 99 cycles, Index 2: 8 cycles, Read 2: 30 cycles).

REFERENCES

1 Rosenberg, A. B. et al. Single-cell profiling of the developing mouse brain and spinal cord with split-pool barcoding. *Science* (2018).
2 Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nat. Methods* 10, 1213-1218, doi:10.1038/nmeth.2688 (2013).

3 Picelli, S. et al. Tn5 transposase and tagmentation procedures for massively scaled sequencing projects. *Genome Res.* 24, 2033-2040, doi:10.1101/gr.177881.114 (2014).

4 Cao, J. et al. Joint profiling of chromatin accessibility and gene expression in thousands of single cells. *Science*, doi: 10.1126/science.aau0730 (2018).

5 Cusanovich, D. A. et al. Multiplex single-cell profiling of chromatin accessibility by combinatorial cellular indexing. *Science* 348, 910-914, doi:10.1126/science.aab1601 (2015).

6 Macosko, Evan Z. et al. Highly Parallel Genome-wide Expression Profiling of Individual Cells Using Nanoliter Droplets. *Cell* 161, 1202-1214, doi:10.1016/j.cell.2015.05.002 (2015).

7 Klein, Allon M. et al. Droplet Barcoding for Single-Cell Transcriptomics Applied to Embryonic Stem Cells. *Cell* 161, 1187-1201, (2015).

8 Gierahn, T. M. et al. Seq-Well: portable, low-cost RNA sequencing of single cells at high throughput. *Nat. Methods* 14, 395, doi: 10.1038/nmeth.4179 (2017).

9 Mezger, A. et al. High-throughput chromatin accessibility profiling at single-cell resolution. *Nat. Commun.* 9, 3647, doi:10.1038/s41467-018-05887-x (2018).

10 Buenrostro, J. D. et al. Single-cell chromatin accessibility reveals principles of regulatory variation. *Nature* 523, 486-490, doi:10.1038/nature14590 (2015).

Example 2—Integrative Single-Cell Chromatin and Transcriptome Profiling Uncovers Cell-Type Specific Regulatory Interactions One central goal of cell biology is to understand the relationship between genome regulation and gene expression. Toward this effort, coincident measurements of different layers of regulation provide opportunities to infer functional relationships. As such, previous efforts have used genomic technologies to profile diverse cell populations or tissues, and together with capable computational approaches, have modeled functional regulatory interactions (Buenrostro et al. *Cell* 173:1535-1548 (2018)). These approaches have been essential in Applicants' effort to reveal the function of the genome, yielding new insights including i) non-coding regulatory elements and their impact on gene expression and ii) the effect of transcription factors (TFs) on chromatin structure (Roadmap Epigenomics Consortium Kundaje et al. *Nature* 518:317-330 (2015)). Together these integrated approaches can expose the molecular drivers defining cell type and state, however, these efforts are limited to breadth and depth due to limits of assay throughput and limitations of isolating pure cell subsets from heterogeneous tissues.

Single-cell genomic technologies provide a unique opportunity to observe diverse regulatory states across heterogeneous tissues. Methods have been developed to assay the epigenome (Buenrostro et al. *Nature* 523:486-490 (2015); Cusanovich et al. *Science* 348:910-914 920165)); Lareau et al. Droplet-based combinatorial indexing for massive scale single-cell epigenomics. Doi:10.1101/612713), transcriptome (Klein et al. *Cell* 161:1187-1201 (2015); Rosenberg et al. *Science* 360:176-182 (2018); Macosko et al. *Cell* 161: 1202-1214 (2015)) and protein (Stoeckius et al. *Nat Methods* 14:865-868 (2017)) at single-cell resolution. Towards integrative analyses, methods to computationally pair these diverse datasets have been developed (Stuart et al. Comprehensive integration of single cell data. doi:10.1101/460147). However, these inference approaches strongly rely on current models of gene regulation and as a consequence are likely to miss new biology. In contrast, direct methods to measure different molecules within the same single-cell, referred to as "multi-omic" methods, have been developed (Clark et al. scNMT-seq enables joint profiling of chromatin accessibility DNA methylation and transcription in single cells. (2017). doi:10.1101/138685; Pott, Simultaneous measurement of chromatin accessibility, DNA methylation, and nucleosome phasing in single cells (2016) doi.10,1101/061739; Dey et al. *Nat Biotechnol* 33:285-289 (2015); Macaulay et al. *Nat Methods* 12:519-522 (2015); Angermueller et al. *Nat Methods* 13:229-232 (2016); Hou et al. *Cell Res* 26:304-319 (2016); Liu et al. Deconvolution of single-cell multi-omics layers reveals regulatory heterogeneity (2018) doi.10.1101/316208; Guo et al. *Cell Res* 27:967-988 (2017); Frei et al. *Nat Methods* 13:269-275 (2016)). Many approaches measuring the epigenome and transcriptome rely on physically isolating single-cells (Clark et al. scNMT-seq enables joint profiling of chromatin accessibility DNA methylation and transcription in single cells. (2017). doi:10.1101/138685; Pott, Simultaneous measurement of chromatin accessibility, DNA methylation, and nucleosome phasing in single cells (2016) doi.10,1101/061739; Dey et al. *Nat Biotechnol* 33:285-289 (2015); Macaulay et al. *Nat Methods* 12:519-522 (2015); Angermueller et al. *Nat Methods* 13:229-232 (2016); Hou et al. *Cell Res* 26:304-319 (2016); Liu et al. Deconvolution of single-cell multi-omics layers reveals regulatory heterogeneity (2018) doi.10.1101/316208; Guo et al. *Cell Res* 27:967-988 (2017)), limiting their throughput (~$10^2$ cells). Methods for pairing chromatin accessibility with gene expression using combinatorial indexing (Cao et al. *Science* 361:1380-1385 (2018)) have improved the throughput of these assays (~$10^3$ cells). However, the highly reduced data quality (number of fragments per cell), cost and throughput limit the application of this method for practical use. Thus, to enable tissue-scale or organism-scale single-cell analyses for defining regulatory interactions across the bread and depth of cellular diversity within tissues, improved multi-omic assays are needed.

Here, Applicants developed a method for Simultaneous High-throughput ATAC and RNA Expression with sequencing (SHARE-seq), which allows individually or jointly profiling of single cell chromatin accessibility and RNA expression at low-cost and massive scale (>$10^4$ cells). Applicants validate the robustness of this approach by profiling four cell lines and adult mouse brain.

SHARE-Seq a Method to Profile Chromatin and Expression at Scale.

Advancements of single cell technologies using multiple rounds of ligation to introduce cell-specific barcodes have enabled transcriptional profiling at large scale (>$10^4$ cells) (Rosenberg et al. *Science* 360:176-182 (2018)). Here, Applicants sought to adapt a split-pool approach to develop SHARE-seq, which utilizes multiple rounds of hybridization-blocking to uniquely and simultaneously label mRNA and chromatin fragments from the same single cells (FIG. 9A). To do this at high-quality, Applicants have significantly optimized the molecular biology steps for each reaction described below. In brief, fixed cells are (i) transposed by Tn5 transposase to mark open chromatin (Buenrostro et al. *Nat Methods* 10:1213-1218 (2013)), (ii) mRNA is reverse transcribed using a poly(T) primer containing a unique molecular identifier (UMI), and a biotin tag, (iii) nuclei are then distributed in a 96-well plate to hybridize well-specific barcoded oligonucleotides. Here, well-specific barcodes hybridize to both transposed chromatin fragments and poly (T) cDNA through a common DNA sequence. (iv) Hybridization is repeated three or more times expanding the barcoding space to approximately 106 barcode combinations or more.

Following hybridization, barcodes are ligated to the cDNA and chromatin fragments. (v) To complete the process Applicants perform reverse crosslinking to release chromatin fragments and cDNA fragments, cDNA fragments are specifically collected using streptavidin beads. Following pulldown, cDNA is prepared using template-switching (Rosenberg et al. Science 360:176-182 (2018)), PCR and tagmentation and transposed chromatin fragments are PCR amplified. Following sequencing, cells are identified using the unique combination of well-specific barcodes, ATAC and RNA data share the same cell-identifying barcodes, and ATAC-seq and RNA-seq reads are distinguished from PCR-based DNA barcodes.

To perform SHARE-seq at large-scale, Applicants designed four barcode sets (three introduced during hybridization and one during PCR) for each sample (FIG. 9B) allowing up to 84,934,656 (96$4$) barcode combinations. Using this barcode space millions of cells can be uniquely labelled in a single experiment with minimal barcode collisions for organism-scale profiling or allowing multiplexing of 96 samples in a single experiment with substantial lower cost compared to other approaches. Further, barcoding is conceptually extendable to even larger experiments by using additional rounds of hybridization.

Applicants performed SHARE-seq on a mixture of cells containing a human cell line (GM12878) and a mouse cell line (NIH/3T3) to validate that cell barcodes represent single-cells. In this proof-of-principle, Applicants found that human and mouse reads are well separated on both chromatin and transcriptional profiles (FIG. 9B-9D). Applicants obtained 903 human and 1,341 mouse cells. Interestingly, there was only one cell doublet (1 cell out of 2,245 barcode combinations) representing 0.04% collision, compared to the expected rate of 0.013%, demonstrated an extraordinarily low collision rate. For cells passing filter, Applicants recovered an average of 2,145 and 2,814 RNA UMIs (8,281 and 10,588 UMIs if sequencing to saturation by estimation) for human and mouse respectively, and an average of 9,369 and 7,499 unique ATAC-seq fragments (67.5% and 63.4% of fragments in peaks) respectively. Consistent with previous studies, Applicants found variations of chromatin accessibility in the cell lines. By comparing the NFkB1 gene expression and chromatin fragments around NFkB1 locus, Applicants observed positive correlation of the two signals at single cell level (FIG. 9E).

SHARE-Seq on the Murine Brain Defines Cell Types.

To determine whether concurrent measurement of chromatin and gene expression enables improved maps of cell type diversity, Applicants applied SHARE-seq to adult mouse brain. Using this approach Applicants recovered SHARE-seq profiles from 3,293 nuclei (an average of 4,119 UMIs for RNA-seq and 2,485 unique fragments for ATAC-seq) with high quality, including an average of 47.0% reads in peaks (FIG. 10A). SHARE-seq could also be used for ATAC-only or RNA-only profiling in complex tissues. To further assess the quality of the SHARE-seq data, Applicants profiled other tissues (human heart, mouse colon, human CD34+ cord blood mononuclear cells (CBMC), and mouse lung) and compared the SHARE-seq profiles to other ATAC-only (sci-ATAC (LaFave et al. under review), SureCell (Lareau et al. Droplet-based combinatorial indexing for massive scale single-cell epigenomics. Doi:10.1101/ 612713), 10× (Satpathy et al. *Nat Biotechnol* 37:925-936 (2019)), FIG. 10B) approaches on adult mouse lung with the sample preparation and RNA-only (Drop-seq, 10×) approaches on adult mouse brain (FIG. 10C). Applicants found the SHARE-seq is similar or better to other scRNA-seq approaches, comparable to other scATAC approaches, and consistent across tissues.

Discussion

Concurrent measurement of chromatin and gene expression enables improved maps of cell type diversity. Applying SHARE-seq to a highly diverse tissue, the mouse brain, Applicants found that both data sets largely reflect similar clusters of cell types demonstrating that cell types in the mouse brain coordinate chromatin structure with transcription. Interestingly, Applicants also found that some cell types have more than expected chromatin change. In one example, Applicants found a transcriptionally silent cell population reflecting Neural Stem and Progenitor cells. Altogether, Applicants expect that improvements in reads per cell, inclusion of more -omic measurements, and improved computational methods for integrative clustering will allow for more robustly defined technical biases from axes of true biological variation, enabling a more accurate approach for defining cell types within heterogeneous tissues.

Applicants found that measurements of chromatin accessibility and gene expression at higher coverage and throughput provides an opportunity to determine regulatory relationships even within highly similar cell types. In contrast to bulk profiling methods that determine regulatory interactions across tissues or purified cell-types (Yoshida et al. *Cell* 176:897-912 (2019)), this single-cell approach, leveraging naturally occurring heterogeneity within a cell type, allows for derivation of cell-type specific regulatory models. As such Applicants have used this approach to i) link variable expression of TFs to putative target sites and ii) chromatin accessibility changes at distal elements to variable expression of genes. Applicants validate distal peak-gene interactions using cis-QTLs, and in agreement with prior reports (Yoshida et al. *Cell* 176:897-912 (2019)) Applicants found peak-gene interactions are largely proximal to genes. Together this single-cell resolved regulatory atlas paves the way toward the unbiased annotation of distal regulatory elements and their target genes.

SHARE-seq provides a generalizable platform and opportunity to layer on additional layers of information per cell. With further development, Applicants expect that other scRNA-seq compatible measurements, such as CITE-seq (Stoeckius et al. *Nat Methods* 14:865-868 (2017)), genotyping (Rodriguez-Meira, et al. *Mol. Cell* 73:1292-1305. (2019); Kong, et al. *Clin Chem* 65:272-281 (2019)) and lineage barcoding (Rodriguez-Fraticelli et al. *Nature* 553: 212-216 (2018)) will be integrated into using this generalizable platform. Furthermore, powered by the massive scalability of this approach, SHARE-seq may be particularly useful for perturbation screens (Dixit et al. *Cell* 167:1853-1866. (2016); Datlinger et al. Pooled CRISPR screening with single-cell transcriptome read-out. doi:10.1101/ 08377429). Further, Applicants envision that extension of this approach to other assays may be realized by replacing ATAC-seq with whole genome transposition (Vitak et al. *Nat Methods* 14:302-308 (2017)) enabling methods for DNA methylation (Mulqueen et al. *Nat Biotechnol* 36:428-431 (2018), chromatin conformation (Ramani et al. *Nat Methods* 14:263-266 (2017)), and DNA sequence (Vitak et al. *Nat Methods* 14:302-308 (2017)). In these efforts, scRNA-seq data could be used as a common scaffold to integrate these data, providing a unique opportunity to understand cells. As such, as Applicants move toward a cell atlas, Applicants anticipate SHARE-seq is likely play a key role in determining the full diversity of cell types and cell states, and the regulators that define them.

REFERENCES

1. Buenrostro, J. D. et al. Integrated Single-Cell Analysis Maps the Continuous Regulatory Landscape of Human Hematopoietic Differentiation. Cell 173, 1535-1548.e16 (2018).
2. Roadmap Epigenomics Consortium et al. Integrative analysis of 111 reference human epigenomes. Nature 518, 317-330 (2015).
3. Buenrostro, J. D. et al. Single-cell chromatin accessibility reveals principles of regulatory variation. Nature 523, 486-490 (2015).
4. Cusanovich, D. A. et al. Multiplex single-cell profiling of chromatin accessibility by combinatorial cellular indexing. Science 348, 910-914 (2015).
5. Lareau, C. A. et al. Droplet-based combinatorial indexing for massive scale single-cell epigenomics. doi: 10.1101/612713
6. Klein, A. M. et al. Droplet barcoding for single-cell transcriptomics applied to embryonic stem cells. Cell 161, 1187-1201 (2015).
7. Rosenberg, A. B. et al. Single-cell profiling of the developing mouse brain and spinal cord with split-pool barcoding. Science 360, 176-182 (2018).
8. Macosko, E. Z. et al. Highly Parallel Genome-wide Expression Profiling of Individual Cells Using Nanoliter Droplets. Cell 161, 1202-1214 (2015).
9. Stoeckius, M. et al. Simultaneous epitope and transcriptome measurement in single cells. Nat. Methods 14, 865-868 (2017).
10. Stuart, T. et al. Comprehensive integration of single cell data. doi:10.1101/460147
11. Clark, S. J. et al. scNMT-seq enables joint profiling of chromatin accessibility DNA methylation and transcription in single cells. (2017). doi:10.1101/138685
12. Pott, S. Simultaneous measurement of chromatin accessibility, DNA methylation, and nucleosome phasing in single cells. (2016). doi:10.1101/061739
13. Dey, S. S., Kester, L., Spanjaard, B., Bienko, M. & van Oudenaarden, A. Integrated genome and transcriptome sequencing of the same cell. Nat. Biotechnol. 33, 285-289 (2015).
14. Macaulay, I. C. et al. G&T-seq: parallel sequencing of single-cell genomes and transcriptomes. Nat. Methods 12, 519-522 (2015).
15. Angermueller, C. et al. Parallel single-cell sequencing links transcriptional and epigenetic heterogeneity. Nat. Methods 13, 229-232 (2016).
16. Hou, Y. et al. Single-cell triple omics sequencing reveals genetic, epigenetic and transcriptomic heterogeneity in hepatocellular carcinomas. Cell Res. 26, 304-319 (2016).
17. Liu, L. et al. Deconvolution of single-cell multi-omics layers reveals regulatory heterogeneity. (2018). doi: 10.1101/316208
18. Guo, F. et al. Single-cell multi-omics sequencing of mouse early embryos and embryonic stem cells. Cell Res. 27, 967-988 (2017).
19. Frei, A. P. et al. Highly multiplexed simultaneous detection of RNAs and proteins in single cells. Nat. Methods 13, 269-275 (2016).
20. Cao, J. et al. Joint profiling of chromatin accessibility and gene expression in thousands of single cells. Science 361, 1380-1385 (2018).
21. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat. Methods 10, 1213-1218 (2013).
22. Satpathy, A. T. et al. Massively parallel single-cell chromatin landscapes of human immune cell development and intratumoral T cell exhaustion. Nat. Biotechnol. 37, 925-936 (2019).
23. Larsson, A. J. M. et al. Genomic encoding of transcriptional burst kinetics. Nature 565, 251-254 (2019).
24. Ludwig, L. S. et al. Lineage Tracing in Humans Enabled by Mitochondrial Mutations and Single-Cell Genomics. Cell 176, 1325-1339.e22 (2019).
25. Yoshida, H. et al. The cis-Regulatory Atlas of the Mouse Immune System. Cell 176, 897-912.e20 (2019).
26. Rodriguez-Meira, A. et al. Unravelling Intratumoral Heterogeneity through High-Sensitivity Single-Cell Mutational Analysis and Parallel RNA Sequencing. Mol. Cell 73, 1292-1305.e8 (2019).
27. Kong, S. L. et al. Concurrent Single-Cell RNA and Targeted DNA Sequencing on an Automated Platform for Comeasurement of Genomic and Transcriptomic Signatures. Clin. Chem. 65, 272-281 (2019).
28. Rodriguez-Fraticelli, A. E. et al. Clonal analysis of lineage fate in native haematopoiesis. Nature 553, 212-216 (2018).
29. Dixit, A. et al. Perturb-Seq: Dissecting Molecular Circuits with Scalable Single-Cell RNA Profiling of Pooled Genetic Screens. Cell 167, 1853-1866.e17 (2016).
30. Datlinger, P. et al. Pooled CRISPR screening with single-cell transcriptome read-out. doi: 10.1101/083774
31. Vitak, S. A. et al. Sequencing thousands of single-cell genomes with combinatorial indexing. Nat. Methods 14, 302-308 (2017).
32. Mulqueen, R. M. et al. Highly scalable generation of DNA methylation profiles in single cells. Nat. Biotechnol. 36, 428-431 (2018).
33. Ramani, V. et al. Massively multiplex single-cell Hi-C. Nat. Methods 14, 263-266 (2017).

Example 3—Chromatin-Mediated Lineage Priming and Chromatin Potential Identified by Shared Single Cell Profiling of RNA and Chromatin Cell differentiation and function are regulated at multiple layers and their simultaneous molecular profiling can help infer their mechanistic relationships and understand their distinct contribution to cellular phenotype. In particular, chromatin organization has been postulated to prime changes in gene expression, especially during differentiation, but tracing this during asynchronous processes has remained challenging. Here, Applicants developed SHARE-seq, a highly scalable, sensitive, and cost-effective approach for measurement of chromatin accessibility and gene expression from the same single cell. Applicants applied SHARE-seq to adult mouse tissues (skin, brain, lung) and directly showed the congruence between cellular diversity as defined by chromatin accessibility or RNA expression. Focusing on an atlas of 34,774 high quality profiles from adult mouse skin—a tissue enriched for cell types from diverse lineages and multiple populations of somatic stem cells—Applicants leverage the variation across cells to infer regulatory relationships between chromatin accessibility and gene expression, developed a broadly-applicable computational strategy to determine the impact of regulatory elements on genes, and identified faithfully correlated cis-regulatory interactions that significantly overlap with super-enhancers at lineage-determining genes. Focusing on hair follicle differentiation, Applicants showed that despite the overall broad congruence between the epigenome and transcriptome, during lineage commitment, chromatin accessibility generally activates before the onset of corresponding gene expression. This provided strong evidence of lineage-priming mediated by chromatin accessibility. Applicants leveraged this finding to define chromatin potential, as the priming between the epigenome and transcriptome and showed that chromatin potential predicts cell fate outcomes. The combined scalability and depth of SHARE-seq provided an extensible platform to study regulatory circuitry and cellular dynamics across diverse cells within tissues.

Regulation of chromatin structure and gene expression underlies key developmental transitions in cell lineages (1-3). In recent years, genome-wide profiling of gene expression and chromatin has helped uncover mechanisms of chromatin change at key points of multi-lineage cell fate decisions (1,2). Prior studies comparing profiles of purified populations at distinct differentiation states have observed that changes in histone modifications and binding of lineage associated transcription factors (TFs) may precede and foreshadow changes in gene expression creating primed or poised chromatin states that bias genes for activation or repression to alter lineage outcomes (4-6).

However, an understanding of the dynamics of chromatin-mediated lineage-priming and lineage fate bias has been limited by the resolution of cell isolation strategies and bulk profiling approaches, which rely on pre-defined markers and do not resolve the asynchronous nature of the underlying differentiation process. Methods for combining measurements of different layers of gene regulation within single cells may serve to determine regulators of cell differentiation and function as sensitive markers of cell identity and cell potential (2,7). Computational methods (8) have had some success in integrating single cell epigenome, transcriptome and protein measurements (9) profiled separately; however, because they assume these distinct measurements align and reflect a common cell identity, they may not be able to correctly recover dynamic changes such as in lineage-priming or lineage-foreshadowing. Emerging single cell "multi-omic" technologies (9) offer a direct means to determine the coordination between layers of gene regulation, including the epigenome and gene expression. However, current multi-omic approaches have either limited throughput (9) or limited sensitivity (10-12), hampering their ability to sample sufficient cells or to recover fine but important distinctions between cells.

Here, Applicants investigated the dynamics of the epigenomic and transcriptomic basis of cellular identity, by developing Simultaneous High-throughput ATAC13 and RNA Expression with sequencing (SHARE-seq), for individual or joint measures of single-cell chromatin accessibility and gene expression at low-cost and massive scale. Using SHARE-seq, Applicants profiled 84,426 cells across 4 different cell lines and 3 tissue types, including mouse lung, brain, and skin. In particular, applying SHARE-seq to mouse skin showed that cell type definitions were congruent between chromatin accessibility and gene expression, with notable exceptions including high expression variability for cell cycle genes with little to no associated changes in chromatin accessibility. Applicants leveraged the heterogeneity across cells to infer chromatin-expression relationships and identify 63,110 peak accessibility-gene expression associations in adult mouse skin. High-density peak-to-gene associated regions, which Applicants referred to as Domains of Regulatory Chromatin (DORCs), were enriched for lineage-determining genes and overlap with known super-enhancers14. Strikingly, during hair follicle differentiation, chromatin at DORC-regulated genes became accessible before induction of the corresponding gene's expression, identifying a role for chromatin accessibility in lineage-priming. Finally, building upon this finding, Applicants used lineage-priming of chromatin accessibility to predict cellular trajectories during cell differentiation. Thus, Applicants described an experimental and analytical basis for integrated measurements of the epigenome and transcriptome enabling new avenues to uncover principles of gene regulation and cell fate specification across single cells in diverse systems.

Results

SHARE-Seq for Joint Profiling of Chromatin Accessibility and Gene Expression at Scale To create a chromatin accessibility and mRNA expression co-profiling approach that is both scalable and sensitive, Applicants built upon SPLiT-seq[15], a combinatorial indexing method for scRNA-seq, to develop SHARE-seq, which used multiple rounds of hybridization-blocking to uniquely and simultaneously label mRNA and chromatin fragments in the same single cell (FIGS. 11A, 15A, 15B). Briefly, in SHARE-seq (i) fixed and permeabilized cells or nuclei were transposed by Tn5 transposase to mark regions of open chromatin; (ii) mRNA was reverse transcribed using a poly(T) primer containing a unique molecular identifier (UMI) and a biotin tag; (iii) permeabilized cells or nuclei were distributed in a 96-well plate to hybridize well-specific barcoded oligonucleotides to transposed chromatin fragments and poly(T) cDNA; (iv) hybridization was repeated three times, expanding the barcoding space to approximately $10^6$ ($96^3$) barcode combinations (FIG. 15B, Tables 6A-6E), and, following hybridization, cell barcodes were simultaneously ligated to cDNA and chromatin fragments; (v) reverse crosslinking was performed to release barcoded molecules; (vi) cDNA was specifically separated from chromatin using streptavidin beads and each library is prepared for sequencing; and finally, (vii) paired profiles were identified using the common combination of well-specific barcodes (FIG. 15A). This barcoding strategy may be extended to even larger experiments, by using additional rounds of hybridization (FIG. 15B).

TABLE 6A

| Name | Sequence | Scale | Purification | Specific oligos | |
|---|---|---|---|---|---|
| Round 1 linker | CCGAGCCCACGAGACTCGGACGATCATGGG (SEQ ID NO: 396) | 1 um | STD | | Note: Oligos specific to ATAC-RNA protocol is labelled with * |

TABLE 6A-continued

| Name | Sequence | Scale | Purification | Specific oligos | |
|---|---|---|---|---|---|
| Round 2 linker | CAAGTATGCAGCGCGCTCAAGCACGTGGAT (SEQ ID NO: 397) | 1 um | STD | | Other oligos are designed for split-pool-ligation |
| Round 3 linker | AGTCGTACGCCGATGCGAAACATCGGCCAC (SEQ ID NO: 398) | 1 um | STD | | |
| Round 1 blocking | CCCATGATCGTCCGAGTCTCGTGGGCTCGG (SEQ ID NO: 399) | 1 um | STD | | |
| Round 2 blocking | ATCCACGTGCTTGAGCGCGCTGCATACTTG (SEQ ID NO: 400) | 1 um | STD | | |
| Round 3 blocking | GTGGCCGATGTTTCGCATCGGCGTACGACT (SEQ ID NO: 401) | 1 um | STD | | |
| Read1 | TCGTCGGCAGCGTCAGATGTGTATAAGAGACAG (SEQ ID NO: 402) | 100 nm | HPLC | * | |
| TSO | AAGCAGTGGTATCAACGCAGAGTGAATrGrG+G (SEQ ID NO: 403) | 100 nm | HPLC | * | |
| RNA_PCR_primer | AAGCAGTGGTATCAACGCAGAGT (SEQ ID NO: 404) | 100 nm | STD | * | |
| P7 | CAAGCAGAAGACGGCATACGAGAT (SEQ ID NO: 405) | 100 nm | STD | * | |
| Phosphorylated_Read2 | /5Phos/GTCTCGTGGGCTCGGAGATGTGTATAAGAGACAG (SEQ ID NO: 406) | 100 nm | HPLC | * | The phosphorylation is used for following ligation step |
| RT_primer | /5Phos/GTCTCGTGGGCTCGGAGATGTGTATAAGAGACAGNNNNNNNNNN/iBiodT/TTTTTTTTTTTTTVN (SEQ ID NO: 407) | 100 nm | HPLC | * | The phosphorylation is used for following ligation step |
| Blocked_ME_Comp | /5Phos/C*T*G* T*C*T* C*T*T* A*T*A* C*A*/3ddC/ (SEQ ID NO: 408) | 100 nm | HPLC | * | The phosphorylation is used for following ligation step; The 3ddC modification reduces extension of oligo by polymerase; The phosphorothioation prevents the tagmentation of the oligo itself |

TABLE 6B

| 96 Well Columns | (plate Ad1) Custom Barcodes Adapter 1 (index i5): | Sequences |
|---|---|---|
| A1 | v2_Ad1.01_TAGATCGC | AATGATACGGCGACCACCGAGATCTACACTAGATCGCTCGTCGGCAGCGTCAGATGTGTAT (SEQ ID NO: 409) |
| B1 | v2_Ad1.02_CTCTCTAT | AATGATACGGCGACCACCGAGATCTACACCTCTCTATTCGTCGGCAGCGTCAGATGTGTAT (SEQ ID NO: 410) |
| C1 | v2_Ad1.03_TATCCTCT | AATGATACGGCGACCACCGAGATCTACACTATCCTCTTCGTCGGCAGCGTCAGATGTGTAT (SEQ ID NO: 411) |
| D1 | v2_Ad1.04_AGAGTAGA | AATGATACGGCGACCACCGAGATCTACACAGAGTAGATCGTCGGCAGCGTCAGATGTGTAT (SEQ ID NO: 412) |

TABLE 6B-continued

| 96 Well Columns | (plate Ad1) Custom Barcodes Adapter 1 (index i5): | Sequences |
|---|---|---|
| E1 | v2_Ad1.05_GTAAGGAG | AATGATACGGCGACCACCGAGATCTACACGTAAGGAGTCGTCGGCAGCGTCAGATGTGTAT (SEQ ID NO: 413) |
| F1 | v2_Ad1.06_ACTGCATA | AATGATACGGCGACCACCGAGATCTACACACTGCATATCGTCGGCAGCGTCAGATGTGTAT (SEQ ID NO: 414) |
| G1 | v2_Ad1.07_AAGGAGTA | AATGATACGGCGACCACCGAGATCTACACAAGGAGTATCGTCGGCAGCGTCAGATGTGTAT (SEQ ID NO: 415) |
| H1 | v2_Ad1.08_CTAAGCCT | AATGATACGGCGACCACCGAGATCTACACCTAAGCCTTCGTCGGCAGCGTCAGATGTGTAT (SEQ ID NO: 416) |
| A2 | v2_Ad1.09_TGGAAATC | AATGATACGGCGACCACCGAGATCTACACTGGAAATCTCGTCGGCAGCGTCAGATGTGTAT (SEQ ID NO: 417) |
| B2 | v2_Ad1.10_AACATGAT | AATGATACGGCGACCACCGAGATCTACACAACATGATTCGTCGGCAGCGTCAGATGTGTAT (SEQ ID NO: 418) |
| C2 | v2_Ad1.11_TGATGAAA | AATGATACGGCGACCACCGAGATCTACACTGATGAAATCGTCGGCAGCGTCAGATGTGTAT (SEQ ID NO: 419) |
| D2 | v2_Ad1.12_GTCGGACT | AATGATACGGCGACCACCGAGATCTACACGTCGGACTTCGTCGGCAGCGTCAGATGTGTAT (SEQ ID NO: 420) |
| E2 | v2_Ad1.13_TTTCTAGC | AATGATACGGCGACCACCGAGATCTACACTTTCTAGCTCGTCGGCAGCGTCAGATGTGTAT (SEQ ID NO: 421) |
| F2 | v2_Ad1.14_TAACCAAG | AATGATACGGCGACCACCGAGATCTACACTAACCAAGTCGTCGGCAGCGTCAGATGTGTAT (SEQ ID NO: 422) |
| G2 | v2_Ad1.15_GTGTATCG | AATGATACGGCGACCACCGAGATCTACACGTGTATCGTCGTCGGCAGCGTCAGATGTGTAT (SEQ ID NO: 423) |
| H2 | v2_Ad1.16_TCCATCAA | AATGATACGGCGACCACCGAGATCTACACTCCATCAATCGTCGGCAGCGTCAGATGTGTAT (SEQ ID NO: 424) |
| A3 | v2_Ad1.17_TTCGTGCA | AATGATACGGCGACCACCGAGATCTACACTTCGTGCATCGTCGGCAGCGTCAGATGTGTAT (SEQ ID NO: 425) |
| B3 | v2_Ad1.18_AGGTTGCC | AATGATACGGCGACCACCGAGATCTACACAGGTTGCCTCGTCGGCAGCGTCAGATGTGTAT (SEQ ID NO: 426) |
| C3 | v2_Ad1.19_CCTTATGT | AATGATACGGCGACCACCGAGATCTACACCCTTATGTTCGTCGGCAGCGTCAGATGTGTAT (SEQ ID NO: 427) |
| D3 | v2_Ad1.20_CAGCAACG | AATGATACGGCGACCACCGAGATCTACACCAGCAACGTCGTCGGCAGCGTCAGATGTGTAT (SEQ ID NO: 428) |
| E3 | v2_Ad1.21_GGTTCAAT | AATGATACGGCGACCACCGAGATCTACACGGTTCAATTCGTCGGCAGCGTCAGATGTGTAT (SEQ ID NO: 429) |
| F3 | v2_Ad1.22_ACATTCGT | AATGATACGGCGACCACCGAGATCTACACACATTCGTTCGTCGGCAGCGTCAGATGTGTAT (SEQ ID NO: 430) |
| G3 | v2_Ad1.23_GATTCCCA | AATGATACGGCGACCACCGAGATCTACACGATTCCCATCGTCGGCAGCGTCAGATGTGTAT (SEQ ID NO: 431) |
| H3 | v2_Ad1.24_CGGACTGC | AATGATACGGCGACCACCGAGATCTACACCGGACTGCTCGTCGGCAGCGTCAGATGTGTAT (SEQ ID NO: 432) |
| A4 | v2_Ad1.25_AGCCGTTC | AATGATACGGCGACCACCGAGATCTACACAGCCGTTCTCGTCGGCAGCGTCAGATGTGTAT (SEQ ID NO: 433) |
| B4 | v2_Ad1.26_ATTGGGTC | AATGATACGGCGACCACCGAGATCTACACATTGGGTCTCGTCGGCAGCGTCAGATGTGTAT (SEQ ID NO: 434) |
| C4 | v2_Ad1.27_TGCATACT | AATGATACGGCGACCACCGAGATCTACACTGCATACTTCGTCGGCAGCGTCAGATGTGTAT (SEQ ID NO: 435) |
| D4 | v2_Ad1.28_GGGCTTGG | AATGATACGGCGACCACCGAGATCTACACGGGCTTGGTCGTCGGCAGCGTCAGATGTGTAT (SEQ ID NO: 436) |
| E4 | v2_Ad1.29_GACGTGGC | AATGATACGGCGACCACCGAGATCTACACGACGTGGCTCGTCGGCAGCGTCAGATGTGTAT (SEQ ID NO: 437) |

TABLE 6B-continued

| 96 Well Columns | (plate Ad1) Custom Barcodes Adapter 1 (index i5): | Sequences |
|---|---|---|
| F4 | v2_Ad1.30_GCAAATTT | AATGATACGGCGACCACCGAGATCTACACGCAAATTTTCGTCGGCAGCGTCAGATGTGTAT (SEQ ID NO: 438) |
| G4 | v2_Ad1.31_GCAGCCTC | AATGATACGGCGACCACCGAGATCTACACGCAGCCTCTCGTCGGCAGCGTCAGATGTGTAT (SEQ ID NO: 439) |
| H4 | v2_Ad1.32_TCCGAGTT | AATGATACGGCGACCACCGAGATCTACACTCCGAGTTTCGTCGGCAGCGTCAGATGTGTAT (SEQ ID NO: 440) |
| A5 | v2_Ad1.33_GCATTAAG | AATGATACGGCGACCACCGAGATCTACACGCATTAAGTCGTCGGCAGCGTCAGATGTGTAT (SEQ ID NO: 441) |
| B5 | v2_Ad1.34_ACGATAAC | AATGATACGGCGACCACCGAGATCTACACACGATAACTCGTCGGCAGCGTCAGATGTGTAT (SEQ ID NO: 442) |
| C5 | v2_Ad1.35_CCTGCGGG | AATGATACGGCGACCACCGAGATCTACACCCTGCGGGTCGTCGGCAGCGTCAGATGTGTAT (SEQ ID NO: 443) |
| D5 | v2_Ad1.36_TGATTGTT | AATGATACGGCGACCACCGAGATCTACACTGATTGTTTCGTCGGCAGCGTCAGATGTGTAT (SEQ ID NO: 444) |
| E5 | v2_Ad1.37_GGCACGGA | AATGATACGGCGACCACCGAGATCTACACGGCACGGATCGTCGGCAGCGTCAGATGTGTAT (SEQ ID NO: 445) |
| F5 | v2_Ad1.38_GATCATTC | AATGATACGGCGACCACCGAGATCTACACGATCATTCTCGTCGGCAGCGTCAGATGTGTAT (SEQ ID NO: 446) |
| G5 | v2_Ad1.39_ATGGTCAT | AATGATACGGCGACCACCGAGATCTACACATGGTCATTCGTCGGCAGCGTCAGATGTGTAT (SEQ ID NO: 447) |
| H5 | v2_Ad1.40_CGTACCAA | AATGATACGGCGACCACCGAGATCTACACCGTACCAATCGTCGGCAGCGTCAGATGTGTAT (SEQ ID NO: 448) |
| A6 | v2_Ad1.41_CCAGTTTA | AATGATACGGCGACCACCGAGATCTACACCCAGTTTATCGTCGGCAGCGTCAGATGTGTAT (SEQ ID NO: 449) |
| B6 | v2_Ad1.42_ACCGGCCC | AATGATACGGCGACCACCGAGATCTACACACCGGCCCTCGTCGGCAGCGTCAGATGTGTAT (SEQ ID NO: 450) |
| C6 | v2_Ad1.43_CTAGAAGT | AATGATACGGCGACCACCGAGATCTACACCTAGAAGTTCGTCGGCAGCGTCAGATGTGTAT (SEQ ID NO: 451) |
| D6 | v2_Ad1.44_CGCCAGAT | AATGATACGGCGACCACCGAGATCTACACCGCCAGATTCGTCGGCAGCGTCAGATGTGTAT (SEQ ID NO: 452) |
| E6 | v2_Ad1.45_TCACATGG | AATGATACGGCGACCACCGAGATCTACACTCACATGGTCGTCGGCAGCGTCAGATGTGTAT (SEQ ID NO: 453) |
| F6 | v2_Ad1.46_GAACTCGA | AATGATACGGCGACCACCGAGATCTACACGAACTCGATCGTCGGCAGCGTCAGATGTGTAT (SEQ ID NO: 454) |
| G6 | v2_Ad1.47_CCACCGTT | AATGATACGGCGACCACCGAGATCTACACCCACCGTTTCGTCGGCAGCGTCAGATGTGTAT (SEQ ID NO: 455) |
| H6 | v2_Ad1.48_TAAGTTAC | AATGATACGGCGACCACCGAGATCTACACTAAGTTACTCGTCGGCAGCGTCAGATGTGTAT (SEQ ID NO: 456) |
| A7 | v2_Ad1.49_GAGACGTG | AATGATACGGCGACCACCGAGATCTACACGAGACGTGTCGTCGGCAGCGTCAGATGTGTAT (SEQ ID NO: 457) |
| B7 | v2_Ad1.50_TTGCCTAA | AATGATACGGCGACCACCGAGATCTACACTTGCCTAATCGTCGGCAGCGTCAGATGTGTAT (SEQ ID NO: 458) |
| C7 | v2_Ad1.51_TTAACTTG | AATGATACGGCGACCACCGAGATCTACACTTAACTTGTCGTCGGCAGCGTCAGATGTGTAT (SEQ ID NO: 459) |
| D7 | v2_Ad1.52_CTTTAACA | AATGATACGGCGACCACCGAGATCTACACCTTTAACATCGTCGGCAGCGTCAGATGTGTAT (SEQ ID NO: 460) |
| E7 | v2_Ad1.53_CGTAGACC | AATGATACGGCGACCACCGAGATCTACACCGTAGACCTCGTCGGCAGCGTCAGATGTGTAT (SEQ ID NO: 461) |
| F7 | v2_Ad1.54_TATTTGCG | AATGATACGGCGACCACCGAGATCTACACTATTTGCGTCGTCGGCAGCGTCAGATGTGTAT (SEQ ID NO: 462) |

TABLE 6B-continued

| 96 Well Columns | (plate Ad1) Custom Barcodes Adapter 1 (index i5): | Sequences |
|---|---|---|
| G7 | v2_Ad1.55_ATCCAGGA | AATGATACGGCGACCACCGAGATCTACACATCCAGGATCGTCGGCAGCGTCAGATGTGTAT (SEQ ID NO: 463) |
| H7 | v2_Ad1.56_TGTTCCTG | AATGATACGGCGACCACCGAGATCTACACTGTTCCTGTCGTCGGCAGCGTCAGATGTGTAT (SEQ ID NO: 464) |
| A8 | v2_Ad1.57_ACGCGCAG | AATGATACGGCGACCACCGAGATCTACACACGCGCAGTCGTCGGCAGCGTCAGATGTGTAT (SEQ ID NO: 465) |
| B8 | v2_Ad1.58_TCTGGCGA | AATGATACGGCGACCACCGAGATCTACACTCTGGCGATCGTCGGCAGCGTCAGATGTGTAT (SEQ ID NO: 466) |
| C8 | v2_Ad1.59_AATCTACA | AATGATACGGCGACCACCGAGATCTACACAATCTACATCGTCGGCAGCGTCAGATGTGTAT (SEQ ID NO: 467) |
| D8 | v2_Ad1.60_TACTGACC | AATGATACGGCGACCACCGAGATCTACACTACTGACCTCGTCGGCAGCGTCAGATGTGTAT (SEQ ID NO: 468) |
| E8 | v2_Ad1.61_CGATAGGG | AATGATACGGCGACCACCGAGATCTACACCGATAGGGTCGTCGGCAGCGTCAGATGTGTAT (SEQ ID NO: 469) |
| F8 | v2_Ad1.62_ACTTAGAA | AATGATACGGCGACCACCGAGATCTACACACTTAGAATCGTCGGCAGCGTCAGATGTGTAT (SEQ ID NO: 470) |
| G8 | v2_Ad1.63_AGAGATCT | AATGATACGGCGACCACCGAGATCTACACAGAGATCTTCGTCGGCAGCGTCAGATGTGTAT (SEQ ID NO: 471) |
| H8 | v2_Ad1.64_GGTGAAGG | AATGATACGGCGACCACCGAGATCTACACGGTGAAGGTCGTCGGCAGCGTCAGATGTGTAT (SEQ ID NO: 472) |
| A9 | v2_Ad1.65_ATCGAATG | AATGATACGGCGACCACCGAGATCTACACATCGAATGTCGTCGGCAGCGTCAGATGTGTAT (SEQ ID NO: 473) |
| B9 | v2_Ad1.66_TCAAGAGC | AATGATACGGCGACCACCGAGATCTACACTCAAGAGCTCGTCGGCAGCGTCAGATGTGTAT (SEQ ID NO: 474) |
| C9 | v2_Ad1.67_GCCCACGT | AATGATACGGCGACCACCGAGATCTACACGCCCACGTTCGTCGGCAGCGTCAGATGTGTAT (SEQ ID NO: 475) |
| D9 | v2_Ad1.68_TGGGCGGT | AATGATACGGCGACCACCGAGATCTACACTGGGCGGTTCGTCGGCAGCGTCAGATGTGTAT (SEQ ID NO: 476) |
| E9 | v2_Ad1.69_CCCTTGGA | AATGATACGGCGACCACCGAGATCTACACCCCTTGGATCGTCGGCAGCGTCAGATGTGTAT (SEQ ID NO: 477) |
| F9 | v2_Ad1.70_ATTACCGT | AATGATACGGCGACCACCGAGATCTACACATTACCGTTCGTCGGCAGCGTCAGATGTGTAT (SEQ ID NO: 478) |
| G9 | v2_Ad1.71_AGTCCGAG | AATGATACGGCGACCACCGAGATCTACACAGTCCGAGTCGTCGGCAGCGTCAGATGTGTAT (SEQ ID NO: 479) |
| H9 | v2_Ad1.72_ACTTGTTG | AATGATACGGCGACCACCGAGATCTACACACTTGTTGTCGTCGGCAGCGTCAGATGTGTAT (SEQ ID NO: 480) |
| A10 | v2_Ad1.73_GTAATACA | AATGATACGGCGACCACCGAGATCTACACGTAATACATCGTCGGCAGCGTCAGATGTGTAT (SEQ ID NO: 481) |
| B10 | v2_Ad1.74_GGCGTCTA | AATGATACGGCGACCACCGAGATCTACACGGCGTCTATCGTCGGCAGCGTCAGATGTGTAT (SEQ ID NO: 482) |
| C10 | v2_Ad1.75_GCGCTGCT | AATGATACGGCGACCACCGAGATCTACACGCGCTGCTTCGTCGGCAGCGTCAGATGTGTAT (SEQ ID NO: 483) |
| D10 | v2_Ad1.76_GTGCCATT | AATGATACGGCGACCACCGAGATCTACACGTGCCATTTCGTCGGCAGCGTCAGATGTGTAT (SEQ ID NO: 484) |
| E10 | v2_Ad1.77_TAGGTATG | AATGATACGGCGACCACCGAGATCTACACTAGGTATGTCGTCGGCAGCGTCAGATGTGTAT (SEQ ID NO: 485) |
| F10 | v2_Ad1.78_AACACCTA | AATGATACGGCGACCACCGAGATCTACACAACACCTATCGTCGGCAGCGTCAGATGTGTAT (SEQ ID NO: 486) |
| G10 | v2_Ad1.79_CTCCGAAC | AATGATACGGCGACCACCGAGATCTACACCTCCGAACTCGTCGGCAGCGTCAGATGTGTAT (SEQ ID NO: 487) |

TABLE 6B-continued

| 96 Well Columns | (plate Ad1) Custom Barcodes Adapter 1 (index i5): | Sequences |
|---|---|---|
| H10 | v2_Ad1.80_CAACGGCA | AATGATACGGCGACCACCGAGATCTACACCAACGGCATCGTCGGCAGCGTCAGATGTGTAT (SEQ ID NO: 488) |
| A11 | v2_Ad1.81_CAATGTAG | AATGATACGGCGACCACCGAGATCTACACCAATGTAGTCGTCGGCAGCGTCAGATGTGTAT (SEQ ID NO: 489) |
| B11 | v2_Ad1.82_GGCTACCC | AATGATACGGCGACCACCGAGATCTACACGGCTACCCTCGTCGGCAGCGTCAGATGTGTAT (SEQ ID NO: 490) |
| C11 | v2_Ad1.83_AAAGTCCG | AATGATACGGCGACCACCGAGATCTACACAAAGTCCGTCGTCGGCAGCGTCAGATGTGTAT (SEQ ID NO: 491) |
| D11 | v2_Ad1.84_TTCCGCGG | AATGATACGGCGACCACCGAGATCTACACTTCCGCGGTCGTCGGCAGCGTCAGATGTGTAT (SEQ ID NO: 492) |
| E11 | v2_Ad1.85_AGGCACTT | AATGATACGGCGACCACCGAGATCTACACAGGCACTTTCGTCGGCAGCGTCAGATGTGTAT (SEQ ID NO: 493) |
| F11 | v2_Ad1.86_CTTCAGTG | AATGATACGGCGACCACCGAGATCTACACCTTCAGTGTCGTCGGCAGCGTCAGATGTGTAT (SEQ ID NO: 494) |
| G11 | v2_Ad1.87_GCCGGTAG | AATGATACGGCGACCACCGAGATCTACACGCCGGTAGTCGTCGGCAGCGTCAGATGTGTAT (SEQ ID NO: 495) |
| H11 | v2_Ad1.88_TTCAATCC | AATGATACGGCGACCACCGAGATCTACACTTCAATCCTCGTCGGCAGCGTCAGATGTGTAT (SEQ ID NO: 496) |
| A12 | v2_Ad1.89_CCACACAC | AATGATACGGCGACCACCGAGATCTACACCCACACACTCGTCGGCAGCGTCAGATGTGTAT (SEQ ID NO: 497) |
| B12 | v2_Ad1.90_ATATTATC | AATGATACGGCGACCACCGAGATCTACACATATTATCTCGTCGGCAGCGTCAGATGTGTAT (SEQ ID NO: 498) |
| C12 | v2_Ad1.91_CCGAAGCA | AATGATACGGCGACCACCGAGATCTACACCCGAAGCATCGTCGGCAGCGTCAGATGTGTAT (SEQ ID NO: 499) |
| D12 | v2_Ad1.92_GTATCGGT | AATGATACGGCGACCACCGAGATCTACACGTATCGGTTCGTCGGCAGCGTCAGATGTGTAT (SEQ ID NO: 500) |

TABLE 6C

| Well Position | Name | Sequence |
|---|---|---|
| A1 | Round1_01 | /5Phos//CGCGCTGCATACTTGAACGTGATCCCATGATCGTCCGA (SEQ ID NO: 501) |
| B1 | Round1_02 | /5Phos//CGCGCTGCATACTTGAAACATCGCCCATGATCGTCCGA (SEQ ID NO: 502) |
| C1 | Round1_03 | /5Phos//CGCGCTGCATACTTGATGCCTAACCCATGATCGTCCGA (SEQ ID NO: 503) |
| D1 | Round1_04 | /5Phos//CGCGCTGCATACTTGAGTGGTCACCCATGATCGTCCGA (SEQ ID NO: 504) |
| E1 | Round1_05 | /5Phos//CGCGCTGCATACTTGACCACTGTCCCATGATCGTCCGA (SEQ ID NO: 505) |
| F1 | Round1_06 | /5Phos//CGCGCTGCATACTTGACATTGGCCCCATGATCGTCCGA (SEQ ID NO: 506) |
| G1 | Round1_07 | /5Phos//CGCGCTGCATACTTGCAGATCTGCCCATGATCGTCCGA (SEQ ID NO: 507) |
| H1 | Round1_08 | /5Phos//CGCGCTGCATACTTGCATCAAGTCCCATGATCGTCCGA (SEQ ID NO: 508) |
| A2 | Round1_09 | /5Phos//CGCGCTGCATACTTGCGCTGATCCCCATGATCGTCCGA (SEQ ID NO: 509) |
| B2 | Round1_10 | /5Phos//CGCGCTGCATACTTGACAAGCTACCCATGATCGTCCGA (SEQ ID NO: 510) |
| C2 | Round1_11 | /5Phos//CGCGCTGCATACTTGCTGTAGCCCCCATGATCGTCCGA (SEQ ID NO: 511) |
| D2 | Round1_12 | /5Phos//CGCGCTGCATACTTGAGTACAAGCCCATGATCGTCCGA (SEQ ID NO: 512) |
| E2 | Round1_13 | /5Phos//CGCGCTGCATACTTGAACAACCACCCATGATCGTCCGA (SEQ ID NO: 513) |
| F2 | Round1_14 | /5Phos//CGCGCTGCATACTTGAACCGAGACCCATGATCGTCCGA (SEQ ID NO: 514) |

TABLE 6C-continued

| Well Position | Name | Sequence |
|---|---|---|
| G2 | Round1_15 | /5Phos//CGCGCTGCATACTTG AACGCTTACCCATGATCGTCCGA (SEQ ID NO: 515) |
| H2 | Round1_16 | /5Phos//CGCGCTGCATACTTG AAGACGGACCCATGATCGTCCGA (SEQ ID NO: 516) |
| A3 | Round1_17 | /5Phos//CGCGCTGCATACTTG AAGGTACACCCATGATCGTCCGA (SEQ ID NO: 517) |
| B3 | Round1_18 | /5Phos//CGCGCTGCATACTTG ACACAGAACCCATGATCGTCCGA (SEQ ID NO: 518) |
| C3 | Round1_19 | /5Phos//CGCGCTGCATACTTG ACAGCAGACCCATGATCGTCCGA (SEQ ID NO: 519) |
| D3 | Round1_20 | /5Phos//CGCGCTGCATACTTG ACCTCCAACCCATGATCGTCCGA (SEQ ID NO: 520) |
| E3 | Round1_21 | /5Phos//CGCGCTGCATACTTG ACGCTCGACCCATGATCGTCCGA (SEQ ID NO: 521) |
| F3 | Round1_22 | /5Phos//CGCGCTGCATACTTG ACGTATCACCCATGATCGTCCGA (SEQ ID NO: 522) |
| G3 | Round1_23 | /5Phos//CGCGCTGCATACTTG ACTATGCACCCATGATCGTCCGA (SEQ ID NO: 523) |
| H3 | Round1_24 | /5Phos//CGCGCTGCATACTTG AGAGTCAACCCATGATCGTCCGA (SEQ ID NO: 524) |
| A4 | Round1_25 | /5Phos//CGCGCTGCATACTTG AGATCGCACCCATGATCGTCCGA (SEQ ID NO: 525) |
| B4 | Round1_26 | /5Phos//CGCGCTGCATACTTG AGCAGGAACCCATGATCGTCCGA (SEQ ID NO: 526) |
| C4 | Round1_27 | /5Phos//CGCGCTGCATACTTG AGTCACTACCCATGATCGTCCGA (SEQ ID NO: 527) |
| D4 | Round1_28 | /5Phos//CGCGCTGCATACTTG ATCCTGTACCCATGATCGTCCGA (SEQ ID NO: 528) |
| E4 | Round1_29 | /5Phos//CGCGCTGCATACTTG ATTGAGGACCCATGATCGTCCGA (SEQ ID NO: 529) |
| F4 | Round1_30 | /5Phos//CGCGCTGCATACTTG CAACCACACCCATGATCGTCCGA (SEQ ID NO: 530) |
| G4 | Round1_31 | /5Phos//CGCGCTGCATACTTG GACTAGTACCCATGATCGTCCGA (SEQ ID NO: 531) |
| H4 | Round1_32 | /5Phos//CGCGCTGCATACTTG CAATGGAACCCATGATCGTCCGA (SEQ ID NO: 532) |
| A5 | Round1_33 | /5Phos//CGCGCTGCATACTTG CACTTCGACCCATGATCGTCCGA (SEQ ID NO: 533) |
| B5 | Round1_34 | /5Phos//CGCGCTGCATACTTG CAGCGTTACCCATGATCGTCCGA (SEQ ID NO: 534) |
| C5 | Round1_35 | /5Phos//CGCGCTGCATACTTG CATACCAACCCATGATCGTCCGA (SEQ ID NO: 535) |
| D5 | Round1_36 | /5Phos//CGCGCTGCATACTTG CCAGTTCACCCATGATCGTCCGA (SEQ ID NO: 536) |
| E5 | Round1_37 | /5Phos//CGCGCTGCATACTTG CCGAAGTACCCATGATCGTCCGA (SEQ ID NO: 537) |
| F5 | Round1_38 | /5Phos//CGCGCTGCATACTTG CCGTGAGACCCATGATCGTCCGA (SEQ ID NO: 538) |
| G5 | Round1_39 | /5Phos//CGCGCTGCATACTTG CCTCCTGACCCATGATCGTCCGA (SEQ ID NO: 539) |
| H5 | Round1_40 | /5Phos//CGCGCTGCATACTTG CGAACTTACCCATGATCGTCCGA (SEQ ID NO: 540) |
| A6 | Round1_41 | /5Phos//CGCGCTGCATACTTG CGACTGGACCCATGATCGTCCGA (SEQ ID NO: 541) |
| B6 | Round1_42 | /5Phos//CGCGCTGCATACTTG CGCATACACCCATGATCGTCCGA (SEQ ID NO: 542) |
| C6 | Round1_43 | /5Phos//CGCGCTGCATACTTG CTCAATGACCCATGATCGTCCGA (SEQ ID NO: 543) |
| D6 | Round1_44 | /5Phos//CGCGCTGCATACTTG CTGAGCCACCCATGATCGTCCGA (SEQ ID NO: 544) |
| E6 | Round1_45 | /5Phos//CGCGCTGCATACTTG CTGGCATACCCATGATCGTCCGA (SEQ ID NO: 545) |
| F6 | Round1_46 | /5Phos//CGCGCTGCATACTTG GAATCTGACCCATGATCGTCCGA (SEQ ID NO: 546) |
| G6 | Round1_47 | /5Phos//CGCGCTGCATACTTG CAAGACTACCCATGATCGTCCGA (SEQ ID NO: 547) |
| H6 | Round1_48 | /5Phos//CGCGCTGCATACTTG GAGCTGAACCCATGATCGTCCGA (SEQ ID NO: 548) |
| A7 | Round1_49 | /5Phos//CGCGCTGCATACTTG GATAGACACCCATGATCGTCCGA (SEQ ID NO: 549) |
| B7 | Round1_50 | /5Phos//CGCGCTGCATACTTG GCCACATACCCATGATCGTCCGA (SEQ ID NO: 550) |
| C7 | Round1_51 | /5Phos//CGCGCTGCATACTTG GCGAGTAACCCATGATCGTCCGA (SEQ ID NO: 551) |
| D7 | Round1_52 | /5Phos//CGCGCTGCATACTTG GCTAACGACCCATGATCGTCCGA (SEQ ID NO: 552) |

TABLE 6C-continued

| Well Position | Name | Sequence |
|---|---|---|
| E7 | Round1_53 | /5Phos//CGCGCTGCATACTTG GCTCGGTACCCATGATCGTCCGA (SEQ ID NO: 553) |
| F7 | Round1_54 | /5Phos//CGCGCTGCATACTTG GGAGAACACCCATGATCGTCCGA (SEQ ID NO: 554) |
| G7 | Round1_55 | /5Phos//CGCGCTGCATACTTG GGTGCGAACCCATGATCGTCCGA (SEQ ID NO: 555) |
| H7 | Round1_56 | /5Phos//CGCGCTGCATACTTG GTACGCAACCCATGATCGTCCGA (SEQ ID NO: 556) |
| A8 | Round1_57 | /5Phos//CGCGCTGCATACTTG GTCGTAGACCCATGATCGTCCGA (SEQ ID NO: 557) |
| B8 | Round1_58 | /5Phos//CGCGCTGCATACTTG GTCTGTCACCCATGATCGTCCGA (SEQ ID NO: 558) |
| C8 | Round1_59 | /5Phos//CGCGCTGCATACTTG GTGTTCTACCCATGATCGTCCGA (SEQ ID NO: 559) |
| D8 | Round1_60 | /5Phos//CGCGCTGCATACTTG TAGGATGACCCATGATCGTCCGA (SEQ ID NO: 560) |
| E8 | Round1_61 | /5Phos//CGCGCTGCATACTTG TATCAGCACCCATGATCGTCCGA (SEQ ID NO: 561) |
| F8 | Round1_62 | /5Phos//CGCGCTGCATACTTG TCCGTCTACCCATGATCGTCCGA (SEQ ID NO: 562) |
| G8 | Round1_63 | /5Phos//CGCGCTGCATACTTG TCTTCACACCCATGATCGTCCGA (SEQ ID NO: 563) |
| H8 | Round1_64 | /5Phos//CGCGCTGCATACTTG TGAAGAGACCCATGATCGTCCGA (SEQ ID NO: 564) |
| A9 | Round1_65 | /5Phos//CGCGCTGCATACTTG TGGAACAACCCATGATCGTCCGA (SEQ ID NO: 565) |
| B9 | Round1_66 | /5Phos//CGCGCTGCATACTTG TGGCTTCACCCATGATCGTCCGA (SEQ ID NO: 566) |
| C9 | Round1_67 | /5Phos//CGCGCTGCATACTTG TGGTGGTACCCATGATCGTCCGA (SEQ ID NO: 567) |
| D9 | Round1_68 | /5Phos//CGCGCTGCATACTTG TTCACGCACCCATGATCGTCCGA (SEQ ID NO: 568) |
| E9 | Round1_69 | /5Phos//CGCGCTGCATACTTG AACTCACCCCCATGATCGTCCGA (SEQ ID NO: 569) |
| F9 | Round1_70 | /5Phos//CGCGCTGCATACTTG AAGAGATCCCCATGATCGTCCGA (SEQ ID NO: 570) |
| G9 | Round1_71 | /5Phos//CGCGCTGCATACTTG AAGGACACCCCATGATCGTCCGA (SEQ ID NO: 571) |
| H9 | Round1_72 | /5Phos//CGCGCTGCATACTTG AATCCGTCCCCATGATCGTCCGA (SEQ ID NO: 572) |
| A10 | Round1_73 | /5Phos//CGCGCTGCATACTTG AATGTTGCCCCATGATCGTCCGA (SEQ ID NO: 573) |
| B10 | Round1_74 | /5Phos//CGCGCTGCATACTTG ACACGACCCCCATGATCGTCCGA (SEQ ID NO: 574) |
| C10 | Round1_75 | /5Phos//CGCGCTGCATACTTG ACAGATTCCCCATGATCGTCCGA (SEQ ID NO: 575) |
| D10 | Round1_76 | /5Phos//CGCGCTGCATACTTG AGATGTACCCCATGATCGTCCGA (SEQ ID NO: 576) |
| E10 | Round1_77 | /5Phos//CGCGCTGCATACTTG AGCACCTCCCCATGATCGTCCGA (SEQ ID NO: 577) |
| F10 | Round1_78 | /5Phos//CGCGCTGCATACTTG AGCCATGCCCCATGATCGTCCGA (SEQ ID NO: 578) |
| G10 | Round1_79 | /5Phos//CGCGCTGCATACTTG AGGCTAACCCCCATGATCGTCCGA (SEQ ID NO: 579) |
| H10 | Round1_80 | /5Phos//CGCGCTGCATACTTG ATAGCGACCCCATGATCGTCCGA (SEQ ID NO: 580) |
| A11 | Round1_81 | /5Phos//CGCGCTGCATACTTG ATCATTCCCCCATGATCGTCCGA (SEQ ID NO: 581) |
| B11 | Round1_82 | /5Phos//CGCGCTGCATACTTG ATTGGCTCCCCATGATCGTCCGA (SEQ ID NO: 582) |
| C11 | Round1_83 | /5Phos//CGCGCTGCATACTTG CAAGGAGCCCCATGATCGTCCGA (SEQ ID NO: 583) |
| D11 | Round1_84 | /5Phos//CGCGCTGCATACTTG CACCTTACCCCATGATCGTCCGA (SEQ ID NO: 584) |
| E11 | Round1_85 | /5Phos//CGCGCTGCATACTTG CCATCCTCCCCATGATCGTCCGA (SEQ ID NO: 585) |
| F11 | Round1_86 | /5Phos//CGCGCTGCATACTTG CCGACAACCCCATGATCGTCCGA (SEQ ID NO: 586) |
| G11 | Round1_87 | /5Phos//CGCGCTGCATACTTG CCTAATCCCCCATGATCGTCCGA (SEQ ID NO: 587) |
| H11 | Round1_88 | /5Phos//CGCGCTGCATACTTG CCTCTATCCCCATGATCGTCCGA (SEQ ID NO: 588) |
| A12 | Round1_89 | /5Phos//CGCGCTGCATACTTG CGACACACCCCATGATCGTCCGA (SEQ ID NO: 589) |
| B12 | Round1_90 | /5Phos//CGCGCTGCATACTTG CGGATTGCCCCATGATCGTCCGA (SEQ ID NO: 590) |

TABLE 6C-continued

| Well Position | Name | Sequence |
|---|---|---|
| C12 | Round1_91 | /5Phos//CGCGCTGCATACTTGCTAAGGTCCCCATGATCGTCCGA (SEQ ID NO: 591) |
| D12 | Round1_92 | /5Phos//CGCGCTGCATACTTGGAACAGGCCCCATGATCGTCCGA (SEQ ID NO: 592) |
| E12 | Round1_93 | /5Phos//CGCGCTGCATACTTGGACAGTGCCCCATGATCGTCCGA (SEQ ID NO: 593) |
| F12 | Round1_94 | /5Phos//CGCGCTGCATACTTGGAGTTAGCCCCATGATCGTCCGA (SEQ ID NO: 594) |
| G12 | Round1_95 | /5Phos//CGCGCTGCATACTTGGATGAATCCCCATGATCGTCCGA (SEQ ID NO: 595) |
| H12 | Round1_96 | /5Phos//CGCGCTGCATACTTGGCCAAGACCCCATGATCGTCCGA (SEQ ID NO: 596) |

TABLE 6D

| Well Position | Name | Sequence |
|---|---|---|
| A1 | Round2_01 | /5Phos/CATCGGCGTACGACTAACGTGATATCCACGTGCTTGAG (SEQ ID NO: 597) |
| B1 | Round2_02 | /5Phos/CATCGGCGTACGACTAAACATCGATCCACGTGCTTGAG (SEQ ID NO: 598) |
| C1 | Round2_03 | /5Phos/CATCGGCGTACGACTATGCCTAAATCCACGTGCTTGAG (SEQ ID NO: 599) |
| D1 | Round2_04 | /5Phos/CATCGGCGTACGACTAGTGGTCAATCCACGTGCTTGAG (SEQ ID NO: 600) |
| E1 | Round2_05 | /5Phos/CATCGGCGTACGACTACCACTGTATCCACGTGCTTGAG (SEQ ID NO: 601) |
| F1 | Round2_06 | /5Phos/CATCGGCGTACGACTACATTGGCATCCACGTGCTTGAG (SEQ ID NO: 602) |
| G1 | Round2_07 | /5Phos/CATCGGCGTACGACTCAGATCTGATCCACGTGCTTGAG (SEQ ID NO: 603) |
| H1 | Round2_08 | /5Phos/CATCGGCGTACGACTCATCAAGTATCCACGTGCTTGAG (SEQ ID NO: 604) |
| A2 | Round2_09 | /5Phos/CATCGGCGTACGACTCGCTGATCATCCACGTGCTTGAG (SEQ ID NO: 605) |
| B2 | Round2_10 | /5Phos/CATCGGCGTACGACTACAAGCTAATCCACGTGCTTGAG (SEQ ID NO: 606) |
| C2 | Round2_11 | /5Phos/CATCGGCGTACGACTCTGTAGCCATCCACGTGCTTGAG (SEQ ID NO: 607) |
| D2 | Round2_12 | /5Phos/CATCGGCGTACGACTAGTACAAGATCCACGTGCTTGAG (SEQ ID NO: 608) |
| E2 | Round2_13 | /5Phos/CATCGGCGTACGACTAACAACCAATCCACGTGCTTGAG (SEQ ID NO: 609) |
| F2 | Round2_14 | /5Phos/CATCGGCGTACGACTAACCGAGAATCCACGTGCTTGAG (SEQ ID NO: 610) |
| G2 | Round2_15 | /5Phos/CATCGGCGTACGACTAACGCTTAATCCACGTGCTTGAG (SEQ ID NO: 611) |
| H2 | Round2_16 | /5Phos/CATCGGCGTACGACTAAGACGGAATCCACGTGCTTGAG (SEQ ID NO: 612) |
| A3 | Round2_17 | /5Phos/CATCGGCGTACGACTAAGGTACAATCCACGTGCTTGAG (SEQ ID NO: 613) |
| B3 | Round2_18 | /5Phos/CATCGGCGTACGACTACACAGAAATCCACGTGCTTGAG (SEQ ID NO: 614) |
| C3 | Round2_19 | /5Phos/CATCGGCGTACGACTACAGCAGAATCCACGTGCTTGAG (SEQ ID NO: 615) |
| D3 | Round2_20 | /5Phos/CATCGGCGTACGACTACCTCCAAATCCACGTGCTTGAG (SEQ ID NO: 616) |
| E3 | Round2_21 | /5Phos/CATCGGCGTACGACTACGCTCGAATCCACGTGCTTGAG (SEQ ID NO: 617) |
| F3 | Round2_22 | /5Phos/CATCGGCGTACGACTACGTATCAATCCACGTGCTTGAG (SEQ ID NO: 618) |
| G3 | Round2_23 | /5Phos/CATCGGCGTACGACTACTATGCAATCCACGTGCTTGAG (SEQ ID NO: 619) |
| H3 | Round2_24 | /5Phos/CATCGGCGTACGACTAGAGTCAAATCCACGTGCTTGAG (SEQ ID NO: 620) |
| A4 | Round2_25 | /5Phos/CATCGGCGTACGACTAGATCGCAATCCACGTGCTTGAG (SEQ ID NO: 621) |
| B4 | Round2_26 | /5Phos/CATCGGCGTACGACTAGCAGGAAATCCACGTGCTTGAG (SEQ ID NO: 622) |
| C4 | Round2_27 | /5Phos/CATCGGCGTACGACTAGTCACTAATCCACGTGCTTGAG (SEQ ID NO: 623) |
| D4 | Round2_28 | /5Phos/CATCGGCGTACGACTATCCTGTAATCCACGTGCTTGAG (SEQ ID NO: 624) |
| E4 | Round2_29 | /5Phos/CATCGGCGTACGACTATTGAGGAATCCACGTGCTTGAG (SEQ ID NO: 625) |
| F4 | Round2_30 | /5Phos/CATCGGCGTACGACTCAACCACAATCCACGTGCTTGAG (SEQ ID NO: 626) |

TABLE 6D-continued

| Well Position | Name | Sequence |
|---|---|---|
| G4 | Round2_31 | /5Phos/CATCGGCGTACGACTGACTAGTAATCCACGTGCTTGAG (SEQ ID NO: 627) |
| H4 | Round2_32 | /5Phos/CATCGGCGTACGACTCAATGGAAATCCACGTGCTTGAG (SEQ ID NO: 628) |
| A5 | Round2_33 | /5Phos/CATCGGCGTACGACTCACTTCGAATCCACGTGCTTGAG (SEQ ID NO: 629) |
| B5 | Round2_34 | /5Phos/CATCGGCGTACGACTCAGCGTTAATCCACGTGCTTGAG (SEQ ID NO: 630) |
| C5 | Round2_35 | /5Phos/CATCGGCGTACGACTCATACCAAATCCACGTGCTTGAG (SEQ ID NO: 631) |
| D5 | Round2_36 | /5Phos/CATCGGCGTACGACTCCAGTTCAATCCACGTGCTTGAG (SEQ ID NO: 632) |
| E5 | Round2_37 | /5Phos/CATCGGCGTACGACTCCGAAGTAATCCACGTGCTTGAG (SEQ ID NO: 633) |
| F5 | Round2_38 | /5Phos/CATCGGCGTACGACTCCGTGAGAATCCACGTGCTTGAG (SEQ ID NO: 634) |
| G5 | Round2_39 | /5Phos/CATCGGCGTACGACTCCTCCTGAATCCACGTGCTTGAG (SEQ ID NO: 635) |
| H5 | Round2_40 | /5Phos/CATCGGCGTACGACTCGAACTTAATCCACGTGCTTGAG (SEQ ID NO: 636) |
| A6 | Round2_41 | /5Phos/CATCGGCGTACGACTCGACTGGAATCCACGTGCTTGAG (SEQ ID NO: 637) |
| B6 | Round2_42 | /5Phos/CATCGGCGTACGACTCGCATACAATCCACGTGCTTGAG (SEQ ID NO: 638) |
| C6 | Round2_43 | /5Phos/CATCGGCGTACGACTCTCAATGAATCCACGTGCTTGAG (SEQ ID NO: 639) |
| D6 | Round2_44 | /5Phos/CATCGGCGTACGACTCTGAGCCAATCCACGTGCTTGAG (SEQ ID NO: 640) |
| E6 | Round2_45 | /5Phos/CATCGGCGTACGACTCTGGCATAATCCACGTGCTTGAG (SEQ ID NO: 641) |
| F6 | Round2_46 | /5Phos/CATCGGCGTACGACTGAATCTGAATCCACGTGCTTGAG (SEQ ID NO: 642) |
| G6 | Round2_47 | /5Phos/CATCGGCGTACGACTCAAGACTAATCCACGTGCTTGAG (SEQ ID NO: 643) |
| H6 | Round2_48 | /5Phos/CATCGGCGTACGACTGAGCTGAAATCCACGTGCTTGAG (SEQ ID NO: 644) |
| A7 | Round2_49 | /5Phos/CATCGGCGTACGACTGATAGACAATCCACGTGCTTGAG (SEQ ID NO: 645) |
| B7 | Round2_50 | /5Phos/CATCGGCGTACGACTGCCACATAATCCACGTGCTTGAG (SEQ ID NO: 646) |
| C7 | Round2_51 | /5Phos/CATCGGCGTACGACTGCGAGTAAATCCACGTGCTTGAG (SEQ ID NO: 647) |
| D7 | Round2_52 | /5Phos/CATCGGCGTACGACTGCTAACGAATCCACGTGCTTGAG (SEQ ID NO: 648) |
| E7 | Round2_53 | /5Phos/CATCGGCGTACGACTGCTCGGTAATCCACGTGCTTGAG (SEQ ID NO: 649) |
| F7 | Round2_54 | /5Phos/CATCGGCGTACGACTGGAGAACAATCCACGTGCTTGAG (SEQ ID NO: 650) |
| G7 | Round2_55 | /5Phos/CATCGGCGTACGACTGGTGCGAAATCCACGTGCTTGAG (SEQ ID NO: 651) |
| H7 | Round2_56 | /5Phos/CATCGGCGTACGACTGTACGCAAATCCACGTGCTTGAG (SEQ ID NO: 652) |
| A8 | Round2_57 | /5Phos/CATCGGCGTACGACTGTCGTAGAATCCACGTGCTTGAG (SEQ ID NO: 653) |
| B8 | Round2_58 | /5Phos/CATCGGCGTACGACTGTCTGTCAATCCACGTGCTTGAG (SEQ ID NO: 654) |
| C8 | Round2_59 | /5Phos/CATCGGCGTACGACTGTGTTCTAATCCACGTGCTTGAG (SEQ ID NO: 655) |
| D8 | Round2_60 | /5Phos/CATCGGCGTACGACTTAGGATGAATCCACGTGCTTGAG (SEQ ID NO: 656) |
| E8 | Round2_61 | /5Phos/CATCGGCGTACGACTTATCAGCAATCCACGTGCTTGAG (SEQ ID NO: 657) |
| F8 | Round2_62 | /5Phos/CATCGGCGTACGACTTCCGTCTAATCCACGTGCTTGAG (SEQ ID NO: 658) |
| G8 | Round2_63 | /5Phos/CATCGGCGTACGACTTCTTCACAATCCACGTGCTTGAG (SEQ ID NO: 659) |
| H8 | Round2_64 | /5Phos/CATCGGCGTACGACTTGAAGAGAATCCACGTGCTTGAG (SEQ ID NO: 660) |
| A9 | Round2_65 | /5Phos/CATCGGCGTACGACTTGGAACAAATCCACGTGCTTGAG (SEQ ID NO: 661) |
| B9 | Round2_66 | /5Phos/CATCGGCGTACGACTTGGCTTCAATCCACGTGCTTGAG (SEQ ID NO: 662) |
| C9 | Round2_67 | /5Phos/CATCGGCGTACGACTTGGTGGTAATCCACGTGCTTGAG (SEQ ID NO: 663) |
| D9 | Round2_68 | /5Phos/CATCGGCGTACGACTTTCACGCAATCCACGTGCTTGAG (SEQ ID NO: 664) |

TABLE 6D-continued

| Well Position | Name | Sequence |
|---|---|---|
| E9 | Round2_69 | /5Phos/CATCGGCGTACGACTAACTCACCATCCACGTGCTTGAG (SEQ ID NO: 665) |
| F9 | Round2_70 | /5Phos/CATCGGCGTACGACTAAGAGATCATCCACGTGCTTGAG (SEQ ID NO: 666) |
| G9 | Round2_71 | /5Phos/CATCGGCGTACGACTAAGGACACATCCACGTGCTTGAG (SEQ ID NO: 667) |
| H9 | Round2_72 | /5Phos/CATCGGCGTACGACTAATCCGTCATCCACGTGCTTGAG (SEQ ID NO: 668) |
| A10 | Round2_73 | /5Phos/CATCGGCGTACGACTAATGTTGCATCCACGTGCTTGAG (SEQ ID NO: 669) |
| B10 | Round2_74 | /5Phos/CATCGGCGTACGACTACACGACCATCCACGTGCTTGAG (SEQ ID NO: 670) |
| C10 | Round2_75 | /5Phos/CATCGGCGTACGACTACAGATTCATCCACGTGCTTGAG (SEQ ID NO: 671) |
| D10 | Round2_76 | /5Phos/CATCGGCGTACGACTAGATGTACATCCACGTGCTTGAG (SEQ ID NO: 672) |
| E10 | Round2_77 | /5Phos/CATCGGCGTACGACTAGCACCTCATCCACGTGCTTGAG (SEQ ID NO: 673) |
| F10 | Round2_78 | /5Phos/CATCGGCGTACGACTAGCCATGCATCCACGTGCTTGAG (SEQ ID NO: 674) |
| G10 | Round2_79 | /5Phos/CATCGGCGTACGACTAGGCTAACATCCACGTGCTTGAG (SEQ ID NO: 675) |
| H10 | Round2_80 | /5Phos/CATCGGCGTACGACTATAGCGACATCCACGTGCTTGAG (SEQ ID NO: 676) |
| A11 | Round2_81 | /5Phos/CATCGGCGTACGACTATCATTCCATCCACGTGCTTGAG (SEQ ID NO: 677) |
| B11 | Round2_82 | /5Phos/CATCGGCGTACGACTATTGGCTCATCCACGTGCTTGAG (SEQ ID NO: 678) |
| C11 | Round2_83 | /5Phos/CATCGGCGTACGACTCAAGGAGCATCCACGTGCTTGAG (SEQ ID NO: 679) |
| D11 | Round2_84 | /5Phos/CATCGGCGTACGACTCACCTTACATCCACGTGCTTGAG (SEQ ID NO: 680) |
| E11 | Round2_85 | /5Phos/CATCGGCGTACGACTCCATCCTCATCCACGTGCTTGAG (SEQ ID NO: 681) |
| F11 | Round2_86 | /5Phos/CATCGGCGTACGACTCCGACAACATCCACGTGCTTGAG (SEQ ID NO: 682) |
| G11 | Round2_87 | /5Phos/CATCGGCGTACGACTCCTAATCCATCCACGTGCTTGAG (SEQ ID NO: 683) |
| H11 | Round2_88 | /5Phos/CATCGGCGTACGACTCCTCTATCATCCACGTGCTTGAG (SEQ ID NO: 684) |
| A12 | Round2_89 | /5Phos/CATCGGCGTACGACTCGACACACATCCACGTGCTTGAG (SEQ ID NO: 685) |
| B12 | Round2_90 | /5Phos/CATCGGCGTACGACTCGGATTGCATCCACGTGCTTGAG (SEQ ID NO: 686) |
| C12 | Round2_91 | /5Phos/CATCGGCGTACGACTCTAAGGTCATCCACGTGCTTGAG (SEQ ID NO: 687) |
| D12 | Round2_92 | /5Phos/CATCGGCGTACGACTGAACAGGCATCCACGTGCTTGAG (SEQ ID NO: 688) |
| E12 | Round2_93 | /5Phos/CATCGGCGTACGACTGACAGTGCATCCACGTGCTTGAG (SEQ ID NO: 689) |
| F12 | Round2_94 | /5Phos/CATCGGCGTACGACTGAGTTAGCATCCACGTGCTTGAG (SEQ ID NO: 690) |
| G12 | Round2_95 | /5Phos/CATCGGCGTACGACTGATGAATCATCCACGTGCTTGAG (SEQ ID NO: 691) |
| H12 | Round2_96 | /5Phos/CATCGGCGTACGACTGCCAAGACATCCACGTGCTTGAG (SEQ ID NO: 692) |

TABLE 6E

| Well Position | Name | Sequence |
|---|---|---|
| A1 | Round3_01 | CAAGCAGAAGACGGCATACGAGATAACGTGATGTGGCCGATGTTTCG (SEQ ID NO: 693) |
| B1 | Round3_02 | CAAGCAGAAGACGGCATACGAGATAAACATCGGTGGCCGATGTTTCG (SEQ ID NO: 694) |
| C1 | Round3_03 | CAAGCAGAAGACGGCATACGAGATATGCCTAAGTGGCCGATGTTTCG (SEQ ID NO: 695) |
| D1 | Round3_04 | CAAGCAGAAGACGGCATACGAGATAGTGGTCAGTGGCCGATGTTTCG (SEQ ID NO: 696) |
| E1 | Round3_05 | CAAGCAGAAGACGGCATACGAGATACCACTGTGTGGCCGATGTTTCG (SEQ ID NO: 697) |
| F1 | Round3_06 | CAAGCAGAAGACGGCATACGAGATACATTGGCGTGGCCGATGTTTCG (SEQ ID NO: 698) |
| G1 | Round3_07 | CAAGCAGAAGACGGCATACGAGATCAGATCTGGTGGCCGATGTTTCG (SEQ ID NO: 699) |
| H1 | Round3_08 | CAAGCAGAAGACGGCATACGAGATCATCAAGTGTGGCCGATGTTTCG (SEQ ID NO: 700) |

TABLE 6E-continued

| Well Position | Name | Sequence |
|---|---|---|
| A2 | Round3_09 | CAAGCAGAAGACGGCATACGAGAT CGCTGATCGTGGCCGATGTTTCG (SEQ ID NO: 701) |
| B2 | Round3_10 | CAAGCAGAAGACGGCATACGAGAT ACAAGCTAGTGGCCGATGTTTCG (SEQ ID NO: 702) |
| C2 | Round3_11 | CAAGCAGAAGACGGCATACGAGAT CTGTAGCCGTGGCCGATGTTTCG (SEQ ID NO: 703) |
| D2 | Round3_12 | CAAGCAGAAGACGGCATACGAGAT AGTACAAGGTGGCCGATGTTTCG (SEQ ID NO: 704) |
| E2 | Round3_13 | CAAGCAGAAGACGGCATACGAGAT AACAACCAGTGGCCGATGTTTCG (SEQ ID NO: 705) |
| F2 | Round3_14 | CAAGCAGAAGACGGCATACGAGAT AACCGAGAGTGGCCGATGTTTCG (SEQ ID NO: 706) |
| G2 | Round3_15 | CAAGCAGAAGACGGCATACGAGAT AACGCTTAGTGGCCGATGTTTCG (SEQ ID NO: 707) |
| H2 | Round3_16 | CAAGCAGAAGACGGCATACGAGAT AAGACGGAGTGGCCGATGTTTCG (SEQ ID NO: 708) |
| A3 | Round3_17 | CAAGCAGAAGACGGCATACGAGAT AAGGTACAGTGGCCGATGTTTCG (SEQ ID NO: 709) |
| B3 | Round3_18 | CAAGCAGAAGACGGCATACGAGAT ACACAGAAGTGGCCGATGTTTCG (SEQ ID NO: 710) |
| C3 | Round3_19 | CAAGCAGAAGACGGCATACGAGAT ACAGCAGAGTGGCCGATGTTTCG (SEQ ID NO: 711) |
| D3 | Round3_20 | CAAGCAGAAGACGGCATACGAGAT ACCTCCAAGTGGCCGATGTTTCG (SEQ ID NO: 712) |
| E3 | Round3_21 | CAAGCAGAAGACGGCATACGAGAT ACGCTCGAGTGGCCGATGTTTCG (SEQ ID NO: 713) |
| F3 | Round3_22 | CAAGCAGAAGACGGCATACGAGAT ACGTATCAGTGGCCGATGTTTCG (SEQ ID NO: 714) |
| G3 | Round3_23 | CAAGCAGAAGACGGCATACGAGAT ACTATGCAGTGGCCGATGTTTCG (SEQ ID NO: 715) |
| H3 | Round3_24 | CAAGCAGAAGACGGCATACGAGAT AGAGTCAAGTGGCCGATGTTTCG (SEQ ID NO: 716) |
| A4 | Round3_25 | CAAGCAGAAGACGGCATACGAGAT AGATCGCAGTGGCCGATGTTTCG (SEQ ID NO: 717) |
| B4 | Round3_26 | CAAGCAGAAGACGGCATACGAGAT AGCAGGAAGTGGCCGATGTTTCG (SEQ ID NO: 718) |
| C4 | Round3_27 | CAAGCAGAAGACGGCATACGAGAT AGTCACTAGTGGCCGATGTTTCG (SEQ ID NO: 719) |
| D4 | Round3_28 | CAAGCAGAAGACGGCATACGAGAT ATCCTGTAGTGGCCGATGTTTCG (SEQ ID NO: 720) |
| E4 | Round3_29 | CAAGCAGAAGACGGCATACGAGAT ATTGAGGAGTGGCCGATGTTTCG (SEQ ID NO: 721) |
| F4 | Round3_30 | CAAGCAGAAGACGGCATACGAGAT CAACCACAGTGGCCGATGTTTCG (SEQ ID NO: 722) |
| G4 | Round3_31 | CAAGCAGAAGACGGCATACGAGAT GACTAGTAGTGGCCGATGTTTCG (SEQ ID NO: 723) |
| H4 | Round3_32 | CAAGCAGAAGACGGCATACGAGAT CAATGGAAGTGGCCGATGTTTCG (SEQ ID NO: 724) |
| A5 | Round3_33 | CAAGCAGAAGACGGCATACGAGAT CACTTCGAGTGGCCGATGTTTCG (SEQ ID NO: 725) |
| B5 | Round3_34 | CAAGCAGAAGACGGCATACGAGAT CAGCGTTAGTGGCCGATGTTTCG (SEQ ID NO: 726) |
| C5 | Round3_35 | CAAGCAGAAGACGGCATACGAGAT CATACCAAGTGGCCGATGTTTCG (SEQ ID NO: 727) |
| D5 | Round3_36 | CAAGCAGAAGACGGCATACGAGAT CCAGTTCAGTGGCCGATGTTTCG (SEQ ID NO: 728) |
| E5 | Round3_37 | CAAGCAGAAGACGGCATACGAGAT CCGAAGTAGTGGCCGATGTTTCG (SEQ ID NO: 729) |
| F5 | Round3_38 | CAAGCAGAAGACGGCATACGAGAT CCGTGAGAGTGGCCGATGTTTCG (SEQ ID NO: 730) |
| G5 | Round3_39 | CAAGCAGAAGACGGCATACGAGAT CCTCCTGAGTGGCCGATGTTTCG (SEQ ID NO: 731) |
| H5 | Round3_40 | CAAGCAGAAGACGGCATACGAGAT CGAACTTAGTGGCCGATGTTTCG (SEQ ID NO: 732) |
| A6 | Round3_41 | CAAGCAGAAGACGGCATACGAGAT CGACTGGAGTGGCCGATGTTTCG (SEQ ID NO: 733) |
| B6 | Round3_42 | CAAGCAGAAGACGGCATACGAGAT CGCATACAGTGGCCGATGTTTCG (SEQ ID NO: 734) |
| C6 | Round3_43 | CAAGCAGAAGACGGCATACGAGAT CTCAATGAGTGGCCGATGTTTCG (SEQ ID NO: 735) |
| D6 | Round3_44 | CAAGCAGAAGACGGCATACGAGAT CTGAGCCAGTGGCCGATGTTTCG (SEQ ID NO: 736) |
| E6 | Round3_45 | CAAGCAGAAGACGGCATACGAGAT CTGGCATAGTGGCCGATGTTTCG (SEQ ID NO: 737) |
| F6 | Round3_46 | CAAGCAGAAGACGGCATACGAGAT GAATCTGAGTGGCCGATGTTTCG (SEQ ID NO: 738) |

TABLE 6E-continued

| Well Position | Name | Sequence |
|---|---|---|
| G6 | Round3_47 | CAAGCAGAAGACGGCATACGAGAT CAAGACTAGTGGCCGATGTTTCG (SEQ ID NO: 739) |
| H6 | Round3_48 | CAAGCAGAAGACGGCATACGAGAT GAGCTGAAGTGGCCGATGTTTCG (SEQ ID NO: 740) |
| A7 | Round3_49 | CAAGCAGAAGACGGCATACGAGAT GATAGACAGTGGCCGATGTTTCG (SEQ ID NO: 741) |
| B7 | Round3_50 | CAAGCAGAAGACGGCATACGAGAT GCCACATAGTGGCCGATGTTTCG (SEQ ID NO: 742) |
| C7 | Round3_51 | CAAGCAGAAGACGGCATACGAGAT GCGAGTAAGTGGCCGATGTTTCG (SEQ ID NO: 743) |
| D7 | Round3_52 | CAAGCAGAAGACGGCATACGAGAT GCTAACGAGTGGCCGATGTTTCG (SEQ ID NO: 744) |
| E7 | Round3_53 | CAAGCAGAAGACGGCATACGAGAT GCTCGGTAGTGGCCGATGTTTCG (SEQ ID NO: 745) |
| F7 | Round3_54 | CAAGCAGAAGACGGCATACGAGAT GGAGAACAGTGGCCGATGTTTCG (SEQ ID NO: 746) |
| G7 | Round3_55 | CAAGCAGAAGACGGCATACGAGAT GGTGCGAAGTGGCCGATGTTTCG (SEQ ID NO: 747) |
| H7 | Round3_56 | CAAGCAGAAGACGGCATACGAGAT GTACGCAAGTGGCCGATGTTTCG (SEQ ID NO: 748) |
| A8 | Round3_57 | CAAGCAGAAGACGGCATACGAGAT GTCGTAGAGTGGCCGATGTTTCG (SEQ ID NO: 749) |
| B8 | Round3_58 | CAAGCAGAAGACGGCATACGAGAT GTCTGTCAGTGGCCGATGTTTCG (SEQ ID NO: 750) |
| C8 | Round3_59 | CAAGCAGAAGACGGCATACGAGAT GTGTTCTAGTGGCCGATGTTTCG (SEQ ID NO: 751) |
| D8 | Round3_60 | CAAGCAGAAGACGGCATACGAGAT TAGGATGAGTGGCCGATGTTTCG (SEQ ID NO: 752) |
| E8 | Round3_61 | CAAGCAGAAGACGGCATACGAGAT TATCAGCAGTGGCCGATGTTTCG (SEQ ID NO: 753) |
| F8 | Round3_62 | CAAGCAGAAGACGGCATACGAGAT TCCGTCTAGTGGCCGATGTTTCG (SEQ ID NO: 754) |
| G8 | Round3_63 | CAAGCAGAAGACGGCATACGAGAT TCTTCACAGTGGCCGATGTTTCG (SEQ ID NO: 755) |
| H8 | Round3_64 | CAAGCAGAAGACGGCATACGAGAT TGAAGAGAGTGGCCGATGTTTCG (SEQ ID NO: 756) |
| A9 | Round3_65 | CAAGCAGAAGACGGCATACGAGAT TGGAACAAGTGGCCGATGTTTCG (SEQ ID NO: 757) |
| B9 | Round3_66 | CAAGCAGAAGACGGCATACGAGAT TGGCTTCAGTGGCCGATGTTTCG (SEQ ID NO: 758) |
| C9 | Round3_67 | CAAGCAGAAGACGGCATACGAGAT TGGTGGTAGTGGCCGATGTTTCG (SEQ ID NO: 759) |
| D9 | Round3_68 | CAAGCAGAAGACGGCATACGAGAT TTCACGCAGTGGCCGATGTTTCG (SEQ ID NO: 760) |
| E9 | Round3_69 | CAAGCAGAAGACGGCATACGAGAT AACTCACCGTGGCCGATGTTTCG (SEQ ID NO: 761) |
| F9 | Round3_70 | CAAGCAGAAGACGGCATACGAGAT AAGAGATCGTGGCCGATGTTTCG (SEQ ID NO: 762) |
| G9 | Round3_71 | CAAGCAGAAGACGGCATACGAGAT AAGGACACGTGGCCGATGTTTCG (SEQ ID NO: 763) |
| H9 | Round3_72 | CAAGCAGAAGACGGCATACGAGAT AATCCGTCGTGGCCGATGTTTCG (SEQ ID NO: 764) |
| A10 | Round3_73 | CAAGCAGAAGACGGCATACGAGAT AATGTTGCGTGGCCGATGTTTCG (SEQ ID NO: 765) |
| B10 | Round3_74 | CAAGCAGAAGACGGCATACGAGAT ACACGACCGTGGCCGATGTTTCG (SEQ ID NO: 766) |
| C10 | Round3_75 | CAAGCAGAAGACGGCATACGAGAT ACAGATTCGTGGCCGATGTTTCG (SEQ ID NO: 767) |
| D10 | Round3_76 | CAAGCAGAAGACGGCATACGAGAT AGATGTACGTGGCCGATGTTTCG (SEQ ID NO: 768) |
| E10 | Round3_77 | CAAGCAGAAGACGGCATACGAGAT AGCACCTCGTGGCCGATGTTTCG (SEQ ID NO: 769) |
| F10 | Round3_78 | CAAGCAGAAGACGGCATACGAGAT AGCCATGCGTGGCCGATGTTTCG (SEQ ID NO: 770) |
| G10 | Round3_79 | CAAGCAGAAGACGGCATACGAGAT AGGCTAACGTGGCCGATGTTTCG (SEQ ID NO: 771) |
| H10 | Round3_80 | CAAGCAGAAGACGGCATACGAGAT ATAGCGACGTGGCCGATGTTTCG (SEQ ID NO: 772) |
| A11 | Round3_81 | CAAGCAGAAGACGGCATACGAGAT ATCATTCCGTGGCCGATGTTTCG (SEQ ID NO: 773) |
| B11 | Round3_82 | CAAGCAGAAGACGGCATACGAGAT ATTGGCTCGTGGCCGATGTTTCG (SEQ ID NO: 774) |
| C11 | Round3_83 | CAAGCAGAAGACGGCATACGAGAT CAAGGAGCGTGGCCGATGTTTCG (SEQ ID NO: 775) |
| D11 | Round3_84 | CAAGCAGAAGACGGCATACGAGAT CACCTTACGTGGCCGATGTTTCG (SEQ ID NO: 776) |

TABLE 6E-continued

| Well Position | Name | Sequence |
|---|---|---|
| E11 | Round3_85 | CAAGCAGAAGACGGCATACGAGAT CCATCCTCGTGGCCGATGTTTCG (SEQ ID NO: 777) |
| F11 | Round3_86 | CAAGCAGAAGACGGCATACGAGAT CCGACAACGTGGCCGATGTTTCG (SEQ ID NO: 778) |
| G11 | Round3_87 | CAAGCAGAAGACGGCATACGAGAT CCTAATCCGTGGCCGATGTTTCG (SEQ ID NO: 779) |
| H11 | Round3_88 | CAAGCAGAAGACGGCATACGAGAT CCTCTATCGTGGCCGATGTTTCG (SEQ ID NO: 780) |
| A12 | Round3_89 | CAAGCAGAAGACGGCATACGAGAT CGACACACGTGGCCGATGTTTCG (SEQ ID NO: 781) |
| B12 | Round3_90 | CAAGCAGAAGACGGCATACGAGAT CGGATTGCGTGGCCGATGTTTCG (SEQ ID NO: 782) |
| C12 | Round3_91 | CAAGCAGAAGACGGCATACGAGAT CTAAGGTCGTGGCCGATGTTTCG (SEQ ID NO: 783) |
| D12 | Round3_92 | CAAGCAGAAGACGGCATACGAGAT GAACAGGCGTGGCCGATGTTTCG (SEQ ID NO: 784) |
| E12 | Round3_93 | CAAGCAGAAGACGGCATACGAGAT GACAGTGCGTGGCCGATGTTTCG (SEQ ID NO: 785) |
| F12 | Round3_94 | CAAGCAGAAGACGGCATACGAGAT GAGTTAGCGTGGCCGATGTTTCG (SEQ ID NO: 786) |
| G12 | Round3_95 | CAAGCAGAAGACGGCATACGAGAT GATGAATCGTGGCCGATGTTTCG (SEQ ID NO: 787) |
| H12 | Round3_96 | CAAGCAGAAGACGGCATACGAGAT GCCAAGACGTGGCCGATGTTTCG (SEQ ID NO: 788) |

SHARE-Seq Generated High-Quality Chromatin and Expression Profiles Across Diverse Cell Lines and Tissues To validate specificity and data quality, Applicants first performed SHARE-seq on a mixture of human (GM12878) and mouse (NIH/3T3) cell lines. Human and mouse reads were well separated on both chromatin and transcriptome profiles resulting in 903 human and 1,341 mouse cells passing filter out of 2,000 expected cells (FIGS. 11B, 11C, and 11D) with low levels of ambient chromatin (~1.5%), and moderate ambient RNA (~5.1%) relative to previous reports (~0.4 to 3.1%)[16] (FIGS. 15D and 15E). Applicants identified only one cell doublet representing a remarkably low 0.04% collision rate (consistent with the expected rate of 0.052%, FIG. 15F), a benefit from the large SHARE-seq barcoding space. Cells passing filter (Methods) had on average 2,545 RNA UMIs (9,660 estimated UMI library size) and 8,252 unique ATAC-seq fragments (19,723 estimated library size with 65.5% fragments in peaks) (FIGS. 15G, 16A).

SHARE-seq had similar performance across replicates and additional cell lines (FIGS. 16B-16I) and showed high concordance with previously published ATAC-seq datasets (Methods, FIG. 16F). SHARE-seq also consistently outperformed previously published joint ATAC-RNA approaches[10-12] (FIG. 16E). Notably, SHARE-seq RNA reads (starting with cells or nuclei) were enriched for intronic regions, similar to single nucleus RNA-seq (snRNA-seq)[17] (FIG. 16J), which may be due to cell membrane lysis and serial washes used in the protocol. Intronic RNA was enriched for nascent RNA, which can be used not only to identify cell types[18], but also to investigate temporal processes within single cells[19]. Finally, chromatin accessibility at the NFkB1 locus and NFkB1 gene expression significantly co-varied across single-cells (Spearman p=0.31, $p<10^{-6}$, Z-test), validating the expectation that increased chromatin accessibility results in higher gene expression and that SHARE-seq can be used to query chromatin-gene expression relationships (FIG. 15F).

Further validating SHARE-seq's utility, Applicants found that it performed well with cells or nuclei from a broad range of tissues, including mouse skin, brain and lung tissues (FIGS. 12A-12C, FIGS. 17A-17I). SHARE-seq performed comparably to scATAC-only approaches[20,21] applied to adult mouse lung (Methods, FIG. 12B), and to snRNA-seq[18,22] and scRNA-seq[23,24] from adult mouse brain (FIG. 12C and FIGS. 17D-17I). Importantly, SHARE-seq also enabled experiments at a substantially lower cost than prior methods. Altogether, these validate the accuracy and utility of this approach for integrated measures of chromatin accessibility and gene expression within cell lines or primary tissues.

Broad Congruence Between Chromatin and RNA Defined Cell Types from SHARE-Seq

To utilize SHARE-seq to query the relationship between chromatin accessibility and gene expression, Applicants focused on murine skin. Mammalian skin is enriched for cell types from diverse lineages (including multiple populations of epithelial cells, fibroblasts, immune cells, and neural crest-derived cells)—some are highly proliferative while others are dormant or slow-cycling. Moreover, multiple populations of stem cells in the skin give rise to well-defined downstream cell types. Thus, the skin is an ideal tissue to resolve cellular and regulatory diversity across cells at different proliferation or differentiation status[25]. Moreover, previous analyses of cellular diversity and chromatin state provide a rich resource to validate SHARE-seq[14,26-30].

Leveraging the increased throughput and resolution of SHARE-seq, Applicants assessed the congruence between the epigenome and transcriptome across an atlas of 34,774 high-quality profiles from adult mouse skin (FIG. 12D, FIGS. 18A-18B). To define cell subsets, Applicants clustered the RNA portion of SHARE-seq data and identified consensus expression signatures for each cluster, highlighting known and novel markers (Table 7). Applicants projected the cells based on the ATAC-seq and RNA-seq independently to a low dimensional space using UMAP (Methods), and found that both projections separated these scRNA-seq defined clusters (FIGS. 12D, 12E). SHARE-seq not only resolved cell types from distinct lineages (epithelium, fibroblasts, melanocytes, immune cells), but could also distinguish between cells of closely related types (for example, $\alpha^{high}$ CD34+ bulge vs. $\alpha^{low}$ CD34+ bulge[31]). Moreover, cell membership in subsets identified by scATAC-seq was highly congruent with their membership within scRNA-seq clusters (FIG. 12F, FIG. 18C), and both measures revealed the same major cell type classes, such as transit-amplifying cells (TACs), inner root sheath (IRS), outer root sheath (ORS), and hair shaft cells (FIGS. 12D-12F).

TABLE 7

| | Fgf18 | Krt15 | Krt24 | Krt71 | Lgr6 | Krt6a | Mki67 | Top2a | Mcm2 | Shh |
|---|---|---|---|---|---|---|---|---|---|---|
| Schwann Cell | 0.1468141 | 0.12481227 | 0.0527404 | 0 | 0.03471412 | 0 | 0.03390725 | 0.09077989 | 0.15018386 | 0.1080147 | 0 |
| Sebaceous Gland | 0 | 0.10000377 | 0 | 0 | 0.22882173 | 0 | 0 | 0.11785507 | 0.25398577 | 0.37435331 | 0 |
| Melanocyte | 0 | 0.05364367 | 0 | 0.01170628 | 0 | 0 | 0.02955552 | 0.07179959 | 0.06792278 | 0.01971223 | 0 |
| Macrophage DC | 0.03024103 | 0.09737105 | 0.03268702 | 0.0065956 | 0.04308214 | 0.08967503 | 0.0604428 | 0.05431778 | 0.0796773 | 0 | 0 |
| Dermal Papilla | 0.21804332 | 0.22655761 | 0.06733696 | 0.03117933 | 0.13596485 | 0.06376133 | 0.05050675 | 0.16194534 | 0.15552103 | 0.21794451 | 0.02760686 |
| Dermal Sheath | 0.19983392 | 0.23550391 | 0.10799856 | 0.04422691 | 0.09601735 | 0.07662181 | 0.01388664 | 0.1804104 | 0.27535359 | 0.36815567 | 0 |
| Dermal Fibroblast | 0.37603003 | 0.10858106 | 0.03067506 | 0.02701808 | 0.05872494 | 0.08426749 | 0.01972126 | 0.09636989 | 0.15362917 | 0.13356567 | 0.00628809 |
| Endothelial | 0.03431883 | 0.1760521 | 0.10201029 | 0.03095127 | 0.07117106 | 0.02991834 | 0.04769693 | 0.11727194 | 0.13099333 | 0.102865 | 0.02281214 |
| Infundibulum | 0.03266674 | 0.14943046 | 0.03946292 | 0.00380444 | 0.03666312 | 0.05426936 | 0.02537104 | 0.00398721 | 0.02626075 | 0.02854603 | 0.00170306 |
| Granular | 0.10932495 | 0.32118967 | 0.059083575 | 0.03767988 | 0.09459124 | 0.08103035 | 0.03798544 | 0.15242238 | 0.13383648 | 0.12683979 | 0 |
| Spinous | 0.03286525 | 0.13268835 | 0.05191895 | 0.00463457 | 0.03015948 | 0.05762622 | 0.01932476 | 0.01335534 | 0.03516492 | 0.02853721 | 0.00672182 |
| Basal | 0.02655556 | 0.30594163 | 0.03201539 | 0 | 0.13208406 | 0.0239865 | 0.02697079 | 0.06495717 | 0.13434095 | 0.06780504 | 0.0090522 |
| ORS | 0.10820939 | 0.45093724 | 0.05012644 | 0.01156784 | 0.13730564 | 0.01722792 | 0.1127935 | 0.20241955 | 0.13388614 | 0.29860363 | 0.02055088 |
| Hair Shaft-Cuticle/Cortex | 0.08185307 | 0.02450787 | 0.0221184 | 0.00457446 | 0.02909923 | 0.04888989 | 0.01896014 | 0.14355019 | 0.12497371 | 0.21405978 | 0.01209083 |
| Medulla | 0.08918174 | 0.135133445 | 0.07886867 | 0.05752738 | 0.0463831 | 0.08156241 | 0.01690178 | 0.18380007 | 0.20985332 | 0.15954889 | 0.04311285 |
| IRS | 0.03550621 | 0 | 0.01279269 | 0.44007159 | 0.02922439 | 0.03650776 | 0 | 0.25026281 | 0.11359033 | 0.44503902 | 0.03146853 |
| TAC-2 | 0.05523187 | 0.03749145 | 0.02558537 | 1 | 0.09451205 | 0.03233142 | 0.02741509 | 0.67720619 | 0.72784903 | 0.59689794 | 1 |
| TAC-1 | 0.06844163 | 0.03805398 | 0.04081512 | 0.0488558 | 0.21440249 | 0.07961653 | 0.0262439 | 1 | 1 | 1 | 0.00836671 |
| K6+/Comp. Layer | 0.03094704 | 0.09459457 | 0 | 0.00440459 | 1 | 0.08156241 | 1 | 0.01829697 | 0.06461601 | 0.07558459 | 0.02742783 |
| Isthmus | 0.02308676 | 0.296071 | 0.14972456 | 0.0037781 | 0.18662363 | 0.03233142 | 0.06417279 | 0.01217892 | 0.05958665 | 0.06258156 | 0.0102307 |
| αhighCD34+Bulge | 0.08689436 | 0.70094017 | 0.11908035 | 0.03979637 | 1 | 0.13497526 | 0.16489365 | 0 | 0 | 0.02577989 | 0.00906035 |
| αlowCD34+Bulge | 1 | 1 | 1 | 1 | 1 | 0.16489365 | 0.01566709 | 0.0298966 | 0.01945784 | 0.0112663 | — |

| | Fbp1 | Krt73 | Krt15 | Krt24 | Krt27 | Krt71 | Lgr6 | Foxq1 | Mki67 | Kit1 | Top2a | Krt75 | Mcm2 | Tnni1 | Shh | Krt31 |
|---|---|---|---|---|---|---|---|---|---|---|---|---|---|---|---|---|
| (bottom) | 0 | 0 | 0 | 0.06087978 | 0 | 0.03763684 | — | 0.0398789 | — | 0.19919883 | — | 0 | — | 0.04166226 | — | 0.26028702 |

Wnt10b: 0.24666808

TABLE 7-continued

| Krt32 | Klk82 | Selenbp1 | Rnaset2b | Lgr5 | Krt5 | Krt14 | Krt1 | Krt10 | Ptgs1 |
|---|---|---|---|---|---|---|---|---|---|
| 0 | 0 | 0 | 0.02741272 | 0.01627696 | 0.08083546 | 0.73581985 | 0.06254102 | 0.04552293 | 0.17888008 |
| 0.21501014 | 0 | 0 | 0.159199 | 0.05912391 | 0.20966182 | 0.09814994 | 0.03087864 | 0.02026884 | 0.02884501 |
| 0.15287793 | 0.13434728 | 0 | 0.09432894 | 0.03502633 | 0.10859437 | 0.15317202 | 0.09991786 | 0.04610123 | 0.16994363 |
| 0 | 0.04612707 | 0.08072237 | 0.0712516 | 0.0847071 | 0.33704034 | 0.37361331 | 0.13878071 | 0.12949967 | 0.22230593 |
| 0.20204471 | 0 | 0.04438861 | 0.08726612 | 0.10249525 | 0.3399167 | 0.41821736 | 0.13551003 | 0.15330224 | 0.29034158 |
| 0.0386699 | 0.06303895 | 0.04727922 | 0.03540911 | 0.1074769 | 0.14613985 | 0.1794749 | 0.06478496 | 0.06576592 | 0.10798883 |
| 0 | 0.03811579 | 0.04764473 | 0.05887672 | 0.05786451 | 0.2096419 | 0.21188634 | 0.07669982 | 0.10145679 | 0.73713675 |
| 0.05828494 | 0 | 0.00426834 | 0.01918029 | 0.0049877 | 0 | 0.14495061 | 0.03336491 | 0.1180114 | 0.40084616 |
| 0.27633606 | 0.24284078 | 0.0607102 | 0.06820209 | 0.05453888 | 0.35285375 | 0.48253211 | 0.22858713 | 0.63133901 | 1 |
| 0.02556065 | 0.01123119 | 0.01684679 | 0.03942866 | 0.01188884 | 0.12774454 | 0.13073943 | 1 | 1 | 0.81580538 |
| 0.06196003 | 0.01361243 | 0.01247806 | 0.04778832 | 0 | 0.62611836 | 1 | 0.02060451 | 0 | 0.03421305 |
| 0.03907376 | 0.10301263 | 0.00858439 | 0.05786242 | 1 | 1 | 0.56450263 | 0.04540054 | 0.03695379 | 0.07186282 |
| 0 | 0 | 0.04502209 | 0.01428195 | 0.01428195 | 0.04986057 | 0.04368063 | 0.01976341 | 0.02221317 | 0.00246574 |
| 0.08197125 | 0.07203534 | 0.01314484 | 0.0455202 | 0.04492801 | 0.16665898 | 0.10996236 | 0.07859706 | 0.08767431 | 0.06053715 |
| 0.11966338 | 0 | 0.00876323 | 0.0516844 | 0.03169942 | 0.05656044 | 0 | 0.01475468 | 0.025521 | 0 |
| 0.03579249 | 0.10515873 | 0.0455984 | 0.13782506 | 0.02487432 | 0.19141956 | 0.10591035 | 0.02928249 | 0.0309831 | 0.01318831 |
| 0 | 0.03145401 | 0.01718547 | 0.05889261 | 0.11727442 | 0.20940845 | 0.07396941 | 0.02645295 | 0.02365323 | 0.03399218 |
| 0.05835544 | 0 | 0.02564103 | 0 | 0.02034904 | 0.48399749 | 0.56820171 | 0.04612796 | 0.04373641 | 0.02026997 |
| 0.02583991 | 0 | 0.0227078 | 0.01440262 | 0.01966783 | 0.57086422 | 0.10691768 | 0.0144499 | 0.0185809 | 0.0112359 |
| 0.04284166 | 0.0564731 | 0.02823655 | 0.03826506 | 0.42200038 | 0.55199584 | 0.14370279 | 0.0154371 | 0.00349796 | 0.02519001 |
| | | 1 | 0.04493817 | 0.28654799 | 0.61776955 | 0.05424395 | 0.03736436 | 0.02237764 | 0.02849152 |

| Lor | Flg2 | Flg | Selenbp1 | Krt17 | Krt79 | Gata6 | Foxc1 | Sox9 | Cd36 | Cd34 |
|---|---|---|---|---|---|---|---|---|---|---|
| 0.01952217 | 0.02803229 | 0.07903289 | | 0.01707221 | 0.08516781 | 0 | 0.06472754 | 0.01521886 | 0.01627812 | 0.09412518 |
| 0.00237185 | 0.00946599 | 0.00463294 | | 0.0056715 | 0 | 0 | 0 | 0.00170914 | 0.0146593 | 0.00997231 |
| 0.0085561 | 0.01416981 | 0.04210245 | | 0.00512196 | 0.03711859 | 0 | 0 | 0.05948313 | 0 | 0.00482617 |
| 0.01536251 | 0.02670167 | 0.01709853 | | 0.03274636 | 0.06598077 | 0.26639734 | 0.04011631 | 0.00787868 | 0.01008872 | 0 |

TABLE 7-continued

| Col3a1 | Fbn1 | Sparc | Crabp1 | Itga9 | Dcn | Gpx3 | Cd14 | Place8 | Pdgfra | Pde3a | Tagln | Acta2 |
|---|---|---|---|---|---|---|---|---|---|---|---|---|
| 0.01880457 | 0.9398773 | 0 | 0 | 0.0081033 | 0.01653641 | 0 | 0 | 0 | 0 | 0 | 0 | 0.00822444 |
| 0.00280936 | 0 | 0 | 0 | 1 | 0.03072312 | 0 | 0 | 0 | 0.00891435 | 0.18162983 | 0.00163473 | 0.00077651 |
| 0.29441585 | 0 | 0 | 0 | 0.0053964 | 0.0418836 | 0.35160428 | 0.01134207 | 0 | 0.0345133 | 0 | 1 | 1 |
| 0.01351275 | 0 | 0 | 0 | 0.00099201 | 0.05993478 | 1 | 0 | 0 | 1 | 1 | 0.00112504 | 0.0013924 |
| 1 | 1 | 1 | 0 | 1 | 1 | 0.08883551 | 0.01661332 | 0 | 0.06108539 | 0.12875326 | 0.00618039 | 0.00416626 |
| 0.08572162 | 0 | 0 | 0 | 0.25730022 | 0 | 0 | 0.01065813 | 0 | 0.01216204 | 0.0826005 | 0.00371716 | 0.00286073 |
| 0.02251586 | 0.13666369 | 0.02204253 | 0 | 0.22396443 | 0.05865299 | 0 | 0.02081235 | 0 | 0.03022608 | 0.08797948 | 0.00184764 | 0.00283883 |
| 0.03855891 | 0 | 0 | 0 | 0.23799317 | 0.2837109 | 0 | 0.02287991 | 0 | 0.02088669 | 0.03546386 | 0.00255349 | 0.00393229 |
| 0.02609172 | 0.03701377 | 0 | 0 | 0.01391926 | 0 | 0 | 0.00358704 | 0 | 0.02066087 | 0.10325562 | 0.0005719 | 0.0094434 |
| 0.0261064 | 0 | 0.08491298 | 0 | 0.12979213 | 0 | 0 | 0.0145771 | 0 | 0.16079523 | 0 | 0.00610074 | 0.02559966 |
| 0.00721618 | 0 | 0.03927158 | 0 | 0.02496416 | 0 | 0 | 0.00471925 | 0 | 0.01436043 | 0.04179911 | 0.00225724 | 0.00177608 |
| 0 | 0.01967382 | 0.00951959 | 0 | 0.00560915 | 0.06389699 | 0 | 0.00381322 | 0 | 0.00331526 | 0.0633267 | 0.00091194 | 0.00085173 |
| 0.00663361 | 0 | 0.04802658 | 0 | 0.0300023 | 0 | 0 | 0.00412239 | 0 | 0.0062721 | 0.19169096 | 0.00143774 | 0.00374509 |
| 0.00680146 | 0 | 0.02119183 | 0.1691681 | 0.05665778 | 0 | 0 | 0.00363802 | 0 | 0.0235244 | 0.22555746 | 0.00177633 | 0.00066426 |
| 0.01068686 | 0.15616718 | 0.02518825 | 0.06702345 | 0.06996939 | 0 | 0 | 0.01729637 | 0 | 0.00657899 | 0.2010734 | 0.00392102 | 0.00246101 |
| 0.00539257 | 0.22797619 | 0 | 0 | 0.02110854 | 0 | 0.06389699 | 0.0063124 | 0 | 0.01440622 | 0.19568452 | 0.00044031 | 0.00090312 |
| 0.00659606 | 0 | 0.04902714 | 0 | 0.01490622 | 0 | 0 | 0.01052067 | 0 | 0.00978422 | 0.09784226 | 0.00176123 | 0.00119691 |
| 0.0031952 | 0 | 0.04399349 | 0 | 0.00895517 | 0 | 0 | 0.00629367 | 0 | 0.00957565 | 0.25363502 | 0.0014926 | 0.00133726 |
| 0.14144654 | 0 | 0.0480733 | 0 | 0.03713193 | 0 | 0 | 0 | 0 | 0.0125564 | 0.12791829 | 0 | 0.0605416 |
| 0.00333007 | 0 | 0 | 0 | 0 | 0 | 0 | 0.00615666 | 0 | 0.00702539 | 0 | 0.00171777 | 0 |
| 0.0028912 | 0 | 0 | 0 | 0.00495868 | 0 | 0 | 0.00272618 | 0 | 0.00414781 | 0.04225578 | 0.00133111 | 0.00123391 |
| 0.00148103 | 0 | 0.02632891 | 0 | 0.00889608 | 0 | 0 | 0.0101698 | 0 | 0.01031538 | 0.0700586 | 0.00063055 | 0.00119143 |

| Enpp2 | Sox2 | | | | | | Ptprc | Dock2 | | Cd68 | Tyr | Tyrp1 |
|---|---|---|---|---|---|---|---|---|---|---|---|---|
| 0.07118138 | | | | | | | 1 | | | | 0.34107113 | |
| 1 | | | | | | | 0.02648684 | | | | 0 | |
| 0.0620458 | | | | | | | 0.43582888 | | | | 1 | |
| 0 | | | | | | | 0 | | | | 0 | |
| 0.26355694 | | | | | | | 0.02503456 | | | | 0.00659798 | |
| 0.06413478 | | | | | | | 0.03613657 | | | | 0.01269863 | |
| 0.13248245 | | | | | | | 0.02138322 | | | | 0.00091705 | |

TABLE 7-continued

| Mgst1 | Scd1 | Plp1 | Sox10 |
|---|---|---|---|
| 0.09262025 | 0.0057023 | 0.02068659 | 0.01090411 |
| 0.02859293 | 0.00128072 | 0.0057914 | 0.00488432 |
| 0.06379417 | 0.01172472 | 0.01647463 | 0 |
| 0.01401454 | 0.00615054 | 0.00914326 | 0.00963901 |
| 0.02175388 | 0.00017016 | 0.01169748 | 0.00259615 |
| 0.09020458 | 0.01225598 | 0.02795404 | 0 |
| 0.29255179 | 0.01977408 | 0.02055797 | 0 |
| 0.12536919 | 0.02142186 | 0.03909576 | 0.00515194 |
| 0.3522207 | 0.01869755 | 0.02140231 | 0 |
| 0.46041921 | 0.02174423 | 0.01902428 | 0 |
| 0.21277106 | 0.02045143 | 0.01991622 | 0.00299944 |
| 0.04063155 | 0.00191588 | 0.00932708 | 0 |
| 0.02694355 | 0 | 0.00695808 | 0 |
| 0.01789599 | 0.00356906 | 0.01232421 | 0.00324811 |
| 0.02967092 | 0.0028734 | 0.02298725 | 0.00538525 |

The cells within the RNA-based clusters can also be distinguished by chromatin accessibility features, further confirming their identity (FIGS. 12G-12I). Applicants annotated clusters by the activity of lineage-determining TFs, which Applicants inferred by TF activity scores from the scATAC-seq data (FIG. 12G)[32], and their correlation to TF expression levels (FIGS. 18D-18F, Methods). This revealed global transcriptional activators Dlx3[14] (a hair follicle differentiation gene) and Sox9[14] (a key regulator of the hair follicle stem cell identity) among many others, and repressors Zeb1[33] and Sox5[34] (FIGS. 18F-18G). Thus, SHARE-seq provided insight into cell identity at multiple scales, including chromatin regulation by key lineage-determining TFs, enabling the analyses of cellular and regulatory atlases at scale.

Nevertheless, some cell subsets (e.g., in differentiation) or states (e.g., cell cycle) may be identified at higher resolution by either chromatin or gene expression features. Specifically, grouping clusters by their aggregate (pseudo-bulk) profiles more distinctively revealed chromatin accessibility differences between permanent portion (clusters 1-4) and regenerative portion (clusters 5-9) of hair follicle. Conversely, cells corresponding to the granular layer were easier to distinguish as a unique cluster at the gene expression level (FIG. 12I and FIG. 18C). Moreover, a subset of actively proliferating basal cells strongly expressing cell-cycle genes (FIG. 12J) was not identified as a coherent cluster by chromatin accessibility (with either of four different dimensionality reduction approaches, FIG. 12J, FIGS. 18H-18J, Methods).

SHARE-seq can be used to directly test the accuracy of computational approaches' that pair data from scATAC-seq and scRNA-seq from separately measured cells; such methods typically assume congruence, and may thus miss asynchrony or distinctions between these features of cellular identity. Applicants tested a Canonical Correlation Analysis (CCA)-based method[8] by providing the computational approach the scATAC-seq and scRNA-seq portions of the SHARE-seq measurements separately, and comparing its inferred pairing (defined as membership in the same cluster) to the correct (measured) coupling. Profiles from the same cell were properly assigned to the same cell subset with variable accuracy (74.9% in skin and 36.7% in mouse brain) (FIGS. 19A-19F), with most mis-assignments between clusters representing similar cell types (e.g., IRS to TACs, FIG. 12D). The mis-assignments may result from chromatin changes preceding or succeeding gene expression during differentiation from TACs to IRS, as discussed below. Such computational errors may be exasperated in differentiating cell types as seen in the skin or across highly diverse populations as seen in the brain. Thus, SHARE-seq can help either train computational pairing approaches across tissues or test their performance and help with further improvements.

Paired Measurements Associate Chromatin Peaks and Target Genes in Cis

Cells exhibit significant variation in both gene expression[35] and the underlying regulation of chromatin[36], due to both intrinsic (e.g., bursts of expression[37]) and extrinsic (e.g., cell size, level of regulatory proteins[38]) factors. Joint measurements in SHARE-seq allowed inference of the relationship between variation in chromatin and gene expression. Applicants developed an analytical framework to link distal peaks to genes in cis, based on the co-variation in chromatin accessibility and gene expression levels across cells, while controlling for technical biases in chromatin accessibility measurements (FIG. 13A, Methods). Applicants first applied this approach to a data set of 23,278 GM12878 cells, identifying 13,277 significant peak-gene associations (FIGS. 20A-20F, p<0.05, FDR=0.11). Down-sampling of either cell numbers or number of detected reads (matching library quality to those of previous chromatin/RNA reports[10]) dramatically reduces the ability to discover peak-gene associations (FIG. 13B).

Applying this framework to murine skin dataset, Applicants identified 63,110 significant peak-gene associations (within ±50 kb around transcription start sites (TSSs), p<0.05, FDR=0.1, after filtering peaks associated with multiple genes,). These peak-gene associations were enriched proximally to the TSS (FIGS. 21A-21B, $p<2.2\times10^{-16}$, KS-test). Only 10,154 additional peaks were associated with more than a single gene (FIGS. 21C-21D). Interestingly, most of the chromatin peaks (82%, FIG. 21E) were not correlated with the expression of any gene, and this was even more pronounced when the analysis is conducted within a single cell type. This may support a previous observation that only a small portion of candidate enhancers significantly alter gene expression[39].

A subset of genes, including key fate-determination genes, were associated with a large number of peaks ($p<2.2\times 10^{-16}$, permutation test, Methods). For example, 83 and 53 peaks were significantly associated (within ±500 kb around TSSs, p<0.05) with Dlx3, highly expressed in TACs (FIG. 13C), and Cxcl14, highly expressed in bulge (FIG. 21F), respectively[14]. These results are reminiscent of previous observations describing regulatory locus complexity at key lineage genes[40]. Further, regions with high-density of peaks associated with a single gene significantly overlap known super-enhancers[14] (FIG. 13C, 2.1 fold enrichment, $p=10^{238}$, hypergeometric test). Super-enhancers were enhancer regions that are cell-type specific and highly enriched in histone H3K27 acetylation[41]. This relationship was not simply driven by super-enhancer length (Spearman p=0.04; FIG. 21G). Furthermore, super-enhancers regulated genes were associated with more peaks compared to all genes (10.9 vs. 4.4 associated peaks per gene on average $p<2.2\times 10^{16}$, KS-test, FIGS. 13D-13E, FIG. 21H). Notably, while peak-gene associations are enriched at known super-enhancers, Applicants found that densely regulated genes also exhibited interactions outside the annotated super-enhancer which may reflect the false discovery of our approach (FDR=0.1) and/or limitations in calling super-enhancers using ChIP-seq which did incorporate the 3D configuration of the locus[42]. Finally, most annotated cell cycle genes (n=97) had lower than expected number of peak-gene interactions (on average 3.4 interactions for cell cycle genes vs. 4.4 interactions for all genes; p=0.026, t-test), further supporting a limited contribution of chromatin accessibility to cell cycle associated gene expression and suggesting that variable expression is not sufficient for determining peak-gene associations.

Domains of Regulatory Chromatin (DORCs) Identified Key Lineage-Determining Genes De Novo Applicants defined the 857 regions with an exceptionally large (>10) number of significant peak-gene associations as "Domains Of Regulatory Chromatin" (DORC), identified as those exceeding an inflection point ("elbow") when ranking genes by the number of significant associations (FIG. 13F). Genes associated with super-enhancers were strongly enriched in DORC-regulated genes ($p=10^7$, hypergeometric test). Applicants quantified the activity of DORCs as the sum of accessibility at peaks significantly associated with the DORC-regulated gene. DORC accessibility scores were highly cell-type specific, and DORC genes were identified when conducting the analysis within a cell type (GM12878 cells) or across diverse cells types in tissues (FIGS. 20A-20F). The DORCs identified within sub-populations strongly overlap with DORCs identified with all alls (p=10$^{-201}$, hypergeometric test, FIG. 21I). Moreover, chromatin accessibility of DORCs were strongly enriched for known key regulators of lineage commitment across the expected lineages (FIG. 13G, FIG. 21J). For example, Sox9, a master regulator of stem cell fate commitment[43], is a DORC-regulated gene, and this DORC has high activity in stem cell populations (FIG. 13G).

There were significant differences between DORCs even in closely related populations, suggesting DORCs may help predict novel regulators that distinguish them. In some cases, high DORC activity in a particular cell subset presented little to no gene expression of the DORC regulated-gene, suggesting a gain of chromatin accessibility does not always equate to productive transcription. For example, while Dlx3 DORC activity and Dlx3 gene expression were generally correlated in TAC/IRS/Hair shaft cells, this was not the case within cuticle/cortex cells (FIG. 13H, FIG. 21K). Thus, DORCs provide an unsupervised, readily accessible approach to simultaneously identify key lineage-determining genes and the regions that regulate them de novo at single-cell resolution, without the need to know the cell type identity in advance, isolate cell subsets, and conduct challenging ChIP-seq experiments.

Lineage Priming at Enhancers Precedes Gene Expression in DORCs

The hair follicle is a highly regenerative epithelial tissue that cycles between growth (anagen), degeneration (catagen), and rest (telogen). At the anagen onset, hair follicle stem cells located at the bulge and hair germ proliferate transiently to produce the short-lived TACs. These TACs are one of the most proliferative cells in adult mammals—they proliferate rapidly to produce multiple morphologically and molecularly distinct downstream differentiated cell types that constitute the mature hair follicle, including the companion layer, IRS (Henle's layer, Huxley's layer, IRS cuticle) and hair shaft (hair shaft cuticle, cortex, medulla) [44,45]. Previous studies have shown that TACs display molecular heterogeneity but still maintain a degree of lineage plasticity[46,47]. The unique features of TACs provide an interesting context to study chromatin-RNA relationship in cells that are required to dynamically change their epigenome to choose lineage fates, while undergoing rapid proliferation.

Applicants readily recovered hair follicle differentiation trajectories from chromatin accessibility (FIG. 14A), whereas similar analysis of the RNA profile led to challenges, due to the strong expression of cell cycle genes in the rapidly proliferating TACs (FIG. 12I, FIG. 22A-22F). Single cell chromatin profiles were ordered into three lineage trajectories, IRS, medulla, and cuticle/cortex, differentiated from TACs (FIG. 14A). The detailed structure in IRS (including Henle's layer, Huxley's layer, and the IRS cuticle) was not fully resolved due to the rareness of these cell types (672 (~2%) IRS cells out of 34,774 cells, consistent with previously reported 1-3.8% cell types[48], although Applicants did identify a subset of cells located between the IRS and medulla lineages (FIG. 14A), which may suggest distinct differentiation routes to these IRS subsets, as explored below.

Figure 23A:
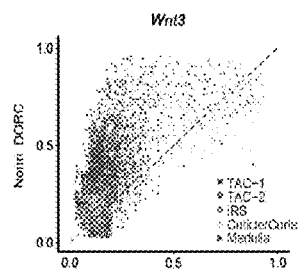
FIGS. 23A-23M. Characterization of lineage-priming and chromatin potential.
Figure 23B:
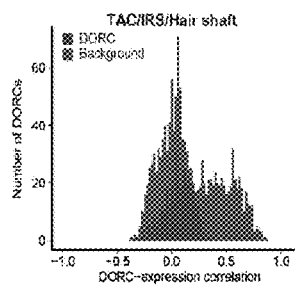

Systematically analyzing the onset of accessibility and gene expression along differentiation pseudotime from TACs to cuticle/cortex cells revealed that DORCs generally become accessible prior to the onset of their associated gene's expression, consistent with lineage-priming. DORCs may play an important role in differentiation. For example, Wnt3 RNA became detectable at late stage of hair shaft differentiation, consistent with previous findings[49]. However, accessibility in the Wnt3 DORC activated at TACs prior to gene expression before lineage commitment (FIG. 14B), which Applicants quantified by computing "residuals" (defined as the difference of chromatin accessibility and expression of the gene). Systematic analysis typically found positive residuals across all DORC-regulated genes and lineages (FIG. 14C, FIG. 23A), despite the overall correlated accessibility of DORCs and the expression of the DORC-regulated genes (by definition, FIG. 23B). Thus, sufficiently high RNA expression may be detectable only within a subset of cells with accessible chromatin at that gene's locus.

Figure 23D:
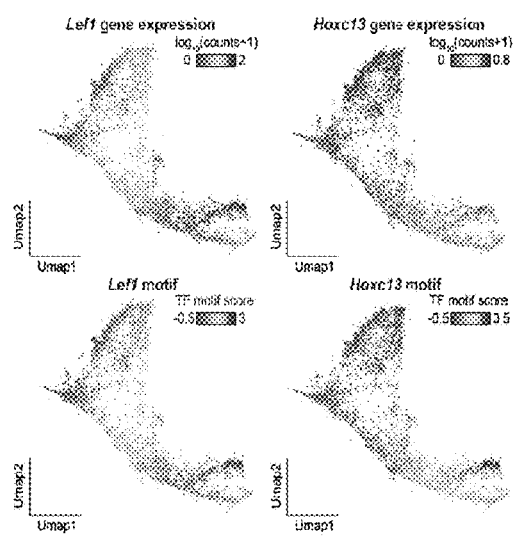
Figure 23C:
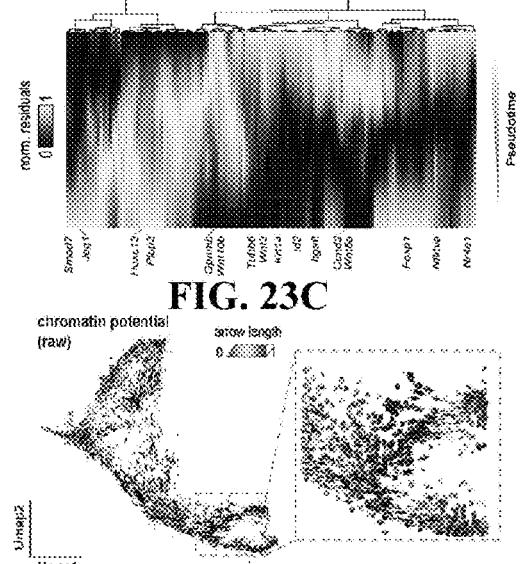

To further understand the possible underlying cause of these residuals, Applicants tracked the changes in accessibility in individual peaks in the Wnt3 DORC along differentiation pseudotime from TACs to cuticle/cortex cells (FIG. 14D). Applicants found a sequential activation of peaks, with enhancer peaks generally activating much earlier (in pseudotime) than the Wnt3 promoter, followed by observed activation of nascent RNA expression (estimated by intron counts) and finally mature RNA expression (estimated by exon counts) (FIG. 14D). This pattern of peak activation in enhancers prior to expression is apparent across many genes, which was referred to as the "lineage-priming module", sharing similar residuals (FIG. 14E, FIG. 23C). For example, there was a lag of 0.20 or 0.13 pseudotime units between the respective onset of accessibility in the Wnt3 or Tubb6 DORCs and the onset of expression of these genes, first at pre-mRNA and then by mRNA (FIG. 14F). Notably, some TACs at late pseudotime were still proliferative (estimated by cell cycle gene expression); however, they already showed activated enhancer peaks, suggesting the proliferation and differentiation switch transitioning from TACs to cuticle/cortex lineage (FIG. 14D). These analyses suggest that enhancer activation foreshadows expression of target genes[5,6] and implicates chromatin accessibility as a marker for lineage-priming[50]

Applicants further investigated the mechanisms leading to chromatin accessibility mediated lineage priming and hypothesized that binding of lineage-specific TFs may lead to lineage-priming. Indeed, Applicants found that binding sites for Lef1 and Hoxc13 TFs are strongly enriched (p<10$^{-4}$, KS-test, FIG. 14G) in hair shaft lineage-priming DORCs (including the Wnt3 DORC). Gene expression and TF motif activity (inferred from ATAC-seq) of Lef1, a regulator of the Wnt signaling pathway[51], activated prior to Hoxc13[52], implicating Lef1 as the lineage-priming TF[52]. This was followed by expression of Hoxc13[53], likely inducing Wnt3 DORC accessibility and promoting Wnt3 gene expression (FIG. 14H, FIG. 23D). Together, this supports a model, whereby lineage defining TFs prime chromatin accessibility and foreshadow lineage choice.

Chromatin potential described chromatin-to-gene expression dynamics during differentiation Empowered by the findings, Applicants explored whether lineage priming by chromatin accessibility may foreshadow gene expression and may be used to predict lineage choice prior to lineage commitment. Applicants focused on DORC-regulated genes, which encompassed lineage-determining genes and coincide with strong chromatin signal.

Figure 23E:
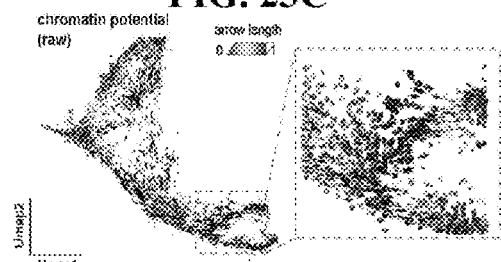
Figure 23F:
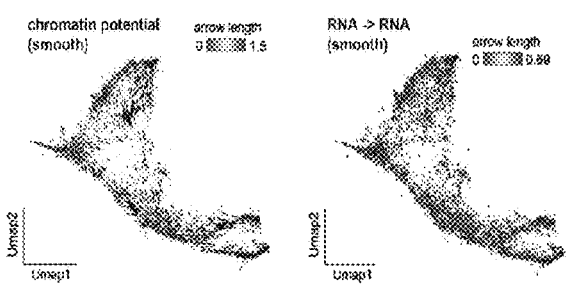

Applicants thus devised an approach to calculate "chromatin potential", defined as the future RNA state most compatible with a cell's current chromatin state. To calculate chromatin potential, Applicants first addressed data sparsity, by smoothing each cell by computing a k-nearest neighbor graph (k-NN defined by chromatin state, k=50) and averaging chromatin and expression profiles for cells in this neighborhood. Next, Applicants computed RNA-chromatin neighbors (k-NN, k=10) whereby Applicants found, for each cell (cell x, chromatin neighborhood), 10 cells (cell y, RNA neighborhood) whose RNA expression of DORC-regulated genes was most correlated to the current chromatin state. Chromatin potential (arrow) was the direction and distance between each cell (cell x, chromatin neighborhood) and 10 nearest cells (cell y, RNA neighborhood) in chromatin low dimensional space (FIG. 14I, FIG. 23E-23F). Applicants noted here that this analysis did not rely on the inferred pseudotime. Chromatin potential related a potential "future" RNA state (observed in another cell) which was best predicted by the chromatin state of a given cell.

In general, chromatin potential flew from progenitor cells (TACs) to differentiated cells (IRS/Hair shaft). Long arrow length represented a chromatin state reflecting a more differentiated transcriptome. Regions of long arrows suggests lineage commitment at these lineage events occurs as a switch rather than as a gradient[46]. Chromatin potential was higher at key multi-lineage defining transitions, including the branch point that defining the cuticle/cortex and medulla lineages.

Figure 23G:
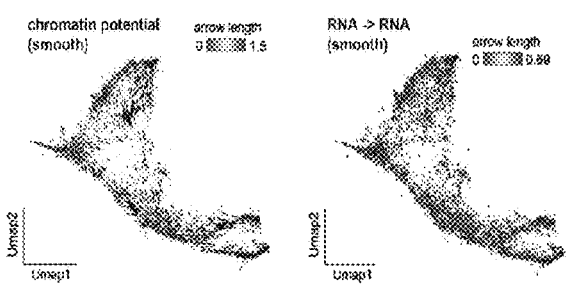
Figure 23H:
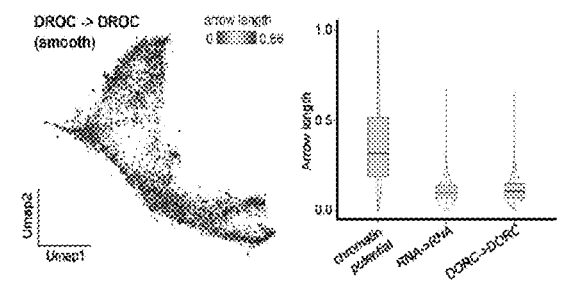
Figure 23I:
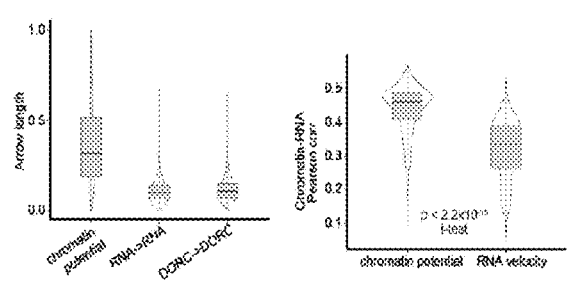
Figure 23J:
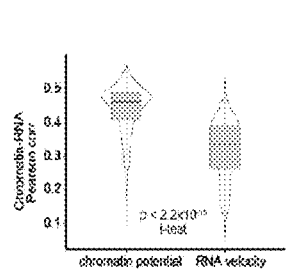
Figure 23K:
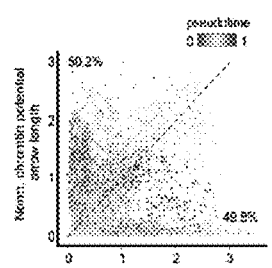

In many key developmental transitions, longer time scales foreshadowed by chromatin states. This is clear by several different measures. First, the "future" RNA state predicted by chromatin potential extended significantly further than that predicted with the current RNA state (FIGS. 23G-23I). Second, RNA velocity derived vectors, which used intronic RNA as a measure of nascent transcription to determine future states, validated the end-point trajectories (FIG. 14J)[19]. In particular, for each cell its RNA velocity (from RNA) and its chromatin potential (from chromatin-RNA), cells reflecting the "future" RNA state (defined by RNA velocity) results in substantially less chromatin-RNA correlation when compared to the "future" state predicted by chromatin potential ($p<2.2\times10^{-16}$, t-test, FIG. 23J). The discrepancy between RNA velocity and chromatin potential was most prominent in TACs (FIG. 14K). Interestingly, chromatin potential had longer reach (prediction timescales) at early stages, whereas RNA velocity (extended to a k-NN neighborhood) had further reach (longer arrows) at late pseudotimes ($p<2.2\times10^{-16}$, KS-test, FIG. 23K). Generally, chromatin potential supported the measure of pseudotime; however, it identified a distinct root-like position, which suggests either an alternative lineage origin or plasticity and route reversal (FIG. 14I). Chromatin potential also suggested an alternative route to the IRS which was not identified by RNA velocity (FIG. 14J); however, additional experiments using lineage tracing were needed to better elucidate the dynamics of this transition. Thus, chromatin potential allowed for relating the chromatin state of one cell to future RNA states not yet realized in that cell, and to span longer time scales especially in early developmental transitions.

Figure 23L:
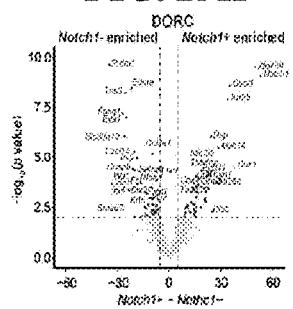
Figure 23M:
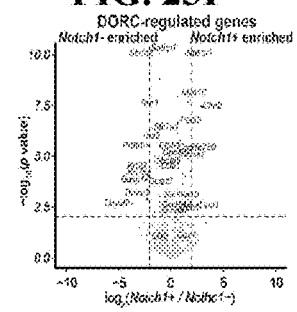

Finally, Applicants sought to see how early markers of lineage commitment could be identified, searching for genes whose chromatin state foreshadows lineage commitment far preceding the lineage choice as reflected in their RNA state. To investigate this, Applicants identified DORCs that were differentially active between cuticle/cortex and medulla cells preceding the lineage decision, including Notch1, Cux1, and Lef1 (FIG. 23L). Interestingly, Notch1 is highly expressed in hair shaft cells, whose DORC encompasses 79 peaks. Notch1 is important in controlling hair follicle differentiation and acts non-autonomously to regulate the formation of hair shaft and IRS[54]. The activation of Notch1 DORC activity coincided with longer arrows associated with cuticle/cortex lineage commitment. (FIG. 14I). When Applicants partitioned the lineage-priming region into 3 sub-regions by the DORCs' accessibility (FIG. 14L), Notch1+ and Notch1- regions showed distinct chromatin patterns with coordinated changes in gene expression, whereas Notch1+ cells were not distinctly identified by their gene expression pattern alone (FIG. 14M, FIGS. 23L and 23M). Notch1+ and Notch1- regions showed chromatin potential to differentiate into cuticle/cortex and medulla lineages, respectively. Applicants observed clear chromatin-gene expression differences (residuals) at multiple loci in the lineage-priming region using aggregated genome tracks (FIG. 14N). A similar differential trend was observed between fully differentiated cells, which clearly highlights the chromatin evidence of lineage-priming events before gene expression activation. Altogether, Applicants demonstrated that analyses of chromatin accessibility mediated lineage-priming enable insight into the chromatin potential of cells and predict lineage fate outcomes.

Discussion

High resolution, massively parallel simultaneous measurement of chromatin landscapes and gene expression in diverse tissues including during differentiation provided four key insights: (1) There was a high degree of congruence in the definition of differentiated cell types by both measures; (2) co-variation of chromatin and RNA across cells—within and between cell types—associated regulatory regions to their target genes; (3) among these, Applicants identified DORCs, which reflected regulatory regions that control key lineage genes; and (4) focusing on DORCs, Applicants found that chromatin activates prior to gene expression during differentiation, with chromatin potential foreshadowing RNA states of cells at longer time scales than RNA velocity. These insights required the improved data quality and throughput (up to $10^6$ cells) of SHARE-seq.

To determine congruence, Applicants found that both datasets largely reflected similar clusters of cell types demonstrating that cell types in tissues largely coordinated chromatin structure with transcription. Nevertheless, some cell states were not reflected equally in both profiles. In one example, a proliferative basal cell population was distinguished specifically in the transcriptional dataset. The joint data in SHARE-seq can also provide excellent training for algorithms that aim to computationally map chromatin and RNA modalities across cells.

To infer transcriptional regulation and recover key regulatory regions in differentiation, SHARE-seq provided a means to infer DORCs reflecting key lineage-determining genes. Leveraging SHARE-seq, it was possible to identify key regulatory regions, including developmental super-enhancers, and their associated target genes, without the need for isolating specific cell subsets or ChIP-seq experiments, which can be challenging for in vivo samples. The inclusion of more layers of measurements, and improved computational methods for illustrating the differences between chromatin regulators and transcriptomic structure, provided a more robust approach for defining chromatin-gene dynamics within complex tissues. This can be important in developmental biology, cancer research, and especially human genetics, where genetic variants associated with complex human diseases are found in non-coding regions, and relating them to specific cell types and target genes can be challenging.

Focusing on the incongruence between chromatin accessibility and gene expression, Applicants demonstrated the existence of chromatin accessibility mediated lineage-priming, and defined chromatin potential to describe the time difference upon hair follicle differentiation. SHARE-seq allowed for stronger predictions on a cell's future potential in several ways. First, when Applicants calculated chromatin potential, Applicants related the chromatin signal of one cell (or neighborhood) to the RNA signal in any cell (or neighborhood) from the same experiment, and can transverse longer time scales and identify cell fates earlier in differentiation. Second, leveraging the joint measurements of RNA (nascent and mature) and chromatin in every single cell, Applicants can relate its current chromatin state to its current and future (by RNA velocity) states, to understand the distinction between its realized (in RNA) and as-yet-unrealized potential.

SHARE-seq provided a generalizable platform and opportunity to include additional layers of information per cell. With further development, Applicants can integrate other scRNA-seq compatible measurements[8], such as protein measurements[55], genotyping, and lineage barcoding. Furthermore, powered by the massive scalability of this approach, SHARE-seq can be adapted for identifying RNA barcodes, particularly useful for CRISPR-based perturbation screens[56]. SHARE-seq can be further extended by replacing ATAC-seq with whole-genome transposition[57] enabling methods for DNA methylation and chromatin conformation. In these efforts, scRNA-seq data may be used as a common scaffold for integration, providing a unique opportunity to comprehensively map between multiple layers of gene regulation, as well as to train algorithms that learn to map between different data modalities in a cell. As such, as Applicants move toward a cell atlas, SHARE-seq can play a key role in determining the full diversity of cell types and cell states, and the regulators that define them.

Methods

Experimental Methods

Mice

Mice were maintained in an Association for Assessment and Accreditation of Laboratory Animal Care (AAALAC) approved animal facility at Harvard University and MIT. Procedures were approved by the Institutional Animal Care and Use Committee of all institutions.

Cell Culture and Tissue Processing (1) Cell Culture

GM12878 cells were cultured in RPMI 1640 medium (11875-093, ThermoFisher) supplemented with 15% FBS (Ser. No. 16/000,044, ThermoFisher) and 1% penicillin-streptomycin (Ser. No. 15/140,122, ThermoFisher). NIH/3T3 and RAW 264.7 cells were cultured in Dulbecco's Modified Eagle Medium (DMEM, 11965092, ThermoFisher) with the addition of 10% FBS and 1% of penicillin-streptomycin. Cells were incubated at 37° C. in 5% $CO_2$ and maintained at the exponential phase. NIH/3T3 and RAW 264.7 cells were digested with accutase for preparing single-cell suspension.

(2) Mouse Skin

Female C57BL/6J mouse dorsal skins were collected at late anagen (P32). The hair cycle stages were confirmed using cryosectioning. To generate whole skin a single cell suspension, skin samples were incubated in 0.25% collagenase in HBSS at 37° C. for 35-45 minutes on an orbital shaker. Samples were gently scraped from the dermal side and the single-cell suspension was collected by filtering through a 70 μm filter followed by a 40 μm filter. The epidermal portion of the skin samples were incubated in 0.25% trypsin-EDTA at 37° C. for 35-45 minutes on the shaker and cells were gently scraped from the epidermal side. Single-cell suspensions were combined and centrifuged for 5 minutes at 4° C., resuspended in 0.25% FBS in PBS, and stained with DAPI (0.05 m/mL). Live cells were enriched by FACS. To enrich for epidermal populations, CD140a negative population were purified by FACS and combined with whole skin cells in a ratio of 1:1.

(3) Mouse Brain

Adult mouse brain was dissected, snap-frozen on dry ice, and stored at −80° C. A single nucleus suspension was prepared following the OMNI-ATAC protocol[58]. Nuclei were resuspended in PBSI (0.1 U/μl Enzymatics RNase Inhibitor, Y9240L, Qiagen; 0.05U4 SUPERase inhibitor, AM2696, ThermoFisher; 0.04% Bovine Serum Albumin, BSA, 15260037, ThermoFisher in PBS).

(4) Mouse Lung

Mouse lung was dissociated with fine scissors followed by proteolytic digestion using the Lung Dissociation kit (Miltenyi Biotech) following the manufacturer's instructions. Dissociated cells were then incubated at 37° C. for 20 minutes with rotation, then filtered using a 100 μm strainer. Red blood cells were lysed using ACK buffer (A1049201, ThermoFisher).

Skin Histology and Immunofluorescence

Mouse skin samples were fixed in 4% paraformaldehyde (PFA) for 15 minutes at room temperature and then washed 6 times using PBS. The samples were immersed in 30% sucrose in PBS overnight at 4° C. Samples were cut and embedded in OCT (Sakura Finetek) and 35 μM sections were harvested on positively charged slides. For immunohistochemistry, sections were fixed in 4% PFA for 2 minutes, washed with PBS and PBST. Sections were blocked using blocking buffer (5% donkey serum, 1% BSA, 2% cold water fish gelatin, 0.3% Triton X-100 in PBS) for 1 hour at room temperature. Primary antibodies (anti-PolII S5, Abcam, ab5131; anti-PolII S2, Abeam, ab5095; anti-PolII, Abeam, ab817) were added and incubated overnight at 4° C. Secondary antibodies (anti-Rabbit IgG Alexa 488, Jackson ImmunoResearch, 711-545-152; anti-Mouse IgG Alexa 488, Jackson ImmunoResearch, 715-545-150) were added and incubated for 4 hours at room temperature.

SHARE-seq (1) Preparing Oligonucleotides for Ligations

There are three barcoding rounds of hybridization reactions in SHARE-seq, with a different 96-well barcoding plate for each round (Tables 6A-6E). Hybridization oligos have a universal linker sequence that is partially complementary to well-specific barcode sequences. These strands were annealed prior to cellular barcoding to create a DNA molecule with three distinct functional domains: a 5' overhang that is complementary to the 3' overhang present on the cDNA molecule or transposed DNA molecules (may originate from RT primer, transposition adapter or previous round of barcoding), a unique well-specific barcode sequence, and a 3' overhang complementary to the 5' overhang present on the DNA molecule to be subsequently ligated. Linker strands and barcode strands for the hybridization rounds were added to RNase-free 96-well plates to a total volume of 10 μl/well with the following concentrations: round 1 plates contained 9 μM round 2 linker strand and 10 μM barcodes, round 2 plates contained 11 μM round 2 linker strand and 12 μM barcodes, and round 3 plates contained 13 μM round 3 linker strand and 14 μM barcodes. The oligos are dissolved in STE buffer (10 mM Tris pH 8.0, 50 mM NaCl, and 1 mM EDTA). Oligos are annealed by heating plates to 95° C. for 2 minutes and cooling down to 20° C. at a rate of −1° C. per minute.

Blocking strands are complementary to the 3' overhang present on the DNA barcodes used during hybridization barcoding rounds. Blocking occurs after well-specific barcodes have hybridized to cDNA molecules, but before all cells are pooled back together. The blocking step minimizes the possibility that unbound DNA barcodes mislabel cells in future barcoding rounds. 10 µl of each blocking strand solution was added to each of the 96 wells after the first, second, and third round of hybridization of DNA barcodes, respectively. Blocking strand solutions were prepared at a concentration of 22 µM for round 1, 26.4 µM for round 2, and 23 µM for round 3. Blocking strands for the first two rounds were in a 2×T4 DNA Ligase buffer (NEB) while the third round was in 0.1% Triton X-100. Both ligation reaction and blocking reaction were incubated with cells for 30 minutes at room temperature with gentle shaking (300 rpm). All the oligos are thawed to room temperature before using.

(2) Fixation

For simplicity, cells and nuclei, which were processed identically for the following steps, are both referred to as cells. Cells were centrifuged at 300 g for 5 minutes and resuspended to 1 million cells/ml in PBSI. Cells were fixed by adding formaldehyde (28906, ThermoFisher, final concentration of 0.1% for cell lines or 0.2% for primary tissues) and incubated at room temperature for 5 minutes. The fixation was stopped by adding 56.1 µl of 2.5M glycine, 50 µl of 1M Tris-HCl pH 8.0, and 13.3 µl of 7.5% BSA on ice. The sample was incubated at room temperature for 5 minutes and then centrifuged at 500 g for 5 minutes to remove supernatant. All centrifugations were performed on a swing bucket centrifuge. The cell pellet was washed twice with 1 ml of PBSI, and centrifuged at 500 g for 5 minutes between washings. The cells were resuspended in PBS with 0.1 U/µl Enzymatics RNase Inhibitor and aliquoted for transposition.

(3) Transposition

The transposition reaction was performed similarly to previous published work[58] with minor modifications. All the oligos used in this protocol can be found in Tables 6A-6E. The 100 µM Read1 and phosphorylated Read2 oligos were annealed with an equal amount of 100 µM blocked ME-complement oligo by heating at 85° C. for 2 minutes and slowly cooling down to 20° C. at a ramp rate of −1° C./minute. The annealed oligos were mixed with an equal volume of cold glycerol and stored at −80° C. until use. In-house produced Tn5[10] was mixed with an equal volume of dilution buffer (50 mM Tris, 100 mM NaCl, 0.1 mM EDTA, 1 mM DTT, 0.1% NP-40, and 50% glycerol). Diluted Tn5 was then mixed with an equal volume of annealed oligos and incubated at room temperature for 30 minutes before transposition.

For each transposition reaction, cells (10,000-20,000 cells in 5 µl PBSI) and 42.5 µl of transposition buffer (38.8 mM Tris-acetate, 77.6 mM K-acetate, 11.8 mM Mg-acetate, 18.8% DIME, 0.12% NP-40, 0.47% Protease Inhibitor Cocktail, and 0.8 U/µl Enzymatics RNase Inhibitor) were mixed and incubated at room temperature for 10 minutes. 2.5 µl of assembled Tn5 was added to the transposition reaction. Depending on the target number of cells to be recovered, the number of transposition reactions can be scaled up. In general, Applicants prepared 10-40 reactions, which were equivalent to 100,000-800,000 cells. The transposition was carried out at 37° C. for 30 minutes with shaking at 500 rpm. The sample was centrifuged at 1,000 g for 3 minutes and then washed with 1 ml Nuclei Isolation Buffer (NIB) (10 mM Tris buffer pH 7.5, 10 mM NaCl, 3 mM $MgCl_2$, 0.1% NP-40, 0.1 U/µl Enzymatics RNase Inhibitor, and 0.05 U/µl SUPERase RI). The sample was then resuspended to 60 µl of NIB and before proceeding to reverse transcription.

(4) Reverse Transcription

Transposed cells (60 µl) were mixed with 240 µl of RT mix (1.25×RT buffer, 0.5 U/µl Enzymatics RNase Inhibitor, 625 µM dNTP, 12.5 µl V1 RT primer with an affinity tag, 18.75% PEG 6000, and 25 U/µl Maxima H Minus Reverse Transcriptase). The RT primer contained a poly-T tail, a Unique Molecular Identifier (UMI), a universal ligation overhang, and a biotin molecule. The sample was heated at 50° C. for 10 minutes, then went through 3 thermal cycles (8° C. for 12s, 15° C. for 45s, 20° C. for 45s, 30° C. for 30s, 42° C. for 120s and 50° C. for 180s), and finally incubated at 50° C. for 5 minutes. After reverse transcription, 300 µl of NIB was added and the sample was centrifuged at 1,000 g for 3 minutes to remove supernatant. Cell pellet was washed with 0.5 ml of NIB and centrifuged at 1,000 g for 3 minutes. Cells were resuspended in 4,608 µl of hybridization mix (1×T4 ligation buffer, 0.32 U/µl Enzymatics RNase Inhibitor, 0.05 U/µl SUPERase RI, 0.1% Triton X-100, and 0.25×NIB).

(5) Hybridization and Ligation

Cells in ligation mix (40 µl) were added to each of the 96 wells in the first-round barcoding plate. Each well already contained 10 µl of the appropriate DNA barcodes. The round 1 barcoding plate was incubated for 30 minutes at room temperature with gentle shaking (300 rpm) to allow hybridization to occur before adding blocking strands. 10 µl of round 1 blocking oligo was added and the plate was incubated for 30 minutes at room temperature with gentle shaking (300 rpm). Cells from all 96 wells were combined into a single multichannel basin. Subsequent steps in round 2 and round 3 were identical to round 1, except that 50 µl and 60 µl of pooled cells were split and added to barcodes in round 2 (total volume of 60 µl/well) and round 3 (total volume of 70 µl/well), respectively. After adding the round 3 blocking oligo, cells from all wells were combined and centrifuged at 1,000 g for 3 minutes to remove supernatant. The cell pellet was washed twice with 1 ml of MB, and centrifuged at 1,000 g for 3 minutes between washings. Cells were re-suspended in the ligation mix (1×T4 ligation buffer, 0.32 U/µl Enzymatics RNase Inhibitor, 20 U/µl T4 DNA ligase (M0202L, NEB), 0.1% Triton X-100, 0.2×NIB) and incubated for 30 minutes at room temperature with gentle shaking (300 rpm). Cells were washed once with 0.5 ml washing buffer and resuspended in 100 µl of NIB, counted and aliquoted to 0.2 ml PCR tubes with 1,000-20,000 cells per tube.

(6) Reverse Crosslinking and Affinity Pull-Down

NIB was added to each sample to bring the volume to 50 µl in total. 50 µl of 2× reverse crosslinking buffer (100 mM Tris pH 8.0, 100 mM NaCl, and 0.04% SDS), 2 µl of 20 mg/ml proteinase K, and 1 µl of SUPERase RI were mixed with each sample and incubated at 55° C. for 1 hour. 5 µl of 100 mM PMSF was added to the reverse crosslinked sample to inactivate proteinase K and incubated at room temperature for 10 minutes. For each sample, 10 µl of MyOne C1 Dynabeads were washed twice with 1×B&W-T buffer (5 mM Tris pH 8.0, 1M NaCl, 0.5 mM EDTA, and 0.05% Tween 20) and once with 1×B&W-T buffer supplemented with 2 U/µl SUPERase RI. After washing, the beads were resuspended in 100 µl of 2×B&W buffer (10 mM Tris pH 8.0, 2M NaCl, 1 mM EDTA, and 4 U/µl SUPERase RI) and mixed with the sample. The mixture was rotated on an end-to-end rotator at 10 rpm for 60 minutes at room temperature. The lysate was put on a magnetic stand to separate supernatant and beads.

(7) scATAC-Seq Library Preparation

The supernatant that contained the transposed DNA fragments was purified with DNA clean and concentrator kit and eluted to 10 µl of Tris buffer (pH 8.0). Fragments were PCR amplified with Ad1 primer with sample barcodes and P7 primer. The amplification procedure was similar to standard bulk ATAC-seq library preparation[58] with minor modifications: the annealing temperature was set to 65° C. instead of 72° C.

(8) cDNA Library Preparation

Beads were washed three times with 1×B&W-T buffer and once with STE (10 mM Tris pH 8.0, 50 mM NaCl, and 1 mM EDTA) both supplemented with 1 U/µl SUPERase inhibitor. Beads were resuspended in 50 µl of template switch mix (15% PEG 6000, 1× Maxima RT buffer, 4% Ficoll PM-400, 1 mM dNTPs, 1 U/µl Enzymatics RNase-In, 2.5 µM TSO, and 10 U/µl Maxima H Minus Reverse Transcriptase). Beads were rotated on an end-to-end rotator at 10 rpm for 30 minutes at room temperature, and then shaken at 300 rpm for 90 minutes at 42° C. Beads were resuspended by pipetting every 30 minutes during agitation. After template switching, 100 µl of STE were added to each tube to dilute the sample. The supernatant was removed by placing the sample on a magnetic stand. Beads were washed with 200 µl of STE without disturbing the bead pellet. Beads were then resuspended in 55 µl of PCR mix (1× Kapa HiFi PCR mix, 400 nM P7 primer, and 400 nM RNA PCR primer). The PCR reaction was carried out at the following conditions: 95° C. for 3 minutes, and then thermocycling 14 cycles at 98° C. for 30s, 65° C. for 45s and 72° C. for 3 minutes. Optionally, Applicants ran 5 cycles of PCR, took 2.5 µl sample, added 7.5 µl of PCR cocktail with 1× EvaGreen (Biotium), and run qPCR. The qPCR reactions were amplified to saturation to determine the number of cycles required for the remaining samples on the plate. The qPCR reaction was carried out at the following conditions: 95° C. for 3 minutes, and then 20 thermal cycles at 98° C. for 30s, 65° C. for 20s and 72° C. for 3 minutes. Libraries were amplified for 12-14 cycles in total for 1,000 cells. Amplified cDNA was purified by 0.8× (for cell line) or 0.6× (for primary tissue) AMPure beads and eluted to 10 µl of Tris pH 8.0 buffer. The amount of cDNA was quantified by Qubit (ThermoFisher).

(9) Tagmentation and scRNA-Seq Library Preparation

100 µM Read1 oligo was annealed with an equal amount of 100 µM blocked ME-complement oligo and assembled with Tn5 as described above. For each sample, 50 ng cDNA was fragmented in 50 µl tagmentation mix (1×TD buffer from Illumina Nextera Kit, and 5 µl assembled Tn5) at 55° C. for 5 minutes. Fragmented cDNA was purified with the DNA Clean and Concentrator Kit (Zymo) and eluted to 10 µl of Tris pH 8.0 buffer. Purified cDNA was then mixed with tagmentation PCR mix (25 µl of NEBNext High-Fidelity 2×PCR Master Mix, 1 µl of 25 µM P7 primer and 1 µl of 25 µM Ad1 primer with sample barcodes). PCR was carried out at the following conditions: 72° C. for 5 minutes, 98° C. for 30s, and then 7 cycles at 98° C. for 10s, 65° C. for 30s and 72° C. for 1 minute. The amplified library was purified by 0.7× AMpure beads and eluted to 10 µl of Tris buffer (pH 8.0).

(10) Quantification and Sequencing

Both scATAC-seq and scRNA-seq libraries were quantified with KAPA Library Quantification Kit and pooled for sequencing. Libraries were sequenced on the Next-seq platform (Illumina) using a 150-cycle High-Output Kit (Read 1: 30 cycles, Index 1: 99 cycles, Index 2: 8 cycles, Read 2: 30 cycles) or the Nova-seq platform (Illumina) using a 200-cycle 51 Kit (Read 1: 50 cycles, Index 1: 99 cycles, Index 2: 8 cycles, Read 2: 50 cycles).

Computational Methods

SHARE-ATAC-Seq Pre-Processing

Raw sequencing reads were trimmed with a custom python script. Reads were aligned to hg19 or mm10 genome using bowtie2 (Langmead et al. 2012) with (–×2000) option. For each read, there are four sets of barcodes (eight bases each) in the indexing reads. The data were demultiplexed tolerating one mismatched base in each 8-base barcode. Reads with alignment quality<Q30, improperly paired, mapped to the unmapped contigs, chrY, and mitochondria, were discarded. Duplicates were removed using Picard tools (broadinstitute.github.io/picard/). Open chromatin regions peaks were called on individual samples using MACS2 peak caller (Zhang et al., 2008) with the following parameters: -nomodel-nolambda-keep-dup-call-summits. Peaks from all samples were merged and peaks overlapping with ENCODE blacklisted regions (sites.google.com/site/anshulkundaje/projects/blacklists) were filtered out. Peak summits were extended by 150 bp on each side and defined as accessible regions. Peaks were annotated to genes using Homer (Heinz et al., 2010). The fragment counts in peaks and TF scores were calculated using chromVAR (Schep et al., 2017).

SHARE-RNA-Seq Pre-Processing

Base calls were converted to the fastq format using bcl2fastq. Reads were trimmed with a custom python script. Applicants removed reads that do not have TTTTTT at the beginning of Read 2 allowing one mismatch. Reads were aligned to the mouse genome (version mm10) using STAR (Dobin et al. 2013) (STAR--chimOutType WithinBAM--outFilterMultimapNmax 20--outFilterMismatchNoverLmax 0.06--limitOutSJcollapsed 2000000). For species mixing experiments, reads were aligned to a combined human (hg19) and mouse (mm10) genome and only primary alignments were considered. Data were demultiplexed tolerating one mismatched base in each 8-base barcode. Aligned reads were annotated to both exons and introns using featurecounts (Liao et al. 2014). To speed up processing, only barcode combinations with >100 reads were retained. UMI-Tools (Smith et al. 2017) was used to collapse UMIs of aligned reads that were within 1 nt mismatch of another UMI. UMIs that were only associated with one read were removed as potential ambient RNA contamination. A matrix of gene counts by cell was created with UMI-Tools. For cell line data, cells that expressed>7,500 genes, <300 genes, or >1% mitochondrial reads were removed. For tissue data, cells that expressed>10,000 genes, <100 genes, or >2% mitochondrial reads were removed. Expression counts (number of transcripts) for a given gene in a given cell were determined by counting unique UMIs and compiling a Digital Gene Expression (DGE) matrix. Mitochondrial genes were removed. Seurat V3 (Stuart et al. 2019) was used to scale the DGE matrix by total UMI counts, multiplied by the mean number of transcripts, and values were log transformed. To visualize data, the top 3,000 variable genes were projected into 2D space by UMAP (McInnes et al. 2018). Ambient RNA level was estimated using a previously reported approach[16].

Peak-Gene Cis-Association and DORC Identification

To calculate peak-gene associations in cis, Applicants considered all ATAC peaks that are located in the ±50 kb or ±500 kb window around each annotated TSS. We used peak counts and gene expression values to calculate the observed Spearman correlation (obs) of each peak-gene pair. To estimate the background, Applicants used chromVAR to generate 100 background peaks for each peak by matching accessibility and GC content, and calculated the Spearman correlation coefficient between those background peaks and the gene, resulting in a null peak-gene Spearman correlation distribution that is independent of peak-gene proximity. Applicants calculated the expected population mean (pop.mean) and expected population standard deviation (pop.sd) from expected Spearman correlations. The Z score was calculated by z=(obs-pop.mean)/pop.sd, and converted to a p-value based on the normal distribution. For peaks associated with multiple genes, Applicants only kept peak-gene associations with the smallest p-value.

To define DORCs (a set of nearby peaks per gene), Applicants ranked genes by the number of significantly associated peaks (±50 kb around TSSs, p<0.05). Applicants used 10 and 5 peaks per gene as cutoffs for skin data and GM12878 data, respectively. Applicants then re-calculate peak-gene association by expanding the window to ±500 kb around TSSs. The DORC score was calculated by summing up all the significantly correlated peak counts per gene, and then normalized by dividing the total unique fragments in peaks.

TF-Gene Correlation in Trans

Applicants used TF scores derived from chromVAR and gene expression values to calculate the observed Spearman correlation (obs) of each TF-gene pair. TF scores were root-mean-square normalized and gene expression values were normalized using the SCtransform function in Seurat. Z scores and p-values were calculated in the same way in the cis-analysis.

Comparison to Other Technologies

Applicants compared the performance of SHARE-seq to sci-CAR[10], SNARE-seq[11] and Paired-seq[12] using cell line data. Applicants used deeply sequenced GM12878 data for SHARE-seq, published A549 cell line data for sci-CAR[10] and published cell line mixture data for SNARE-seq[11] and Paired-seq[12]. Applicants used the authors' count matrices, which was obtained on libraries that were sequenced to saturation. For SHARE-seq and sci-CAR, Applicants set cutoff and removed debris barcode combinations by evaluating the performance of each assay. For SNARE-seq and Paired-seq, Applicants used all the cell barcodes without filtering.

To compare SHARE-seq with other high-throughput scATAC-seq methods using cell line data, Applicants used the approach described in previous paper[21], and compared with published datasets, including Cusanovich et al.[59] (GSE67446), Pliner et al.[60] (GSE109828), Preissl et al.[61] (GSE1000333), Lareau et al.[21] (GSE123581), and Buenrostro et al.[36] (GSE65360).

To compare scATAC-seq technologies in primary tissue, Applicants generated sci-ATAC, SHARE-seq, and 10× Genomics scATAC-seq datasets on adult mouse lung using the same sample processing method (above).

To compare SHARE-seq with other high-throughput scRNA-seq/snRNA-seq methods, Applicants processed four adult mouse brain datasets the same way as SHARE-seq. Applicants downloaded count matrix for nuclei[22] and cells[24] processed by 10× Genomics (P60 cortex, SRP135960), cells processed by Drop-seq[23] (P60 Cortex, GSE116470), and nuclei processed by DroNc-seq[18] (PFC, GSE71585).

Cell Cycle Signature

To calculate the cell cycle signature, Applicants used their previously published cell cycle gene list (Tirosh et al. 2016) and summed up the normalized cell cycle gene counts per cell. Applicants did not regress out the cell cycle signature, because it is one of the most important signatures in TACs.

Computational Pairing

To confirm if computational pairing methods correctly predict cell type in scATAC-seq based on a scRNA-seq profile, Applicants used Seurat v3.0 (Stuart et al. 2019) to calculate gene activity scores from scATAC-seq. Next, Applicants identified anchors between the scATAC-seq and scRNA-seq datasets using CCA (Stuart et al. 2019) and used these anchors to transfer cell-type labels from scRNA-seq to scATAC-seq. Applicants calculated the percent of mismatch between the predicted cell type to the actual cell type.

Brain Data Analysis

For the brain sample, Applicants aggregated scATAC-seq data generated using SureCell[21] as pseudo-bulk samples, then extracted a small number of principal components (PCs) from the normalized pseudo-bulk count matrix. Applicants next projected the scATAC-seq data to the space spanned by the PCs. The projected data was then visualized using tSNE and UMAP. To jointly cluster on ATAC and RNA signal, Applicants used Similarity NEtwork FUSION (Wang et al. 2014) to combine the distance matrix in chromatin space and RNA space. After generating the fused distance matrix, Applicants then calculated k-nearest neighbor graph and found clusters using Louvain community detection algorithm. The clusters were assigned based on both marker gene and scATAC-seq signal.

Skin scATAC-Seq Peak Count Matrix

To ensure that a peak set in skin includes ATAC peaks from rare populations, Applicants performed two rounds of peak calling. Applicants first called peaks on filtered reads from all cells and generated $1^{st}$-round cell-peak count matrix. Applicants then filtered cells based on both ATAC and RNA profiles and identified clusters based on RNA profiles. Applicants next called peaks again on aggregated pseudo bulk samples from each cluster and merged all peak summits, to generate a $2^{nd}$-round cell-peak count matrix.

Skin scATAC-Seq Dimension Reduction

To reduce the dimension of ATAC-seq data, Applicants tested cisTopic (Gonzalez-Blas et al. 2019), chromVAR motif score and Kmer (Schep et al. 2017), and snapATAC (Fang et al. 2019) approaches.

Pseudotime Inference

To calculate pseudotime based on scATAC-seq data of TACs, IRS and Hair Shaft populations, Applicants provided 55 normalized topics from cisTopic as input to Palantir (Setty et al. 2019). Applicants then defined lineages based on the probability of lineage assignment.

Residual Analysis

Both DORC scores and gene expression were smoothed over pseudotime with local polynomial regression fitting (loess) separately, then min-max normalized. The residual for each gene was calculated by subtracting normalized gene expression from normalized DORC scores.

Chromatin Potential

To calculate chromatin potential, Applicants first smoothed DORC scores (chromatin space) and corresponding gene expression (RNA space) over a k-nearest neighbor graph (k-NN, k=50), calculated using normalized ATAC topics from cisTopic. Next, Applicants calculated another k-NN (k=10), between smoothed chromatin profile of a given cell ($C_{atac,i}$), and smoothed gene expression profile of each cell ($C_{rna,i,j}$). Applicants then calculated the distance ($D_{i,j}$) between the $C_{atac,\ i}$ and the average of $C_{rna,\ j}$ in chromatin space. The arrow length was defined by normalizing $D_{i,\ j}$. For visualization, Applicant smoothed arrows with the 15 k-NNs in low dimensional space. For grid view, Applicants divided the UMAP space into 40×40 grid, then averaged the arrows for all the cells within each grid.

RNA Velocity

RNA velocity was calculated using Velocyto (La Manno et al. 2018) with default settings. For visualization, we smoothed arrows with the 15 RNA k-NNs. For grid view, Applicants divided the UMAP space into 40×40 grid, then averaged the arrows for all the cells within each grid.

REFERENCES

1. Spitz, F. & Furlong, E. E. M. Transcription factors: from enhancer binding to developmental control. Nat. Rev. Genet. 13, 613-626 (2012).
2. Shema, E., Bernstein, B. E. & Buenrostro, J. D. Single-cell and single-molecule epigenomics to uncover genome regulation at unprecedented resolution. Nat. Genet. 51, 19-25 (2018).
3. Novershtern, N. et al. Densely interconnected transcriptional circuits control cell states in human hematopoiesis. Cell 144, 296-309 (2011).
4. Bernstein, B. E. et al. A Bivalent Chromatin Structure Marks Key Developmental Genes in Embryonic Stem Cells. Cell vol. 125 315-326 (2006).
5. Rada-Iglesias, A. et al. A unique chromatin signature uncovers early developmental enhancers in humans. Nature 470, 279-283 (2011).
6. Lara-Astiaso, D. et al. Chromatin state dynamics during blood formation. Science 345, 943 (2014).
7. Kelsey, G., Stegle, O. & Reik, W. Single-cell epigenomics: Recording the past and predicting the future. Science 358, 69-75 (2017).
8. Stuart, T. et al. Comprehensive Integration of Single-Cell Data. Cell 177, 1888-1902.e21 (2019).
9. Rusk, N. Multi-omics single-cell analysis. Nat. Methods 16, 679 (2019).
10. Cao, J. et al. Joint profiling of chromatin accessibility and gene expression in thousands of single cells. Science 361, 1380-1385 (2018).
11. Chen, S., Lake, B. B. & Zhang, K. High-throughput sequencing of the transcriptome and chromatin accessibility in the same cell. Nat. Biotechnol. (2019) doi: 10.1038/s41587-019-0290-0.
12. Zhu, C. et al. An ultra high-throughput method for single-cell joint analysis of open chromatin and transcriptome. Nat. Struct. Mol. Biol. 26, 1063-1070 (2019).
13. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat. Methods 10, 1213-1218 (2013).
14. Adam, R. C. et al. Pioneer factors govern super-enhancer dynamics in stem cell plasticity and lineage choice. Nature 521, 366-370 (2015).
15. Rosenberg, A. B. et al. Single-cell profiling of the developing mouse brain and spinal cord with split-pool barcoding. Science 360, 176-182 (2018).
16. Ding, J. et al. Systematic comparative analysis of single cell RNA-sequencing methods. bioRxiv 632216 (2019) doi:10.1101/632216.
17. Habib, N. et al. Div-Seq: Single-nucleus RNA-Seq reveals dynamics of rare adult newborn neurons. Science 353, 925-928 (2016).
18. Habib, N. et al. Massively parallel single-nucleus RNA-seq with DroNc-seq. Nat. Methods 14, 955-958 (2017).
19. La Manno, G. et al. RNA velocity of single cells. Nature 560, 494-498 (2018).
20. Mezger, A. et al. High-throughput chromatin accessibility profiling at single-cell resolution. Nat. Commun. 9, 3647 (2018).
21. Lareau, C. A. et al. Droplet-based combinatorial indexing for massive-scale single-cell chromatin accessibility. Nat. Biotechnol. 37, 916-924 (2019).
22. Datasets-Single Cell Gene Expression-Official 10× Genomics Support. support. 10×genomics com/single-cell-gene-expression/datasets/2.1.0/nuclei2k.
23. Saunders, A. et al. Molecular Diversity and Specializations among the Cells of the Adult Mouse Brain. Cell 174, 1015-1030.e16 (2018).
24. Zeisel, A. et al. Molecular Architecture of the Mouse Nervous System. Cell 174, 999-1014.e22 (2018).
25. Hsu, Y.-C., Li, L. & Fuchs, E. Emerging interactions between skin stem cells and their niches. Nat. Med. 20, 847-856 (2014).
26. Fan, X. et al. Single Cell and Open Chromatin Analysis Reveals Molecular Origin of Epidermal Cells of the Skin. Dev. Cell 47, 133 (2018).
27. Salzer, M. C. et al. Identity Noise and Adipogenic Traits Characterize Dermal Fibroblast Aging. Cell 175, 1575-1590.e22 (2018).
28. Joost, S. et al. Single-Cell Transcriptomics of Traced Epidermal and Hair Follicle Stem Cells Reveals Rapid Adaptations during Wound Healing. Cell Rep. 25, 585-597.e7 (2018).
29. Lien, W.-H. et al. Genome-wide maps of histone modifications unwind in vivo chromatin states of the hair follicle lineage. Cell Stem Cell 9, 219-232 (2011).
30. Cohen, I. et al. PRC1 Fine-tunes Gene Repression and Activation to Safeguard Skin Development and Stem Cell Specification. Cell Stem Cell 22, 726-739.e7 (2018).
31. Blanpain, C., Lowry, W. E., Geoghegan, A., Polak, L. & Fuchs, E. Self-renewal, multipotency, and the existence of two cell populations within an epithelial stem cell niche. Cell 118, 635-648 (2004).
32. Schep, A. N., Wu, B., Buenrostro, J. D. & Greenleaf, W. J. chromVAR: inferring transcription-factor-associated accessibility from single-cell epigenomic data. Nat. Methods 14, 975-978 (2017).
33. Spaderna, S. et al. The transcriptional repressor ZEB1 promotes metastasis and loss of cell polarity in cancer. Cancer Res. 68, 537-544 (2008).
34. Huang, D.-Y. et al. Transcription factor SOX-5 enhances nasopharyngeal carcinoma progression by down-regulating SPARC gene expression. J. Pathol. 214, 445-455 (2008).
35. Marinov, G. K. et al. From single-cell to cell-pool transcriptomes: stochasticity in gene expression and RNA splicing. Genome Res. 24, 496-510 (2014).
36. Buenrostro, J. D. et al. Single-cell chromatin accessibility reveals principles of regulatory variation. Nature 523, 486-490 (2015).
37. Larsson, A. J. M. et al. Genomic encoding of transcriptional burst kinetics. Nature 565, 251-254 (2019).
38. Lin, J. & Amir, A. Homeostasis of protein and mRNA concentrations in growing cells. Nat. Commun. 9, 4496 (2018).
39. Gasperini, M. et al. A Genome-wide Framework for Mapping Gene Regulation via Cellular Genetic Screens. Cell 176, 1516 (2019).
40. Gonzalez, A. J., Setty, M. & Leslie, C. S. Early enhancer establishment and regulatory locus complexity shape transcriptional programs in hematopoietic differentiation. Nat. Genet. 47, 1249-1259 (2015).

41. Whyte, W. A. et al. Master transcription factors and mediator establish super-enhancers at key cell identity genes. *Cell* 153, 307-319 (2013).
42. Schoenfelder, S. & Fraser, P. Long-range enhancer-promoter contacts in gene expression control. *Nat. Rev. Genet.* 20, 437-455 (2019).
43. Nowak, J. A., Polak, L., Pasolli, H. A. & Fuchs, E. Hair follicle stem cells are specified and function in early skin morphogenesis. *Cell Stem Cell* 3, 33-43 (2008).
44. Zhang, B. & Hsu, Y.-C. Emerging roles of transit-amplifying cells in tissue regeneration and cancer. *Wiley Interdiscip. Rev. Dev. Biol.* 6, (2017).
45. Zhang, B. et al. Hair follicles' transit-amplifying cells govern concurrent dermal adipocyte production through Sonic Hedgehog. *Genes & Development* vol. 30 2325-2338 (2016).
46. Yang, H., Adam, R. C., Ge, Y., Hua, Z. L. & Fuchs, E. Epithelial-Mesenchymal Micro-niches Govern Stem Cell Lineage Choices. *Cell* 169, 483-496.e13 (2017).
47. Xin, T., Gonzalez, D., Rompolas, P. & Greco, V. Flexible fate determination ensures robust differentiation in the hair follicle. *Nat. Cell Biol.* 20, 1361-1369 (2018).
48. Joost, S. et al. Single-Cell Transcriptomics Reveals that Differentiation and Spatial Signatures Shape Epidermal and Hair Follicle Heterogeneity. *Cell Syst* 3, 221-237.e9 (2016).
49. Millar, S. E. et al. WNT signaling in the control of hair growth and structure. *Dev. Biol.* 207, 133-149 (1999).
50. Olsson, A. et al. Single-cell analysis of mixed-lineage states leading to a binary cell fate choice. *Nature* 537, 698-702 (2016).
51. Clevers, H. Wnt/β-Catenin Signaling in Development and Disease. *Cell* vol. 127 469-480 (2006).
52. Merrill, B. J., Gat, U., DasGupta, R. & Fuchs, E. Tcf3 and Lef1 regulate lineage differentiation of multipotent stem cells in skin. *Genes Dev.* 15, 1688-1705 (2001).
53. Godwin, A. R. & Capecchi, M. R. Hoxc13 mutant mice lack external hair. *Genes Dev.* 12, 11-20 (1998).
54. Pan, Y. et al. γ-Secretase Functions through Notch Signaling to Maintain Skin Appendages but Is Not Required for Their Patterning or Initial Morphogenesis. *Developmental Cell* vol. 7 731-743 (2004).
55. Stoeckius, M. et al. Simultaneous epitope and transcriptome measurement in single cells. *Nat. Methods* 14, 865-868 (2017).
56. Dixit, A. et al. Perturb-Seq: Dissecting Molecular Circuits with Scalable Single-Cell RNA Profiling of Pooled Genetic Screens. *Cell* 167, 1853-1866.e17 (2016).
57. Vitak, S. A. et al. Sequencing thousands of single-cell genomes with combinatorial indexing Nat. *Methods* 14, 302-308 (2017).
58. Corces, M. R. et al. An improved ATAC-seq protocol reduces background and enables interrogation of frozen tissues. *Nat. Methods* 14, 959-962 (2017).
59. Cusanovich, D. A. et al. Multiplex single-cell profiling of chromatin accessibility by combinatorial cellular indexing. *Science* vol. 348 910-914 (2015).
60. Pliner, H. A. et al. Cicero Predicts cis-Regulatory DNA Interactions from Single-Cell Chromatin Accessibility Data. *Mol. Cell* 71, 858-871.e8 (2018).
61. Preissl, S. et al. Single-nucleus analysis of accessible chromatin in developing mouse forebrain reveals cell-type-specific transcriptional regulation. *Nat. Neurosci.* 21, 432-439 (2018).
62. Hnisz, D. et al. Super-enhancers in the control of cell identity and disease. *Cell* 155, 934-947 (2013).

Additional Notes

To improve library yield and minimize interference between assays, Applicants systematically optimized SHARE-seq, including fixation, operation order, buffer condition, selection of RNase inhibitors, and hybridization temperatures. To reduce cost and improve performance compared to SPLiT-seq, Applicants optimized SHARE-seq library structure and significantly reduced the number of ligation reactions. To demonstrate the technical advancement of SHARE-seq, Applicants comprehensively compared SHARE-seq with sci-CAR[10], another combinatorial indexing approach, in terms of data quality, time, throughput, barcode collision rate, cell recovery, and cost.

1. Data Quality

To compare with another combinatorial indexing approach (sci-CAR[10]), Applicants downloaded published sci-CAR cell line data (A549)[10]. Applicants set a cutoff to filter low-quality cells based on the distribution of the total number of reads per cell. For sci-CAR-ATAC, Applicants filtered low-quality cells with fewer than 100 reads in peaks. To reduce bias in peak calling, Applicants took the top 100,000 peaks in each of the sci-CAR A549 dataset and SHARE-seq's GM12878 dataset. Sci-CAR recovers median 364 reads in peaks and SHARE-seq recovers 4,631 reads in peaks. (Applicants used the authors' count matrix, which was obtained on a library that was sequenced to saturation[10]). When normalized to copy number in both cell lines, Applicants showed a 17-fold improvement of reads per cell in SHARE-seq. For comparison to RNA-seq, Applicants filtered cells with less than 800 UMIs for sci-CAR and 2,500 UMIs for SHARE-seq. Sci-CAR recovers a median of 2,623 UMIs per cell and SHARE-seq recovers 6,742 UMIs per cell.

2. Throughput

To generate paired profiles from 10,000 cells, SHARE-seq and sci-CAR both took about two days. Sci-CAR needed fluorescence activated cell sorting (FACS) to accurately deposit a small number of cells to each well[10]. SHARE-seq processed samples in bulk so that FACS or any other special equipment is not needed, which simplified use and makes SHARE-seq applicable to cells that are difficult to sort. SHARE-seq could generate more single-cell profiles (100,000 to 1 million) without additional labor and time.

3. Barcode Collision

Sci-CAR inherently had about 10% barcode collision rate because of the number of barcoding combinations[10]. SHARE-seq had 1-0.01% of the expected barcoding collision rate depending on the targeted number of cells.

4. Cell Recovery

Sci-CAR was reported to start with 5 million cells to recover roughly 6,000 cells[10], likely because of cell loss during FACS (about 0.1% cell recovery) and manipulation of a very small number of cells. SHARE-seq, in general, needed a minimum of 200,000 cells, and expects to recover about 10% of cells.

5. Cost

Figure 24:
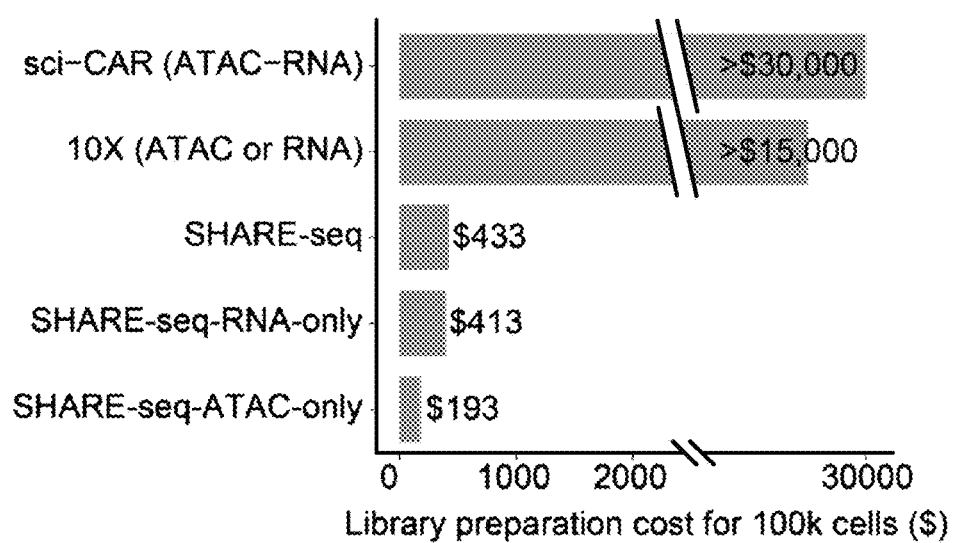
FIG. 24 shows exemplary cost of SHARE-seq library preparation compares to 10× and sci-CAR.

SHARE-seq significantly reduced the amount of consumed enzyme by performing all reactions (including ligation, transposition, reverse transcription, and tagmentation) in bulk (about 10,000 cells per reaction), which dramatically reduced cost. The library preparation cost for SHARE-seq in Applicants hands was only about $433 for 100,000 cells (FIG. 24), including $50 oligos, $50 enzymes (Tn5, ligase, etc.), $121 RNase inhibitors and other consumables. By comparison, the cost of sci-CAR scaled with the number of cells to be recovered. For each experiment, 96 RT reactions, 96 transposition reactions, one tagmentation reaction per 25 nuclei and 2 PCR reactions per 25 nuclei were needed. It would cost more than $30,000 to prepare a sequencing library for 100,000 cells for sci-CAR.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for single cell analysis of genomic DNA accessibility and RNA expression in a cell, comprising:
   a. fragmenting, within individual fixed cells, by a transposase, cellular genomic DNA;
   b. generating cDNA copies of cellular RNA molecules by reverse transcription;
   c. isolating the individual fixed cells in separate individual discrete volumes;
   d. barcoding with a primer pair and a volume-specific barcode, the primer pair and volume-specific barcode hybridizes to both fragmented cellular genomic DNA and cDNA such that the genomic DNA and the cDNA from the same cell receive the same unique cell barcode sequence;
   e. reverse crosslinking the individual fixed cells;
   f. isolating the barcoded genomic DNA and the cDNA; and
   g. characterizing one or more features of the individual cells based, at least in part, on sequencing of the isolated barcoded genomic DNA and the cDNA.

2. The method of claim 1, wherein the transposase is an engineered transposase with an activity higher than a wild type counterpart.

3. The method of claim 1, wherein the transposase comprises two or more enzymatic moieties.

4. The method of claim 1, wherein the transposase forms a complex with a phosphorylated oligonucleotide.

5. The method of claim 1, further comprising generating cDNA from the RNA in the cell using a primer comprising i) a unique molecular identifier (UMI), (ii) an affinity tag, and/or (iii) a poly(T) sequence.

6. The method of claim 1, wherein the cDNA comprises an affinity tag.

7. The method of claim 5, wherein the barcoded cDNA is isolated by capturing the affinity tag on a solid support.

8. The method of claim 1, wherein, before isolation, the genomic DNA forms a complex with one or more proteins, and the genomic DNA is isolated by capturing the one or more proteins on a solid support.

9. The method of claim 1, further comprising amplifying the genomic DNA, the cDNA, or a combination thereof.

10. The method of claim 1, wherein the sequencing comprises sequencing a portion of the genomic DNA fragments, a portion of the cDNA molecules, and/or a portion of the barcode attached thereof.

11. The method of claim 1, wherein the one or more features comprise an epigenetic feature of a genomic DNA region in the cell.

12. The method of claim 11, wherein the epigenetic feature comprises:
   a profile of chromatin accessibility along the genomic DNA region;
   a DNA binding protein occupancy for a binding site in the genomic DNA region;
   a nucleosome-free DNA in the genomic DNA region;
   a positioning of nucleosomes along the genomic DNA region;
   chromatin states; or
   a combination thereof.

13. The method of claim 11, wherein the one or more features comprise an expression profile of the cellular RNA.

14. The method of claim 1, wherein the genomic DNA is tagged.

15. The method of claim 1, further comprising fixing the individual cells before generating the genomic DNA and cDNA.

16. The method of claim 1, further comprising lysing the individual cells in the presence of an RNase inhibitor.

17. The method of claim 16, wherein the RNase inhibitor is compatible with an insertional enzyme.

18. A method of diagnosing a condition in a subject, comprising:
   characterizing a feature of one or more cells in the subject using the method of claim 1; and
   providing a diagnosis or prognosis based on the feature.

* * * * *